(12) United States Patent
Zhang et al.

(10) Patent No.: US 9,873,700 B2
(45) Date of Patent: Jan. 23, 2018

(54) COMPOUNDS FOR KINASE MODULATION, AND INDICATIONS THEREFOR

(71) Applicant: Plexxikon Inc., Berkeley, CA (US)

(72) Inventors: Chao Zhang, Moraga, CA (US); Klaus-Peter Hirth, San Francisco, CA (US); Prabha N. Ibrahim, Mountain View, CA (US); Marika Nespi, Berkeley, CA (US); Songyuan Shi, Fremont, CA (US); Wayne Spevak, Berkeley, CA (US); Gaston G. Habets, Pleasant Hill, CA (US); Elizabeth A. Burton, El Cerrito, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

(21) Appl. No.: 14/290,786

(22) Filed: May 29, 2014

(65) Prior Publication Data

US 2014/0357612 A1    Dec. 4, 2014

Related U.S. Application Data

(60) Provisional application No. 61/829,190, filed on May 30, 2013.

(51) Int. Cl.
| | |
|---|---|
| *A01N 43/00* | (2006.01) |
| *A61K 31/397* | (2006.01) |
| *C07D 487/04* | (2006.01) |
| *A61K 31/5377* | (2006.01) |
| *A61K 31/519* | (2006.01) |
| *A61K 31/506* | (2006.01) |
| *A61K 31/437* | (2006.01) |
| *A61K 31/4439* | (2006.01) |
| *C07D 417/04* | (2006.01) |
| *C07D 471/04* | (2006.01) |
| *C07D 213/75* | (2006.01) |

(52) U.S. Cl.
CPC .......... *C07D 487/04* (2013.01); *A61K 31/437* (2013.01); *A61K 31/4439* (2013.01); *A61K 31/506* (2013.01); *A61K 31/519* (2013.01); *A61K 31/5377* (2013.01); *C07D 213/75* (2013.01); *C07D 417/04* (2013.01); *C07D 471/04* (2013.01)

(58) Field of Classification Search
USPC ....................................................... 514/210.2
See application file for complete search history.

(56) References Cited

U.S. PATENT DOCUMENTS

| | | | |
|---|---|---|---|
| 7,202,266 B2 | 4/2007 | Arnold et al. | |
| 7,348,338 B2 | 3/2008 | Arnold et al. | |
| 7,476,746 B2 | 1/2009 | Artis et al. | |
| 7,491,831 B2 | 2/2009 | Artis et al. | |
| 7,498,342 B2 | 3/2009 | Ibrahim et al. | |
| 7,504,509 B2 | 3/2009 | Ibrahim et al. | |
| 7,517,970 B2 | 4/2009 | West et al. | |
| 7,531,568 B2 | 5/2009 | Lin et al. | |
| 7,572,806 B2 | 8/2009 | Arnold et al. | |
| 7,585,859 B2 | 9/2009 | Ibrahim et al. | |
| 7,605,168 B2 | 10/2009 | Ibrahim et al. | |
| 7,723,374 B2 | 5/2010 | Artis et al. | |
| 7,759,475 B2 | 7/2010 | West | |
| 7,846,941 B2 | 12/2010 | Zhang et al. | |
| 7,863,288 B2 | 1/2011 | Ibrahim et al. | |
| 7,863,289 B2 | 1/2011 | Spevak et al. | |
| 7,872,018 B2 | 1/2011 | Ibrahim et al. | |
| 7,893,075 B2 | 2/2011 | Zhang et al. | |
| 7,947,708 B2 | 5/2011 | Ibrahim et al. | |
| 7,994,185 B2 * | 8/2011 | Rheault .................... | 514/275 |
| 8,053,463 B2 | 11/2011 | Lin et al. | |
| 8,067,434 B2 | 11/2011 | Ibrahim et al. | |
| 8,110,576 B2 | 2/2012 | Ibrahim et al. | |
| 8,119,637 B2 | 2/2012 | Ibrahim et al. | |
| 8,129,404 B2 | 3/2012 | Ibrahim et al. | |
| 8,143,271 B2 | 3/2012 | Ibrahim et al. | |
| 8,153,641 B2 | 4/2012 | Ibrahim et al. | |
| 8,158,636 B2 | 4/2012 | Ibrahim et al. | |
| 8,198,273 B2 | 6/2012 | Ibrahim et al. | |
| 8,268,858 B2 | 9/2012 | Wu et al. | |
| 8,367,828 B2 | 2/2013 | Arnold et al. | |
| 8,404,700 B2 | 3/2013 | Ibrahim et al. | |
| 8,415,469 B2 | 4/2013 | Ibrahim et al. | |
| 8,461,169 B2 | 6/2013 | Zhang et al. | |
| 8,470,818 B2 | 6/2013 | Ibrahim et al. | |
| 8,470,821 B2 | 6/2013 | Ibrahim et al. | |
| 8,642,606 B2 | 2/2014 | Ibrahim et al. | |
| 8,673,928 B2 | 3/2014 | Ibrahim et al. | |

(Continued)

FOREIGN PATENT DOCUMENTS

| | | |
|---|---|---|
| WO | WO 2007/013896 | 5/2007 |
| WO | WO 2009/012283 | 1/2009 |

(Continued)

OTHER PUBLICATIONS

International Search Report (ISR) and Written Opinion (WO) in PCT/US2014/040076 dated Oct. 22, 2014.
U.S. Appl. No. 14/602,119, filed Jan. 21, 2015, Ibrahim et al.
U.S. Appl. No. 14/637,303, filed Mar. 3, 2015, Lin et al.
U.S. Appl. No. 14/798,167, filed Jul. 13, 2015, Ibrahim et al.
U.S. Appl. No. 14/733,830, filed Jun. 8, 2015, Zhang et al.
U.S. Appl. No. 14/839,668, filed Aug. 28, 2015, Ibrahim.
U.S. Appl. No. 14/846,545, filed Sep. 4, 2015, Zhang et al.
U.S. Appl. No. 14/850,912, filed Sep. 10, 2015, Shi et al.

(Continued)

*Primary Examiner* — Marcos Sznaidman
(74) *Attorney, Agent, or Firm* — Sheppard Mullin Richter & Hampton LLP

(57) ABSTRACT

Compounds active on protein kinases and methods for regulating protein kinase pathways are described, as well as methods of using such compounds to treat diseases and conditions associated with aberrant activity of protein kinases.

8 Claims, 9 Drawing Sheets

(56) References Cited

U.S. PATENT DOCUMENTS

| | | |
|---|---|---|
| 8,722,702 B2 | 5/2014 | Zhang et al. |
| 8,865,735 B2 | 10/2014 | Ibrahim et al. |
| 8,901,118 B2 | 12/2014 | Zhang et al. |
| 8,901,301 B2 | 12/2014 | Ibrahim et al. |
| 8,912,204 B2 | 12/2014 | Ibrahim et al. |
| 9,469,640 B2 | 10/2016 | Wu et al. |
| 9,487,515 B2 | 11/2016 | Zhang et al. |
| 9,695,169 B2 | 7/2017 | Ibrahim |
| 2004/0142864 A1 | 7/2004 | Bremer et al. |
| 2004/0171062 A1 | 9/2004 | Hirth et al. |
| 2005/0048573 A1 | 3/2005 | Artis et al. |
| 2005/0079548 A1 | 4/2005 | Artis et al. |
| 2005/0164300 A1 | 7/2005 | Artis et al. |
| 2005/0170431 A1 | 8/2005 | Ibrahim et al. |
| 2006/0058339 A1 | 3/2006 | Ibrahim et al. |
| 2006/0135540 A1 | 6/2006 | Lin et al. |
| 2006/0160135 A1 | 7/2006 | Wang et al. |
| 2007/0066641 A1 | 3/2007 | Ibrahim et al. |
| 2007/0072904 A1 | 3/2007 | Lin et al. |
| 2008/0221127 A1 | 9/2008 | Lin et al. |
| 2008/0234349 A1 | 9/2008 | Lin et al. |
| 2008/0249137 A1 | 10/2008 | Lin et al. |
| 2010/0190777 A1 | 7/2010 | Wu et al. |
| 2010/0310659 A1 | 12/2010 | Desai et al. |
| 2011/0092538 A1 | 4/2011 | Spevak et al. |
| 2011/0112127 A1 | 5/2011 | Zhang et al. |
| 2011/0166174 A1 | 7/2011 | Zhang et al. |
| 2011/0183988 A1 | 7/2011 | Ibrahim et al. |
| 2012/0015966 A1 | 1/2012 | Lin et al. |
| 2012/0053177 A1 | 3/2012 | Ibrahim et al. |
| 2012/0122860 A1 | 5/2012 | Visor et al. |
| 2012/0165366 A1 | 6/2012 | Ibrahim et al. |
| 2012/0245174 A1 | 9/2012 | Ibrahim et al. |
| 2013/0237531 A1 | 9/2013 | Wu et al. |
| 2013/0261117 A1 | 10/2013 | Ibrahim et al. |
| 2013/0274259 A1 | 10/2013 | Zhang et al. |
| 2013/0303534 A1 | 11/2013 | Ibrahim et al. |
| 2014/0037617 A1 | 2/2014 | Bollag et al. |
| 2014/0038948 A1 | 2/2014 | Wu et al. |
| 2014/0045840 A1 | 2/2014 | Zhang et al. |
| 2014/0094611 A1 | 4/2014 | Ibrahim et al. |
| 2014/0128373 A1 | 5/2014 | Ibrahim et al. |
| 2014/0128390 A1 | 5/2014 | Lin et al. |
| 2014/0213554 A1 | 7/2014 | Wu et al. |
| 2014/0243365 A1 | 8/2014 | Zhang et al. |
| 2014/0288070 A1 | 9/2014 | Bollag et al. |
| 2014/0303121 A1 | 10/2014 | Zhang et al. |
| 2014/0303187 A1 | 10/2014 | Wu et al. |
| 2015/0080372 A1 | 3/2015 | Ibrahim et al. |
| 2015/0133400 A1 | 5/2015 | Zhang et al. |
| 2015/0166547 A1 | 6/2015 | Ibrahim et al. |
| 2015/0183793 A1 | 7/2015 | Zhang et al. |
| 2016/0075712 A1 | 3/2016 | Shi et al. |
| 2016/0243092 A1 | 8/2016 | Bollag et al. |
| 2016/0326162 A1 | 11/2016 | Lin et al. |
| 2016/0326168 A1 | 11/2016 | Ibrahim et al. |
| 2016/0326169 A1 | 11/2016 | Ibrahim et al. |
| 2016/0339025 A1 | 11/2016 | Ibrahim et al. |
| 2016/0340357 A1 | 11/2016 | Ibrahim et al. |
| 2016/0340358 A1 | 11/2016 | Ibrahim et al. |
| 2016/0355513 A1 | 12/2016 | Desai et al. |
| 2017/0029413 A1 | 2/2017 | Holladay et al. |
| 2017/0056382 A1 | 3/2017 | Wu et al. |
| 2017/0157120 A1 | 6/2017 | Ibrahim et al. |
| 2017/0158690 A1 | 6/2017 | Wu et al. |

FOREIGN PATENT DOCUMENTS

| | | |
|---|---|---|
| WO | WO 2009/111278 | 9/2009 |
| WO | WO 2009/111279 | 9/2009 |
| WO | WO 2009/137391 | 11/2009 |
| WO | WO 2010/111527 | 9/2010 |
| WO | WO 2010/129467 | 11/2010 |
| WO | WO 2011/023773 | 3/2011 |
| WO | WO 2011/025938 | 3/2011 |
| WO | WO 2011/059610 | 5/2011 |
| WO | WO 2012/109075 | 8/2012 |
| WO | WO 2013/043935 | 3/2013 |
| WO | WO 2014/039714 | 3/2014 |

OTHER PUBLICATIONS

U.S. Appl. No. 15/221,474, filed Jul. 27, 2016, Holladay et al.
U.S. Appl. No. 15/260,042, filed Sep. 8, 2016, Wu et al.
U.S. Appl. No. 15/269,054, filed Sep. 19, 2016, Ibrahim et al.
U.S. Appl. No. 15/288,558, filed Oct. 7, 2016, Zhang et al.
U.S. Appl. No. 15/370,631, filed Dec. 6, 2016, Wu et al.
International Preliminary Report on Patentability for International Application No. PCT/US2014/040076, dated Dec. 1, 2015. (8 pages).
U.S. Appl. No. 15/460,095, filed Mar. 15, 2017, Lin et al.
U.S. Appl. No. 15/605,856, filed May 25, 2017, Ibrahim et al.
U.S. Appl. No. 15/606,682, filed May 26, 2017, Desai et al.
U.S. Appl. No. 15/620,396, filed Jun. 12, 2017, Wu et al.
U.S. Appl. No. 15/627,223, filed Jun. 19, 2017, Zhang et al.

* cited by examiner a

COMPOUNDS FOR KINASE MODULATION, AND INDICATIONS THEREFOR

CROSS-REFERENCE TO RELATED APPLICATION

This application claims the benefit under 35 U.S.C. § 119(e) to U.S. Provisional Application No. 61/829,190, filed on May 30, 2013, the entirety of which is incorporated herein by reference.

FIELD

The present disclosure relates to kinase inhibitors which selectively modulate kinases, and uses therefor. Particular embodiments contemplate disease indications which are amenable to treatment by modulation of kinase activity.

BACKGROUND

Receptor protein kinases regulate key signal transduction cascades that control or are involved in the control of a plethora of physiological functions including cellular growth and proliferation, cell differentiation, cellular development, cell division, cell adhesion, stress response, short-range contact-mediated axonal guidance, transcription regulation, aberrant mitogenesis, angiogenesis, abnormal endothelial cell-cell or cell-matrix interactions during vascular development, inflammation, lymphohematopoietic stem cell activity, protective immunity against specific bacteria, allergic asthma, aberrant tissue-specific responses to the activation of the JNK signal transduction pathway, cell transformation, memory, apoptosis, competitive activity-dependent synapse modification at the neuromuscular synapse, immunological mediation of disease, and calcium regulation.

Exemplary disease states associated with aberrant regulation of protein kinases include, for example without limitation, acrocephalo-syndactyly type I, acute myeloid leukemia, AIDS-induced non-Hodgkin's lymphoma, Alzheimer's disease, amyotrophic lateral sclerosis, arthritis, asthma, atherosclerosis, atopic dermatitis, autoimmune diseases, bacterial infection, bladder cancer, cancer of the breast, cancer of the central nervous system, cancer of the colon, cancer of the endometrium, cancer of the fallopian tube, cancer of the gastrointestinal tract, cancer of the ovary, heart failure, chronic myeloid leukemia, colon carcinoma, colorectal cancer, chronic obstructive pulmonary disease (COPD), Crouzon Syndrome, diabetes, diabetic nephropathy, emphysema, endometriosis, epidermoid cancer, fibrotic disorders, gastrointestinal stromal tumor (GIST), glomerulonephritis, Graves' disease, head injury, hepatocellular carcinoma, Hirschsprung's disease, human gliomas, immunodeficiency diseases, inflammatory disorders, ischemic stroke, Jackson-Weiss syndrome, leiomyosarcoma, leukemias, lupus nephritis, malignant melanoma, malignant nephrosclerosis, mastocytosis, mast cell tumors, melanoma of the colon, MEN2 syndromes, metabolic disorders, migraine, multiple sclerosis, myeloproliferative disorders, nephritis, neurodegenerative diseases, neurotraumatic diseases, lung cancer, non small cell lung cancer, organ transplant rejection, osteoporosis, pain, Parkinson's disease, Pfeiffer Syndrome, polycystic kidney disease, primary lymphoedema, prostate cancer, psoriasis, vascular restenosis, rheumatoid arthritis, dermal and tissue scarring, selective T-cell defect (STD), severe combined immunodeficiency (SCID), small cell lung cancer, spinal cord injury, squamous cell carcinoma, systemic lupus erythematosis, testicular cancer, thrombotic microangiopathy syndromes, Wegener's granulomatosis, X-linked agammaglobulinemia, viral infection, diabetic retinopathy, alopecia, erectile dysfunction, macular degeneration, chronic lymphocytic leukemia (CLL), myelodysplastic syndrome (MDS), neurofibromatosis, and tuberous sclerosis.

The identification of activating BRAF mutations (primarily missense substitutions for Valine-600 or BRAF$^{V600}$ in cancer supports a functionally important role for BRAF in the pathogenesis of these malignancies (Davies, H. et al. *Nature* 417, 949-954 (2002)). Specific BRAF inhibitors including vemurafenib and dabrafenib have demonstrated both objective tumor response and, in the case of vemurafenib, overall survival benefit in mutant BRAF$^{V600}$ driven melanoma (Flaherty, K. T. et al. *N Engl J Med* 363, 809-819 (2010); Chapman, P. B. et al. *N Engl J Med* 364, 2507-2516 (2011); Sosman, J. A. et al. *N Engl J Med* 366, 707-714 (2012); Hauschild, A. et al. *Lancet* 380, 358-365 (2012); Bollag, G. et al. *Nature* 467, 596-599 (2010); and Stellwagen, J. C. et al. *Bioorg Med Chem Lett* 21, 4436-4440 (2011)). The clinical effectiveness of BRAF inhibitor-based therapy depends on complete abolition of the MAPK pathway output in tumors harboring BRAF mutations (Bollag, G. et al. *Nature* 467, 596-599 (2010)). However these compounds paradoxically activate the MAPK pathway in cells bearing oncogenic RAS or elevated upstream receptor signaling (Hatzivassiliou, G. et al. *Nature* 464, 431-435 (2010); Heidorn, S. J. et al. *Cell* 140, 209-221 (2010); and Poulikakos, P. I., Zhang, C., Bollag, G., Shokat, K. M. & Rosen, N. *Nature* 464, 427-430 (2010)). This activation can lead to cellular proliferation and has been associated clinically with appearance of cutaneous squamous cell carcinomas (cuSCC) and keratoacanthomas (KAs), sometimes within weeks of initiation of therapy (Hauschild, A. et al. *Lancet* 380, 358-365 (2012); Bollag, G. et al. *Nature* 467, 596-599 (2010); Huang, V., Hepper, D., Anadkat, M. & Cornelius, L. *Arch Dermatol* 148, 628-633 (2012); and Anforth, R. M. et al. *Br J Dermatol* 167, 1153-1160 (2012)). Accordingly, there is a need in the art for compounds and methods of use thereof for modulation of receptor protein kinases. The disclosure herein meets this and other needs.

SUMMARY

In one aspect, provided herewith is a compound having formula (I'):

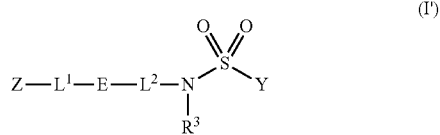

or a pharmaceutically acceptable salt, a prodrug, a solvate, a tautomer or an isomer thereof, Y is —N(R$^1$)(R$^2$) or —C(R$^8$)(R$^9$)(R$^{10}$);

R$^1$ and R$^2$ are each independently optionally substituted alkyl, optionally substituted aryl, optionally substituted heteroaryl, optionally substituted cycloalkyl; or R$^1$ and R$^2$ are taken together to form an optionally substituted 4-, 5- or 6-membered heterocycloalkyl ring having from 0-1 additional heteroatoms selected from O, N or S;

R$^8$, R$^9$ and R$^{10}$ are each independently H, optionally substituted C$_{1-6}$ alkyl, optionally substituted C$_{1-6}$ haloalkyl, optionally substituted C$_{1-6}$ haloalkoxy, optionally substituted C$_{3-8}$ cycloalkyl, optionally substituted aryl, optionally substituted heterocycloalkyl, optionally substituted heteroaryl; or any of two of the R$^8$, R$^9$ and R$^{10}$ groups taken together with the carbon atom to which they are attached form a 3 to 8-membered optionally substituted non-aromatic ring having from 0 to 2 heteroatoms as ring members selected from N, O or S; provided at each occurrence, at least two of the R$^8$, R$^9$ and R$^{10}$ groups are not simultaneously hydrogen;

R$^3$ is H or C$_{1-6}$alkyl;

L$^1$ and L$^2$ are each independently a bond, —C(O)—, —C(S)—, —C(O)NH—, —NHC(O)— or optionally substituted —C(=CH$_2$)—, wherein two substituents attached to the same methylene carbon in the —C(=CH$_2$)— group are optionally taken together to form an optionally substituted 5- or 6-membered ring having from 0-4 heteroatoms selected from O, N or S, where N and S are optionally oxidized; E is an optionally substituted aryl or optionally substituted 5- or 6-membered heteroaryl; Z is an optionally substituted aryl or optionally substituted heteroaryl, when L$^2$ is a bond and E is

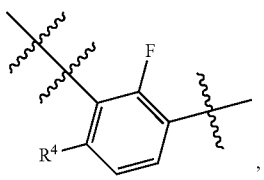

then Z is other than a 5-position optionally substituted

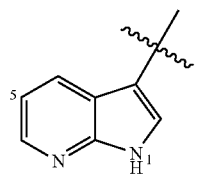 [SMILES: *c1c[nH]c2ncccc12]

core, and wherein the wavy line in

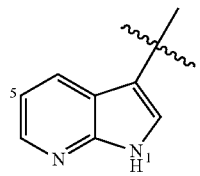 [SMILES: *c1c[nH]c2ncccc12]

indicates the attachment to the rest of the molecule, wherein the single wavy line in

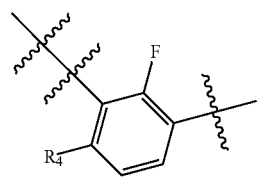

indicates the attachment to —N(R$^3$)SO$_2$Y group and the double wavy line indicates the attachment to E and wherein R$^4$ is H or F.

In some embodiments, provided herewith is a compound of formula (I):

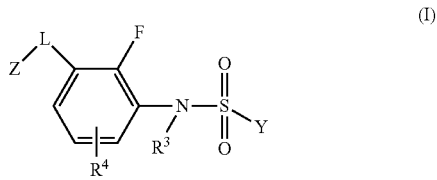

or a pharmaceutically acceptable salt, a prodrug, a solvate, a tautomer or an isomer thereof, Y is —N(R$^1$)(R$^2$) or —C(R$^8$)(R$^9$)(R$^{10}$);

R$^1$ and R$^2$ are each independently optionally substituted alkyl, optionally substituted aryl, optionally substituted heteroaryl, optionally substituted cycloalkyl; or R$^1$ and R$^2$ taken together with the nitrogen to which they attach form an optionally substituted 5- or 6-membered heterocycloalkyl ring having from 0-1 additional heteroatoms as ring members selected from O, N or S;

R$^8$, R$^9$ and R$^{10}$ are each independently H, optionally substituted C$_{1-6}$ alkyl, optionally substituted C$_{1-6}$ haloalkyl, optionally substituted C$_{1-6}$ haloalkoxy, optionally substituted C$_{3-8}$ cycloalkyl, optionally substituted aryl, optionally substituted heterocycloalkyl, optionally substituted heteroaryl; or any of two of the R$^8$, R$^9$ and R$^{10}$ groups taken together with the carbon atom to which they are attached form a 3 to 8-membered optionally substituted non-aromatic ring having from 0 to 2 heteroatoms as ring members selected from N, O or S; provided at each occurrence, at least two of the R$^8$, R$^9$ and R$^{10}$ groups are not simultaneously hydrogen;

R$^3$ is H or C$_{1-6}$alkyl;

R$^4$ is halogen, hydrogen, C$_{1-2}$alkyl, C$_{1-2}$haloalkyl, CN, C$_{1-2}$haloalkoxy or C$_{1-2}$alkoxy;

L is a bond, —C(O)—, —C(S)—, —C(O)NH—, —NHC(O)— or optionally substituted —C(=CH$_2$)—, wherein two substituents attached to the same methylene carbon in the —C(=CH$_2$)— group are optionally taken together to form an optionally substituted 5- or 6-membered ring having from 0-4 heteroatoms selected from O, N or S, where N and S are optionally oxidized;

Z is an optionally substituted aryl or optionally substituted heteroaryl, provided that Z is other than an optionally substituted

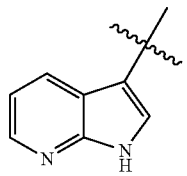 [SMILES: *c1c[nH]c2ncccc12]

core when R$^4$ is attached at the ortho position with respect to the -L-Z substituent on the phenyl ring, wherein the wavy line indicates the point of attachment to the rest of the molecule; and provided that the compound is not 4-[[(1S)-1-cyclopropylethyl]amino]-5-[3-[[ethyl(methyl)sulfamoyl]amino]-2-fluoro-benzoyl]-7H-pyrrolo[2,3-d]pyrimidine or 4-[[(1R)-1-cyclopropylethyl]amino]-5-[3-[[ethyl(methyl)sulfamoyl]amino]-2-fluoro-benzoyl]-7H-pyrrolo[2,3-d]pyrimidine.

In another aspect, provided herewith is a method for regulating or modulating a MAPK pathway signaling. The method includes selectively inhibiting a mutant RAF kinase, wherein the inhibition of mutant kinase does not cause or induce the activation of pERK and expression of upstream EGFR ligands. In some embodiments, the mutant RAF kinase is a mutant BRAF kinase. In certain embodiments, the method includes the use of a compound as described herein in regulating or modulating a MAPK pathway signaling.

In another aspect, provided herewith is a composition. The composition includes a compound having a sulfamoylamino moiety, a compound of formula (I) or (I'), or any sub-generic formulas of formula (I), a compound as recited in any of the claims and described herein or a pharmaceutically acceptable salt or solvate thereof, and a pharmaceutically acceptable excipient or carrier. The disclosure also provides a composition, which includes a compound as recited in the claims and described herein, a pharmaceutically acceptable excipient or carrier, and another therapeutic agent.

DETAILED DESCRIPTION

I. Definitions

Figure 1:
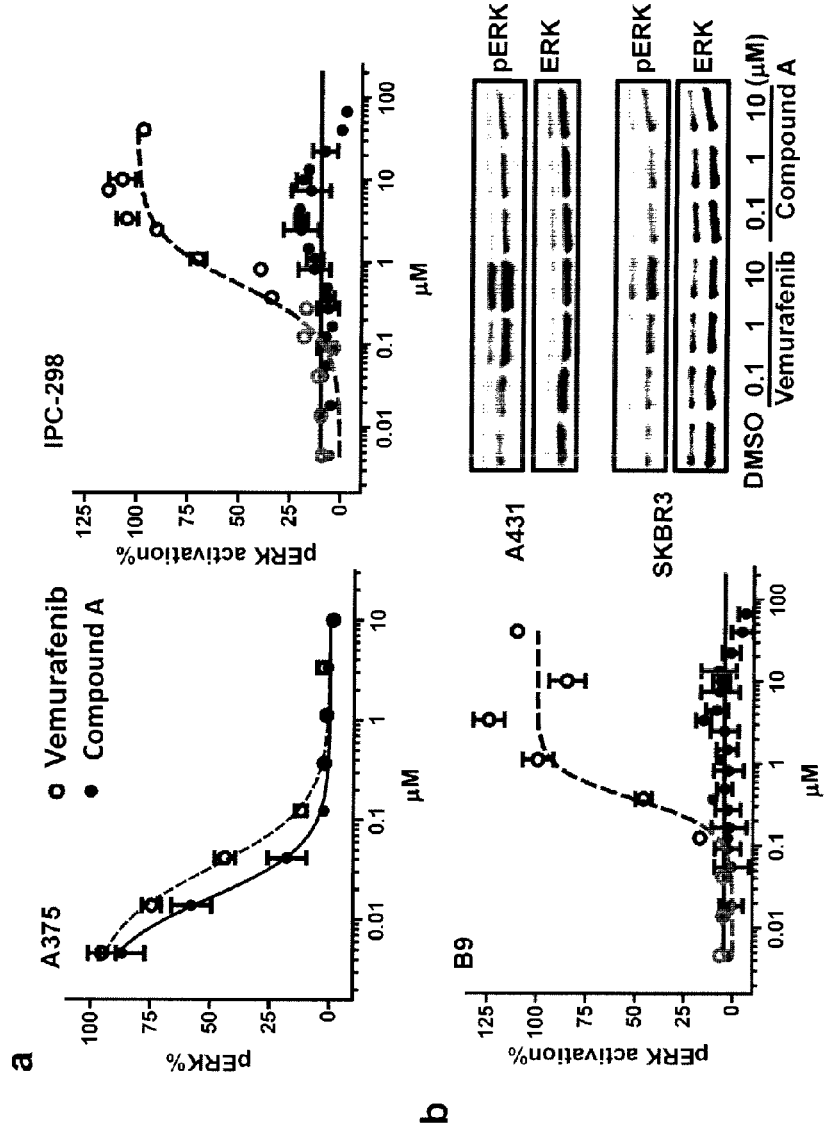
FIG. 1. Paradox Breakers, e.g. compounds containing —N(R$^3$)S(O)$_2$Y moiety dissociate MAPK pathway inhibition from the opposing pathway activation property. (a) pERK IC$_{50}$ curves in the A375 (BRAF$^{V600E}$) cell line and pERK EC$_{50}$ curves in the B9 (HRAS$^{Q61L}$) and IPC-298 (NRAS$^{Q61L}$) cell lines. For EC$_{50}$, the data were normalized to the pERK level induced by 10 µM compound P-1000 (set as 100%). (b) Immunoblot analysis of pERK in human SCC cell line A431 and human breast carcinoma cell line SKBR3 treated by vemurafenib or a compound of formula (I), e.g. compound A. (c) Compound A and vemurafenib treatments inhibited the growth of COLO205 human colorectal cancer xenografts. (d) B9 cells displayed increased anchorage independent cell growth in the presence of increasing concentrations of vemurafenib and compound P-1000 whereas a compound of formula (I), e.g. compound A had no effect. (e) B9 subcutaneous xenografts were stimulated by vemurafenib administered at 50 mg/kg, but not by compound A at the same dose (and exposure).
Figure 1:
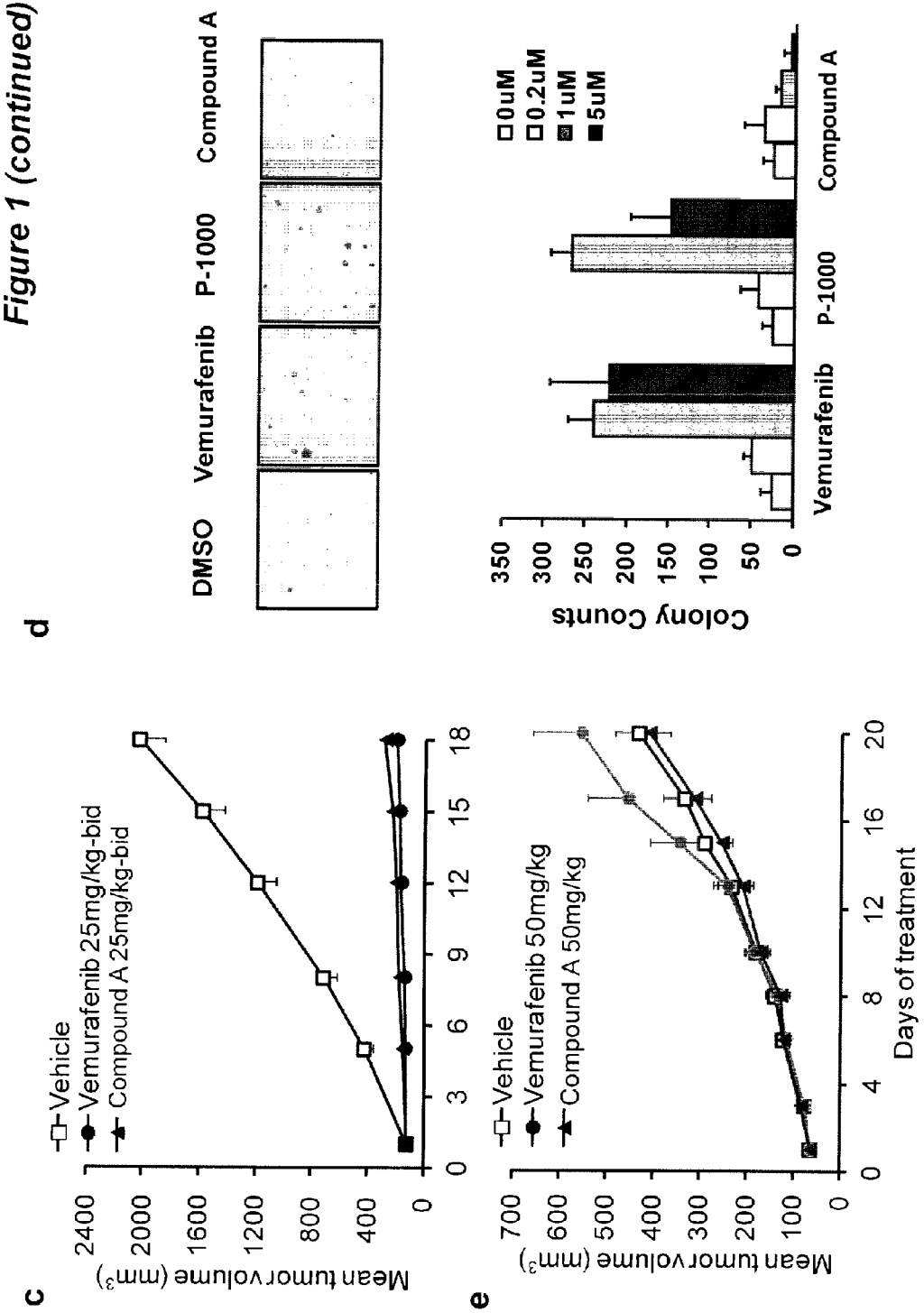

As used herein the following definitions apply unless clearly indicated otherwise:

It is noted here that as used in this specification and the appended claims, the singular forms "a," "an," and "the" include plural reference unless the context clearly dictates otherwise.

"Halogen" or "halo" refers to all halogens, that is, chloro (Cl), fluoro (F), bromo (Br), or iodo (I).

"Hydroxyl" or "hydroxy" refers to the group —OH.

"Thiol" refers to the group —SH.

The term "alkyl", by itself or as part of another substituent, means, unless otherwise stated, a straight or branched chain hydrocarbon, having the number of carbon atoms designated (i.e. $C_{1-6}$ means one to six carbons). Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, alkylamino, alkylthio, alkylene, haloalkyl, arylalkyl, cycloalkylalkyl, heterocycloalkylalkyl, heteroarylalkyl), when a prefix is not included to indicate the number of carbon atoms in an alkyl portion, the alkyl moiety or portion thereof will have 12 or fewer main chain carbon atoms or 8 or fewer main chain carbon atoms or 6 or fewer main chain carbon atoms. For example, $C_{1-6}$ alkyl refers to a straight or branched hydrocarbon having 1, 2, 3, 4, 5 or 6 carbon atoms and includes, but is not limited to, $C_{1-2}$ alkyl, $C_{1-4}$ alkyl, $C_{2-6}$ alkyl, $C_{2-4}$ alkyl, $C_{1-6}$ alkyl, $C_{2-8}$ alkyl, $C_{1-7}$ alkyl, $C_{2-7}$ alkyl and $C_{3-6}$ alkyl. "Fluoro substituted alkyl" denotes an alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. While it is understood that substitutions are attached at any available atom to produce a stable compound, when optionally substituted alkyl is an R group of a moiety such as —OR (e.g. alkoxy), —SR (e.g. thioalkyl), —NHR (e.g. alkylamino), —C(O)NHR, and the like, substitution of the alkyl R group is such that substitution of the alkyl carbon bound to any O, S, or N of the moiety (except where N is a heteroaryl ring atom) excludes substituents that would result in any O, S, or N of the substituent (except where N is a heteroaryl ring atom) being bound to the alkyl carbon bound to any O, S, or N of the moiety. As used herein, "deuterated $C_{1-6}$alkyl" is meant to include partially deuterated or perdeuterated $C_{1-6}$alkyl groups. Non-limiting examples include —$CD_3$, $CD_3CH_2$—, $CD_3CD_2$-, —$CD(CD_3)_2$, —$CD(CH_3)_2$, and the like.

The term "alkylene" by itself or as part of another substituent means a linear or branched saturated divalent hydrocarbon moiety derived from an alkane having the number of carbon atoms indicated in the prefix. For example, (i.e., $C_{1-6}$ means one to six carbons; $C_{1-6}$ alkylene is meant to include methylene, ethylene, propylene, 2-methylpropylene, pentylene, hexylene and the like). $C_{1-4}$ alkylene includes methylene —$CH_2$—, ethylene —$CH_2CH_2$—, propylene —$CH_2CH_2CH_2$—, and isopropylene —$CH(CH_3)CH_2$—, —$CH_2CH(CH_3)$—, —$CH_2$—$(CH_2)_2CH_2$—, —$CH_2$—$CH(CH_3)CH_2$—, —$CH_2$—$C(CH_3)_2$, —$CH_2$—$CH_2CH(CH_3)$—. Typically, an alkyl (or alkylene) group will have from 1 to 24 carbon atoms, with those groups having 10 or fewer, 8 or fewer, or 6 or fewer carbon atoms being preferred in the present disclosure. When a prefix is not included to indicate the number of carbon atoms in an alkylene portion, the alkylene moiety or portion thereof will have 12 or fewer main chain carbon atoms or 8 or fewer main chain carbon atoms, 6 or fewer main chain carbon atoms or 4 or fewer main chain carbon atoms.

The term "alkenylene" means a linear bivalent hydrocarbon radical or a branched divalent hydrocarbon radical having the number of carbon atoms indicated in the prefix and containing at least one double bond. For example, i.e., $C_{2-6}$ means two to six carbons; $C_{2-6}$ alkenylene is meant to include, but is not limited to, —CH=CH—, —$CH_2$—CH=CH—, —$CH_2$—CH=C($CH_3$)—, —CH=CH—CH=CH—, and the like. Similarly, the term "alkynylene" refers to a linear bivalent hydrocarbon radical or a branched divalent hydrocarbon radical containing at least one triple bond and having the number of carbon atoms indicated in the prefix. For example, $C_{2-6}$ means two to six carbons; $C_{2-6}$ alkynlene is meant to include, but is not limited to, —C≡C—, —C≡CCH$_2$—, —CH$_2$—C≡CCH$_2$—, —C≡CCH(CH$_3$)—, and the like. When a prefix is not included to indicate the number of carbon atoms in an alkenylene or alkynlene portion, the alkenylene moiety or portion thereof will have 12 or fewer main chain carbon atoms, or 8 or fewer main chain carbon atoms, or 6 or fewer main chain carbon atoms, or 4 or fewer main chain carbon atoms.

"Cycloalkyl", "Carbocyclic" or "Carbocycle" by itself or as part of another substituent, means saturated or unsaturated, non-aromatic monocyclic, bicyclic or tricyclic carbon ring systems having the number of carbon atoms indicated in the prefix or if unspecified having 3-10, also 3-8, more preferably 3-6, ring members per ring, such as cyclopropyl, cyclopentyl, cyclohexyl, 1-cyclohexenyl, adamantyl, and the like, where one or two ring carbon atoms may optionally be replaced by a carbonyl. Cycloalkyl refers to hydrocarbon rings having the indicated number of ring atoms (e.g., $C_{3-8}$ cycloalkyl means three to eight ring carbon atoms). "Cycloalkyl" or "carbocycle" refers to a mono-bicyclic or polycyclic group such as, for example, bicyclo[2.2.1]heptane, bicyclo[2.2.2]octane, etc. When used in connection with cycloalkyl substituents, the term "polycyclic" refers herein to fused and non-fused alkyl cyclic structures. "Cycloalkyl" or "carbocycle" may form a bridged ring or a spiro ring. The cycloalkyl group may have one or more ring double or triple bond(s).

"Cycloalkylalkyl" means an -(alkylene)-cycloalkyl group where alkylene as defined herein has the indicated number of carbon atoms or if unspecified having six or fewer, preferably four or fewer main chain carbon atoms; and cycloalkyl is as defined herein has the indicated number of carbon atoms or if unspecified having 3-10, also 3-8, more preferably 3-6, ring members per ring. $C_{3-8}$cycloalkyl-$C_{1-2}$alkyl is meant to have 3 to 8 ring carbon atoms and 1 to 2 alkylene chain carbon atoms. Exemplary cycloalkylalkyl includes, e.g., cyclopropylmethylene, cyclobutylethylene, cyclobutylmethylene, and the like.

"Haloalkyl," is meant to include alkyl substituted by one to seven halogen atoms. Haloalkyl includes monohaloalkyl and polyhaloalkyl. For example, the term "$C_{1-6}$ haloalkyl" is meant to include trifluoromethyl, difluoromethyl, 2,2,2-trifluoroethyl, 4-chlorobutyl, 3-bromopropyl, and the like.

"Haloalkoxy" means a —O-haloalkyl group, where haloalkyl is as defined herein, e.g., trifluoromethoxy, 2,2,2-trifluoroethoxy, difluoromethoxy, and the like.

"Alkoxy" means a —O-alkyl group, where alkyl is as defined herein. "Cycloalkoxy" refers to a —O-cycloalkyl group, where cycloalkyl is as defined herein. "Fluoro substituted alkoxy" denotes alkoxy in which the alkyl is substituted with one or more fluoro atoms, where preferably the alkoxy is substituted with 1, 2, 3, 4 or 5 fluoro atoms, also 1, 2, or 3 fluoro atoms. While it is understood that substitutions on alkoxy are attached at any available atom to produce a stable compound, substitution of alkoxy is such that O, S, or N (except where N is a heteroaryl ring atom), are not bound to the alkyl carbon bound to the alkoxy O. Further, where alkoxy is described as a substituent of another moiety, the alkoxy oxygen is not bound to a carbon atom that is bound to an O, S, or N of the other moiety (except where N is a heteroaryl ring atom), or to an alkene or alkyne carbon of the other moiety.

"Amino" or "amine" denotes the group —NH$_2$.

"Alkylamino" means a —NH-alkyl group, where alkyl is as defined herein. Exemplary alkylamino groups include CH$_3$NH—, ethylamino, and the like.

"Dialkylamino" refers to a —N(alkyl)(alkyl) group, where each alkyl is independently as defined herein. Exemplary dialkylamino groups include dimethylamino, diethylamino, ethylmethylamino, and the like.

"Cycloalkylamino" denotes the group —NR$^{dd}$R$^{ee}$, where R$^{dd}$ and R$^{ee}$ combine with the nitrogen to form a 5-7 membered heterocycloalkyl ring, where the heterocycloalkyl may contain an additional heteroatom within the ring, such as O, N, or S, and may also be further substituted with alkyl. Alternatively, "cycloalkylamino" refers to a —NH-cycloalkyl group, where cycloalkyl is as defined herein.

"Alkylthio" refers to —S-alkyl, where alkyl is as defined herein. Exemplary alkylthio groups include CH$_3$S—, ethylthio, and the like.

"Aryl" by itself or as part of another substituent means a monocyclic, bicyclic or polycyclic polyunsaturated aromatic hydrocarbon radical containing 6 to 14 ring carbon atoms, which can be a single ring or multiple rings (up to three rings) which are fused together or linked covalently. Non-limiting examples of unsubstituted aryl groups include phenyl, 1-naphthyl, 2-naphthyl and 4-biphenyl. Exemplary aryl groups, such as phenyl or naphthyl, may be optionally fused with a cycloalkyl of preferably 5-7, more preferably 5-6, ring members.

"Arylalkyl" refers to -(alkylene)-aryl, where the alkylene group is as defined herein and has the indicated number of carbon atoms, or if unspecified having six or fewer main chain carbon atoms or four or fewer main chain carbon atoms; and aryl is as defined herein. Examples of arylalkyl include benzyl, phenethyl, 1-methylbenzyl and the like.

"Heteroaryl" by itself or as part of another substituent refers to a monocyclic aromatic ring radical containing 5 or 6 ring atoms, or a bicyclic aromatic radical having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, indolyl, triazinyl, quinoxalinyl, cinnolinyl, phthalaziniyl, benzotriazinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridinyl, benzothiazolyl, benzothienyl, quinolyl, isoquinolyl, indazolyl, pteridinyl and thiadiazolyl. "Nitrogen containing heteroaryl" refers to heteroaryl wherein any of the heteroatoms is N. As used herein, "heterocyclic aromatic ring" is meant to be a heteroaryl ring.

"Heteroarylalkyl" refers to -(alkylene)-heteroaryl, where the alkylene group is as defined herein and has the indicated number of carbon atoms, or if unspecified having six or fewer main chain carbon atoms or four or fewer main chain carbon atoms; and heteroaryl is as defined herein. Examples of heteroarylalkyl include 2-pyridylmethyl, 2-thiazolylethyl, and the like.

"Heterocycloalkyl" refers to a saturated or unsaturated non-aromatic cycloalkyl group that contains from one to five ring heteroatoms selected from N, O, and S, wherein the nitrogen and sulfur atoms are optionally oxidized, and the nitrogen atom(s) are optionally quaternized, the remaining ring atoms being C, where one or two C atoms may optionally be replaced by a carbonyl. The heterocycloalkyl may be a monocyclic, a bicyclic or a polycyclic ring system of 3 to 12, preferably 4 to 10 ring atoms, more preferably 5 to 8 ring atoms in which one to five ring atoms are heteroatoms selected from —N═, —N—, —O—, —S—, —S(O)—, or —S(O)$_2$— and further wherein one or two ring atoms are optionally replaced by a —C(O)— group. The heterocycloalkyl can also be a heterocyclic alkyl ring fused with a cycloalkyl, an aryl or a heteroaryl ring. When multiple rings are present, they can be fused together or linked covalently. Each heterocycle typically contains 1, 2, 3, 4 or 5, independently selected heteroatoms. Preferably, these groups contain 1, 2, 3, 4, 5, 6, 7, 8, 9 or 10 carbon atoms, 0, 1, 2, 3, 4 or 5 nitrogen atoms, 0, 1 or 2 sulfur atoms and 0, 1 or 2 oxygen atoms. More preferably, these groups contain 1, 2 or 3 nitrogen atoms, 0-1 sulfur atoms and 0-1 oxygen atoms. Non limiting examples of heterocycloalkyl groups include oxetanyl, azetidinyl, pyrrolidinyl, piperidinyl, imidazolidinyl, pyrazolidinyl, butyrolactam moiety, valerolactam moiety, imidazolidinone moiety, hydantoin, dioxolane moiety, phthalimide moiety, piperidine, 1,4-dioxane moiety, morpholinyl, thiomorpholinyl, thiomorpholinyl-S-oxide, thiomorpholinyl-S,S-oxide, piperazinyl, pyranyl, pyridine moiety, 3-pyrrolinyl, thiopyranyl, pyrone moiety, tetrahydrofuranyl, tetrahydrothiophenyl, quinuclidinyl, 1-methylpyridin-2-one moiety, 1-methyl-2-oxo-3-pyridyl, 1-methyl-2-oxo-4-pyridyl, 1-methyl-2-oxo-5-pyridyl, 1-methyl-2-oxo-6-pyridyl, and the like. A heterocycloalkyl group can be attached to the remainder of the molecule through a ring carbon or a heteroatom. As used herein, the term "heterocycloalkylene" by itself or as part of another substituent, refers to a divalent heterocycloalkyl, where the heterocycloalkyl is as defined herein. Non-limiting examples of heterocycloalkylene include piperazine-1,4-diyl, piperidine-1,4-diyl, 1,2,3,6-tetrahydropyridine-1,4-diyl, 1,2,3,6-tetrahydropyridine-1,5-diyl, 2,3,6,7-tetrahydro-1H-azepine-1,4-diyl, 2,3,6,7-tetrahydro-1H-azepine-1,5-diyl, 2,5-dihydro-1H-pyrrole-1,3-diyl, azabicyclo[3.2.1]octane-3,8-diyl, 3,8-diazabicyclo[3.2.1]octane-3,8-diyl, 8-azabicyclo[3.2.1]octane-3,8-diyl, 2-azabicyclo[2.2.2]octane-2,5-diyl, 2,5-diazabicyclo[2.2.2]octane-2,5-diyl, 3-oxomorpholin-2-yl, 3-oxomorpholin-4-yl, 3-oxomorpholin-5-yl, 3-oxomorpholin-6-yl, 2-oxopiperazin-3-yl, 2-oxopiperazin-4-yl, 2-oxopiperazin-5-yl, 2-oxopiperazin-6-yl, 2-oxopiperazin-7-yl, piperazin-1-oxide-2-yl, piperazin-1-oxide-3-yl, piperazin-1-oxide-4-yl, pyridine-2-one-3-yl, pyridine-2-one-4-yl, pyridine-2-one-5-yl, pyridine-2-one-6-yl, pyridine-2-one-7-yl, piperidinyl, morpholinyl, piperazinyl, isoxazolinyl, pyrazolinyl, imidazolinyl, pyrazol-5-one-3-yl, pyrazol-5-one-4-yl, pyrrolidine-2,5-dione-1-yl, pyrrolidine-2,5-dione-3-yl, pyrrolidine-2,5-dione-4-yl, imidazolidine-2,4-dione-1-yl, imidazolidine-2,4-dione-3-yl, imidazolidine-2,4-dione-5-yl, pyrrolidinyl, tetrahydroquinolinyl, decahydroquinolinyl, tetrahydrobenzooxazepinyl, dihydrodibenzooxepinyl, and the like.

"Heterocycloalkylalkyl" refers to -(alkylene)-heterocycloalkyl, where the alkylene group is as defined herein and has the indicated number of carbon atoms, or if unspecified having six or fewer main chain carbon atoms or four or fewer main chain carbon atoms; and heterocycloalkyl is as defined herein. Non-limiting examples of heterocycloalkyl include, e.g., 2-pyridylmethyl, 2-thiazolylethyl, pyrrolidin-1-ylmethyl, 2-piperidinylmethyl, and the like.

The substituents for alkyl, alkoxy, haloalkyl, haloalkoxy, cycloalkyl, cycloalkylalkyl, alkylene, alkenylene, alkynylene, heterocycloalkyl, heterocycloalkylalkyl, arylalkyl, or heteroarylalkyl include, but are not limited to, R', halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR', —SR', —OC(O)R', —OC(S)R', —C(O)R', —C(S)R', —C(O)OR, —C(S)OR', —S(O)R', —S(O)$_2$R', —C(O)NHR', —C(S)NHR', —C(O)NR'R', —C(S)NR"R", —S(O)$_2$NHR', —S(O)$_2$NR'R", —C(NH)NHR', —C(NH)NR'R", —NHC(O)R', —NHC(S)R', —NR"C(O)R', —NR'C(S) R", —NHS(O)$_2$R', —NR'S(O)$_2$R", —NHC(O)NHR', —NHC(S)NHR', —NR'C(O)NH$_2$, —NR'C(S)NH$_2$, —NR'C(O) NHR", —NR'C(S)NHR", —NHC(O)NR'R", —NHC(S) NR'R", —NR'C(O)NR"R"', —NR"'C(S)NR'R", —NHS(O)$_2$N HR', —NR'S(O)$_2$NH$_2$, —NR'S(O)$_2$NHR", —NHS(O)$_2$NR'R", —NR'S(O)$_2$NR'R"', —NHR', and —NR'R" in a number ranging from zero to (2m'+1), where m' is the total number of carbon atoms in such group. R', R" and R"' each independently refer to hydrogen, C$_{1-8}$ alkyl, heterocycloalkyl, aryl, heteroaryl, arylalkyl, heteroarylalkyl, aryl substituted with 1-3 halogens, C$_{1-8}$ alkoxy, haloalkyl, haloalkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. R', R" and R"' can be further substituted with R$^{a1}$, halogen, —OH, —NH$_2$, —NO$_2$, —CN, —C(O)OH, —C(S) OH, —C(O)NH$_2$, —C(S)NH$_2$, —S(O)$_2$NH$_2$, —NHC(O) NH$_2$, —NHC(S)NH$_2$, —NHS(O)$_2$NH$_2$, —C(NH)NH$_2$, —OR$^{a1}$, —SR$^{a1}$, —OC(O)R$^{a1}$, —OC(S)R$^{a1}$, —C(O)R$^{a1}$, —C(S)R$^{a1}$, —C(O) OR$^{a1}$, —C(S)OR$^{a1}$, —S(O)R$^{a1}$, —S(O)$_2$R$^{a1}$, —C(O)NHR$^{a1}$, —C(S)NHR$^{a1}$, —C(O) NR$^1$R$^{a2}$, —C(S)NR$^{a1}$R$^{a2}$, —S(O)$_2$NHR$^{a1}$, —S(O)$_2$NR$^{a1}$R$^{a2}$, —C(NH)NHR$^{a1}$, —C(NH)NR$^{a1}$R$^{a2}$, —NHC(O)R$^{a1}$, —NHC(S)R$^{a1}$, —NR$^{a2}$C(O)R$^{a1}$, —NR$^{a1}$C(S)R$^{a2}$, —NHS(O)$_2$R$^{a1}$, —NR$^{a1}$S(O)$_2$R$^{a2}$, —NHC(O) NHR$^{a1}$, —NHC(S)NHR$^{a1}$, —NR$^{a1}$C(O)NH$_2$, —NR$^{a1}$C(S) NH$_2$, —NR$^{a1}$C(O) NHR$^{a2}$, —NR$^{a1}$C(S)NHR$^{a2}$, —NHC(O) NR$^{a1}$R$^{a2}$, —NHC(S)NR$^{a1}$R$^{a2}$, —NR$^{a1}$C(O)NR$^{a2}$R$^{a3}$, —NR$^{a3}$C(S)NR$^{a1}$R$^{a2}$, —NH S(O)$_2$NHR$^{a1}$, —NR$^{a1}$ S(O)$_2$NH$_2$, —NR$^{a1}$ S(O)$_2$NHR$^{a2}$, —NHS(O)$_2$NR$^{a1}$R$^{a2}$, —NR$^{a1}$ S(O)$_2$NR$^{a2}$R$^{a3}$, —NHR$^{a1}$, and —NR$^{a1}$R$^{a2}$ in a number ranging from zero to (2n'+1), where n' is the total number of carbon atoms in such group. R$^{a1}$, R$^{a2}$ and R$^{a3}$ each independently refer to hydrogen, C$_{1-8}$ alkyl, heterocycloalkyl, aryl, heteroaryl, arylalkyl, heteroarylalkyl, aryl substituted with 1-3 halogens, C$_{1-8}$ alkoxy, haloalkyl, haloalkoxy or C$_{1-8}$ thioalkoxy groups, or unsubstituted aryl-C$_{1-4}$ alkyl groups. R$^{a1}$, R$^{a2}$ and R$^{a3}$ can be further substituted with R$^{b1}$, halogen, —OH, —NH$_2$, —NO$_2$, —CN, —C(O) OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^{b1}$, —SR$^{b1}$, —OC(O)R$^{b1}$, —OC(S) R$^{b1}$, —C(O)R$^{b1}$, —C(S)R$^{b1}$, —C(O)OR$^{b1}$, —C(S)OR$^{b1}$, —S(O)R$^{b1}$, —S(O)$_2$R$^{b1}$, —C(O)NHR$^{b1}$, —C(S)NHR$^{b1}$, —C(O)NR$^{b1}$R$^{b2}$, —C(S)NR$^{b1}$R$^{b2}$, —S(O)$_2$NHR$^{b1}$, —S(O)$_2$NR$^{b1}$R$^{b2}$, —C(NH)NHR$^{b1}$, —C(NH)NR$^{b1}$R$^{b2}$, —NHC(O)R$^{b1}$, —NHC(S)R$^{b1}$, —NR$^{b2}$C(O)R$^{b1}$, —NR$^{b1}$C (S)R$^{b2}$, —NHS(O)$_2$R$^{b1}$, —NR$^{b1}$ S(O)$_2$R$^{b2}$, —NHC(O) NHR$^{b1}$, —NHC(S)NHR$^{b1}$, —NR$^{b1}$C(O)NH$_2$, —NR$^{b1}$C(S) NH, —NR$^{b1}$C(O)NHR$^{b2}$, —NR$^{b1}$C(S)NHR$^{b2}$, —NHC(O) NR$^{b1}$R$^{b2}$, —NHC(S)NR$^{b1}$R$^{b2}$, —NR$^{b1}$C(O)NR$^{b2}$R$^{b3}$, —NR$^{b3}$C(S)NR$^{b1}$R$^{b2}$, —NHS(O)$_2$NHR$^{b1}$, —NR$^{b1}$ S(O)$_2$NH$_2$, —NR$^{b1}$S(O)$_2$NHR$^{b2}$, —NHS(O)$_2$NR$^{b1}$R$^{b2}$, —NR$^{b1}$ S(O)$_2$NR$^{b2}$R$^{b3}$, —NHR$^{b1}$, and —NR$^{b1}$R$^{b2}$ in a number ranging from zero to (2p'+1), where p' is the total number of carbon atoms in such group. R$^{b1}$, R$^{b2}$ and R$^{b3}$ each independently refer to hydrogen, C$_{1-8}$ alkyl, heterocycloalkyl, aryl, heteroaryl, arylalkyl, heteroarylalkyl, aryl substituted with 1-3 halogens, C$_{1-8}$ alkoxy, haloalkyl, haloalkoxy or C$_{1-8}$ thioalkoxy groups, or unsubstituted aryl-C$_{1-4}$ alkyl groups.

Substituents for the aryl and heteroaryl groups are varied and are generally selected from: R', halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR', —SR', —OC(O)R', —OC(S)R', —C(O)R', —C(S)R', —C(O)OR, —C(S)OR', —S(O)R', —S(O)$_2$R', —C(O)NHR', —C(S)NHR', —C(O) NR'R", —C(S)NR'R", —S(O)$_2$NHR', —S(O)$_2$NR'R", —C(NH)NHR', —C(NH)NR'R", —NHC(O)R', —NHC(S) R', —NR"C(O)R', —NR'C(S)R", —NHS(O)$_2$R', —NR'S (O)$_2$R", —NHC(O)NHR', —NHC(S)NHR', —NR'C(O) NH$_2$, —NR'C(S)NH$_2$, —NR'C(O)NHR", —NR'C(S)NH R", —NHC(O)NR'R", —NHC(S)NR'R", —NR'C(O) NR'R"', —NR"'C(S)NR'R", —NHS(O)$_2$NHR', —NR'S(O)$_2$N H$_2$, —NR'S(O)$_2$NHR", —NHS(O)$_2$NR'R", —NR'S(O)$_2$NR"R"', —NHR', —NR'R", —N$_3$, perfluoro (C$_1$-C$_4$)alkoxy, and perfluoro(C$_1$-C$_4$)alkyl, in a number ranging from zero to the total number of open valences on the aromatic ring system; and where R', R" and R"' are independently selected from hydrogen, haloalkyl, haloalkoxy, C$_{1-8}$ alkyl, C$_{3-6}$ cycloalkyl, cycloalkylalkyl, C$_{2-8}$ alkenyl, C$_{2-8}$ alkynyl, aryl, arylalkyl, heteroaryl, heteroarylalkyl, aryl-C$_{1-4}$ alkyl, and aryloxy-C$_{1-4}$ alkyl. Other suitable substituents include each of the above aryl substituents attached to a ring atom by an alkylene tether of from 1-4 carbon atoms. R', R" and R"' can be further substituted with R$^{a1}$, halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^{a1}$, —SR$^{a1}$, —OC(O) R$^{a1}$, —OC(S) R$^{a1}$, —C(O)R$^{a1}$, —C(S)R$^{a1}$, —C(O)OR$^{a1}$, —C(S)OR$^{a1}$, —S(O)R$^{a1}$, —S(O)$_2$R$^{a1}$, —C(O)NHR$^{a1}$, —C(S)NHR$^{a1}$, —C(O)NR$^{a1}$R$^{a2}$, —C(S)NR$^{a1}$R$^{a2}$, —S(O)$_2$NHR$^{a1}$, —S(O)$_2$NR$^{a1}$R$^{a2}$, —C(NH)NHR$^{a1}$, —C(NH)NR$^{a1}$R$^{a2}$, —NHC(O)R$^{a1}$, —NHC(S)R$^{a1}$, —NR$^{a2}$C(O)R$^{a1}$, —NR$^{a1}$C (S)R$^{a2}$, —NHS(O)$_2$R$^{a1}$, —NR$^{a1}$ S(O)$_2$R$^{a2}$, —NHC(O) NHR$^{a1}$, —NHC(S)NHR$^{a1}$, —NR$^{a1}$C(O)NH$_2$, —NR$^{a1}$C(S) NH$_2$, —NR$^{a1}$C(O)NHR$^{a2}$, —NR$^{a1}$C(S)NHR$^{a2}$, —NHC(O) NR$^{a1}$R$^{a2}$, —NHC(S)NR$^{a1}$R$^{a2}$, —NR$^{a1}$C(O)NR$^{a2}$R$^{a3}$, —NR$^{a3}$C(S)NR$^{a1}$R$^{a2}$, —NHS(O)$_2$NHR$^{a1}$, —NR$^{a1}$ S(O)$_2$NH$_2$, —NR$^{a1}$ S(O)$_2$NHR$^{a2}$, —NHS(O)$_2$NR$^{a1}$R$^{a2}$, —NR$^{a1}$S(O)$_2$NR$^{a2}$R$^{a3}$, —NHR$^{a1}$, —NR$^{a1}$R$^{a2}$, —N$_3$, perfluoro(C$_1$-C$_4$)alkoxy, and perfluoro(C$_1$-C$_4$)alkyl, in a number ranging from zero to the total number of open valences on the aromatic ring system; and where R$^{a1}$, R$^{a2}$ and R$^{a3}$ are each independently selected from hydrogen, haloalkyl, haloalkoxy, C$_{1-8}$ alkyl, C$_{3-6}$ cycloalkyl, cycloalkylalkyl, C$_2$ alkenyl, C$_{2-8}$ alkynyl, aryl, arylalkyl, heteroaryl, heteroarylalkyl, aryl-C$_{1-4}$ alkyl, or aryloxy-C$_{1-4}$ alkyl. Other suitable substituents include each of the above aryl substituents attached to a ring atom by an alkylene tether of from 1-4 carbon atoms.

When two substituents are present on adjacent atoms of a substituted aryl or a substituted heteroaryl ring, such substituents may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, when two substituents are present on adjacent atoms of a substituted aryl or a substituted heteroaryl ring, such substituents may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, when two substituents are present on adjacent atoms of a substituted aryl or a substituted heteroaryl ring, such substituents may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

"Protecting group" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 4th ed. 2006), Beaucage and Iyer, *Tetrahedron* 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), tri-isopropylsilyl (TIPS), phenylsulphonyl and the like (see also, Boyle, A. L. (Editor), carbamates, amides, N-sulfonyl derivatives, groups of formula —C(O)OR, wherein R is, for example, methyl, ethyl, t-butyl, benzyl, phenylethyl, CH$_2$=CHCH$_2$—, and the like, groups of the formula —C(O)R', wherein R' is, for example, methyl, phenyl, trifluoromethyl, and the like, groups of the formula —SO$_2$R", wherein R" is, for example, tolyl, phenyl, trifluoromethyl, 2,2,5,7,8-pentamethylchroman-6-yl, 2,3,6-trimethyl-4-methoxyphenyl, and the like, and silanyl containing groups, such as 2-trimethylsilylethoxymethyl, t-butyldimethylsilyl, triisopropylsilyl, and the like, CURRENT PROTOCOLS IN NUCLEIC ACID CHEMISTRY, John Wiley and Sons, New York, Volume 1, 2000).

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

"Pharmaceutically acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds disclosed herein contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N, N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds disclosed herein contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like (see, for example, Berge, S. M. et al, "Pharmaceutical Salts", J. Pharmaceutical Science, 1977, 66:1-19). Certain specific compounds disclosed herein contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the disclosure.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated. The therapeutically effective amount will vary depending on the compound, the disease, disorder or condition and its severity and the age, weight, etc., of the mammal to be treated. In general, satisfactory results in subjects are indicated to be obtained at a daily dosage of from about 0.1 to about 10 g/kg subject body weight. In some embodiments, a daily dose ranges from about 0.10 to 10.0 mg/kg of body weight, from about 1.0 to 3.0 mg/kg of body weight, from about 3 to 10 mg/kg of body weight, from about 3 to 150 mg/kg of body weight, from about 3 to 100 mg/kg of body weight, from about 10 to 100 mg/kg of body weight, from about 10 to 150 mg/kg of body weight, or from about 150 to 1000 mg/kg of body weight. The dosage can be conveniently administered, e.g., in divided doses up to four times a day or in sustained-release form.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

By "assaying" is meant the creation of experimental conditions and the gathering of data regarding a particular result of the exposure to specific experimental conditions. For example, enzymes can be assayed based on their ability to act upon a detectable substrate. A compound can be assayed based on its ability to bind to a particular target molecule or molecules.

As used herein, the terms "ligand" and "modulator" are used equivalently to refer to a compound that changes (i.e., increases or decreases) the activity of a target biomolecule, e.g., an enzyme such as a kinase. Generally a ligand or modulator will be a small molecule, where "small molecule refers to a compound with a molecular weight of 1500 Daltons or less, or preferably 1000 Daltons or less, 800 Daltons or less, or 600 Daltons or less. Thus, an "improved ligand" is one that possesses better pharmacological and/or pharmacokinetic properties than a reference compound, where "better" can be defined by one skilled in the relevant art for a particular biological system or therapeutic use.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. Preferably a binding compound interacts with a specified target with a dissociation constant ($K_D$) of 1 mM or less, 1 µM or less, 100 nM or less, 10 nM or less, or 1 nM or less.

In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10,000-fold greater affinity. The term "selective" also refers to a compound that selectively inhibits RAF kinase relative to other 287 kinases, i.e. a compound having an $IC_{50}$ of less than 500 nm, less than 100 nM, less than 50 nM, less than 20 nM, less than 10 nM, less than 5 nM, or less than 1 nM as determined in a generally accepted RAF kinase activity assay and when determined in a comparable generally accepted other kinases activity assay will have a ratio of $IC_{50}$ for other kinases divided by the $IC_{50}$ for RAF kinase of >20, also >30, also >40, also >50, also >60, also >70, also >80, also >90, also >100. Such compounds are effective in treating a disease or condition that is RAF protein kinase mediated, without effecting other protein kinases. Such compounds are preferably, but not necessarily, selective with respect to other protein kinases, i.e. when compared to another protein kinase, the $IC_{50}$ for the other kinase divided by the $IC_{50}$ for RAF kinase is >20, also >30, also >40, also >50, also >60, also >70, also >80, also >90, also >100.

Preferably, the compounds are selective relative to other protein kinases including, but not limited to, wild type BRAF and CRAF kinases. While it is understood that a RAF selective inhibitor may be used to treat any RAF protein kinase mediated disease or condition, the RAF selectivity provides beneficial effects in treating certain diseases or conditions, including, but not limiting to, melanoma, metastatic melanoma, thyroid cancer, lung cancer, colorectal cancer and ovarian cancer.

As used herein in connection with compounds disclosed herein, the term "synthesizing" and like terms means chemical synthesis from one or more precursor materials. Further, by "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

As used herein, the term "modulating" or "modulate" or "regulating" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

"Prodrugs" means any compound which releases an active parent drug according to Formula I in vivo when such prodrug is administered to a mammalian subject. Prodrugs of a compound of Formula I or a compound of any of the subgeneric formulas are prepared by modifying functional groups present in the compound of Formula I or a compound of any of the subgeneric formulas in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds of Formula I or a compound of any of the subgeneric formulas, wherein a hydroxy, amino, carboxyl or sulfhydryl group in a compound of Formula I is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds of Formula I, or a compound of any of the subgeneric formulas, and the like. Preparation, selection, and use of prodrugs is discussed in T. Higuchi and V. Stella, "Pro-drugs as Novel Delivery Systems," Vol. 14 of the A.C.S. Symposium Series; "Design of Prodrugs", ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

Esters a compound of Formula I or a compound of any of the subgeneric formulas can be prepared through functionalization of hydroxyl and/or carboxyl groups that may be present within the molecular structure of the compound. Amides and prodrugs can also be prepared using techniques known to those skilled in the art. For example, amides may be prepared from esters, using suitable amine reactants, or they may be prepared from anhydride or an acid chloride by reaction with ammonia or a lower alkyl amine. Moreover, esters, urease, sulfonamides, and amides of a compound of Formula I or a compound of any of the subgeneric formulas can be made by reaction with a carbonylating agent (e.g., ethyl formate, acetic anhydride, methoxyacetyl chloride, benzoyl chloride, methyl isocyanate, ethyl chloroformate) or methanesulfonyl chloride and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of from 0 to 60° C. Prodrugs are typically prepared by covalent attachment of a moiety, which results in a compound that is therapeutically inactive until modified by an individual's metabolic system.

"Tautomer" means compounds produced by the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol, imine-enamine tautomers and the like, ring-chain tautomers, such as glucose/2,3,4,5,6-pentahydroxy-hexanal and the like, the tautomeric forms of heteroaryl groups containing a —N═C(H)—NH— ring atom arrangement, such as pyrazoles, imidazoles, benzimidazoles, triazoles, and tetrazoles. Where the compound contains, for example, a keto or oxime group or an aromatic moiety, tautomeric isomerism ('tautomerism') can occur. The compounds described herein may have one or more tautomers and therefore include various isomers. A person of ordinary skill in the art would recognize that other tautomeric ring atom arrangements are possible. All such isomeric forms of these compounds are expressly included in the this disclosure.

"Isomers" mean compounds having identical molecular formulae but differ in the nature or sequence of bonding of their atoms or in the arrangement of their atoms in space. Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 6th edition J. March, John Wiley and Sons, New York, 2007) differ in the chirality of one or more stereocenters.

Certain compounds disclosed herein can exist in unsolvated forms as well as solvated forms, including hydrated forms. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure. Certain compounds disclosed herein may exist in multiple crystalline or amorphous forms. In general, all physical forms are equivalent for the uses contemplated by this disclosure and are intended to be within the scope of the present disclosure.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

"Solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

"Pain" or a "pain condition" can be acute and/or chronic pain, including, without limitation, arachnoiditis; arthritis (e.g. osteoarthritis, rheumatoid arthritis, ankylosing spondylitis, gout); back pain (e.g. sciatica, ruptured disc, spondylolisthesis, radiculopathy); burn pain; cancer pain; dysmenorrhea; headaches (e.g. migraine, cluster headaches, tension headaches); head and facial pain (e.g. cranial neuralgia, trigeminal neuralgia); hyperalgesia; hyperpathia; inflammatory pain (e.g. pain associated with irritable bowel syndrome, inflammatory bowel disease, ulcerative colitis, Crohn's disease, cystitis, pain from bacterial, fungal or viral infection); keloid or scar tissue formation; labor or delivery pain; muscle pain (e.g. as a result of polymyositis, dermatomyositis, inclusion body myositis, repetitive stress injury (e.g. writer's cramp, carpal tunnel syndrome, tendonitis, tenosynovitis)); myofascial pain syndromes (e.g. fibromyalgia); neuropathic pain (e.g. diabetic neuropathy, causalgia, entrapment neuropathy, brachial plexus avulsion, occipital neuralgia, gout, reflex sympathetic dystrophy syndrome, phantom limb or post-amputation pain, postherpetic neuralgia, central pain syndrome, or nerve pain resulting from trauma (e.g. nerve injury), disease (e.g. diabetes, multiple sclerosis, Guillan-Barre Syndrome, myasthenia gravis, neurodegenerative diseases such as Parkinson's disease, Alzheimer's disease, amyotrophic lateral sclerosis, or cancer treatment); pain associated with skin disorders (e.g. shingles, herpes simplex, skin tumors, cysts, neurofibromatosis); sports injuries (e.g. cuts, sprains, strains, bruises, dislocations, fractures, spinal cord, head); spinal stenosis; surgical pain; tactile allodynia; temporomandibular disorders; vascular disease or injury (e.g. vasculitis, coronary artery disease, reperfusion injury (e.g. following ischemia, stroke, or myocardial infarcts)); other specific organ or tissue pain (e.g. ocular pain, corneal pain, bone pain, heart pain, visceral pain (e.g. kidney, gallbladder, gastrointestinal), joint pain, dental pain, pelvic hypersensitivity, pelvic pain, renal colic, urinary incontinence); other disease associated pain (e.g. sickle cell anemia, AIDS, herpes zoster, psoriasis, endometriosis, asthma, chronic obstructive pulmonary disease (COPD), silicosis, pulmonary sarcoidosis, esophagitis, heart burn, gastroesophageal reflux disorder, stomach and duodenal ulcers, functional dyspepsia, bone resorption disease, osteoporosis, cerebral malaria, bacterial meningitis); or pain due to graft v. host rejection or allograft rejections.

As used herein, "MAPK" refers to the mitogen-activated protein kinase. MAPK pathway is an important second signal transduction pathway that affects HIF-1α level and activity, and may also affect MN/CA9 expression. Multiple lines of evidence indicate that the MAPK pathway is important in human cancer. This pivotal pathway relays extracellular signals to the nucleus via a cascade of specific phosphorylation events involving Ras, Raf, MEK, and ERK to regulate fundamental cellular processes, including proliferation, differentiation, and cell survival (Kolch, W., *Biochem. J*, 351: 289-305 (2000); and Lu and Xu, *IUBMB Life*, 58(11): 621-631 (2006)). Inappropriate Ras activation is associated with nearly a third of all human cancers (Downward, J. *Nat Rev Cancer*, 3: 11-22 (2003)). One of the Raf isoforms, BRAF, is mutated in many cancers, including malignant melanoma (27-70%), papillary thyroid cancer (36-53%), ovarian cancer (30%) and colorectal cancer (5-22%), and the mutations are frequently gain-of-function substitutions that result in constitutive activity Messersmith et al., *Clin Adv. Hematol. Oncol.*, 4(11): 831-836 (2006); Garnett and Marais, Cancer Cell, 6: 313-319 (2004)). ERK is elevated in nearly 50% of breast cancers and is associated with a poor prognosis (Messersmith et al. (2006)).

"Unit dosage form" refers to a composition intended for a single administration to treat a subject suffering from a disease or medical condition. Each unit dosage form typically comprises each of the active ingredients of this disclosure plus pharmaceutically acceptable excipients. Examples of unit dosage forms are individual tablets, individual capsules, bulk powders, liquid solutions, ointments, creams, eye drops, suppositories, emulsions or suspensions. Treatment of the disease or condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds disclosed herein, whether radioactive or not, are intended to be encompassed within the scope of the disclosure.

The term "deuterated" as used herein alone or as part of a group, means substituted deuterium atoms. When a particular position is designated as holding deuterium (stated as "D" or "deuterium"), it is understood that the abundance of deuterium at that position is substantially greater than the natural abundance of deuterium, which is 0.015% (i.e., at least 50.1% incorporation of deuterium).

The term "deuterated analog" as used herein alone or as part of a group, means substituted deuterium atoms in place of hydrogen. The deuterated analog of a compound may be a fully or partially deuterium substituted derivative. Preferably the deuterium substituted compound holds a fully or partially deuterium substituted alkyl, aryl or heteroaryl group. In one embodiment, the deuterium substituted compound holds a fully or partially deuterium substituted alkyl group, e.g., —CD$_3$, CD$_2$CD$_3$, —CD$_2$CD$_2$CD$_3$ (n-propyl-D7), —CD(CD$_3$)$_2$ (iso-propyl-D7), —CD$_2$CD$_2$CD$_2$CD$_3$ (n-butyl-D9), —CD$_2$-CD(CD$_3$)$_2$ (iso-butyl-D9) and the like. In another embodiment, the deuterium substituted compound holds a fully or partially deuterium substituted aryl, such as phenyl, e.g., C$_6$D$_5$ or a fully or partially deuterium substituted heteroaryl, e.g., pyrazoly-d$_2$, thiazoly-d$_2$, pyridyl-d$_3$, and the like.

As used in connection with binding of a compound with a RAF kinase, e.g., BRAF kinase, the term "interact" means that the distance from a bound compound to a particular amino acid residue will be 5.0 angstroms or less. In particular embodiments, the distance from the compound to the particular amino acid residue is 4.5 angstroms or less, 4.0 angstroms or less, 3.5 angstroms or less, or 3 angstroms or less. Such distances can be determined, for example, using co-crystallography, or estimated using computer fitting of a compound in a BRAF active site.

By "binding site" is meant an area of a target molecule to which a ligand can bind non-covalently. Binding sites embody particular shapes and often contain multiple binding pockets' present within the binding site. The particular shapes are often conserved within a class of molecules, such as a molecular family. Binding sites within a class also can contain conserved structures such as, for example, chemical moieties, the presence of a binding pocket, and/or an electrostatic charge at the binding site or some portion of the binding site, all of which can influence the shape of the binding site.

As used herein, "binding pocket" is meant a specific volume within a binding site. A binding pocket can often be a particular shape, indentation, or cavity in the binding site. Binding pockets can contain particular chemical groups or structures that are important in the noncovalent binding of another molecule such as, for example, groups that contribute to ionic, hydrogen bonding, or van der Waals interactions between the molecules.

As used herein in connection with amino acid or nucleic acid sequence, the term "isolate" indicates that the sequence is separated from at least a portion of the amino acid and/or nucleic acid sequences with which it would normally be associated.

In connection with amino acid or nucleic sequences, the term "purified" indicates that the subject molecule constitutes a significantly greater proportion of the biomolecules in a composition than the proportion observed in a prior composition, e.g., in a cell culture. The greater proportion can be 2-fold, 5-fold, 10-fold, or more than 10-fold, with respect to the proportion found in the prior composition.

The disclosure also embraces isotopically-labeled compounds disclosed herein which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Unless otherwise stated, when a position is designated specifically as "H" or "hydrogen", the position is understood to have hydrogen at its natural abundance isotopic composition or its isotopes, such as deuterium (D) or tritium ($^3$H). Certain isotopically-labeled compounds disclosed herein (e.g., those labeled with $^3$H and $^{14}$C) are useful in compound and/or substrate tissue distribution assays. Tritiated (i.e., $^3$H) and carbon-14 (i.e., $^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds disclosed herein can generally be prepared by following procedures analogous to those disclosed in the Schemes and in the Examples herein below, by substituting an isotopically labeled reagent for a non-isotopically labeled reagent.

II. General

The present disclosure concerns compounds and methods for modulating, regulating, mediating or inhibiting MAPK pathway signaling by regulating the interaction of a RAF inhibitor with a mutant RAF kinase, for example, by selective inhibition of mutant BRAF protein kinases. Surprisingly, the inhibition of a wild type RAF kinase with the compounds as described herein does not induce or cause the activation of MAPK pathway as observed by pERK or pMEK, for instance, in cells having RAS mutation or upstream receptor tyrosine kinase activation.

III. Compounds

In one aspect, the disclosure provides a compound having formula (I):

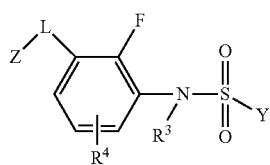

(I)

wherein the variables and substituents are as defined in the Summary

In some embodiments of compounds of formula (I), the compounds have molecular weights less than 800, preferably, the compounds have molecular weights less than 750, more preferably, the compounds have molecular weights less than 700, even more preferably, the compounds have molecular weights less than 650, still more preferably, the compounds have molecular weights less than 600. In certain preferred embodiments, the compounds have molecular weights less than 550. In other preferred embodiments, the compounds have molecular weights less than 500. In yet other preferred embodiments, the compounds have molecular weights less than 450.

In some embodiments of compounds of formula (I), Z is optionally substituted aryl or optionally substituted heteroaryl, with the proviso that Z is other than an optionally substituted

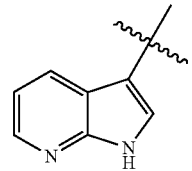 [SMILES: *c1c[nH]c2ncccc12]

core when R$^4$ is attached at the ortho position with respect to the -L-Z substituent on the phenyl ring, wherein the wavy line indicates the point of attachment to the rest of the molecule. In certain embodiments, Z is other than an optionally substituted

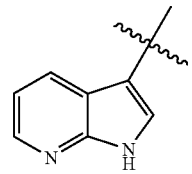 [SMILES: *c1c[nH]c2ncccc12]

core. In certain embodiments, Z is other than a 5-position optionally substituted

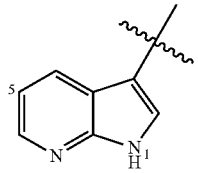 [SMILES: *c1c[nH]c2ncccc12]

core when R$^4$ is attached at the ortho position with respect to the -L-Z substituent on the phenyl ring. In one embodiment, Z is an optionally substituted aryl. In another embodiment, Z is an optionally substituted heteroaryl. All the other variables in formula (I) are as defined in any of the embodiments as described herein.

In some embodiments of compounds of formula (I), Z is an aryl or heteroaryl, each of which is independently optionally substituted with from 1-5 R$^7$ substituents; each R$^7$ is independently selected from $C_{1-6}$ alkyl, $C_{1-6}$ alkoxy, $C_{1-6}$ haloalkyl, $C_{1-6}$ haloalkoxy, $C_{3-8}$ cycloalkyl, $C_{3-8}$ cycloalkyl-$C_{1-4}$-alkyl, aryl, arylalkyl, heteroaryl, heteroarylalkyl, heterocycloalkyl, heterocycloalkyl-$C_{1-4}$ alkyl or —R$^a$, wherein R$^a$ is selected from halogen, —CH=CH$_2$, —CN, —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^b$, —SR$^b$, —OC(O) R$^b$, —OC(S)R$^b$, —C(O)R$^b$, —C(S)R$^b$, —C(O)OR$^b$, —C(S) OR$^b$, —S(O)R$^b$, —S(O)$_2$R$^b$, —C(O)NHR$^b$, —C(S)NHR$^b$, —C(O)NR$^b$R$^b$, —C(S)NR$^b$R$^b$, —S(O)$_2$NHR$^b$, —S(O)$_2$NR$^b$R$^b$, —C(NH)NHR$^b$, —C(NH)NR$^b$R$^b$, —NHC (O)R$^b$, —NHC(S)R$^b$, —NR$^b$C(O)R$^b$, —NR$^b$C(S)R$^b$, —NHS(O)$_2$R$^b$, —NR$^b$S(O)$_2$R$^b$, —NHC(O)N HR$^b$, —NHC (S)NHR$^b$, —NR$^b$C(O)NH$_2$, —NR$^b$C(S)NH$_2$, —NR$^b$C(O) NHR$^b$, —NR$^b$C(S)NHR$^b$, —NHC(O)NR$^b$R$^b$, —NHC(S) NR$^b$R$^b$, —NR$^b$C(O)NR$^b$R$^b$, —NR$^b$C(S)NR$^b$R$^b$, —NHS(O)$_2$NHR$^b$, —NR$^b$S(O)$_2$NH$_2$, —NR$^b$S(O)$_2$NHR$^b$, —NHS(O)$_2$NR$^b$R$^b$, —NR$^b$S(O)$_2$NR$^b$R$^b$, —NHR$^b$ or —NR$^b$R$^b$, wherein each R$^b$ is independently selected from the group consisting of C$_{1-6}$alkyl, halogen, —CN, C$_{1-6}$alkoxy, C$_{3-8}$cycloalkyl, C$_{3-8}$cycloalkyl-C$_{1-4}$-alkyl, —OH, C$_{1-6}$haloalkyl, C$_{1-6}$haloalkoxy, aryl, aryl-C$_{1-4}$alkyl, heteroaryl and heteroarylalkyl; or two R$^b$ substituents when attached to the same nitrogen atom taken together with the nitrogen atom form a three to eight-membered ring having from 0-2 additional heteroatoms as ring members selected from N, O or S; wherein the aliphatic or aromatic portion of R$^7$ is further optionally substituted with from 1-3 groups selected from C$_{1-6}$ alkyl, C$_{1-6}$ alkoxy, C$_{1-6}$ haloalkyl, C$_{1-6}$ haloalkoxy, aryl, arylalkyl, heteroaryl, heteroarylalkyl, heterocycloalkyl, heterocycloalkyl-C$_{1-4}$alkyl or —R$^c$, wherein each R$^c$ is independently selected from halogen, —CH=CH$_2$, —CN, —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^d$, —SR$^d$, —OC(O)R$^d$, —OC(S)R$^d$, —C(O)R$^d$, —C(S)R$^d$, —C(O)OR$^d$, —C(S)OR$^d$, —S(O)R$^d$, —S(O)$_2$R$^d$, —C(O)NHR$^d$, —C(S)NHR$^d$, —C(O)NR$^d$R$^d$, —C(S)NR$^d$R$^d$, —S(O)$_2$NHR$^d$, —S(O)$_2$NR$^d$R$^d$, —C(NH)NHR$^d$, —C(NH)NR$^d$R$^d$, —NHC(O)R$^d$, —NHC(S)R$^d$, —NR$^d$C(O)R$^d$, —NR$^d$C(S)R$^d$, —NHS(O)$_2$R$^d$, —NR$^d$S(O)$_2$R$^d$, —NHC(O)NHR$^d$, —NHC(S)NHR$^d$, —NR$^d$C(O)NH$_2$, —NR$^d$C(S)NH$_2$, —NR$^d$C(O)NHR$^d$, —NR$^d$C(S)NHR$^d$, —NHC(O)NR$^d$R$^d$, —NHC(S)NR$^d$R$^d$, —NR$^d$C(O)NR$^d$R$^d$, —NR$^d$C(S)NR$^d$R$^d$, —NHS(O)$_2$NHR$^d$, —NR$^d$S(O)$_2$NH$_2$, —NR$^d$S(O)$_2$NHR$^d$, —NHS(O)$_2$NR$^d$R$^d$, —NR$^d$S(O)$_2$NR$^d$R$^d$, —NHR$^d$, R$^f$ or —NR$^d$R$^d$, wherein each R$^d$ is independently selected from C$_{1-6}$ alkyl, arylalkyl, aryl, heteroaryl, heteroarylalkyl, cycloalkyl, cycloalkylalkyl, heterocycloalkyl or heterocycloalkylalkyl; and wherein the aromatic portion of R$^d$ is optionally substituted with from 1-3 substituents independently selected from R$^e$, wherein R$^e$ is selected from the group consisting of halogen, —CH=CH$_2$, —CN, —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^f$, —SR$^f$, —OC(O)R$^f$, —OC(S)R$^f$, —C(O)R$^f$, —C(S)R$^f$, —C(O)OR$^f$, —C(S)OR$^f$, —S(O)R$^f$, —S(O)$_2$R$^f$, —C(O)NHR$^f$, —C(S)NHR$^f$, —C(O)NR$^f$R$^f$, —C(S)NR$^f$R$^f$, —S(O)$_2$NHR$^f$, —S(O)$_2$NR$^f$R$^f$, —C(NH) NHR$^f$, —C(NH) NR$^f$R$^f$, —NHC(O)R$^f$, —NHC(S)R$^f$, —NR$^f$C(O)R$^f$, —NR$^f$C(S)R$^f$, —NHS(O)$_2$R$^f$, —NR$^f$S(O)$_2$R$^f$, —NHC(O)NHR$^f$, —NHC(S)NHR$^f$, —NR$^f$C(O)NH$_2$, —NR$^f$C(S)NH$_2$, —NR$^f$C(O)NHR$^f$, —NR$^f$C(S)NHR$^f$, —NHC(O)NR$^f$R$^f$, —NHC(S)NR$^f$R$^f$, —NR$^f$C(O)NR$^f$R$^f$, —NR$^f$C(S)NR$^f$R$^f$, —NHS(O)$_2$NHR$^f$, —NR$^f$S(O)$_2$NH$_2$, —NR$^f$S(O)$_2$NHR$^f$, —NHS(O)$_2$NR$^f$R$^f$, —NR$^f$S(O)$_2$NR$^f$R$^f$, —NHR$^f$, —NR$^f$R$^f$ and R$^f$, wherein R is C$_{1-6}$alkyl or aryl; or two adjacent R$^7$ groups on the aryl or heteroaryl ring together with the atoms to which they are attached form a 5- or 6-membered ring having from 0 to 2 additional heteroatoms selected from N, O or S, optionally substituted with from 1 to 3 R$^d$ or R$^e$ substituents. In some instances, R$^f$ is C$_{1-6}$alkyl. In other instances, R$^f$ is aryl, such as phenyl. In some instances, Z is a heteroaryl optionally substituted with from 1-2 R$^7$. In other instances, R$^7$ is an optionally substituted 6-membered heteroaryl. The other variables are as defined in any of the embodiments of compounds of formula (I).

In some embodiments of compounds of formula (I), Z is aryl or heteroaryl group, wherein the heteroaryl group has from 1 to 4 heteroatoms as ring members selected from N, O or S; and wherein the aryl or heteroaryl groups are optionally substituted with from 1 to 3 R$^7$ substituents. In one embodiment, Z is a heteroaryl having from 1-4 heteroatoms as ring members selected from N, O or S; and wherein the heteroaryl group is optionally substituted with from 1 to 2 independently selected R$^7$ substituents; or 1-2 independently selected R$^a$ substituents; or 1-2 independently selected R$^b$ substituents; or 1-2 independently selected R$^c$ substituents; or 1-2 independently selected R$^d$ substituents; or 1-2 independently selected R$^e$ substituents. In some instances, Z is an optionally substituted 5-membered heteroaryl. In other instances, Z is an optionally substituted 6-membered heteroaryl. In other instances, Z is an optionally substituted bicyclic heteroaryl. The other variables are as defined in any of the embodiments of compounds of formula (I).

In some embodiments of compounds of formula (I), Z is 2-pyridyl, 3-pyridyl, 4-pyridyl, 2-thiazolyl, 4-thiazolyl, 5-thiazolyl, 3-pyrazolyl, 1-pyrazolyl, 4-imidazolyl

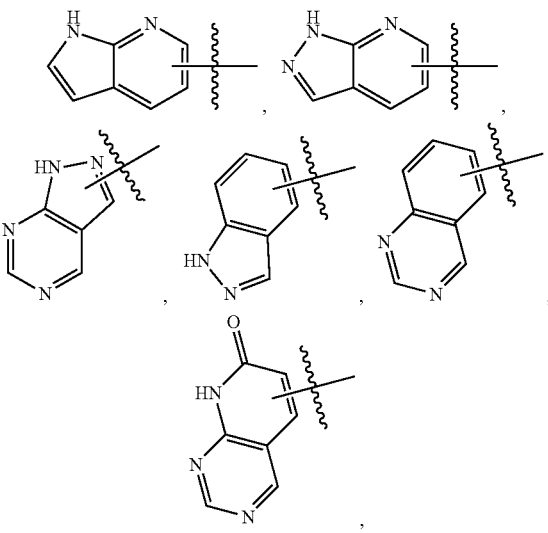

, each of which is optionally substituted, for example, each of which is optionally substituted with from 1 to 3 independently selected R$^7$ substituents; or 1-3 independently selected R$^a$ substituents; or 1-3 independently selected R$^b$ substituents; or 1-3 independently selected R$^c$ substituents; or 1-3 independently selected R$^d$ substituents; or 1-3 independently selected R$^e$ substituents; or 1-3 independently selected R$^f$ substituents. The wavy line indicates the point of attachment to the rest of the molecule. In certain embodiments, Z is optionally substituted 4-thiazolyl. In other embodiments, Z is optionally substituted 3-pyrazolyl. The other variables are as defined in any of the embodiments of compounds of formula (I).

In some embodiments of compounds of formula (I), Z is selected from:

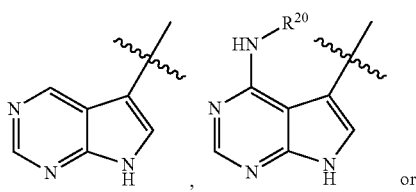

, or

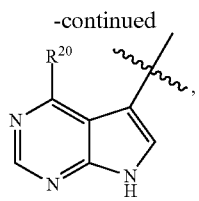

wherein each $R^{20}$ is independently $R^7$; or $R^a$; or $R^b$; or $R^c$; or $R^d$; or $R^e$; or $R^f$; or $R^g$, wherein $R^{20}$ is further optionally substituted with from 1-3 $R^e$ or 1-3 $R^g$ substituents as defined herein. The wavy line indicates the point of attachment to the rest of the molecule. In one embodiment, Z is

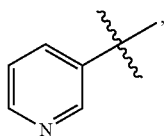 [SMILES: *c1cccnc1]

optionally substituted with from 1-3 independently selected $R^7$ substituents; or 1-3 independently selected $R^a$ substituents; or 1-3 independently selected $R^b$ substituents; or 1-3 independently selected $R^c$ substituents; or 1-3 independently selected $R^d$ substituents; or 1-3 independently selected $R^e$ substituents; or 1-3 independently selected $R^f$ substituents. The wavy line indicates the point of attachment to the rest of the molecule. The other variables are as defined in any of the embodiments of compounds of formula (I).

In some embodiments of compounds of formula (I), Z is 5-pyrimidinyl, 2-pyrimidinyl, 4-pyrimidinyl, 2-pyridyl, 3-pyridyl, 4-pyridyl, 2-pyrazinyl, 2-pyridazinyl, 3-pyridazinyl, 1-pyrrolyl, 2-pyrrolyl, 3-pyrrolyl, 2-imidazolyl, 4-imidazolyl, 1-pyrazolyl, 2-pyrazolyl, 3-pyrazolyl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1,2,3-triazol-1-yl, 1,2,3-triazol-2-yl, 1,2,3-triazol-3-yl, 1,2,3-triazol-4-yl, 1,2,3-triazol-5-yl, 1,2,4-triazol-1-yl, 1,2,4-triazol-2-yl, 1,2,4-triazol-3-yl, 1,2,4-triazol-4-yl, 1,2,4-triazol-5-yl, 1-oxa-2,3-diazol-4-yl, 1-oxa-2,3-diazol-5-yl, 1-oxa-2,4-diazol-3-yl, 1-oxa-2,4-diazol-5-yl, 1-oxa-2,5-diazol-3-yl, 1-oxa-2,5-diazol-4-yl, 1-thia-2,3-diazol-4-yl, 1-thia-2,3-diazol-5-yl, 1-thia-2,4-diazol-3-yl, 1-thia-2,4-diazol-5-yl, 1-thia-2,5-diazol-3-yl, 1-thia-2,5-diazol-4-yl, 1-tetrazolyl, 3-tetrazolyl, 1H-5-tetrazolyl, 3H-5-tetrazolyl, 2-furanyl, 3-furanyl, 2-thiopenyl or 3-thiophenyl, each of which is optionally substituted with from 1 to 3 independently selected $R^7$ substituents; or 1 to 3 independently selected $R^a$ substituents; or 1 to 3 independently selected $R^b$ substituents; or 1 to 3 independently selected $R^c$ substituents; or 1 to 3 independently selected $R^d$ substituents; or 1 to 3 independently selected $R^e$ substituents; 1 to 3 independently selected $R^f$ substituents; or 1 to 3 independently selected $R^g$ substituents selected from F, Cl, Br, I, —CN, —OH, —CF$_3$, —NH$_2$, CF$_3$O—, $C_{1-6}$alkyl, $C_{1-6}$alkoxy, CH$_3$—, CH$_3$O, —NO$_2$, t-butyl, phenyl, cyclopropyl, cyclopropylmethyl, cyclopropylamino, pyrimidinyl, 4-pyrimidinyl, cyclopropylmethylamino, 1-cyanocyclopropyl, methylamino, dimethylamino, methylthio, acetoxy, acetyl, methoxycarbonyl, acetamido, 1-cyclopropylethyl, 2-cyclopropylethyl, 1-cyclopropylethylamino, 2-cyclopropylethylamino, 1-hydroxy-1-methylethyl, methylcarbamoyl, 1-carboxycyclopropyl, 1-carbamoylcyclopropyl, 1-methoxycarbonylcyclopropyl, 1-cyanoisopropyl, 1-hydroxycyclopropyl, 1-hydoxyisopropyl, cyclobutoxy, cyclopentoxy, cycloheyloxy, 4-morpholino, thiomorpholin-4-yl, 4-hydroxypiperidinyl, 1-piperidinyl, piperazinyl, 4-methylpiperazinyl, 4-t-butoxycarbonylpiperazinyl, azetidinyl, pyrrolidinyl, cyclopropylcarbamoyl, 5-methyl-1,2,4-oxadiazol-3-yl, 5-methyl-1,3,4-oxadiazol-2yl, 5-dimethylamino-1,3,4-oxadiazol-2yl, 2-(methoxycarbonylamino)propyl or 5-methylamino-1,3,4-thiadiazol-2-yl. In some instances, $R^g$ is further optionally substituted with 1-3 $R^e$ groups.

In some embodiments of compounds of formula (I), Z is 1-pyrrolyl, 2-pyrrolyl, 3-pyrrolyl, 2-imidazolyl, 4-imidazolyl, 1-pyrazolyl, 2-pyrazolyl, 3-pyrazolyl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1,2,3-triazol-1-yl, 1,2,3-triazol-2-yl, 1,2,3-triazol-3-yl, 1,2,3-triazol-4-yl, 1,2,3-triazol-5-yl, 1,2,4-triazol-1-yl, 1,2,4-triazol-2-yl, 1,2,4-triazol-3-yl, 1,2,4-triazol-4-yl, 1,2,4-triazol-5-yl, 1-oxa-2,3-diazol-4-yl, 1-oxa-2,3-diazol-5-yl, 1-oxa-2,4-diazol-3-yl, 1-oxa-2,4-diazol-5-yl, 1-oxa-2,5-diazol-3-yl, 1-oxa-2,5-diazol-4-yl, 1-thia-2,3-diazol-4-yl, 1-thia-2,3-diazol-5-yl, 1-thia-2,4-diazol-3-yl, 1-thia-2,4-diazol-5-yl, 1-thia-2,5-diazol-3-yl, 1-thia-2,5-diazol-4-yl, 1-tetrazolyl, 3-tetrazolyl, 1H-5-tetrazolyl, 3H-5-tetrazolyl, 2-furanyl, 3-furanyl, 2-thiopenyl or 3-thiophenyl, each of which is optionally substituted with from 1 to 3 independently selected $R^7$ substituents; or 1 to 3 independently selected $R^a$ substituents; or 1 to 3 independently selected $R^b$ substituents; or 1 to 3 independently selected $R^c$ substituents; or 1 to 3 independently selected $R^d$ substituents; or 1 to 3 independently selected $R^e$ substituents; 1 to 3 independently selected $R^f$ substituents; or 1 to 3 independently selected $R^g$ substituents selected from F, Cl, Br, I, —CN, —OH, —CF$_3$, NH$_2$, CF$_3$O—, $C_{1-6}$alkyl, $C_{1-6}$alkoxy, CH$_3$—, CH$_3$O, —NO$_2$, t-butyl, phenyl, cyclopropyl, cyclopropylmethyl, cyclopropylamino, pyrimidinyl, 4-pyrimidinyl, cyclopropylmethylamino, 1-cyanocyclopropyl, methylamino, dimethylamino, methylthio, acetoxy, acetyl, methoxycarbonyl, acetamido, 1-cyclopropylethyl, 2-cyclopropylethyl, 1-cyclopropylethylamino, 2-cyclopropylethylamino, 1-hydroxy-1-methylethyl, methylcarbamoyl, 1-carboxycyclopropyl, 1-carbamoylcyclopropyl, 1-methoxycarbonylcyclopropyl, 1-cyanoisopropyl, 1-hydroxycyclopropyl, 1-hydoxyisopropyl, cyclobutoxy, cyclopentoxy, cycloheyloxy, 4-morpholino, thiomorpholin-4-yl, 4-hydroxypiperidinyl,1-piperidinyl, piperazinyl, 4-methylpiperazinyl, 4-t-butoxycarbonylpiperazinyl, azetidinyl, pyrrolidinyl, cyclopropylcarbamoyl, 5-methyl-1,2,4-oxadiazol-3-yl, 5-methyl-1,3,4-oxadiazol-2yl, 5-dimethylamino-1,3,4-oxadiazol-2yl, 2-(methoxycarbonylamino)propyl or 5-methylamino-1,3,4-thiadiazol-2-yl. In some instances, $R^g$ is optionally substituted with 1-3 $R^e$ groups. In one instance, Z is 4-thiazolyl optionally substituted with 1-2 independently selected $R^7$ groups; or 1-2 independently selected $R^a$ groups; or 1-2 independently selected $R^b$ groups; or 1-2 independently selected $R^c$ groups; or 1-2 independently selected $R^d$ groups; or 1-2 independently selected $R^e$ groups; or 1-2 independently selected $R^f$ groups; or 1-2 independently selected $R^g$ groups. In another instance, Z is 3-pyrazolyl optionally substituted with 1-2 independently selected $R^7$ groups; or 1-2 independently selected $R^a$ groups; or 1-2 independently selected $R^b$ groups; or 1-2 independently selected $R^c$ groups; or 1-2 independently selected $R^d$ groups; or 1-2 independently selected $R^e$ groups; or 1-2 independently selected $R^f$ groups; or 1-2 independently selected $R^g$ groups. In another instances, Z is 2-imidazolyl optionally substituted with 1-2 independently selected $R^7$ groups; or 1-2 independently selected $R^a$ groups; or 1-2 independently selected $R^b$ groups; or 1-2 independently selected $R^c$ groups; or 1-2 independently selected $R^d$ groups; or 1-2 independently selected $R^e$ groups; or 1-2 independently selected $R^f$ groups; or 1-2 independently selected $R^g$ groups. In one instance, Z is 5(2-aminopyrimidin-4-yl)-4-thiazolyl substituted with from 1-2 independently selected $R^7$ groups; or 1-2 independently selected $R^a$ groups; or 1-2 independently selected $R^b$ groups; or 1-2 independently selected $R^c$ groups; or 1-2 independently selected $R^d$ groups; or 1-2 independently selected $R^e$ groups; or 1-2 independently selected $R^f$ groups; or 1-2 independently selected $R^g$ groups In some embodiments, $R^g$ is 4-pyrimidinyl optionally substituted with from 1-3 $R^e$.

In some embodiments of compounds of formula (I), Z is 2-pyridyl, 3-pyridyl, 4-pyridyl, 2-thiazolyl, 4-thiazolyl, 5-thiazolyl, 1H-pyrrolo[2,3-b]pyridine-5-yl, 1H-pyrrolo[2,3-b]pyridine-6-yl, 1H-pyrrolo[2,3-b]pyridine-4-yl, 1H-pyrrolo[2,3-b]pyridine-3-yl, 1H-pyrrolo[2,3-b]pyridine-2-yl, 1H-pyrrolo[2,3-b]pyridine-1-yl, 1H-pyrazolo[5,4-b]pyridine-4-yl, 1H-pyrazolo[5,4-b]pyridine-5-yl, 1H-pyrazolo[5,4-b]pyridine-6-yl, 1H-pyrazolo[5,4-d]pyrimidin-3-yl, 1H-pyrazolo[5,4-d]pyrimidin-1-yl, 1H-indazol-4-yl, 1H-indazol-5-yl, 1H-indazol-6-yl, 1H-indazol-7-yl, quinazolin-5-yl, quinazolin-6-yl, 7-oxo-8H-pyrido[2,3-d]pyrimidin-5-yl, 7-oxo-8H-pyrido[2,3-d]pyrimidin-6-yl, each of which is optionally substituted, for example, each of which is optionally substituted with from 1 to 3 independently selected $R^7$ substituents; or 1 to 3 independently selected $R^a$ substituents; or 1 to 3 independently selected $R^b$ substituents; or 1 to 3 independently selected $R^c$ substituents; or 1 to 3 independently selected $R^d$ substituents; or 1 to 3 independently selected $R^e$ substituents; 1 to 3 independently selected $R^f$ substituents; or 1 to 3 independently selected $R^g$ substituents. In some instances, $R^g$ is further optionally substituted with 1-3 $R^e$ groups.

In some embodiments of the compounds of formula (I), Z is an optionally substituted heteroaryl having the formula:

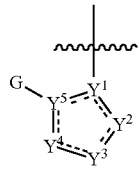

$Y^1$ and $Y^5$ are each independently C or N; $Y^2$, $Y^3$ and $Y^4$ are each independently a carbon atom or a heteroatom selected from O, N or S, wherein N and S are optionally oxidized; G is an optionally substituted heteroaryl; and === is a single bond or a double bond to maintain Z being aromatic, with the proviso that $Y^1$, $Y^2$, $Y^3$, $Y^4$ and $Y^5$ are not simultaneously an optionally substituted carbon; the wavy line indicates the point of attachment to the rest of the molecule. In one embodiment, G is halogen. In some instances, G is an optionally substituted 6-membered heteroaryl. In other instances, G is a pyridyl, pyrimidinyl, pyrazinyl or pyridazinyl, each of which is optionally substituted. In some embodiments, G is a pyridyl, pyrimidinyl, pyrazinyl or pyridazinyl, each of which is optionally substituted with from 1-2 independently selected $R^7$ groups; or 1-2 independently selected $R^a$ groups; or 1-2 independently selected $R^b$ groups; or 1-2 independently selected $R^c$ groups; or 1-2 independently selected $R^d$ groups; or 1-2 independently selected $R^e$ groups; or 1-2 independently selected $R^f$ groups; or 1-2 independently selected $R^g$ groups. In one instance, G is an optionally substituted 4-pyrimidinyl. In another instance, G is an optionally substituted 2-amino-4-pyrimidinyl. In another instance, G is 4-pyrimidinyl optionally substituted with from 1-2 independently selected $R^7$ groups; or 1-2 independently selected $R^a$ groups; or 1-2 independently selected $R^b$ groups; or 1-2 independently selected $R^c$ groups; or 1-2 independently selected $R^d$ groups; or 1-2 independently selected $R^e$ groups; or 1-2 independently selected $R^f$ groups; or 1-2 independently selected $R^g$ groups. In another instance, G is 2-amino-4-pyrimidinyl optionally substituted with from 1-2 independently selected $R^7$ groups; or 1-2 independently selected $R^a$ groups; or 1-2 independently selected $R^b$ groups; or 1-2 independently selected $R^c$ groups; or 1-2 independently selected $R^d$ groups; or 1-2 independently selected $R^e$ groups; or 1-2 independently selected $R^f$ groups; or 1-2 independently selected $R^g$ groups. In some embodiments, G is heteroaryl substituted with —$OCH_3$, —$NH_2$ or —$NH[CH_2CH(CH_3)NHC(O)OCH_3]$.

In some embodiments of the compounds of formula (I), G is selected from 3-pyridyl, 4-pyrimidinyl, 2-amino-4-pyrimidinyl, 2-methoxy-4-pyrimidinyl,

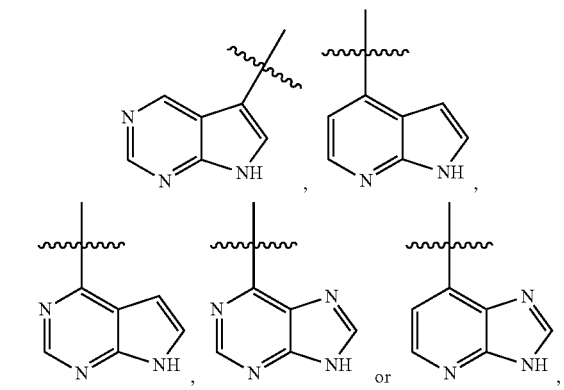

each of which is optionally substituted with from 1-2 independently selected $R^7$ groups; or 1-2 independently selected $R^a$ groups; or 1-2 independently selected $R^b$ groups; or 1-2 independently selected $R^c$ groups; or 1-2 independently selected $R^d$ groups; or 1-2 independently selected $R^e$ groups; or 1-2 independently selected $R^f$ groups; or 1-2 independently selected $R^g$ groups.

In some embodiments of the compounds of formula (I), Z is

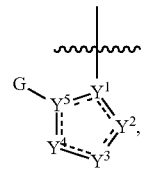

which is optionally substituted with from 1 to 3 independently selected $R^7$ substituents; or 1 to 3 independently selected $R^a$ substituents; or 1 to 3 independently selected $R^b$ substituents; or 1 to 3 independently selected $R^c$ substituents; or 1 to 3 independently selected $R^d$ substituents; or 1 to 3 independently selected $R^e$ substituents; 1 to 3 independently selected $R^f$ substituents; or 1 to 3 independently selected $R^g$ substituents selected from F, Cl, Br, I, —CN, —OH, —$CF_3$, $NH_2$, $CF_3O$—, $CH_3$—, ethyl, propyl, isopropyl, CH₃O, —NO₂, t-butyl, cyclopropyl, cyclopropylmethyl, cyclopropylamino, pyrimidinyl, 4-pyrimidinyl, cyclopropylmethylamino, 1-cyanocyclopropyl, methylamino, dimethylamino, methylthio, acetoxy, acetyl, methoxycarbonyl, acetamido, 1-cyclopropylethyl, 2-cyclopropylethyl, 1-cyclopropylethylamino, 2-cyclopropylethylamino, 1-hydroxy-1-methylethyl, methylcarbamoyl, 1-carboxycyclopropyl, 1-carbamoylcyclopropyl, 1-methoxycarbonylcyclopropyl, 1-cyanoisopropyl, 1-hydroxycyclopropyl, 1-hydoxyisopropyl, cyclobutoxy, cyclopentoxy, cycloheyloxy, 4-morpholino, 4-hydroxypiperidinyl, 1-piperidinyl, piperazinyl, 4-methylpiperazinyl, 4-t-butoxycarbonylpiperazinyl, azetidinyl, pyrrolidinyl, cyclopropylcarbamoyl, 5-methyl-1,2,4-oxadiazol-3-yl, 5-methyl-1,3,4-oxadiazol-2yl, 5-dimethylamino-1,3,4-oxadiazol-2yl, 2-(methoxycarbonylamino)propyl or 5-methylamino-1,3,4-thiadiazol-2-yl. In some instances, $R^g$ is optionally substituted with 1-3 $R^e$ groups. $Y^1$, $Y^2$, $Y^3$, $Y^4$, $Y^5$ and G are as defined in any of the embodiments disclosed herein.

In some embodiments of the compounds of formula (I), Z is

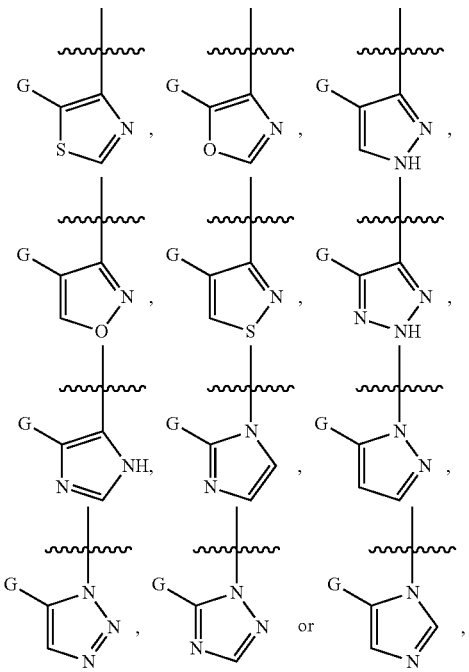

each of which is optionally substituted with from 1 to 3 independently selected $R^7$ substituents; or 1 to 3 independently selected $R^a$ substituents; or 1 to 3 independently selected $R^b$ substituents; or 1 to 3 independently selected $R^c$ substituents; or 1 to 3 independently selected $R^d$ substituents; or 1 to 3 independently selected $R^e$ substituents; 1 to 3 independently selected $R^f$ substituents; or 1 to 3 independently selected $R^g$ substituents, wherein the $R^g$ group is optionally further substituted with 1-3 $R^e$. In one embodiment, G is 4-pyrimidinyl optionally substituted with from 1-2 independently selected $R^7$ groups; or 1-2 independently selected $R^a$ groups; or 1-2 independently selected $R^b$ groups; or 1-2 independently selected $R^c$ groups; or 1-2 independently selected $R^d$ groups; or 1-2 independently selected $R^e$ groups; or 1-2 independently selected $R^f$ groups; or 1-2 independently selected $R^g$ groups. In another embodiment, G is 2-amino-4-pyrimidinyl optionally substituted with from 1-2 independently selected $R^7$ groups; or 1-2 independently selected $R^a$ groups; or 1-2 independently selected $R^b$ groups; or 1-2 independently selected $R^c$ groups; or 1-2 independently selected $R^d$ groups; or 1-2 independently selected $R^e$ groups; or 1-2 independently selected $R^f$ groups; or 1-2 independently selected $R^g$ groups.

In some embodiments of compounds of formula (I), Z is

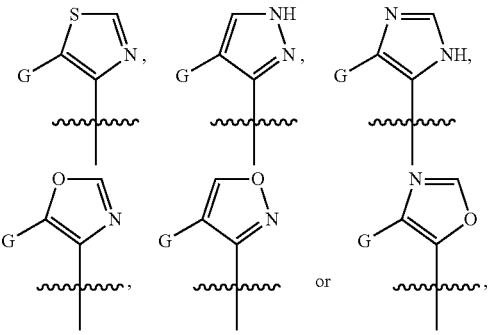

each of which is optionally substituted, for example, with from 1 to 3 independently selected $R^7$ substituents; or 1 to 3 independently selected $R^a$ substituents; or 1 to 3 independently selected $R^b$ substituents; or 1 to 3 independently selected $R^c$ substituents; or 1 to 3 independently selected $R^d$ substituents; or 1 to 3 independently selected $R^e$ substituents; 1 to 3 independently selected $R^f$ substituents; or 1 to 3 independently selected $R^g$ substituents, wherein the $R^g$ group is optionally further substituted with 1-3 $R^e$.

In some embodiments of compounds of formula (I), Y is as defined in the Summary. All the other variables of formula (I) and Z, L, $R^3$ and $R^4$ are as defined in any of the embodiments of compounds of formula (I) as described herein.

In some embodiments of compounds of formula (I), Y is —N($R^1$)($R^2$) or —C($R^8$)($R^9$)($R^{10}$), wherein $R^1$ and $R^2$ are each independently selected from the group consisting of optionally substituted $C_{1-6}$alkyl, optionally substituted $C_{3-8}$cycloalkyl, optionally substituted $C_{3-8}$cycloalkylalkyl, optionally substituted heterocycloalkyl, optionally substituted heterocycloalkylalkyl, optionally substituted aryl, optionally substituted arylalkyl, optionally substituted heteroaryl and optionally substituted heteroarylalkyl; or $R^1$ and $R^2$ taken together with the nitrogen atom to which they are attached form an optionally substituted four to eight-membered ring having from 0-2 additional heteroatoms as ring members selected from N, O or S, wherein N and S are optionally oxidized, wherein the four to eight-membered ring is optionally substituted with from one to three groups independently selected from halogen, $C_{1-6}$ haloalkyl, $C_{1-6}$ haloalkoxy, $C_{1-6}$ alkyl, $C_{3-8}$ cycloalkyl, $C_{3-8}$ cycloalkylalkyl, aryl, arylalkyl or $R^e$. $R^8$, $R^9$ and $R^{10}$ are each independently H, $C_{1-6}$ alkyl, $C_{1-6}$ haloalkyl, $C_{1-6}$ haloalkoxy, $C_{3-8}$ cycloalkyl, $C_{3-8}$ cycloalkylalkyl, aryl, arylalkyl, heterocycloalkyl, heterocycloalkylalkyl, heteroaryl, heteroarylalkyl or —$X^1R^5$; wherein $X^1$ is —N$R^6$, O or S; $R^6$ is H, $C_{1-6}$ alkyl or aryl; and $R^5$ is H, $C_{1-6}$ alkyl, $C_{1-6}$ haloalkyl, $C_{1-6}$ haloalkoxy, $C_{3-8}$ cycloalkyl, $C_{3-8}$ cycloalkylalkyl, aryl, arylalkyl, heteroaryl or heteroarylalkyl, wherein $R^5$ is optionally substituted with from 1 to 3 $R^e$ substituents, wherein the aliphatic or aromatic portion of $R^8$, $R^9$ and $R^{10}$ are each optionally substituted with from 1 to 3 members independently selected from the group consisting of $C_{3-8}$cycloalkyl, $C_{3-8}$cycloalkylalkyl, aryl, arylalkyl, heterocycloalkyl, heterocycloalkylalkyl, heteroaryl, heteroarylalkyl and $R^e$; or any two of the $R^8$, $R^9$ and $R^{10}$ groups taken together with the carbon atom to which they are attached form a 3 to 8-membered carbocyclic ring or a 4 to 8-membered heterocyclic ring having from 1 to 2 heteroatoms as ring members selected from N, O or S, wherein the 3 to 8-membered carbocyclic ring or the 4 to 8-membered heterocyclic ring is optionally substituted with from one to three groups independently selected from $C_{1-6}$haloalkyl, $C_{1-6}$haloalkoxy, $C_{1-6}$alkyl, $C_{3-8}$cycloalkyl, $C_{3-8}$cycloalkylalkyl, aryl, arylalkyl, heteroaryl or heteroarylalkyl or $R^e$, provided at each occurrence, at least two of the $R^8$, $R^9$ and $R^{10}$ groups are not simultaneously hydrogen. All the other variables Z, L, $R^3$ and $R^4$ of formula (I) are as defined in any of the embodiments described herein.

In some embodiments of compounds of formula (I), Y is —N($R^1$)($R^2$), wherein $R^1$ and $R^2$ are each independently selected from $C_{1-6}$alkyl, $C_{3-8}$cycloalkyl, $C_{3-8}$cycloalkylalkyl, aryl, aryl-$C_{1-4}$alkyl, heteroaryl or heteroaryl-$C_{1-4}$alkyl, each of which is optionally substituted with from (i) 1-3 substituents independently selected from $C_{1-6}$alkoxy, $C_{1-6}$haloalkyl, $C_{1-6}$haloalkoxy, $C_{1-6}$alkyl, $C_{3-8}$cycloalkyl, $C_{3-8}$ cycloalkylalkyl, aryl, arylalkyl, heteroaryl, heteroarylalkyl or $R^e$; or (ii) 1, 2 or 3 independently selected $R^a$ substituents; or (iii) 1, 2 or 3 independently selected $R^b$ substituents; or (iv) 1, 2 or 3 independently selected $R^c$ substituents; or (v) 1, 2 or 3 independently selected $R^d$ substituents; or (vi) 1, 2 or 3 independently selected $R^f$ groups. All the other variables Z, L, $R^3$ and $R^4$ of formula (I) are as defined in any of the embodiments described herein.

In some embodiments of compounds of formula (I), $R^1$ is —$CH_3$ and $R^2$ is $C_{2-6}$alkyl, $C_{3-8}$cycloalkyl, $C_{3-8}$cycloalkylalkyl, aryl, aryl-$C_{1-4}$alkyl, heteroaryl or heteroaryl-$C_{1-4}$alkyl, each of which is optionally substituted with from (i) 1-3 substituents independently selected from $C_{1-6}$alkoxy, $C_{1-6}$haloalkyl, $C_{1-6}$haloalkoxy, $C_{1-6}$alkyl, $C_{3-8}$cycloalkyl, $C_{3-8}$cycloalkylalkyl, aryl, arylalkyl, heteroaryl, heteroarylalkyl or $R^e$; or (ii) 1, 2 or 3 $R^a$ substituents; or (iii) 1, 2 or 3 $R^b$ substituents; or (iv) 1, 2 or 3 $R^c$ substituents; or (v) 1, 2 or 3 $R^d$ substituents; or (vi) 1, 2 or 3 $R^f$ groups. In certain instances, R' is —$CH_3$ and $R^2$ is $C_{2-6}$alkyl. All the other variables Z, L, $R^3$ and $R^4$ of formula (I) are as defined in any of the embodiments described herein.

In some embodiments of compounds of formula (I), $R^1$ and $R^2$ are each independently selected from $C_{1-6}$alkyl, $C_{3-8}$cycloalkyl, $C_{3-8}$cycloalkylalkyl, aryl, aryl-$C_{1-4}$alkyl, heteroaryl or heteroaryl-$C_{1-4}$alkyl, each of which is optionally substituted with from 1, 2 or 3 $R^h$ members selected from F, Cl, Br, I, —CN, —OH, —$CF_3$, $NH_2$, $CF_3O$—, $CH_3$—, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In certain instances, $R^h$ is F, Cl, —CN, —OH, —$CF_3$, $NH_2$, $CF_3O$—, $CH_3$—, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In one embodiment, $R^h$ is halogen. All the other variables Z, L, $R^3$ and $R^4$ of formula (I) are as defined in any of the embodiments described herein.

In some embodiments of compounds of formula (I), $R^1$ is —$CH_3$ and $R^2$ is $C_{2-6}$alkyl, $C_{3-8}$cycloalkyl, $C_{3-8}$cycloalkylalkyl, aryl, aryl-$C_{1-4}$alkyl, heteroaryl or heteroaryl-$C_{1-4}$alkyl, each of which is optionally substituted with from 1, 2 or 3 $R^h$ members selected from F, Cl, Br, I, —CN, —OH, —$CF_3$, $NH_2$, $CF_3O$—, $CH_3$—, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. All the other variables Z, L, $R^3$ and $R^4$ of formula (I) are as defined in any of the embodiments described herein.

In some embodiments of compounds of formula (I), $R^1$ is —$CH_3$ and $R^2$ is selected from ethyl, propyl, butyl, pentyl, cyclopropyl, cyclopropylmethyl, cyclobutyl, cyclobutylmethyl, cyclopentyl, cyclopentylmethyl, cyclohexyl, cyclohexylmethyl, phenyl or benzyl, each of which is optionally substituted with from 1-3 substituents independently selected from F, Cl, —CN, —OH, —$CF_3$, $NH_2$, $CF_3O$—, $CH_3$—, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. All the other variables Z, L, $R^3$ and $R^4$ of formula (I) are as defined in any of the embodiments described herein.

In some embodiments of compounds of formula (I), Y is —N($R^1$)($R^2$), wherein $R^1$ and $R^2$ taken together with the nitrogen to which they attach form an optionally substituted 5- or 6-membered heterocycloalkyl ring having from 0-1 additional heteroatoms as ring members selected from O, N or S, wherein N or S is optionally oxidized. In some embodiments, $R^1$ and $R^2$ taken together with the nitrogen to which they attach form a 5-membered heterocycloalkyl having from 0-1 additional heteroatoms as ring members selected from O, N or S, wherein the 5-membered heterocycloalkyl is optionally substituted with from 1-2 independently selected $R^7$ groups; or 1-2 independently selected $R^a$ groups; or 1-2 independently selected $R^b$ groups; or 1-2 independently selected $R^c$ groups; or 1-2 independently selected $R^d$ groups; or 1-2 independently selected $R^e$ groups; or 1-2 independently selected $R^f$ groups; or 1-2 independently selected $R^g$ groups. In other embodiments, $R^1$ and $R^2$ taken together with the nitrogen to which they attach form a 6-membered heterocycloalkyl having from 0-1 additional heteroatoms as ring members selected from O, N or S, wherein the 6-membered heterocycloalkyl is optionally substituted with from 1-2 independently selected $R^7$ groups; or 1-2 independently selected $R^a$ groups; or 1-2 independently selected $R^b$ groups; or 1-2 independently selected $R^c$ groups; or 1-2 independently selected $R^d$ groups; or 1-2 independently selected $R^e$ groups; or 1-2 independently selected $R^f$ groups; or 1-2 independently selected $R^g$ groups.

In some embodiments of compounds of formula (I), Y is —N($R^1$)($R^2$), wherein —N($R^1$)($R^2$) is selected from 1-azetindinyl, 1-pyrrolidinyl, 1-piperidinyl, 4-morpholinyl, 4-thiomorpholinyl, 3-oxazolidinyl, 3-thiazolidinyl, 2-isoxazolidinyl, 2-isothiazolidinyl, 1-pyrazolidinyl, 1-piperazinyl, 1-hexahydropyrimidinyl or 1-hexahydropyridazinyl, each of which is (i) optionally substituted with from 1 to 3 $R^{11}$ substituents independently selected from the group consisting of halogen, $C_{1-6}$alkyl, $C_{1-6}$alkoxy, $C_{1-6}$haloalkyl, $C_{1-6}$haloalkoxy, $C_{1-6}$alkyl, $C_{3-8}$cycloalkyl, $C_{3-8}$cycloalkylalkyl, heterocycloalkyl, heterocycloalkylalkyl, aryl, arylalkyl, heteroaryl, heteroarylalkyl and $R^c$; or (ii) two adjacent $R^{11}$ substituents together with the atom to which they are attached form a 5 or 6-membered aromatic ring having from 0 to 2 additional atoms as ring members selected from O, N or S or (iii) optionally substituted with from 1 to 8 deuteriums with at least 52.5%, 60%, 70%, 75%, 80%, 90%, 95%, 99%, 99.5% or 99.9% deuterium incorporation for each deuterium. In certain instances, $R^{11}$ is F, Cl, Br, I, —CN, —OH, —$CF_3$, $NH_2$, $CF_3O$—, $CH_3$—, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In other instances, $R^{11}$ is F, Cl, —CN, —OH, —$CF_3$, $NH_2$, $CF_3O$—, $CH_3$—, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In other instances, $R^{11}$ is F, $CH_3$, methoxycarbonyl, ethoxycarbonyl, —$CH_3$, $CH_3(CO)NH$—, vinyl, propen-3-yl or $CH_3(CO)(CH_3)N$—. In some embodiments, each hydrogen atom in Y is optionally replaced by a deuterium atom with at least 52.5%, 60%, 70%, 75%, 80%, 90%, 95%, 99%, 99.5% or 99.9% deuterium incorporation for each deuterium. In certain embodiments, Y is 1-azetindinyl, 1-pyrrolidinyl, 1-piperidinyl or 1-piperazinyl, each of which is optionally substituted with from 1-3 independently selected $R^{11}$ groups. All the other variables Z, L, $R^3$ and $R^4$ of formula (I) are as defined in any of the embodiments described herein.

In some embodiments of compounds of formula (I), Y is —C($R^8$)($R^9$)($R^{10}$), where $R^8$ is H and $R^9$ and $R^{10}$ are each independently $C_{1-6}$alkyl, optionally substituted with from 1 to 3 $R^d$ or 1-3 $R^e$ groups. In some embodiments, $R^8$, $R^9$ and $R^{10}$ are each independently $C_{1-6}$alkyl, optionally substituted with from 1 to 3 $R^d$ or 1-3 $R^e$. In some embodiments, —C($R^8$)($R^9$)($R^{10}$) is cyclopropyl, cyclobutyl, cyclohexyl, cyclopentyl, cycloheptyl, cyclooctyl, each of which is optionally substituted with from 1-3 $R^{12}$ substituents independently selected from F, Cl, Br, I, —CN, —OH, —$CF_3$, $NH_2$, $CF_3O$—, $CH_3$—, $CH_3O$, —$CH_2CH=CH_2$, —$NO_2$, cyclopropyl, cyclopropylmethyl, cyclopropylamino, cyclopropylmethylamino, 1-cyanocyclopropyl, vinyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In some instances, $R^{12}$ is F, —CN, —OH, —$CF_3$, $NH_2$, $CF_3O$—, $CH_3$—, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In some embodiments, —C($R^8$)($R^9$)($R^{10}$) is 2-azetindinyl, 3-azetindinyl, 3-pyrrolidinyl, 2-pyrrolidinyl, 2-piperidinyl, 3-piperidinyl, 4-piperidinyl, 2-morpholinyl, 3-morpholinyl, 2-thiomorpholinyl, 3-thiomorpholinyl, 2-oxazolidinyl, 4-oxazolidinyl, 5-oxazolidinyl, 2-thiazolidinyl, 4-thiazolidinyl, 5-thiazolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 2-piperazinyl, 2-hexahydropyrimidinyl, 4-hexahydropyrimidinyl, 5-hexahydropyrimidinyl, 3-hexahydropyridazinyl or 4-hexahydropyridazinyl, each of which is optionally substituted with 1 to 3 $R^{12}$ substituents. In certain embodiments, —C($R^8$)($R^9$)($R^{10}$) is cyclopropyl, cyclobutyl, cyclopentyl or cyclohexyl, each of which is optionally substituted with 1 to 3 $R^{12}$ substituents. In some embodiments, each hydrogen atom in Y is optionally replaced by a deuterium atom with at least 52.5%, 60%, 70%, 75%, 80%, 90%, 95%, 99%, 99.5% or 99.9% deuterium incorporation for each deuterium. All the other variables Z, L, $R^3$ and $R^4$ of formula (I) are as defined in any of the embodiments described herein.

In some embodiments of compounds of formula (I), Y is 1-piperazinyl, 1-pyrrolidinyl, 2-oxo-1-pyrrolidinyl, 3-oxo-1-pyrrolidinyl 1-piperidinyl, 4-morpholino or 4-thiomorpholino, each of which is optionally substituted. In some embodiments of compounds of formula (I), is Y is selected from the group consisting of cyclopropyl, cyclobutyl, cyclohexyl, cyclopentyl, cycloheptyl, cyclooctyl, 1-azetindinyl, 1-pyrrolidinyl, 1-piperidinyl, 4-morpholinyl, 4-thiomorpholinyl 3-oxazolidinyl, 3-thiazolidinyl, 2-isoxazolidinyl, 2-isothiazolidinyl, 1-pyrazolidinyl, 1-piperazinyl, 1-hexahydropyrimidinyl, 1-hexahydropyridazinyl, $(CH_3)(CF_3CH_2)N—$, cyloproyplmethylamino, sec-butyl, pentan-2-yl and pentan-3-yl, each of which is (i) optionally substituted with from one to three $R^{13}$ substituents independently selected from the group consisting of halogen, $C_{1-6}$alkyl, $C_{1-6}$alkoxy, $C_{1-6}$haloalkyl, $C_{1-6}$haloalkoxy, $C_{1-6}$alkyl, $C_{3-8}$ cycloalkyl, $C_{3-8}$ cycloalkylalkyl, heterocycloalkyl, heterocycloalkylalkyl, aryl, arylalkyl, heteroaryl, heteroarylalkyl and $R^c$; or (ii) two adjacent $R^{13}$ substituents together with the atom to which they are attached form a 5 or 6-membered aromatic ring having from 0 to 2 additional atoms as ring members selected from O, N or S; or (iii) optionally substituted with from 1 to 11 deuteriums having at least 52.5%, 60%, 70%, 75%, 80%, 90%, 95%, 99%, 99.5% or 99.9% deuterium incorporation for each deuterium. In one embodiment, Y is cyclopropyl optionally substituted with 1 to 2 $R^{13}$ groups. In another embodiment, Y is cyclopentyl optionally substituted with 1 to 2 $R^{13}$ groups. In yet another embodiment Y is 1-pyrrolidinyl optionally substituted with 1 to 2 $R^{13}$ groups. In other embodiment, Y is 1-piperidinyl optionally substituted with 1 to 2 $R^{13}$ groups. In another embodiment, Y is 1-pyrrolidinyl, 3-fluoro-1-pyrrolidinyl, (3S)-3-fluoro-1-pyrrolidinyl, (3R)-3-fluoro-1-pyrrolidinyl, 3,3-difluoro-1-pyrrolidinyl, 3-$C_{1-6}$alkyl-C(O)—$C_{1-6}$alkyl-N-1-pyrrolidinyl, 3-$C_{1-6}$alkyl-C(O)NH-1-pyrrolidinyl, $C_{1-6}$alkoxycarbonyl-1-pyrrolidinyl or 3,3-dimethyl-1-pyrrolidinyl. In certain instances, $R^{13}$ is F, Cl, Br, I, —CN, —OH, —$CF_3$, $NH_2$, $CF_3O—$, $CH_3—$, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxtetanyl, 2-oxetanylmethyl, 3-oxtetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In one instance, $R^{13}$ is —F, methoxycarbonyl, ethoxycarbonyl, —$CH_3$, $CH_3(CO)NH—$, vinyl, propen-3-yl or $CH_3(CO)(CH_3)N—$. In another instance, $R^{13}$ is —F, methoxycarbonyl, ethoxycarbonyl, —$CH_3$, $CH_3(CO)NH—$ or $CH_3(CO)(CH_3)N—$. In yet another instance, $R^{13}$ is vinyl or propen-3-yl. All the other variables Z, L, $R^3$ and $R^4$ of formula (I) are as defined in any of the embodiments described herein.

In some embodiments of compounds of formula (I), L is a bond, —C(O)—, —C(S)—, —C(O)NH—, —NHC(O)— or optionally substituted —C(=$CH_2$)—, wherein two substituents attached to the same methylene carbon in the —C(=$CH_2$)— group are optionally taken together to form an optionally substituted 5- or 6-membered ring having from 0-4 heteroatoms selected from O, N or S, where N and S are optionally oxidized. In certain embodiments, L is a bond, —C(O)—, —C(O)NH— or —NHC(O)—. In certain instances, L is —C(—C=$CH_2$)—, optionally substituted with from 1-2 $R^c$; or 1-2 $R^e$ substituents. In some instances, L is —C[=C($R^{14}$)($R^{15}$)]—, wherein $R^{14}$ and $R^{15}$ are taken together with the carbon atom to which they attach form 5- or 6-membered ring having from 0-4 heteroatoms selected from O, N or S, where N and S are optionally oxidized. In some embodiments, L is a bond. In other embodiments, L is —C(O)—. In yet other embodiments, L is —C(O)NH— or —NHC(O)—. All the other variables Z, Y, $R^3$ and $R^4$ of formula (I) are as defined in any of the embodiments described herein.

In some embodiments of compounds of formula (I), $R^3$ is H. In certain embodiments, $R^3$ is $C_{1-6}$alkyl. All the other variables Z, Y, L and $R^4$ of formula (I) are as defined in any of the embodiments described herein.

In some embodiments of compounds of formula (I), $R^4$ is halogen, hydrogen, $C_{1-2}$alkyl, $C_{1-2}$haloalkyl, CN, $C_{1-2}$haloalkoxy or $C_{1-2}$alkoxy. In one instance, $R^4$ of formula (I) is attached to the phenyl ring at the meta position with respect to the fluoro substituent. In another instance, $R^4$ of formula (I) is attached to the phenyl ring at the para position with respect to the fluoro substituent. In certain embodiments, $R^4$ is H, F, Cl, $CH_3$, —$CH_2CH_3$, —$OCH_3$, —$CF_3$, —$CHF_2$, —$CH_2F$, CN, —$OCF_3$, —$OCHF_2$ or —$OCH_2F$. In one embodiment, $R^4$ is F. In another embodiment, $R^4$ is Cl. In yet another embodiment, $R^4$ is H. In another embodiment, $R^4$ is $CH_3$. All the other variables Z, Y, $R^3$ and L of formula (I) are as defined in any of the embodiments described herein.

In some embodiments, the disclosure provides a compound of formula (I'):

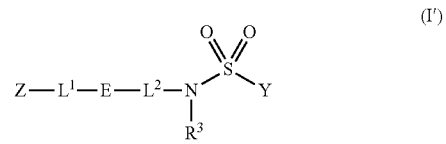

Z, Y and $R^3$ are as defined in any of the embodiments of compounds of formula (I) or subgeneric formulas of formula (I). In one embodiment, Y is —N($R^1$)($R^2$). In another embodiment, Y is —C($R^8$)($R^9$)($R^{10}$), where $R^1$, $R^2$, $R^8$, $R^9$ and $R^{10}$ are as defined in any of embodiments of formula (I) or subgeneric formulas of formula (I) as described herein. $L^1$ and $L^2$ are each independently a bond, —C(O)—, —C(S)—, —C(O)NH—, —NHC(O)— or optionally substituted —C(=$CH_2$)—, wherein two substituents attached to the same methylene carbon in the —C(=$CH_2$)— group are optionally taken together to form an optionally substituted 5- or 6-membered ring having from 0-4 heteroatoms selected from O, N or S, where N and S are optionally oxidized. E is an optionally substituted aryl or optionally substituted 5- or 6-membered heteroaryl. In some instances, E is an aryl or 5- or 6-membered heteroaryl, each of which is optionally substituted with from 1 to 3 independently selected $R^7$ substituents; or 1-3 independently selected $R^a$ substituents; or 1-3 independently selected $R^b$ substituents; or 1-3 independently selected $R^c$ substituents; or 1-3 independently selected $R^d$ substituents; or 1-3 independently selected $R^e$ substituents; or 1-3 independently selected $R^f$ substituents; or 1-3 independently selected $R^g$ substituents; or 1-3 independently selected halogens. In certain instances, when $L^2$ is a bond and E is

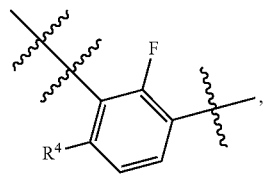

then Z is other than a 5-position optionally substituted

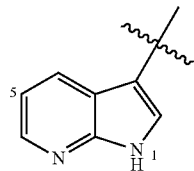 [SMILES: *c1c[nH]c2ncccc12]

core, wherein the single wavy line in

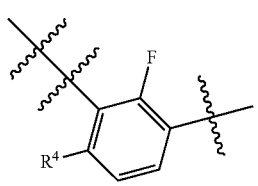

indicates the attachment to —N(R³)SO₂Y group and the double wavy line in

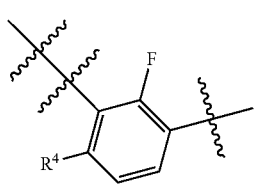

indicates the attachment to E, wherein the wavy line in

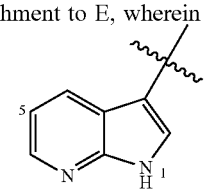

indicates the attachment to L¹ and wherein R⁴ is H or F. In certain embodiments, when L² is a bond and E is

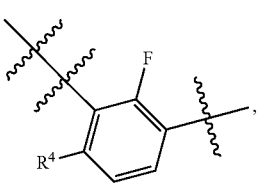

then Z is other than an optionally substituted

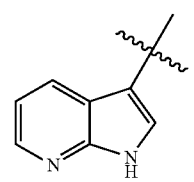 [SMILES: *c1c[nH]c2ncccc12]

core.

Subformulas

In one group of embodiments, compounds of formula (I) have subformula (Ia):

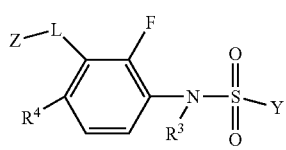

(Ia)

Y is —N(R¹)(R²) or —C(R⁸)(R⁹)(R¹⁰). R⁴ is H, F, CH₃ or Cl. In one instance, R⁴ is H. In another instance, R⁴ is F. The variables R¹, R², R³, R⁴, Y, Z, R⁸, R⁹, R¹⁰, and L are as defined in formula (I) and any embodiments as described herein.

In a second group of embodiments, compounds of formula (I) or (Ia) have subformulas (Ia-1) or (Ia-2):

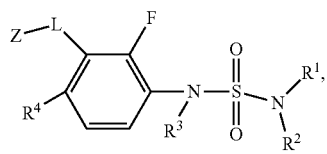

(Ia-1)

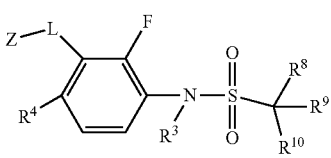

(Ia-2)

The variables R¹, R², R³, R⁴, R⁸, R⁹, R¹⁰, Z and L are as defined in formulas (I) or (Ia) and any embodiments as described herein.

In a third group of embodiments, compounds of formula (I) have subformula (Ib):

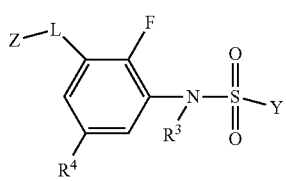

(Ib)

Y is —N(R¹)(R²) or —C(R⁸)(R⁹)(R¹⁰). R⁴ is F, CH₃, CN, CF₃ or Cl. In one instance, R⁴ is F. In another instance, R⁴ is Cl. In yet another instance, R⁴ is CH₃. In some embodiments, R³ is H and L is a bond or —C(O)—. Other variables Y, R¹, R², R³, R⁸, R⁹, R¹⁰, Z and L are as defined in formula (I) and any embodiments as described herein.

In a fourth group of embodiments, compounds of formula (I) or (Ib) have subformulas (Ib-1) or (Ib-2):

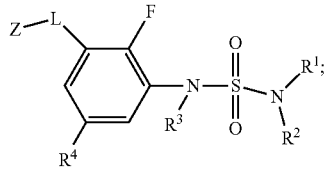

(Ib-1)

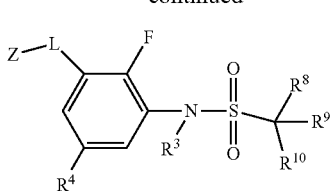

(Ib-2)

In some embodiments, $R^3$ is H. In one embodiment, L is —C(O)—. In another embodiment, $R^4$ is F, Cl, $CH_3$, CN or $CF_3$. In certain embodiments of compounds of formula (Ib-1) or (Ib-2), Z is an optionally substituted 1H-pyrrolo[2,3-b]pyridine-3-yl. The variables $R^1$, $R^2$, $R^3$, $R^4$, $R^8$, $R^9$, $R^{10}$, Z and L are as defined in formula (I) and any embodiments as described herein.

In a fifth group embodiments, compounds of formulas (I), (Ib) or (Ib-1) have subformula (Ib-1a):

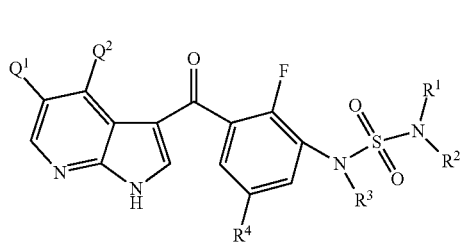

(Ib-1a)

$Q^1$ is CN, halogen, —OH, optionally substituted $C_{1-6}$ alkyl, optionally substituted $C_{1-6}$ alkoxy, optionally substituted $C_{3-6}$cycloalkyl, optionally substituted $C_{1-6}$ haloalkyl, optionally substituted $C_{1-6}$ haloalkoxy, optionally substituted aryl and optionally substituted heteroaryl; optionally wherein two adjacent substituents on a substituted aryl or a substituted heteroaryl ring together with the atoms to which they are attached form an optionally substituted 5- or 6-membered ring having from 0 to 3 additional heteroatoms selected from N, O or S. $Q^2$ is H, halogen, CN, $C_{1-6}$ alkyl, $C_{1-6}$ alkoxy, $C_{1-6}$ haloalkyl, $C_{1-6}$ haloalkoxy, aryl, arylalkyl, heteroaryl, heteroarylalkyl, $C_{3-8}$ cycloalkyl-$C_{0-4}$ alkyl or $(R^{17})(R^{18})N$—, wherein $R^{17}$ and $R^{18}$ are each independently selected from the group consisting of H, $C_{1-6}$ alkyl, $C_{1-6}$ alkoxy, aryl, arylalkyl, heteroaryl, heteroarylalkyl, $C_{3-8}$ cycloalkyl-$C_{0-4}$ alkyl, heterocycloalkyl and heterocycloalkyl-$C_{1-4}$ alkyl; or $R^{17}$ and $R^{18}$ taken together with the nitrogen atom to which they are attached form a four to eight-membered ring having from 0-2 additional heteroatoms as ring members selected from N, O or S; wherein $Q^2$ is optionally substituted with from one to three groups independently selected from $R^e$. In some embodiments, $Q^1$ is CN, halogen, —OH, $C_{1-6}$ alkyl, $C_{1-6}$ alkoxy, $C_{3-6}$cycloalkyl, $C_{1-6}$ haloalkyl, $C_{1-6}$ haloalkoxy, aryl or heteroaryl, wherein the aliphatic or aromatic portion of $Q^1$ is each independently optionally substituted with from 1-5 independently selected $R^7$; or 1 to 5 independently selected $R^a$ substituents; or 1 to 5 independently selected $R^b$ substituents; or 1 to 5 independently selected $R^c$ substituents; or 1 to 5 independently selected $R^d$ substituents; or 1 to 5 independently selected $R^e$ substituents; 1 to 5 independently selected $R^f$ substituents; or 1 to 5 independently selected $R^g$ substituents. In some embodiments, $Q^2$ is H, F, Cl, I, CN, $CH_3$, $CH_3O$—, cyclopropylamino or cyclopropylmethylamino. In other embodiments, $Q^2$ is H. In some embodiments, $R^3$ is H.

In other embodiments, $R^4$ is F, Cl, $CH_3$, CN or $CF_3$. In other embodiments, $R^4$ is F or Cl. In one embodiment, $R^4$ is F. The variables $R^1$, $R^2$, $R^3$ and $R^4$ are as defined in formula (I) and any embodiments as described herein.

In some embodiments of compounds of formula (Ib-1a), $Q^1$ is phenyl, 1-naphthyl or 2-naphthyl, each of which is optionally substituted with from 1 to 3 independently selected $R^7$ substituents; 1 to 3 independently selected $R^a$ substituents; or 1 to 3 independently selected $R^b$ substituents; or 1 to 3 independently selected $R^c$ substituents; or 1 to 3 independently selected $R^d$ substituents; or 1 to 3 independently selected $R^e$ substituents; 1 to 3 independently selected $R^f$ substituents; or 1 to 3 independently selected $R^g$ substituents. In some instance, $Q^1$ is phenyl, 1-naphthyl or 2-naphthyl, F, Cl, Br, I, —CN, —OH, —$CF_3$, $NH_2$, $CF_3O$—, $CH_3$—, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, 1-cyclopropylethyl, 2-cyclopropylethyl, 1-cyclopropylethylamino, 2-cyclopropylethylamino or 1-hydroxy-1-methylethyl or methylcarbamoyl. All the other variables $Q^2$, $R^1$, $R^2$, $R^3$ and $R^4$ are as defined in formula (I) and any embodiments as described herein.

In some embodiments of compounds of formula (Ib-1a), $Q^1$ is 1H-4-benzotriazolyl, 1H-5-benzotriazolyl, 1H-4-benzimidazolyl, 1H-5-benzimidazolyl, 1H-4-indazolyl, 1H-5-indazolyl, 1H-6-indazolyl, 1H-7-indazolyl, 1H-4-indolyl, 1H-5-indolyl, 1H-6-indolyl, 1H-7-indolyl, 2-oxo-6-indolinyl, 2-oxo-4-indolinyl, 2-oxo-5-indolinyl, 2-oxo-7-indolinyl, 1,2-benzoxazol-4-yl, 1,2-benzoxazol-5-yl, 1,2-benzoxazol-6-yl, 1,2-benzoxazol-7-yl, 1,3-benzoxazol-4-yl, 1,3-benzoxazol-5-yl, 1,3-benzoxazol-6-yl, 1,3-benzoxazol-7-yl, 1,2-benzothiazol-4-yl, 1,2-benzothiazol-5-yl, 1,2-benzothiazol-6-yl, 1,2-benzothiazol-7-yl, 5-quinolinyl, 6-quinolinyl, 7-quinolinyl, 8-quinolinyl, 5-isoquinolinyl, 6-isoquinolinyl, 7-isoquinolinyl, 8-isoquinolinyl, 5-cinnolinyl, 6-cinnolinyl, 7-cinnolinyl, 8-cinnolinyl, 5-quinazolinyl, 6-quinazolinyl, 7-quinazolinyl, 8-quinazolinyl, 5-quinoxalinyl, 6-quinoxalinyl, 7-quinoxalinyl, 8-quinoxalinyl, 4-indanyl, 5-indanyl, 5-tetralinyl, 6-tetralinyl, 1,3-dihydroisobenzofuran-4-yl, 1,3-dihydroisobenzofuran-5-yl, 2,3-dihydrobenzofuran-4-yl, 2,3-dihydrobenzofuran-5-yl, 2,3-dihydrobenzofuran-6-yl, 2,3-dihydrobenzofuran-7-yl, 1,3-dihydroisobenzothiophen-4-yl, 1,3-dihydroisobenzothiophen-5-yl, 2,3-dihydrobenzothiophen-4-yl, 2,3-dihydrobenzothiophen-5-yl, 2,3-dihydrobenzothiophen-6-yl, 2,3-dihydrobenzothiophen-7-yl, 4-indolinyl, 5-indolinyl, 6-indolinyl, 7-indolinyl, 5-isochromanyl, 6-isochromanyl, 7-isochromanyl, 8-isochromanyl, 5-chromanyl, 6-chromanyl, 7-chromanyl, 8-chromanyl, 2,3-dihydro-1,3-benzothiazo-4-yl, 2,3-dihydro-1,3-benzothiazo-5-yl, 2,3-dihydro-1,3-benzothiazo-6-yl, 2,3-dihydro-1,3-benzothiazo-7-yl, 2,3-dihydro-1,2-benzothiazo-4-yl, 2,3-dihydro-1,2-benzothiazo-5-yl, 2,3-dihydro-1,2-benzothiazo-6-yl, 2,3-dihydro-1,2-benzothiazo-7-yl, 2,3-dihydro-1,3-benzoxazol-4-yl, 2,3-dihydro-1,3-benzoxazol-5-yl, 2,3-dihydro-1,3-benzoxazol-6-yl, 2,3-dihydro-1,3-benzoxazol-7-yl, 2,3-dihydro-1,2-benzoxazol-4-yl, 2,3-dihydro-1,2-benzoxazol-5-yl, 2,3-dihydro-1,2-benzoxazol-6-yl, 2,3-dihydro-1,2-benzoxazol-7-yl, 4-benzofuranyl, 5-benzofuranyl, 6-benzofuranyl, 7-benzofuranyl, 4-benzothiophenyl, 5-benzothiophenyl, 6-benzothiophenyl or 7-benzothiophenyl, each of which is optionally substituted with from 1 to 3 independently selected $R^7$ substituents; or 1 to 3 independently selected $R^a$ substituents; or 1 to 3 independently selected $R^b$ substituents; or 1 to 3 independently selected $R^c$ substituents; or 1 to 3 independently selected $R^d$ substituents; or 1 to 3 independently selected $R^e$ substituents; 1 to 3 independently selected $R^f$ substituents; or 1 to 3 independently selected $R^g$ substituents. All the other variables $Q^2$, $R^1$, $R^2$, $R^3$ and $R^4$ are as defined in formula (I) and any embodiments as described herein.

In some embodiments of compounds of formula (Ib-1a), $Q^1$ is 5-pyrimidinyl, 2-pyrimidinyl, 4-pyrimidinyl, 2-pyridyl, 3-pyridyl, 4-pyridyl, 2-pyrazinyl, 2-pyridazinyl, 3-pyridazinyl, 1-pyrrolyl, 2-pyrrolyl, 3-pyrrolyl, 2-imidazolyl, 4-imidazolyl, 1-pyrazolyl, 2-pyrazolyl, 3-pyrazolyl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1,2,3-triazol-1-yl, 1,2,3-triazol-2-yl, 1,2,3-triazol-3-yl, 1,2,3-triazol-4-yl, 1,2,3-triazol-5-yl, 1,2,4-triazol-1-yl, 1,2,4-triazol-2-yl, 1,2,4-triazol-3-yl, 1,2,4-triazol-4-yl, 1,2,4-triazol-5-yl, 1-oxa-2,3-diazol-4-yl, 1-oxa-2,3-diazol-5-yl, 1-oxa-2,4-diazol-3-yl, 1-oxa-2,4-diazol-5-yl, 1-oxa-2,5-diazol-3-yl, 1-oxa-2,5-diazol-4-yl, 1-thia-2,3-diazol-4-yl, 1-thia-2,3-diazol-5-yl, 1-thia-2,4-diazol-3-yl, 1-thia-2,4-diazol-5-yl, 1-thia-2,5-diazol-3-yl, 1-thia-2,5-diazol-4-yl, 1-tetrazolyl, 3-tetrazolyl, 1H-5-tetrazolyl, 3H-5-tetrazolyl, 2-furanyl, 3-furanyl, 2-thiopenyl or 3-thiophenyl, each of which is optionally substituted with from 1 to 3 independently selected $R^7$ substituents; or 1 to 3 independently selected $R^a$ substituents; or 1 to 3 independently selected $R^b$ substituents; or 1 to 3 independently selected $R^c$ substituents; or 1 to 3 independently selected $R^d$ substituents; or 1 to 3 independently selected $R^e$ substituents; 1 to 3 independently selected $R^f$ substituents; or 1 to 3 independently selected $R^g$ substituents. All the other variables $Q^2$, $R^1$, $R^2$, $R^3$ and $R^4$ are as defined in formula (I) and any embodiments as described herein.

In some embodiments of compounds of formula (Ib-1a), $Q^1$ is 1-benzotriazolyl, 1-benzimidazolyl, 1H-2-benzimidazolyl, 1-indazolyl, 1H-3-indazolyl, 1-indolyl, 1H-2-indolyl, 1H-3-indolyl, 1,2-benzoxazol-3-yl, 1,3-benzoxazol-2-yl, 1,2-benzothiazol-3-yl, 1,3-benzothiazol-2-yl, 2-quinolinyl, 3-quinolinyl, 4-quinolinyl, 1-isoquinolinyl, 3-isoquinolinyl, 4-isoquinolinyl, 3-cinnolinyl, 4-cinnolinyl, 2-quinazolinyl, 4-quinazolinyl, 2-quinoxalinyl, 2-benzofuranyl, 3-benzofuranyl, 2-benzothiophenyl or 3-benzothiophenyl, each of which is optionally substituted with from 1 to 3 independently selected $R^7$ substituents; or 1 to 3 independently selected $R^a$ substituents; or 1 to 3 independently selected $R^b$ substituents; or 1 to 3 independently selected $R^c$ substituents; or 1 to 3 independently selected $R^d$ substituents; or 1 to 3 independently selected $R^e$ substituents; 1 to 3 independently selected $R^f$ substituents; or 1 to 3 independently selected $R^g$ substituents. All the other variables $Q^2$, $R^1$, $R^2$, $R^3$ and $R^4$ are as defined in formula (I) and any embodiments as described herein.

In a sixth group of embodiments, compounds of formulas (I), (Ib) or (Ib-1) have subformula (Ib-1b):

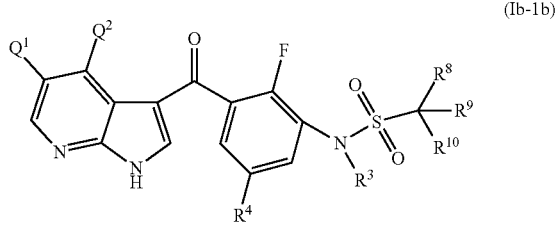

(Ib-1b)

In some embodiments, $R^3$ is H. In other embodiments, $R^4$ is F, Cl, $CH_3$, CN or $CF_3$. In other embodiments, $R^4$ is F or Cl. In one embodiment, $R^4$ is F. In another embodiment, $R^4$ is $CH_3$. In one embodiment, $Q^2$ is H. The variables $Q^1$, $Q^2$, $R^3$, $R^4$, $R^8$, $R^9$ and $R^{10}$ are as defined in any embodiments of formulas (I) or (Ib) or (Ib-1b) as described herein.

In a seventh group of embodiments, compounds of formula (I) have subformula (Ic):

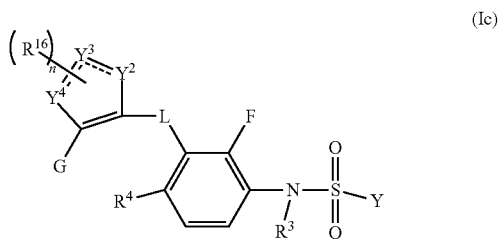

(Ic)

Y is $-N(R^1)(R^2)$ or $-C(R^8)(R^9)(R^{10})$. $R^4$ is H or F. ==== is a single bond or a double bond to maintain that the 5-membered ring containing $Y^2$, $Y^3$ and $Y^4$ being aromatic. $Y^2$, $Y^3$ and $Y^4$ are each independently selected from C, O, N, or S, with the proviso at least one of $Y^2$, $Y^3$ and $Y^4$ is a heteroatom, where N and S are optionally oxidized. $R^{16}$ is H, optionally substituted aryl or optionally substituted $C_{1-6}$alkyl; or $R^7$; or $R^a$; or $R^b$; or $R^c$; or $R^d$; or $R^e$; or $R^f$; or $R^g$. The subscript n is 1, 2 or 3. The variables $R^1$, $R^2$, $R^3$, L and G are as defined in any of the embodiments of formula (I) described herein. In one instance, $R^3$ is H. In one instance, L is a bond. In one instance, $Y^2$ is N. In another instance, G is 6-membered-heteroaryl optionally substituted with a $R^7$ substituent; or a $R^a$ substituent; or a $R^b$ substituent; or a $R^c$ substituent; or a $R^d$ substituent; or a $R^e$ substituent; or a $R^f$ substituent; or a $R^g$ substituent. In another instance, G is 4-pyrimidinyl optionally substituted with a $R^7$ substituent; or a $R^a$ substituent; or a $R^b$ substituent; or a $R^c$ substituent; or a $R^d$ substituent; or a $R^e$ substituent; or a $R^f$ substituent; or a $R^g$ substituent. In another instance, G is 2-amino-4-pyrimidinyl optionally substituted with a $R^7$ substituent; or a $R^a$ substituent; or a $R^b$ substituent; or a $R^c$ substituent; or a $R^d$ substituent; or a $R^e$ substituent; or a $R^f$ substituent; or a $R^g$ substituent. The variables Y, $R^3$, $R^4$, L, $Y^2$, $Y^3$ and $Y^4$ are as defined in any of embodiments of formula (I) as described herein.

In an eighth group of embodiments, compounds of formula (I) or (Ic) have subformula (Ic-1):

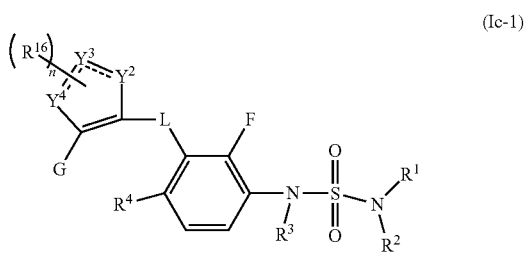

(Ic-1)

In one embodiment, $R^3$ is H. In some instances, both $R^3$ and $R^4$ are H. In one embodiment, $Y^2$ is N. In one embodiment, the subscript n is 1. In another embodiment, the subscript is 2. In another embodiment, the subscript is 3. In some embodiments, $Y^2$ is N, $Y^3$ is C and $Y^4$ is S. In other embodiments, $Y^2$ is N, $Y^3$ is C and $Y^4$ is O. In other embodiments, $Y^2$ is S, $Y^3$ is C and $Y^4$ is N. In other embodiments, $Y^2$ is O, $Y^3$ is C and $Y^4$ is N. In other embodiments, $Y^2$ is N, $Y^3$ is C and $Y^4$ is N. In certain embodiments, —N($R^1$)($R^2$) is 1-azetidinyl, 1-pyrrolidinyl or 1-piperidinyl, each of which is optionally substituted. In certain instances, —N($R^1$)($R^2$) is 1-azetidinyl, 1-pyrrolidinyl or 1-piperidinyl, each of which is optionally substituted with from 1-2 independently selected $R^7$ substituents; or 1 to 2 independently selected $R^a$ substituents; or 1 to 2 independently selected $R^b$ substituents; or 1 to 2 independently selected $R^c$ substituents; or 1 to 2 independently selected $R^d$ substituents; or 1 to 2 independently selected $R^e$ substituents; or 1 to 2 independently selected $R^f$ substituents; or 1 to 2 independently selected $R^g$ substituents; or 1-2 halogen. In other instances, $R^1$ is $CH_3$ and $R^2$ is $C_{1-6}$alkyl. In other instances, $R^1$ is $CH_3$ and $R^2$ is ethyl. In other instances, $R^1$ and $R^2$ are $CH_3$. In other instances, $R^1$ and $R^2$ are ethyl. The variables $R^1$, $R^2$, $R^3$, $R^4$, $R^{16}$, L, n, G, $Y^2$, $Y^3$ and $Y^4$ are as defined in any of embodiments of formula (I) or (Ic) as described herein.

In a ninth group of embodiments, compounds of formulas (I), (Ic) or (Ic-1) have subformula (Ic-1a):

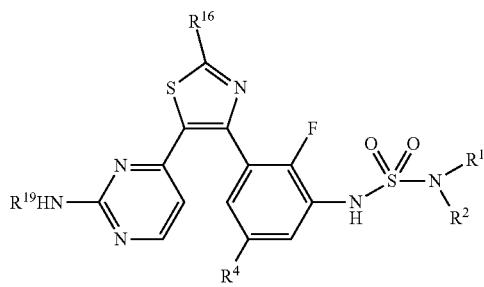

(Ic-1a)

$R^{19}$ is H; or $R^7$; or $R^a$; or $R^b$; or $R^c$; or $R^d$; or $R^e$; $R^f$; or $R^g$ substituent. In one embodiment, $R^{19}$ is H. In another embodiment, $R^{19}$ is 2-(methoxycarbonylamino)propyl. In yet another embodiment, $R^{19}$ is (R)-2-(methoxycarbonylamino)propyl. In still another embodiment, $R^{19}$ is (S)-2-(methoxycarbonylamino)propyl. The variables $R^1$, $R^2$, $R^4$ and $R^{16}$ are as defined in any of the embodiments of formula (I) or its subformulas as described herein. In one embodiment, $R^{16}$ is H, phenyl or $C_{1-6}$alkyl, wherein the phenyl or alkyl is optionally substituted with from 1 to 3 independently selected $R^7$ substituents; or 1 to 3 independently selected $R^a$ substituents; or 1 to 3 independently selected $R^b$ substituents; or 1 to 3 independently selected $R^c$ substituents; or 1 to 3 independently selected $R^d$ substituents; or 1 to 3 independently selected $R^e$ substituents; 1 to 3 independently selected $R^f$ substituents; or 1 to 3 independently selected $R^g$ substituents. In one embodiment, $R^4$ is H. In another embodiment, $R^4$ is F or Cl. In yet another embodiment, $R^4$ is F, Cl, $CH_3$, CN or $CF_3$. In certain embodiments, $R^1$ and $R^2$ taken together with the nitrogen atom to which they attach form 1-azetidinyl, 1-pyrrolidinyl or 1-piperidinyl, each of which is optionally substituted with from 1-2 independently selected $R^7$ substituents; or 1 to 2 independently selected $R^a$ substituents; or 1 to 2 independently selected $R^b$ substituents; or 1 to 2 independently selected $R^c$ substituents; or 1 to 2 independently selected $R^d$ substituents; or 1 to 2 independently selected $R^e$ substituents; or 1 to 2 independently selected $R^f$ substituents; or 1 to 2 independently selected $R^g$ substituents; or 1-2 halogen. In other instances, $R^1$ is $CH_3$ and $R^2$ is $C_{1-6}$alkyl. In other instances, $R^1$ is $CH_3$ and $R^2$ is ethyl. In other instances, $R^1$ and $R^2$ are $CH_3$. In other instances, $R^1$ and $R^2$ are ethyl.

In a tenth group of embodiments, compounds of formula (I) or (Ic) have subformula (Ic-2):

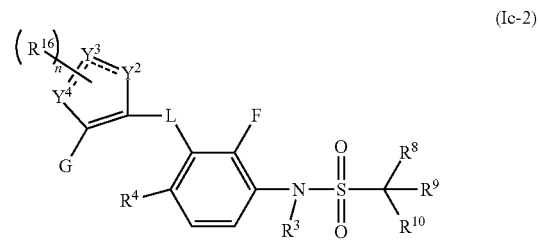

(Ic-2)

In one embodiment, $R^3$ is H. In certain embodiments, —C($R^8$)($R^9$)($R^{10}$) is cyclopropyl, cyclobutyl, cyclopentyl or cyclohexyl, each of which is optionally substituted. In certain instances, —C($R^8$)($R^9$)($R^{10}$) is cyclopropyl, cyclobutyl, cyclopentyl or cyclohexyl, each of which is optionally substituted with from 1-2 independently selected $R^7$ substituents; or 1 to 2 independently selected $R^a$ substituents; or 1 to 2 independently selected $R^b$ substituents; or 1 to 2 independently selected $R^c$ substituents; or 1 to 2 independently selected $R^d$ substituents; or 1 to 2 independently selected $R^e$ substituents; or 1 to 2 independently selected $R^f$ substituents; or 1 to 2 independently selected $R^g$ substituents. The variables $R^8$, $R^9$, $R^{10}$, $R^3$, $R^4$, $R^{16}$, L, n, G, $Y^2$, $Y^3$ and $Y^4$ are as defined in any of embodiments of formula (I) or any of the subgeneric formulas of formula (I) as described herein.

In an eleventh group of embodiments, compounds of formulas (I), (Ic) or (Ic-2) have subformula (Ic-2a):

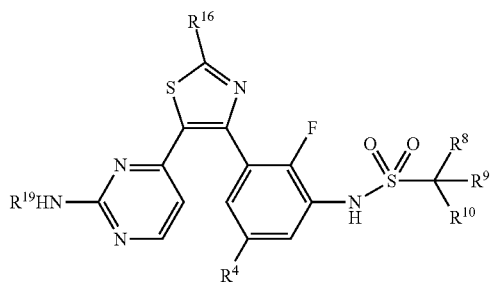

(Ic-2a)

$R^{19}$ is H; or $R^7$; or $R^a$; or $R^b$; or $R^c$; or $R^d$; or $R^e$; $R^f$; or $R^g$ substituent. In one embodiment, $R^{19}$ is H. In another embodiment, $R^{19}$ is 2-(methoxycarbonylamino)propyl. $R^{16}$ is H, phenyl or $C_{1-6}$alkyl, wherein the phenyl or alkyl is optionally substituted with from 1 to 3 independently selected $R^7$ substituents; or 1 to 3 independently selected $R^a$ substituents; or 1 to 3 independently selected $R^b$ substituents; or 1 to 3 independently selected $R^c$ substituents; or 1 to 3 independently selected $R^d$ substituents; or 1 to 3 independently selected $R^e$ substituents; 1 to 3 independently selected $R^f$ substituents; or 1 to 3 independently selected $R^g$ substituents. The variables $R^8$, $R^9$, $R^{10}$, $R^{16}$, and $R^4$ are as defined in any of the embodiments of formula (I) or its subformulas as described herein. In one embodiment, $R^4$ is H. In another embodiment, $R^4$ is F or Cl. In yet another embodiment, $R^4$ is F, Cl, $CH_3$, CN or $CF_3$. In certain embodiments, $R^{10}$ is H and $R^8$ and $R^9$ taken together with the carbon atom to which they attach form cyclopropyl, cyclobutyl, cyclopentyl or cyclohexyl, each of which is optionally substituted with from 1-2 independently selected $R^7$ substituents; or 1 to 2 independently selected $R^a$ substituents; or 1 to 2 independently selected $R^b$ substituents; or 1 to 2 independently selected $R^c$ substituents; or 1 to 2 independently selected $R^d$ substituents; or 1 to 2 independently selected $R^e$ substituents; or 1 to 2 independently selected $R^f$ substituents; or 1 to 2 independently selected $R^g$ substituents.

In a twelfth group of embodiments, compounds of formula (I) have subformula (Id):

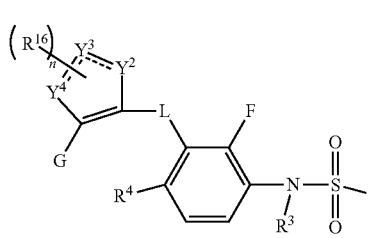
(Id)

$R^4$ is H, Cl or F. The subscript n is 1 or 2. The variables Y, $R^3$, $R^4$, $Y^2$, $Y^3$, $Y^4$, $R^{16}$, L, n and G are as defined in any of the embodiments of formulas (I), (Ic) or (Ic-1) as described herein. In one embodiment, L is a bond. In some instances, $Y^2$ is N, $Y^3$ is N and $Y^4$ is C. In other instances, $Y^2$ is C, $Y^3$ is N and $Y^4$ is N. In other instances, $Y^2$ is N, $Y^3$ is O and $Y^4$ is C. In other instances, $Y^2$ is C, $Y^3$ is O and $Y^4$ is N. In other instances, $Y^2$ is N, $Y^3$ is S and $Y^4$ is C. In other instances, $Y^2$ is C, $Y^3$ is S and $Y^4$ is N. In other instances, $Y^2$ is N, $Y^3$ is N and $Y^4$ is N.

In a thirteenth group of embodiments, compounds of formulas (I) or (Id) have subformula (Id-1):

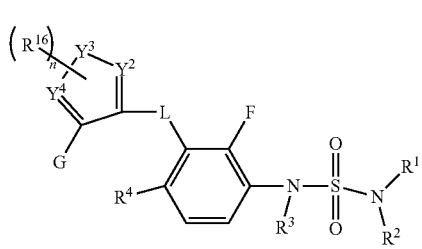
(Id-1)

The subscript n is 1, 2 or 3. The variables $R^1$, $R^2$, $R^3$, $R^4$, $Y^2$, $Y^3$, $Y^4$, $R^{16}$, n and G are as defined in any of the embodiments of formulas (I), (Ic), (Ic-1) or (Id) as described herein.

In a fourteenth group of embodiments, compounds of formulas (I), (Id) or (Id-1) have sub formula (Id-1a):

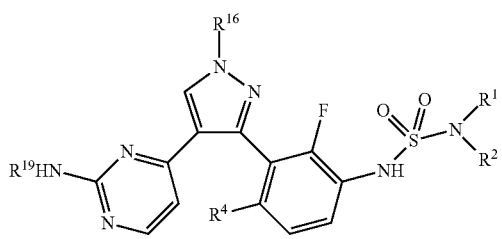
(Id-1a)

The variables $R^1$, $R^2$, $R^4$, $R^{16}$ and $R^{19}$ are as defined in any of the embodiments of formulas (I) or its subgeneric formulas as described herein. In one embodiment, $R^4$ is H or F. In another embodiment, $R^4$ is H, F, Cl, $CH_3$, CN or $CF_3$. In another embodiment, $R^{16}$ is H, phenyl or $C_{1-6}$alkyl, wherein the phenyl or alkyl is optionally substituted with from 1 to 3 independently selected $R^7$ substituents; or 1 to 3 independently selected $R^a$ substituents; or 1 to 3 independently selected $R^b$ substituents; or 1 to 3 independently selected $R^c$ substituents; or 1 to 3 independently selected $R^d$ substituents; or 1 to 3 independently selected $R^e$ substituents; 1 to 3 independently selected $R^f$ substituents; or 1 to 3 independently selected $R^g$ substituents. In one embodiment, $R^{19}$ is H; or $R^7$; or $R^a$; or $R^b$; or $R^c$; or $R^d$; or $R^e$; $R^f$; or $R^g$ substituent; or 2-(methoxycarbonylamino)propyl. In another embodiment, $R^{19}$ is (R)-2-(methoxycarbonylamino)propyl. In yet another embodiment, $R^{19}$ is (S)-2-(methoxycarbonylamino)propyl. In some embodiments, $R^1$ and $R^2$ taken together with the nitrogen atom to which they attach form 1-azetidinyl, 1-pyrrolidinyl or 1-piperidinyl, each of which is optionally substituted with from 1-2 independently selected $R^7$ substituents; or 1 to 2 independently selected $R^a$ substituents; or 1 to 2 independently selected $R^b$ substituents; or 1 to 2 independently selected $R^c$ substituents; or 1 to 2 independently selected $R^d$ substituents; or 1 to 2 independently selected $R^e$ substituents; or 1 to 2 independently selected $R^f$ substituents; or 1 to 2 independently selected $R^g$ substituents; or 1-2 halogen. In other instances, $R^1$ is $CH_3$ and $R^2$ is $C_{1-6}$alkyl. In other instances, $R^1$ is $CH_3$ and $R^2$ is ethyl. In other instances, $R^1$ and $R^2$ are $CH_3$. In other instances, $R^1$ and $R^2$ are ethyl.

In a fifteenth group of embodiments, compounds of formulas (I) or (Id) have subformula (Id-2):

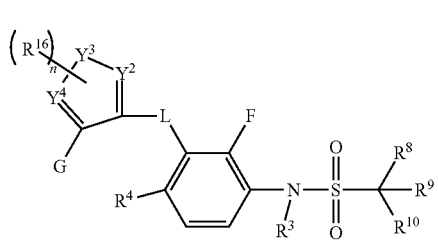
(Id-2)

The variables $R^8$, $R^9$, $R^{10}$, $R^3$, $R^4$, L, $Y^2$, $Y^3$, $Y^4$, $R^{16}$, n and G are as defined in any of the embodiments of formulas (I) or its subgeneric formulas, for example, formulas (Ic), (Ic-1), (Id) or (Id-1) as described herein.

In a sixteenth group of embodiments, compounds of formulas (I), (Id) or (Id-2) have subformula (Id-2a):

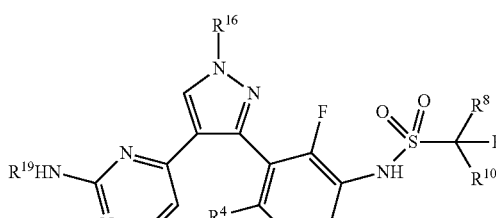
(Id-2a)

The variables $R^8$, $R^9$, $R^{10}$, $R^4$, $R^{16}$ and $R^{19}$ are as defined in any of the embodiments of formulas (I) or its subgeneric formulas, for example, formulas (Ic), (Ic-1), (Id), (Id-1) or (Id-2) as described herein.

In a seventeenth group of embodiments, compounds of formula (I) have subformula (Ie):

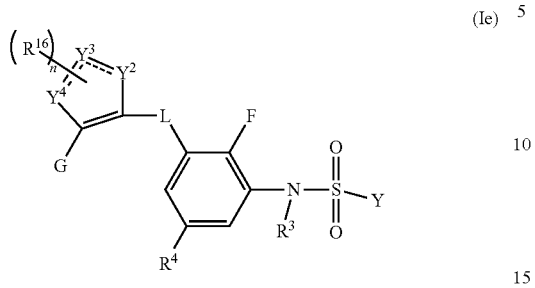

(Ie)

The variables Y, $R^3$, $R^4$, L, $Y^2$, $Y^3$, $Y^4$, $R^{16}$, n and G are as defined in any of embodiments of formula (I) or any of the subgeneric formulas of formula (I) as described herein. In some embodiments, Y is —N($R^1$)($R^2$) or —C($R^8$)($R^9$)($R^{10}$), where $R^1$, $R^2$, $R^8$, $R^9$ and $R^{10}$ are as defined any of the embodiments of formula (I) described herein. In other embodiments, $R^4$ is F, Cl, CN, $CH_3$ or $CF_3$. In one instance, $R^4$ is F or Cl. In one embodiment, L is a bond. ==== is a single bond or a double bond. $Y^2$, $Y^3$ and $Y^4$ are each independently selected from C, O, N, or S, with the proviso at least one of $Y^2$, $Y^3$ and $Y^4$ is a heteroatom, where N and S are optionally oxidized. $R^{16}$ is H, optionally substituted aryl or optionally substituted $C_{1-6}$alkyl; or $R^7$; or $R^a$; or $R^b$; or $R^c$; or $R^d$; or $R^e$; or $R^f$; or $R^g$. The subscript n is 1, 2 or 3. The variables $R^1$, $R^2$, $R^3$, L and G are as defined in any of the embodiments of formula (I) described herein. In one instance, $R^3$ is H. In one instance, L is a bond. In one instance, $Y^2$ is N. In another instance, G is 6-membered-heteroaryl optionally substituted with a $R^7$ substituent; or a $R^a$ substituent; or a $R^b$ substituent; or a $R^c$ substituent; or a $R^d$ substituent; or a $R^e$ substituent; or a $R^f$ substituent; or a $R^g$ substituent. In another instance, G is 4-pyrimidinyl optionally substituted with a $R^7$ substituent; or a $R^a$ substituent; or a $R^b$ substituent; or a $R^c$ substituent; or a $R^d$ substituent; or a $R^e$ substituent; or a $R^f$ substituent; or a $R^g$ substituent. In another instance, G is 2-amino-4-pyrimidinyl optionally substituted with a $R^7$ substituent; or a $R^a$ substituent; or a $R^b$ substituent; or a $R^c$ substituent; or a $R^d$ substituent; or a $R^e$ substituent; or a $R^f$ substituent; or a $R^g$ substituent.

In an eighteenth group of embodiments, compounds of formula (I) or (Ie) have subformula (Ie-1):

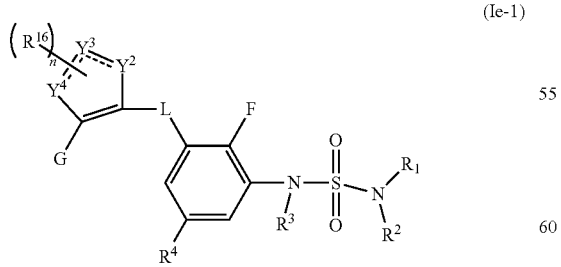

(Ie-1)

The subscript n is 1, 2 or 3. The variables $R^1$, $R^2$, $R^3$, $R^4$, $Y^2$, $Y^3$, $Y^4$, L, $R^{16}$, n and G are as defined in any of the embodiments of formulas (I), (Ic), (Ic-1), (Id), (Id-1), (Id-1a) or (Ie) as described herein.

In a nineteenth group of embodiments, compounds of formula (I), (Ie) or (Ie-1) have subformula (Ie-1a):

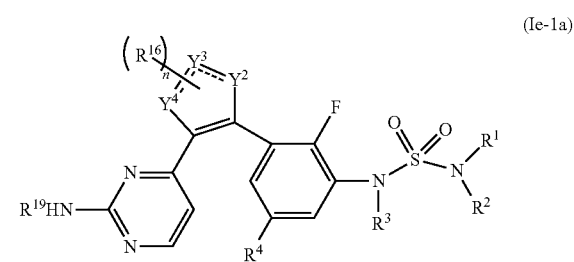

(Ie-1a)

The variables $R^1$, $R^2$, $R^3$, $R^4$, $R^{16}$, $R^{19}$, n, $Y^2$, $Y^3$ and $Y^4$ are as defined in any of the embodiments of formulas (I) or its subgeneric formulas as described herein. In one embodiment, $R^3$ is H. In another embodiment, $R^4$ is F or Cl. In some embodiments, $R^{19}$ is H; or $R^7$; or $R^a$; or $R^b$; or $R^c$; or $R^d$; or $R^e$; $R^f$; or $R^g$ substituent; or 2-(methoxycarbonylamino)propyl. In another embodiment, $R^{19}$ is (R)-2-(methoxycarbonylamino)propyl. In yet another embodiment, $R^{19}$ is (S)-2-(methoxycarbonylamino)propyl. In one embodiment, $Y^2$ is N, $Y^3$ and $Y^4$ are C. In another embodiment, $Y^2$ is O, $Y^3$ and $Y^4$ are C. In another embodiment, $Y^4$ is N, $Y^3$ and $Y^2$ are C. In another embodiment, $Y^4$ is O, $Y^3$ and $Y^2$ are C. In another embodiment, $Y^4$ is O, $Y^3$ is C and $Y^2$ is N. In another embodiment, $Y^3$ is N, $Y^2$ is N and $Y^4$ are C. In another embodiment, $Y^3$ is N, $Y^2$ is O and $Y^4$ are C. In another embodiment, $Y^3$ is N, $Y^2$ is N and $Y^4$ is N. In another embodiment, $Y^3$ is N, $Y^2$ is O and $Y^4$ is N. In another embodiment, $Y^3$ is C, $Y^2$ is C and $Y^4$ is N. In another embodiment, $Y^3$ is C, $Y^2$ is N and $Y^4$ is N. In another embodiment, $Y^3$ is N, $Y^2$ is C and $Y^4$ is N. In another embodiment, $Y^4$ is S, $Y^3$ is C and $Y^2$ is N.

In a twentieth group of embodiments, compounds of formula (I) or (Ie) have subformula (Ie-2):

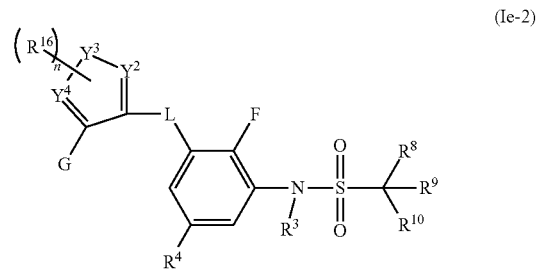

(Ie-2)

The variables $R^8$, $R^9$, $R^{10}$, $R^3$, $R^4$, L, $Y^2$, $Y^3$, $Y^4$, $R^{16}$, n and G are as defined in any of the embodiments of formulas (I) or its subgeneric formulas, for example, formulas (Ic), (Ic-1), (Id), (Id-1), (Ie) or (Ie-1) as described herein.

In a twenty-first group of embodiments, compounds of formula (I), (Ie) or (Ie-2) have subformula (Ie-2a):

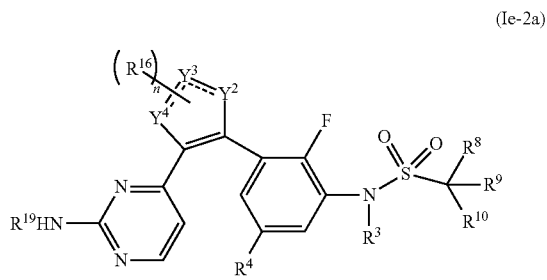

(Ie-2a)

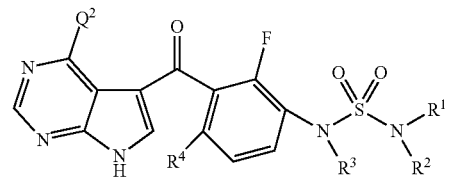

(If-1)

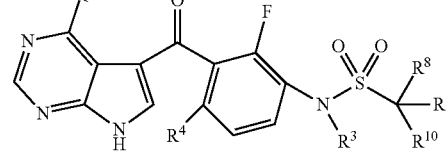

(If-2)

The variables $R^8$, $R^9$, $R^{10}$, $R^3$, $R^4$, L, $Y^2$, $Y^3$, $Y^4$, $R^{16}$, n and G are as defined in any of the embodiments of formulas (I) or its subgeneric formulas as described herein. In one embodiment, $R^4$ is Cl or F. In another embodiment, $R^3$ is H. In some embodiments, $R^{19}$ is H; or $R^7$; or $R^a$; or $R^b$; or $R^c$; or $R^d$; or $R^e$; $R^f$; or $R^g$ substituent; or 2-(methoxycarbonylamino)propyl. In another embodiment, $R^{19}$ is (R)-2-(methoxycarbonylamino)propyl. In yet another embodiment, $R^{19}$ is (S)-2-(methoxycarbonylamino)propyl. In one embodiment, $Y^2$ is N, $Y^3$ and $Y^4$ are C. In another embodiment, $Y^2$ is O, $Y^3$ and $Y^4$ are C. In another embodiment, $Y^4$ is N, $Y^3$ and $Y^2$ are C. In another embodiment, $Y^4$ is O, $Y^3$ and $Y^2$ are C. In another embodiment, $Y^4$ is O, $Y^3$ is C and $Y^2$ is N. In another embodiment, $Y^3$ is N, $Y^2$ is N and $Y^4$ are C. In another embodiment, $Y^3$ is N, $Y^2$ is O and $Y^4$ are C. In another embodiment, $Y^3$ is N, $Y^2$ is N and $Y^4$ is N. In another embodiment, $Y^3$ is N, $Y^2$ is O and $Y^4$ is N. In another embodiment, $Y^3$ is C, $Y^2$ is C and $Y^4$ is N. In another embodiment, $Y^3$ is C, $Y^2$ is N and $Y^4$ is N. In another embodiment, $Y^3$ is N, $Y^2$ is C and $Y^4$ is N. In another embodiment, $Y^4$ is S, $Y^3$ is C and $Y^2$ is N. In certain embodiments, $R^{10}$ is H and $R^8$ and $R^9$ taken together with the carbon atom to which they attach form cyclopropyl, cyclobutyl, cyclopentyl or cyclohexyl, each of which is optionally substituted with from 1-2 independently selected $R^7$ substituents; or 1 to 2 independently selected $R^a$ substituents; or 1 to 2 independently selected $R^b$ substituents; or 1 to 2 independently selected $R^c$ substituents; or 1 to 2 independently selected $R^d$ substituents; or 1 to 2 independently selected $R^e$ substituents; or 1 to 2 independently selected $R^f$ substituents; or 1 to 2 independently selected $R^g$ substituents.

In a twenty-second group of embodiments, compounds of formula (I) have subformula (If):

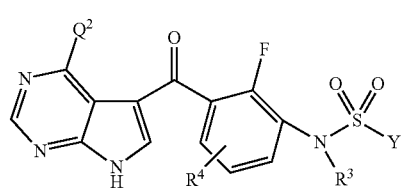

(If)

The variables $Q^2$, $R^3$, $R^4$ and Y are as defined in any of the embodiments of compounds of formula (I) and its subgeneric formulas as described herein. In some instances, $R^3$ is H. In other instances, $R^4$ is H, F or Cl.

In a twenty-third group of embodiments, compounds of formula (I) or (If) have subformula (If-1) or (If-2):

$R^4$ is H, F or Cl. The variables $Q^2$, $R^3$, $R^1$, $R^2$, $R^8$, $R^9$ and $R^{10}$ are as defined in any of the embodiments of compounds of formula (I) and its subgeneric formulas as described herein.

In a twenty-fourth group of embodiments, compounds of formula (I) or (If) have subformula (If-3) or (If-4):

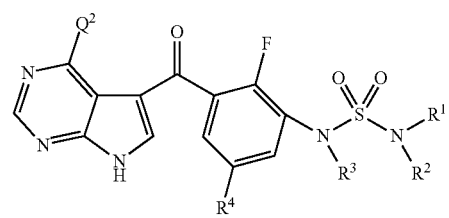

(If-3)

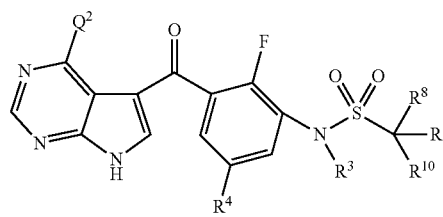

(If-4)

The variables $Q^2$, $R^3$, $R^4$, $R^1$, $R^2$, $R^8$, $R^9$ and $R^{10}$ are as defined in any of the embodiments of compounds of formula (I) and its subgeneric formulas as described herein. In some embodiments, $R^4$ is F or Cl. In other embodiments, $R^3$ is H.

In a twenty-fifth group of embodiments, compounds of formula (I) have subformula (Ig):

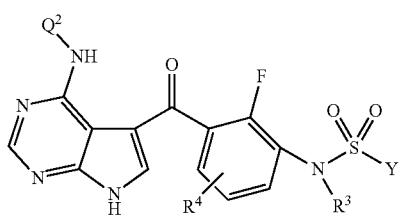

(Ig)

The variables $Q^2$, $R^3$, $R^4$ and Y are as defined in any of the embodiments of compounds of formula (I) and its subgeneric formulas as described herein. In some instances, $R^3$ is H. In other instances, $R^4$ is H, F or Cl. In some instances, when $Q^2$ is optionally substituted cycloalkylalkyl, Y is not —N($R^1$)($R^2$), wherein $R^1$ and $R^2$ are each independently alkyl. In other instances, when $Q^2$ is cycloalkylalkyl, Y is not —N(CH$_3$)(CH$_2$CH$_3$). In some instances, when $Q^2$ is 1-cyclopropylethyl and Y is not —N(CH$_3$)(CH$_2$CH$_3$). In some embodiments, $Q^2$ is $C_{1-6}$ alkyl, $C_{1-6}$ alkoxy, $C_{1-6}$ haloalkyl, $C_{1-6}$ haloalkoxy, aryl, arylalkyl, heteroaryl or heteroarylalkyl, each of which is optionally substituted and Y is an optionally substituted heterocycloalkyl as defined herein. In certain instances, Y is —N($R^1$)($R^2$) or —C($R^8$)($R^9$)($R^{10}$), where $R^1$ and $R^2$ taken together with the nitrogen atom to which they are attached form an optionally substituted 5-membered heterocycloalkyl ring.

In a twenty-sixth group of embodiments, compounds of formula (I) or (Ig) have subformulas (Ig-1) or (Ig-2):

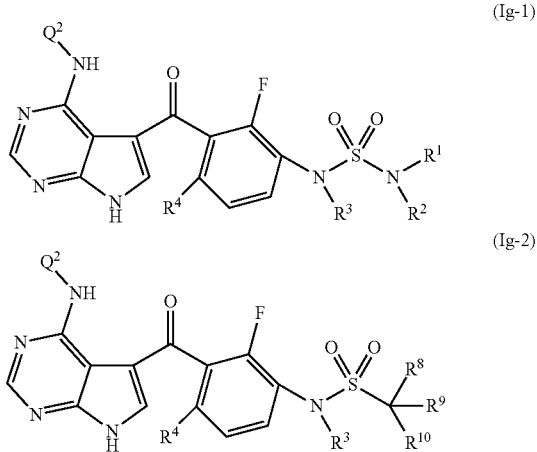

$R^4$ is H, F or Cl. The variables $Q^2$, $R^3$, $R^1$, $R^2$, $R^8$, $R^9$ and $R^{10}$ are as defined in any of the embodiments of compounds of formula (I) and its subgeneric formulas as described herein.

In a twenty-seventh group of embodiments, compounds of formula (I) or (Ig) have subformulas (Ig-3) or (Ig-4):

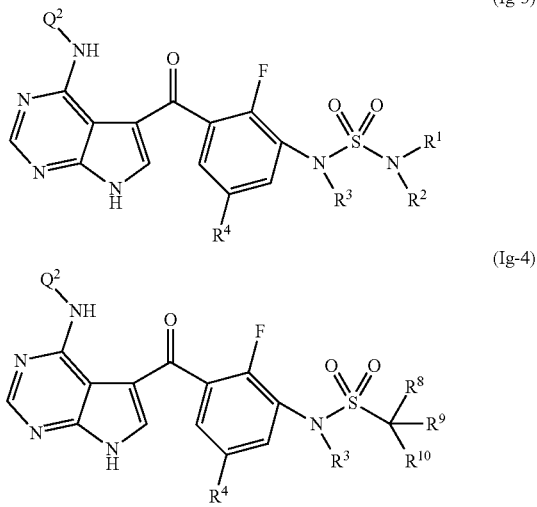

The variables $Q^2$, $R^3$, $R^4$, $R^1$, $R^2$, $R^8$, $R^9$ and $R^{10}$ are as defined in any of the embodiments of compounds of formula (I) and its subgeneric formulas as described herein. In some embodiments, $R^4$ is F or Cl. In other embodiments, $R^3$ is H. In some embodiments, $Q^2$ is $C_{1-6}$alkyl, $C_{3-6}$ cycloalkyl, $C_{3-6}$ cycloalkyl-$C_{1-4}$alkyl, heterocycloalkyl or heterocycloalkyl$C_{1-4}$alkyl, each of which is optionally substituted with from 1-3 independently selected $R^7$; or 1 to 3 independently selected $R^a$ substituents; or 1 to 3 independently selected $R^b$ substituents; or 1 to 3 independently selected $R^c$ substituents; or 1 to 3 independently selected $R^d$ substituents; or 1 to 3 independently selected $R^e$ substituents; or 1 to 3 independently selected $R^f$ substituents; or 1 to 3 independently selected $R^g$ substituents.

In a twenty-eighth group of embodiments, compounds of formula (I) have subformula (Ih):

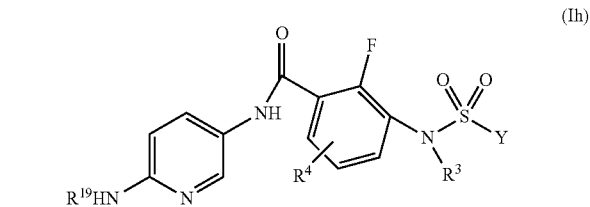

The variables Y, $R^3$, $R^4$ and $R^{19}$ are as defined in any of the embodiments of compounds of formula (I) and its subgeneric formulas as described herein. In one embodiment, le is $C_{1-6}$alkyl-C(O)—. In another embodiment, $R^{19}$ is CH$_3$C(O)—.

In a twenty-ninth group of embodiments, compounds of formula (I) have subformulas (Ih-1) or (Ih-2):

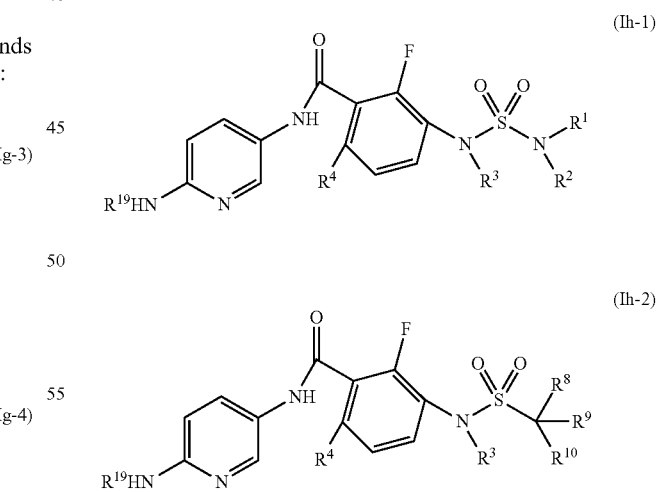

$R^4$ is H, F or Cl. The variables $R^3$, $R^1$, $R^2$, $R^8$, $R^9$, $R^{10}$ and $R^{19}$ are as defined in any of the embodiments of compounds of formula (I) or any of subgeneric formulas of formula (I) as described herein.

In a thirtieth group of embodiments, compounds of formula (I) have subformulas (Ih-3) or (Ih-4):

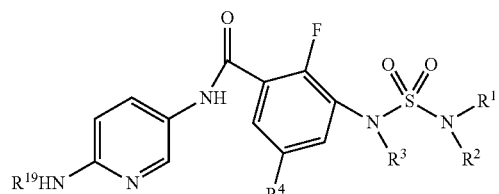

(Ih-3)

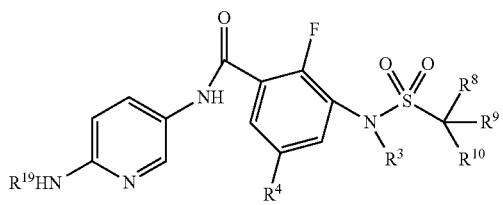

(Ih-4)

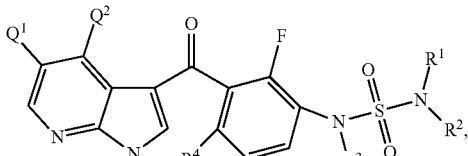

(Ij-1)

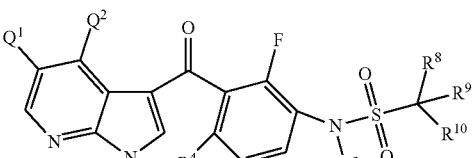

(Ij-2)

$R^4$ is F, Cl, CH$_3$, CN, CF$_3$, CHF$_2$, CH$_2$F or CH$_3$O. In some embodiments, $R^4$ is F or Cl. In other embodiments, $R^4$ is F, Cl or CH$_3$. The variables $R^3$, $R^1$, $R^2$, $R^8$, $R^9$, $R^{10}$ and $R^{19}$ are as defined in any of the embodiments of compounds of formula (I) or any of subgeneric formulas of formula (I) as described herein.

In a thirty-first group of embodiments, compounds of formula (I) have subformulas (Ij), (Ij-1) or (Ij-2):

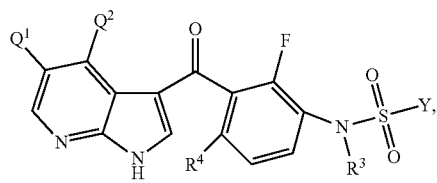

(Ij)

The variables $R^3$, $R^4$, $R^1$, $R^2$, $R^8$, $R^9$, $R^{10}$, $Q^1$, $Q^2$ and Y are as defined in any of the embodiments of compounds of formula (I) or any of subgeneric formulas of formula (I) as described herein. In one embodiment, $Q^1$ is H or halogen. In another embodiment, $Q^1$ is H. In one embodiment, $Q^2$ is halogen, CN, CH$_3$O— or cyclopropylmethylamino. In one embodiment, $R^4$ is H or F. In one embodiment, $R^3$ is H.

Some embodiments disclosed herein can include compound as set forth in Table 1 or a pharmaceutically acceptable salt, hydrates, solvates, isomers, tautomers or deuterated analogs thereof.

TABLE 1

| Compound No. | Name | Structure | (MS (ESI) [M + H$^+$]$^+$) |
|---|---|---|---|
| P-2001 | N-[2,4-difluoro-3-(4-methoxy-1H-pyrrolo[2,3-b]pyridine-3-carbonyl)phenyl]propane-2-sulfonamide | 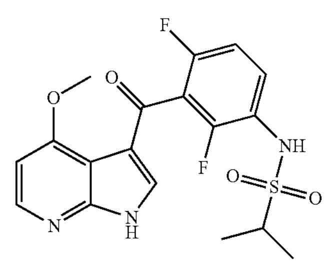 [SMILES: COc1ccnc2[nH]cc(C(=O)c3c(F)ccc(NS(=O)(=O)C(C)C)c3F)c12] | 409.9 |
| P-2002 | 3-[3-(dimethylsulfamoylamino)-2,6-difluoro-benzoyl]-4-methoxy-1H-pyrrolo[2,3-b]pyridine | 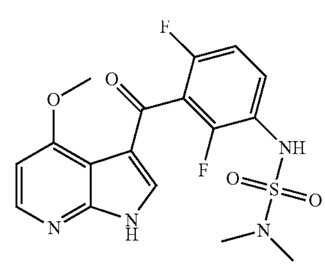 [SMILES: COc1ccnc2[nH]cc(C(=O)c3c(F)ccc(NS(=O)(=O)N(C)C)c3F)c12] | 411.1 |

TABLE 1-continued

| Compound No. | Name | Structure | (MS (ESI) [M + H⁺]⁺) |
|---|---|---|---|
| P-2003 | N-[2,4-difluoro-3-(4-methoxy-1H-pyrrolo[2,3-b]pyridine-3-carbonyl)phenyl]pyrrolidine-1-sulfonamide | 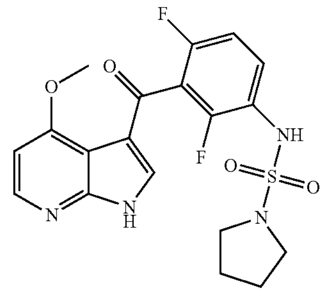 [SMILES: COc1ccnc2[nH]cc(C(=O)c3c(F)ccc(NS(=O)(=O)N4CCCC4)c3F)c12] | 437.1 |
| P-2004 | 3-[3-(diethylsulfamoylamino)-2,6-difluoro-benzoyl]-4-methoxy-1H-pyrrolo[2,3-b]pyridine | 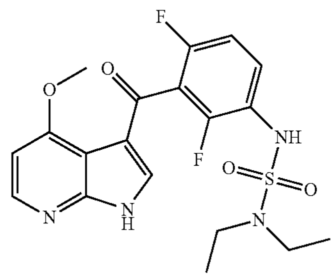 [SMILES: CCN(CC)S(=O)(=O)Nc1ccc(F)c(C(=O)c2c[nH]c3nccc(OC)c23)c1F] | 439.1 |
| P-2005 | N-[2,4-difluoro-3-(4-methoxy-1H-pyrrolo[2,3-b]pyridine-3-carbonyl)phenyl]cyclohexanesulfonamide | 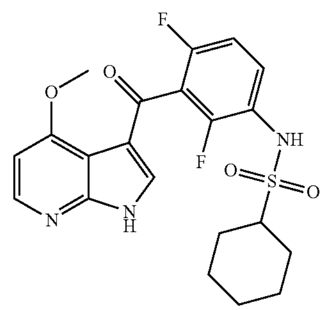 [SMILES: COc1ccnc2[nH]cc(C(=O)c3c(F)ccc(NS(=O)(=O)C4CCCCC4)c3F)c12] | 449.9 |
| P-2006 | N-[2,4-difluoro-3-(4-methoxy-1H-pyrrolo[2,3-b]pyridine-3-carbonyl)phenyl]butane-2-sulfonamide | 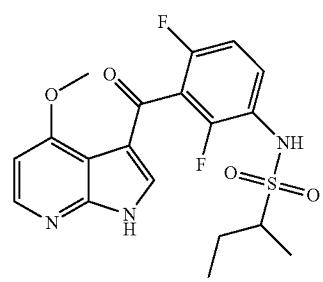 [SMILES: CCC(C)S(=O)(=O)Nc1ccc(F)c(C(=O)c2c[nH]c3nccc(OC)c23)c1F] | 423.9 |
| P-2007 | 4-chloro-3-[3-(dimethylsulfamoylamino)-2,6-difluoro-benzoyl]-1H-pyrrolo[2,3-b]pyridine | 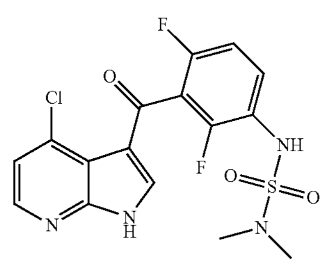 [SMILES: CN(C)S(=O)(=O)Nc1ccc(F)c(C(=O)c2c[nH]c3nccc(Cl)c23)c1F] | 415.1 |

TABLE 1-continued

| Compound No. | Name | Structure | (MS (ESI) [M + H+]+) |
|---|---|---|---|
| P-2008 | N-[3-(4-chloro-1H-pyrrolo[2,3-b]pyridine-3-carbonyl)-2,4-difluorophenyl]cyclobutanesulfonamide | 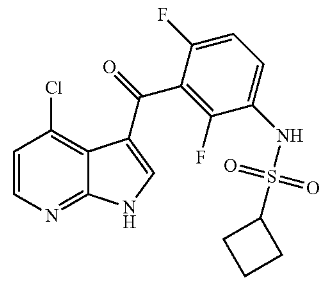 [SMILES: O=C(c1c(F)ccc(NS(=O)(=O)C2CCC2)c1F)c1c[nH]c2nccc(Cl)c12] | 425.9 |
| P-2009 | N-[2,4-difluoro-3-(4-methoxy-1H-pyrrolo[2,3-b]pyridine-3-carbonyl)phenyl]pentane-2-sulfonamide | 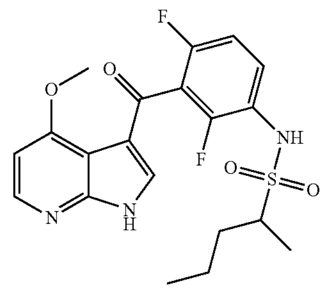 [SMILES: CCCC(C)S(=O)(=O)Nc1ccc(F)c(C(=O)c2c[nH]c3nccc(OC)c23)c1F] | 437.9 |
| P-2010 | N-[2,4-difluoro-3-(4-methoxy-1H-pyrrolo[2,3-b]pyridine-3-carbonyl)phenyl]cyclobutanesulfonamide | 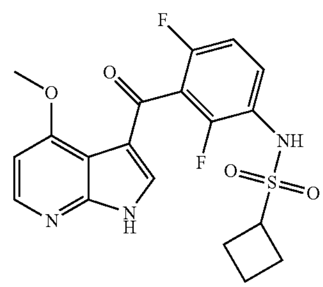 [SMILES: COc1ccnc2[nH]cc(C(=O)c3c(F)ccc(NS(=O)(=O)C4CCC4)c3F)c12] | 421.9 |
| P-2011 | 4-chloro-3-[3-(diethylsulfamoylamino)-2,6-difluoro-benzoyl]-1H-pyrrolo[2,3-b]pyridine | 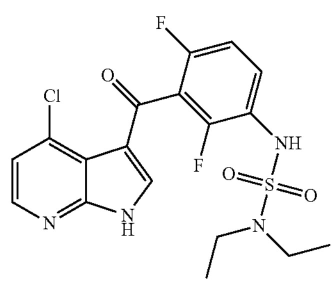 [SMILES: CCN(CC)S(=O)(=O)Nc1ccc(F)c(C(=O)c2c[nH]c3nccc(Cl)c23)c1F] | 443.1 |
| P-2012 | 4-cyano-3-[3-(diethylsulfamoylamino)-2,6-difluoro-benzoyl]-1H-pyrrolo[2,3-b]pyridine | 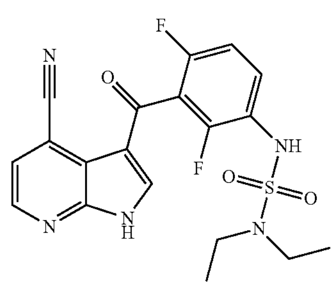 [SMILES: CCN(CC)S(=O)(=O)Nc1ccc(F)c(C(=O)c2c[nH]c3nccc(C#N)c23)c1F] | 433.9 |

TABLE 1-continued

| Compound No. | Name | Structure | (MS (ESI) [M + H+]+) |
|---|---|---|---|
| P-2013 | N-[3-(4-chloro-1H-pyrrolo[2,3-b]pyridine-3-carbonyl)-2,4-difluoro-phenyl]propane-2-sulfonamide | 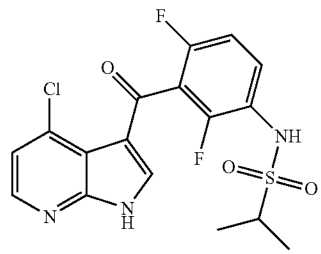 [SMILES: CC(C)S(=O)(=O)Nc1ccc(F)c(C(=O)c2c[nH]c3nccc(Cl)c23)c1F] | 413.9 |
| P-2014 | N-[3-(4-chloro-1H-pyrrolo[2,3-b]pyridine-3-carbonyl)-2,4-difluoro-phenyl]cyclohexanesulfonamide | 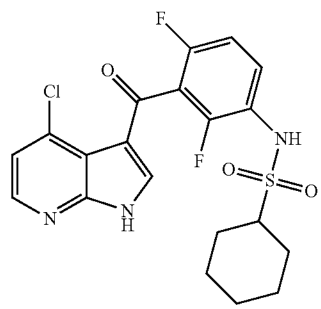 [SMILES: O=C(c1c(F)ccc(NS(=O)(=O)C2CCCCC2)c1F)c1c[nH]c2nccc(Cl)c12] | 453.9 |
| P-2015 | N-[3-(4-chloro-1H-pyrrolo[2,3-b]pyridine-3-carbonyl)-2,4-difluoro-phenyl]cyclopentanesulfonamide | 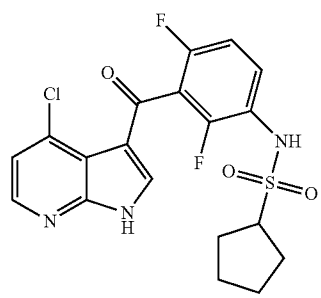 [SMILES: O=C(c1c(F)ccc(NS(=O)(=O)C2CCCC2)c1F)c1c[nH]c2nccc(Cl)c12] | 439.9 |
| P-2016 | N-[3-(4-chloro-1H-pyrrolo[2,3-b]pyridine-3-carbonyl)-2,4-difluoro-phenyl]butane-2-sulfonamide | 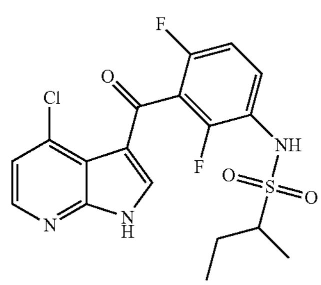 [SMILES: CCC(C)S(=O)(=O)Nc1ccc(F)c(C(=O)c2c[nH]c3nccc(Cl)c23)c1F] | 427.9 |
| P-2017 | N-[3-(4-cyano-1H-pyrrolo[2,3-b]pyridine-3-carbonyl)-2,4-difluoro-phenyl]propane-2-sulfonamide | 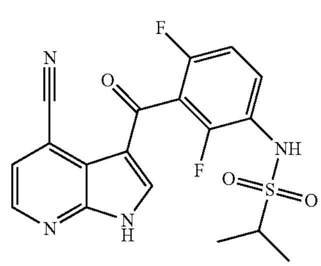 [SMILES: CC(C)S(=O)(=O)Nc1ccc(F)c(C(=O)c2c[nH]c3nccc(C#N)c23)c1F] | 405.1 |

TABLE 1-continued

| Compound No. | Name | Structure | (MS (ESI) [M + H+]+) |
|---|---|---|---|
| P-2018 | N-[3-(4-cyano-1H-pyrrolo[2,3-b]pyridine-3-carbonyl)-2,4-difluoro-phenyl]cyclohexanesulfonamide | 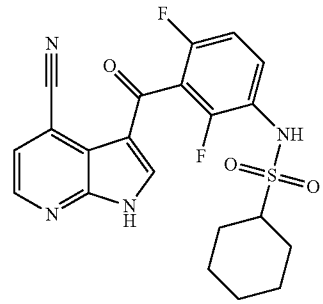 [SMILES: N#Cc1ccnc2[nH]cc(C(=O)c3c(F)ccc(NS(=O)(=O)C4CCCCC4)c3F)c12] | 445.1 |
| P-2019 | N-[3-(4-cyano-1H-pyrrolo[2,3-b]pyridine-3-carbonyl)-2,4-difluoro-phenyl]pyrrolidine-1-sulfonamide | 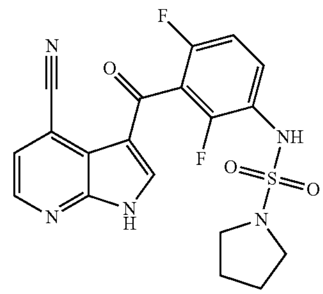 [SMILES: N#Cc1ccnc2[nH]cc(C(=O)c3c(F)ccc(NS(=O)(=O)N4CCCC4)c3F)c12] | 431.9 |
| P-2020 | N-[3-(4-cyano-1H-pyrrolo[2,3-b]pyridine-3-carbonyl)-2,4-difluoro-phenyl]butane-2-sulfonamide | 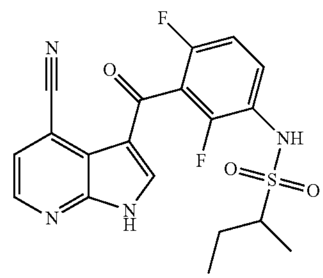 [SMILES: CCC(C)S(=O)(=O)Nc1ccc(F)c(C(=O)c2c[nH]c3nccc(C#N)c23)c1F] | 419.1 |
| P-2021 | N-[3-(4-cyano-1H-pyrrolo[2,3-b]pyridine-3-carbonyl)-2,4-difluoro-phenyl]cyclobutanesulfonamide | 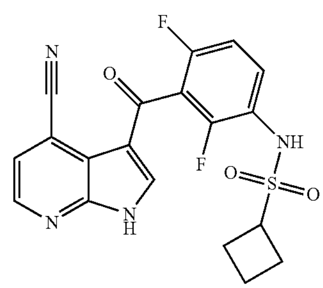 [SMILES: N#Cc1ccnc2[nH]cc(C(=O)c3c(F)ccc(NS(=O)(=O)C4CCC4)c3F)c12] | 417.5 |
| P-2022 | N-[3-(4-cyano-1H-pyrrolo[2,3-b]pyridine-3-carbonyl)-2,4-difluoro-phenyl]morpholine-4-sulfonamide | 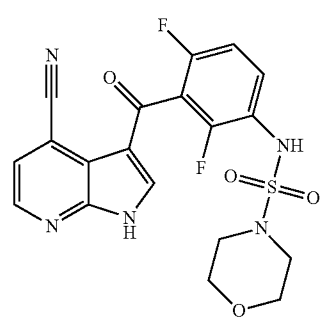 [SMILES: N#Cc1ccnc2[nH]cc(C(=O)c3c(F)ccc(NS(=O)(=O)N4CCOCC4)c3F)c12] | 447.9 |

TABLE 1-continued

| Compound No. | Name | Structure | (MS (ESI) [M + H+]+) |
|---|---|---|---|
| P-2023 | N-[2,4-difluoro-3-(4-methoxy-1H-pyrrolo[2,3-b]pyridine-3-carbonyl)phenyl]morpholine-4-sulfonamide | 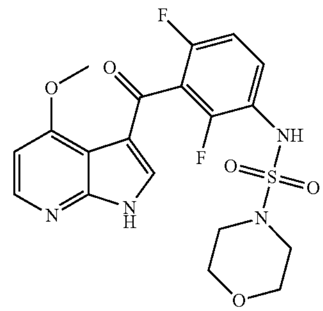 [SMILES: COc1ccnc2[nH]cc(C(=O)c3c(F)ccc(NS(=O)(=O)N4CCOCC4)c3F)c12] | 453.1 |
| P-2024 | N-[3-(4-chloro-1H-pyrrolo[2,3-b]pyridine-3-carbonyl)-2,4-difluoro-phenyl]morpholine-4-sulfonamide | 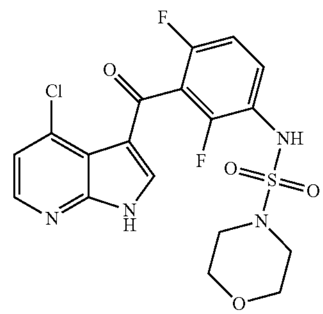 [SMILES: O=C(c1c(F)ccc(NS(=O)(=O)N2CCOCC2)c1F)c1c[nH]c2nccc(Cl)c12] | 457.1 |
| P-2025 | N-[3-(4-chloro-1H-pyrrolo[2,3-b]pyridine-3-carbonyl)-2,4-difluoro-phenyl]pyrrolidine-1-sulfonamide | 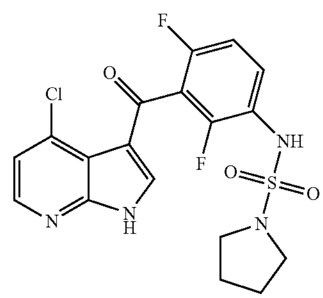 [SMILES: O=C(c1c(F)ccc(NS(=O)(=O)N2CCCC2)c1F)c1c[nH]c2nccc(Cl)c12] | 441.1 |
| P-2026 | 5-[3-(dimethylsulfamoylamino)-2,6-difluoro-benzoyl]-7H-pyrrolo[2,3-d]pyrimidine | 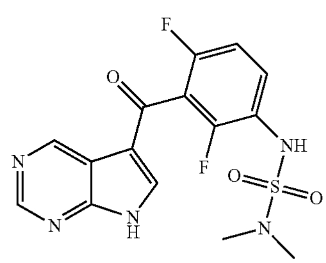 [SMILES: CN(C)S(=O)(=O)Nc1ccc(F)c(C(=O)c2c[nH]c3ncncc23)c1F] | 381.9 |
| P-2027 | N-[2,4-difluoro-3-(7H-pyrrolo[2,3-d]pyrimidine-5-carbonyl)phenyl]cyclohexanesulfonamide | 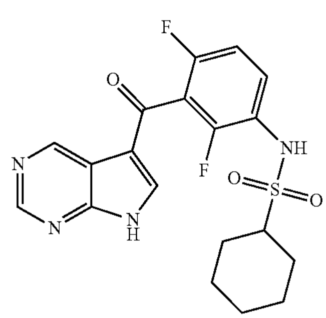 [SMILES: O=C(c1c(F)ccc(NS(=O)(=O)C2CCCCC2)c1F)c1c[nH]c2ncncc12] | 421.1 |

TABLE 1-continued

| Compound No. | Name | Structure | (MS (ESI) [M + H⁺]⁺) |
|---|---|---|---|
| P-2028 | N-[2,4-difluoro-3-(7H-pyrrolo[2,3-d]pyrimidine-5-carbonyl)phenyl]cyclopentanesulfonamide | 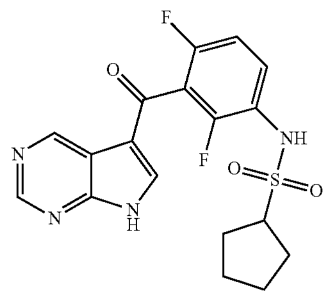 [SMILES: O=C(c1c(F)ccc(NS(=O)(=O)C2CCCC2)c1F)c1c[nH]c2ncncc12] | 407.1 |
| P-2029 | N-[2,4-difluoro-3-(7H-pyrrolo[2,3-d]pyrimidine-5-carbonyl)phenyl]pyrrolidine-1-sulfonamide | 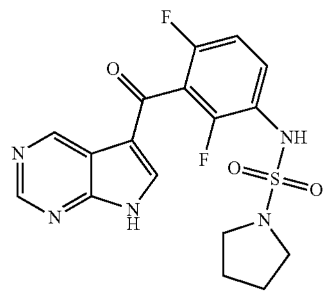 [SMILES: O=C(c1c(F)ccc(NS(=O)(=O)N2CCCC2)c1F)c1c[nH]c2ncncc12] | 408.3 |
| P-2030 | N-[2,4-difluoro-3-(7H-pyrrolo[2,3-d]pyrimidine-5-carbonyl)phenyl]cyclobutanesulfonamide | 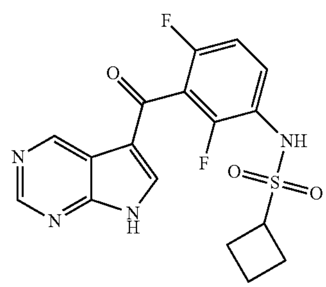 [SMILES: O=C(c1c(F)ccc(NS(=O)(=O)C2CCC2)c1F)c1c[nH]c2ncncc12] | 393.1 |
| P-2031 | N-[2,4-difluoro-3-(7H-pyrrolo[2,3-d]pyrimidine-5-carbonyl)phenyl]morpholine-4-sulfonamide | 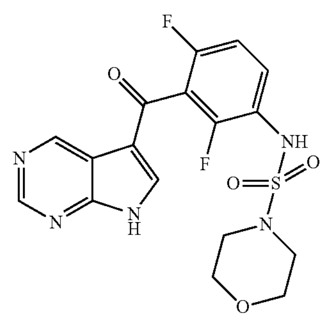 [SMILES: O=C(c1c(F)ccc(NS(=O)(=O)N2CCOCC2)c1F)c1c[nH]c2ncncc12] | 424.3 |
| P-2032 | N-[2-fluoro-3-(7H-pyrrolo[2,3-d]pyrimidine-5-carbonyl)phenyl]pyrrolidine-1-sulfonamide | 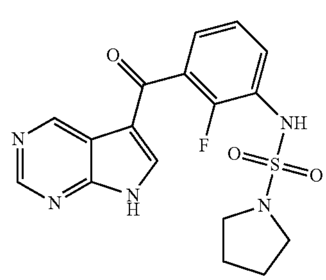 [SMILES: O=C(c1cccc(NS(=O)(=O)N2CCCC2)c1F)c1c[nH]c2ncncc12] | 390.3 |

TABLE 1-continued

| Compound No. | Name | Structure | (MS (ESI) [M + H+]+) |
|---|---|---|---|
| P-2033 | N-(6-acetamido-3-pyridyl)-2,6-difluoro-3-(1-piperidylsulfonylamino)benzamide | 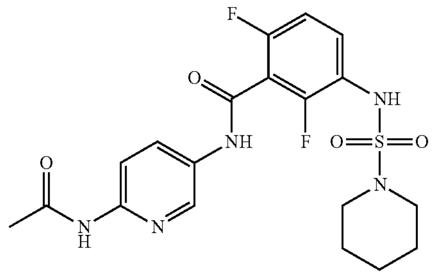 [SMILES: CC(=O)Nc1ccc(NC(=O)c2c(F)ccc(NS(=O)(=O)N3CCCCC3)c2F)cn1] | 454.3 |
| P-2034 | N-(6-acetamido-3-pyridyl)-3-(dimethylsulfamoylamino)-2,6-difluoro-benzamide | 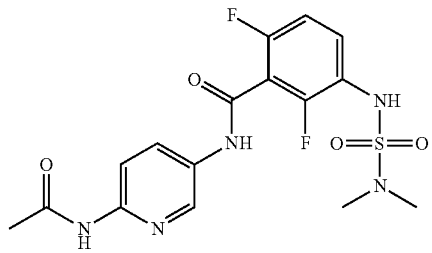 [SMILES: CC(=O)Nc1ccc(NC(=O)c2c(F)ccc(NS(=O)(=O)N(C)C)c2F)cn1] | 414.3 |
| P-2035 | N-(6-acetamido-3-pyridyl)-3-(cyclopentylsulfonylamino)-2,6-difluoro-benzamide | 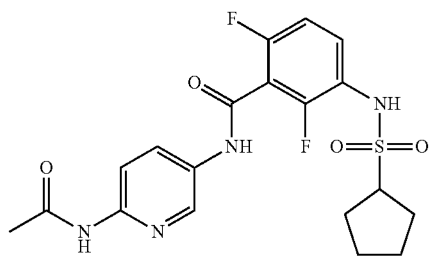 [SMILES: CC(=O)Nc1ccc(NC(=O)c2c(F)ccc(NS(=O)(=O)C3CCCC3)c2F)cn1] | 439.1 |
| P-2036 | N-(6-acetamido-3-pyridyl)-2,6-difluoro-3-(pyrrolidin-1-ylsulfonylamino)benzamide | 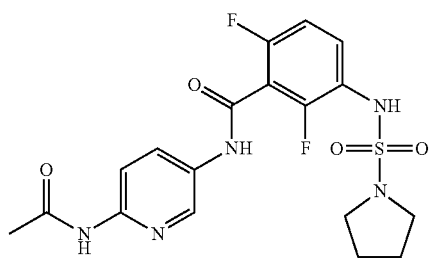 [SMILES: CC(=O)Nc1ccc(NC(=O)c2c(F)ccc(NS(=O)(=O)N3CCCC3)c2F)cn1] | |
| P-2037 | N-[2,4-difluoro-3-[4-(isopropylamino)-7H-pyrrolo[2,3-d]pyrimidine-5-carbonyl]phenyl]propane-2-sulfonamide | 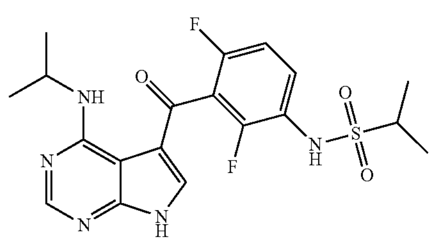 [SMILES: CC(C)Nc1ncnc2[nH]cc(C(=O)c3c(F)ccc(NS(=O)(=O)C(C)C)c3F)c12] | 438.0 |
| P-2038 | N-[2,4-difluoro-3-[4-(isopropylamino)-7H-pyrrolo[2,3-d]pyrimidine-5-carbonyl]phenyl]piperidine-1-sulfonamide | 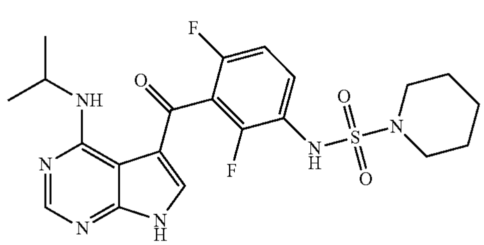 [SMILES: CC(C)Nc1ncnc2[nH]cc(C(=O)c3c(F)ccc(NS(=O)(=O)N4CCCCC4)c3F)c12] | 479.0 |

TABLE 1-continued

| Compound No. | Name | Structure | (MS (ESI) [M + H+]+) |
|---|---|---|---|
| P-2039 | N-[2,4-difluoro-3-[4-(isopropylamino)-7H-pyrrolo[2,3-d]pyrimidine-5-carbonyl]phenyl]cyclohexanesulfonamide | 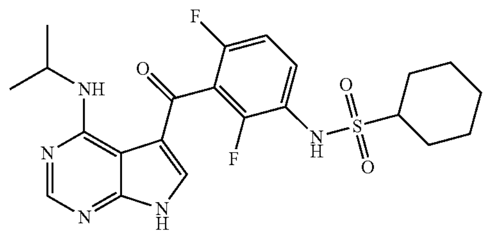 [SMILES: CC(C)Nc1ncnc2[nH]cc(C(=O)c3c(F)ccc(NS(=O)(=O)C4CCCCC4)c3F)c12] | 478.0 |
| P-2040 | N-[2,4-difluoro-3-[4-(isopropylamino)-7H-pyrrolo[2,3-d]pyrimidine-5-carbonyl]phenyl]cyclopentanesulfonamide | 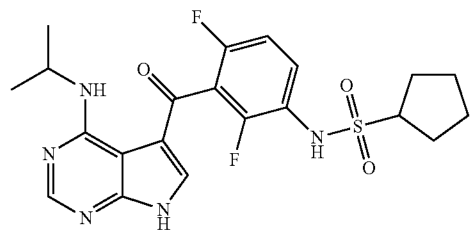 [SMILES: CC(C)Nc1ncnc2[nH]cc(C(=O)c3c(F)ccc(NS(=O)(=O)C4CCCC4)c3F)c12] | 464.0 |
| P-2041 | N-[2,4-difluoro-3-[4-(isopropylamino)-7H-pyrrolo[2,3-d]pyrimidine-5-carbonyl]phenyl]pyrrolidine-1-sulfonamide | 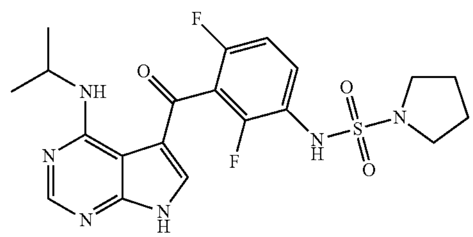 | 465.0 |
| P-2042 | 5-[3-(diethylsulfamoylamino)-2,6-difluoro-benzoyl]-4-(isopropylamino)-7H-pyrrolo[2,3-d]pyrimidine | 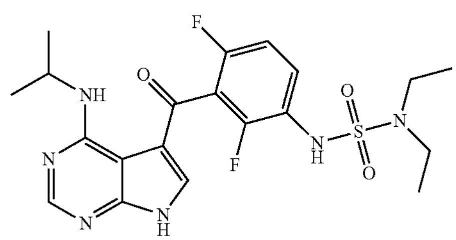 [SMILES: CCN(CC)S(=O)(=O)Nc1ccc(F)c(C(=O)c2c[nH]c3ncnc(NC(C)C)c23)c1F] | 467.5 |
| P-2043 | N-[2,4-difluoro-3-[4-(isopropylamino)-7H-pyrrolo[2,3-d]pyrimidine-5-carbonyl]phenyl]cyclobutanesulfonamide | 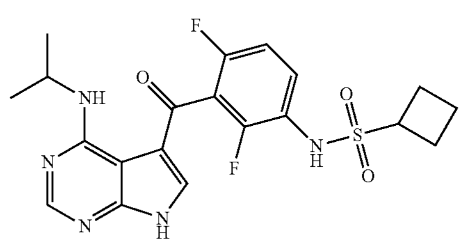 [SMILES: CC(C)Nc1ncnc2[nH]cc(C(=O)c3c(F)ccc(NS(=O)(=O)C4CCC4)c3F)c12] | 450.0 |
| P-2044 | N-[2,4-difluoro-3-[4-(isopropylamino)-7H-pyrrolo[2,3-d]pyrimidine-5-carbonyl]phenyl]morpholine-4-sulfonamide | 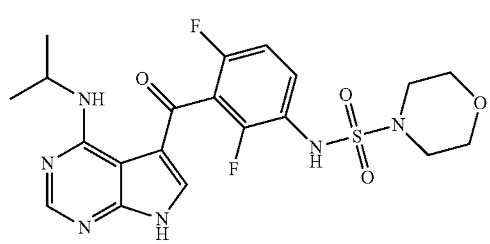 [SMILES: CC(C)Nc1ncnc2[nH]cc(C(=O)c3c(F)ccc(NS(=O)(=O)N4CCOCC4)c3F)c12] | 481.0 |

TABLE 1-continued

| Compound No. | Name | Structure | (MS (ESI) [M + H⁺]⁺) |
|---|---|---|---|
| P-2045 | 5-[3-(dimethylsulfamoylamino)-2,6-difluoro-benzoyl]-4-(isopropylamino)-7H-pyrrolo[2,3-d]pyrimidine | 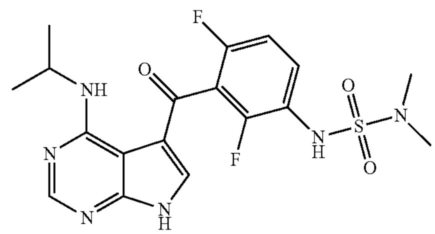 | 439.0 |
| P-2046 | N-[3-[4-(cyclopropylmethylamino)-7H-pyrrolo[2,3-d]pyrimidine-5-carbonyl]-2,4-difluoro-phenyl]cyclopropanesulfonamide | 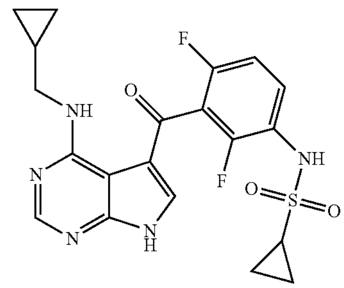 [SMILES: O=C(c1c(F)ccc(NS(=O)(=O)C2CC2)c1F)c1c[nH]c2ncnc(NCC3CC3)c12] | 448.0 |
| P-2047 | N-[3-[4-(cyclopropylmethylamino)-7H-pyrrolo[2,3-d]pyrimidine-5-carbonyl]-2,4-difluoro-phenyl]propane-2-sulfonamide | 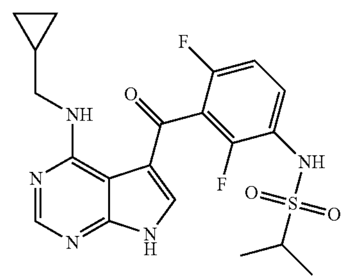 [SMILES: CC(C)S(=O)(=O)Nc1ccc(F)c(C(=O)c2c[nH]c3ncnc(NCC4CC4)c23)c1F] | 450.0 |
| P-2048 | 4-(cyclopropylmethylamino)-5-[3-(dimethylsulfamoylamino)-2,6-difluoro-benzoyl]-7H-pyrrolo[2,3-d]pyrimidine | 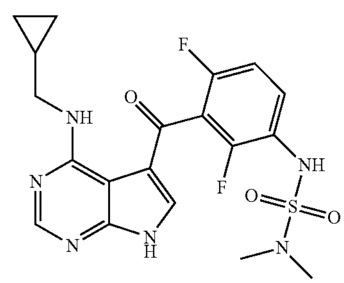 [SMILES: CN(C)S(=O)(=O)Nc1ccc(F)c(C(=O)c2c[nH]c3ncnc(NCC4CC4)c23)c1F] | |
| P-2049 | N-[3-[4-(cyclopropylmethylamino)-7H-pyrrolo[2,3-d]pyrimidine-5-carbonyl]-2,4-difluoro-phenyl]cyclohexanesulfonamide | 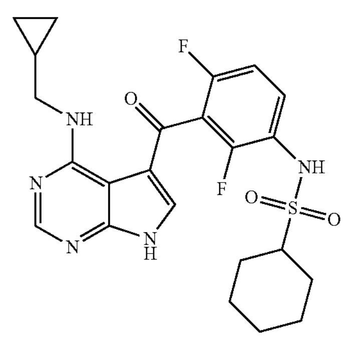 [SMILES: O=C(c1c(F)ccc(NS(=O)(=O)C2CCCCC2)c1F)c1c[nH]c2ncnc(NCC3CC3)c12] | 490.5 |

TABLE 1-continued

| Compound No. | Name | Structure | (MS (ESI) [M + H+]+) |
|---|---|---|---|
| P-2050 | N-[3-[4-(cyclopropylmethylamino)-7H-pyrrolo[2,3-d]pyrimidine-5-carbonyl]-2,4-difluoro-phenyl]cyclopentanesulfonamide | 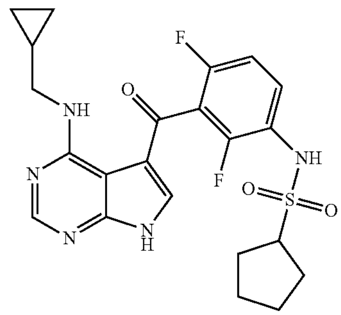 [SMILES: O=C(c1c(F)ccc(NS(=O)(=O)C2CCCC2)c1F)c1c[nH]c2ncnc(NCC3CC3)c12] | 476.5 |
| P-2051 | N-[3-[4-(cyclopropylmethylamino)-7H-pyrrolo[2,3-d]pyrimidine-5-carbonyl]-2,4-difluoro-phenyl]pentane-2-sulfonamide | 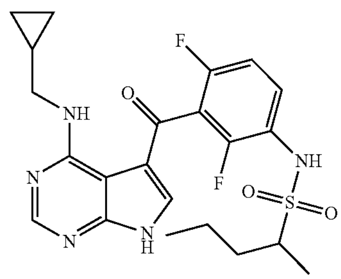 [SMILES: CCCC(C)S(=O)(=O)Nc1ccc(F)c(C(=O)c2c[nH]c3ncnc(NCC4CC4)c23)c1F] | 478.0 |
| P-2052 | 4-(cyclopropylmethylamino)-5-[3-(diethylsulfamoylamino)-2,6-difluoro-benzoyl]-7H-pyrrolo[2,3-d]pyrimidine | 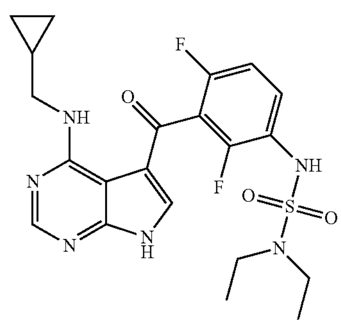 [SMILES: CCN(CC)S(=O)(=O)Nc1ccc(F)c(C(=O)c2c[nH]c3ncnc(NCC4CC4)c23)c1F] | 479.0 |
| P-2053 | N-[3-[4-(cyclopropylmethylamino)-7H-pyrrolo[2,3-d]pyrimidine-5-carbonyl]-2,4-difluoro-phenyl]cyclobutanesulfonamide | 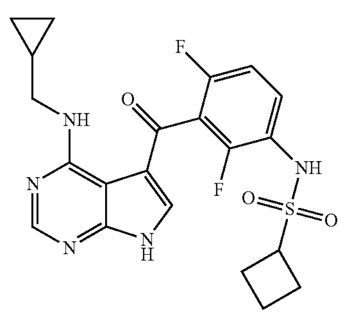 [SMILES: O=C(c1c(F)ccc(NS(=O)(=O)C2CCC2)c1F)c1c[nH]c2ncnc(NCC3CC3)c12] | 462.5 |
| P-2054 | N-[3-[4-(cyclopropylmethylamino)-7H-pyrrolo[2,3-d]pyrimidine-5-carbonyl]-2,4-difluoro-phenyl]morpholine-4-sulfonamide | 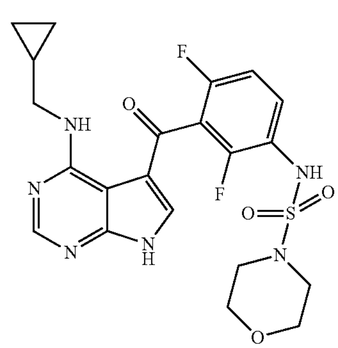 [SMILES: O=C(c1c(F)ccc(NS(=O)(=O)N2CCOCC2)c1F)c1c[nH]c2ncnc(NCC3CC3)c12] | 493.1 |

TABLE 1-continued

| Compound No. | Name | Structure | (MS (ESI) [M + H+]+) |
|---|---|---|---|
| P-2055 | N-[3-[4-(cyclopropylmethylamino)-7H-pyrrolo[2,3-d]pyrimidine-5-carbonyl]-2,4-difluoro-phenyl]pyrrolidine-1-sulfonamide | 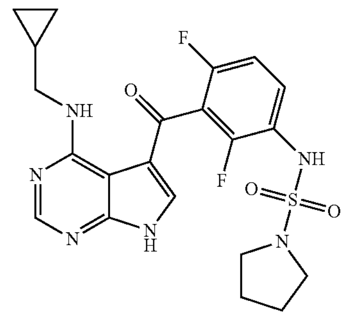 [SMILES: O=C(c1c(F)ccc(NS(=O)(=O)N2CCCC2)c1F)c1c[nH]c2ncnc(NCC3CC3)c12] | 477.1 |
| P-2056 | N-[3-[4-(cyclopropylmethylamino)-7H-pyrrolo[2,3-d]pyrimidine-5-carbonyl]-2,4-difluoro-phenyl]butane-2-sulfonamide | 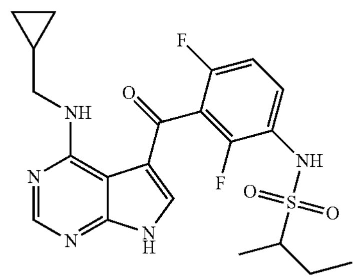 | 464.3 |
| P-2057 | N-[3-[4-(cyclopropylmethylamino)-7H-pyrrolo[2,3-d]pyrimidine-5-carbonyl]-2-fluoro-phenyl]pyrrolidine-1-sulfonamide | 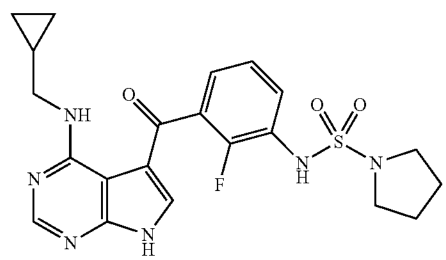 [SMILES: O=C(c1cccc(NS(=O)(=O)N2CCCC2)c1F)c1c[nH]c2ncnc(NCC3CC3)c12] | 459.4 |
| P-2058 | N-[3-[4-(cyclopropylmethylamino)-7H-pyrrolo[2,3-d]pyrimidine-5-carbonyl]-2,4-difluoro-phenyl]tetrahydropyran-4-sulfonamide | 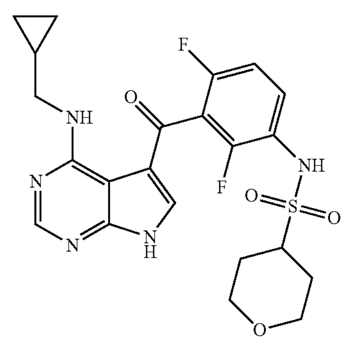 [SMILES: O=C(c1c(F)ccc(NS(=O)(=O)C2CCOCC2)c1F)c1c[nH]c2ncnc(NCC3CC3)c12] | 492.5 |
| P-2060 | N-[3-[4-(cyclopropylmethylamino)-5-fluoro-1H-pyrrolo[2,3-b]pyridine-3-carbonyl]-2,4-difluoro-phenyl]pyrrolidine-1-sulfonamide | 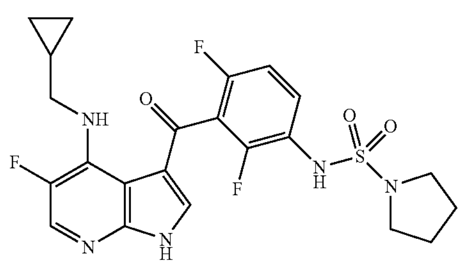 [SMILES: O=C(c1c(F)ccc(NS(=O)(=O)N2CCCC2)c1F)c1c[nH]c2ncc(F)c(NCC3CC3)c12] | 465.1 |

TABLE 1-continued

| Compound No. | Name | Structure | (MS (ESI) [M + H+]+) |
|---|---|---|---|
| P-2061 | 4-(cyclopropylmethylamino)-5-[3-[[ethyl(methyl)sulfamoyl]amino]-2,6-difluoro-benzoyl]-7H-pyrrolo[2,3-d]pyrimidine | 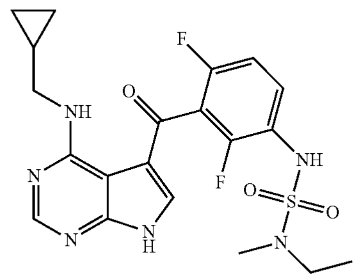 [SMILES: CCN(C)S(=O)(=O)Nc1ccc(F)c(C(=O)c2c[nH]c3ncnc(NCC4CC4)c23)c1F] | 407.1 |
| P-2062 | 5-[3-[[ethyl(methyl)sulfamoyl]amino]-2-fluoro-benzoyl]-4-(methylamino)-7H-pyrrolo[2,3-d]pyrimidine | 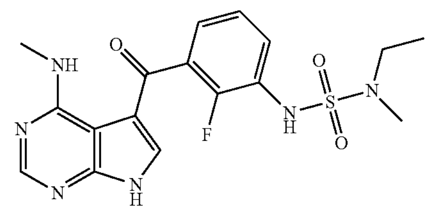 | 433.2 |
| P-2063 | 4-(cyclopropylamino)-5-[3-[[ethyl(methyl)sulfamoyl]amino]-2-fluoro-benzoyl]-7H-pyrrolo[2,3-d]pyrimidine | 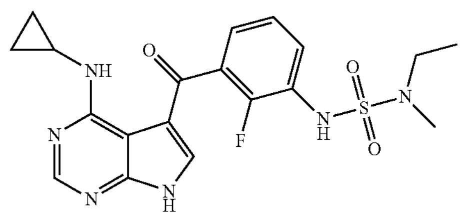 [SMILES: CCN(C)S(=O)(=O)Nc1cccc(C(=O)c2c[nH]c3ncnc(NC4CC4)c23)c1F] | 447.0 |
| P-2064 | 4-(cyclopropylmethylamino)-5-[3-[[ethyl(methyl)sulfamoyl]amino]-2-fluoro-benzoyl]-7H-pyrrolo[2,3-d]pyrimidine | 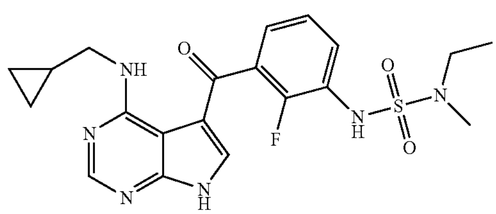 [SMILES: CCN(C)S(=O)(=O)Nc1cccc(C(=O)c2c[nH]c3ncnc(NCC4CC4)c23)c1F] | 475.0 |
| P-2065 | 5-[3-[[ethyl(methyl)sulfamoyl]amino]-2-fluoro-benzoyl]-4-(2,2,2-trifluoroethylamino)-7H-pyrrolo[2,3-d]pyrimidine | 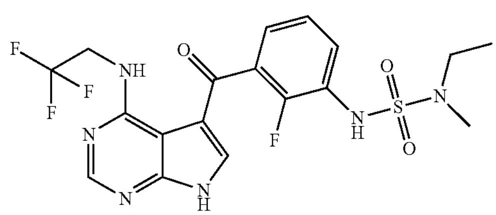 [SMILES: CCN(C)S(=O)(=O)Nc1cccc(C(=O)c2c[nH]c3ncnc(NCC(F)(F)F)c23)c1F] | 435.2 |
| P-2066 | 5-[3-[[ethyl(methyl)sulfamoyl]amino]-2-fluoro-benzoyl]-4-(propylamino)-7H-pyrrolo[2,3-d]pyrimidine | 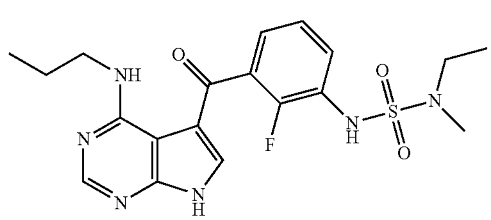 [SMILES: CCCNc1ncnc2[nH]cc(C(=O)c3cccc(NS(=O)(=O)N(C)CC)c3F)c12] | 435.4 |

TABLE 1-continued

| Compound No. | Name | Structure | (MS (ESI) [M + H+]+) |
|---|---|---|---|
| P-2067 | 5-[3-[[ethyl(methyl)sulfamoyl]amino]-2-fluoro-benzoyl]-4-(isopropylamino)-7H-pyrrolo[2,3-d]pyrimidine | 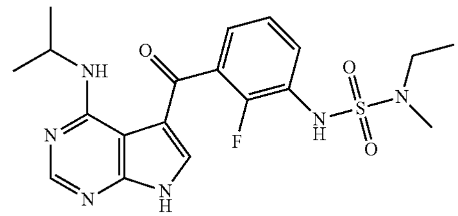 [SMILES: CCN(C)S(=O)(=O)Nc1cccc(C(=O)c2c[nH]c3ncnc(NC(C)C)c23)c1F] | 511.1 |
| P-2068 | 4-[(4,4-difluorocyclohexyl)amino]-5-[3-[[ethyl(methyl)sulfamoyl]amino]-2-fluoro-benzoyl]-7H-pyrrolo[2,3-d]pyrimidine | 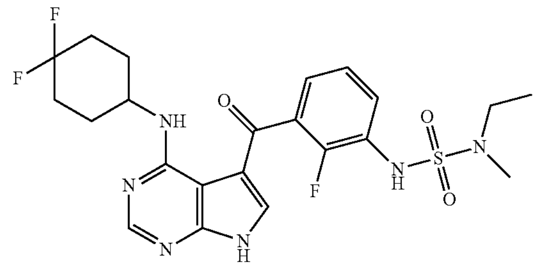 [SMILES: CCN(C)S(=O)(=O)Nc1cccc(C(=O)c2c[nH]c3ncnc(NC4CCC(F)(F)CC4)c23)c1F] | 465.1 |
| P-2069 | 5-[3-[[ethyl(methyl)sulfamoyl]amino]-2-fluoro-benzoyl]-4-[(2-hydroxy-2-methyl-propyl)amino]-7H-pyrrolo[2,3-d]pyrimidine | 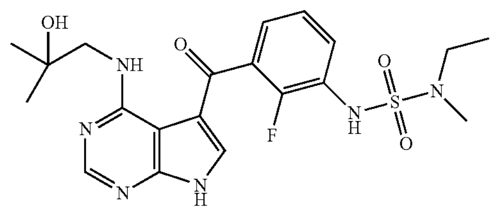 [SMILES: CCN(C)S(=O)(=O)Nc1cccc(C(=O)c2c[nH]c3ncnc(NCC(C)(C)O)c23)c1F] | 445.4 |
| P-2070 | N-[3-[4-(cyclopropylamino)-7H-pyrrolo[2,3-d]pyrimidine-5-carbonyl]-2-fluoro-phenyl]pyrrolidine-1-sulfonamide | 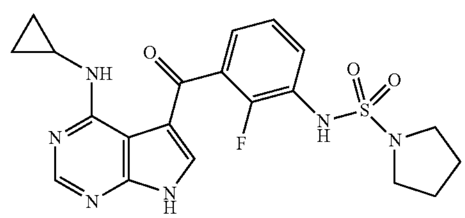 [SMILES: O=C(c1cccc(NS(=O)(=O)N2CCCC2)c1F)c1c[nH]c2ncnc(NC3CC3)c12] | 419.3 |
| P-2071 | N-[2-fluoro-3-[4-(methylamino)-7H-pyrrolo[2,3-d]pyrimidine-5-carbonyl]phenyl]pyrrolidine-1-sulfonamide | 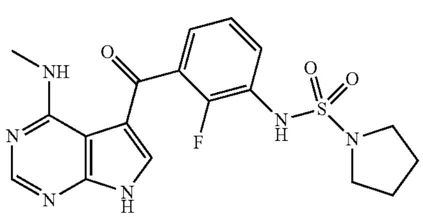 [SMILES: CNc1ncnc2[nH]cc(C(=O)c3cccc(NS(=O)(=O)N4CCCC4)c3F)c12] | 447.3 |
| P-2072 | 4-(cyclobutylamino)-5-[3-[[ethyl(methyl)sulfamoyl]amino]-2-fluoro-benzoyl]-7H-pyrrolo[2,3-d]pyrimidine | 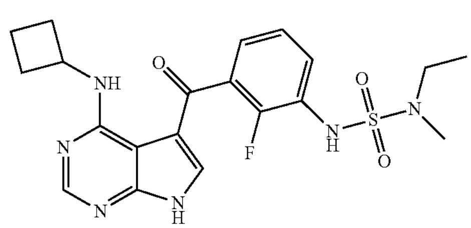 [SMILES: CCN(C)S(=O)(=O)Nc1cccc(C(=O)c2c[nH]c3ncnc(NC4CCC4)c23)c1F] | 451.3 |

TABLE 1-continued

| Compound No. | Name | Structure | (MS (ESI) [M + H+]+) |
|---|---|---|---|
| P-2073 | 5-[3-[[ethyl(methyl)sulfamoyl]amino]-2-fluoro-benzoyl]-4-(2-methoxyethylamino)-7H-pyrrolo[2,3-d]pyrimidine | 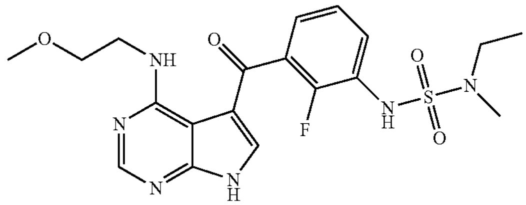 [SMILES: CCN(C)S(=O)(=O)Nc1cccc(C(=O)c2c[nH]c3ncnc(NCCOC)c23)c1F] | 477.1 |
| P-2074 | 5-[3-[[ethyl(methyl)sulfamoyl]amino]-2-fluoro-benzoyl]-4-[[(2S)-tetrahydrofuran-2-yl]methylamino]-7H-pyrrolo[2,3-d]pyrimidine | 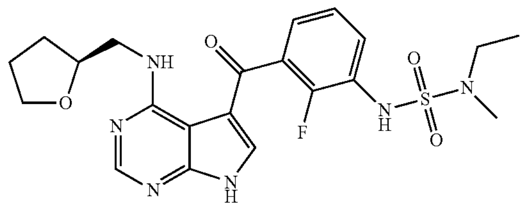 [SMILES: CCN(C)S(=O)(=O)Nc1cccc(C(=O)c2c[nH]c3ncnc(NC[C@@H]4CCCO4)c23)c1F] | 477.0 |
| P-2075 | 5-[3-[[ethyl(methyl)sulfamoyl]amino]-2-fluoro-benzoyl]-4-(tetrahydropyran-4-ylamino)-7H-pyrrolo[2,3-d]pyrimidine | 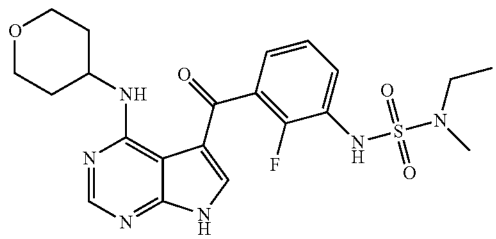 [SMILES: CCN(C)S(=O)(=O)Nc1cccc(C(=O)c2c[nH]c3ncnc(NC4CCOCC4)c23)c1F] | 465.1 |
| P-2076 | N-[2-fluoro-3-(4-methyl-7H-pyrrolo[2,3-d]pyrimidine-5-carbonyl)phenyl]pyrrolidine-1-sulfonamide | 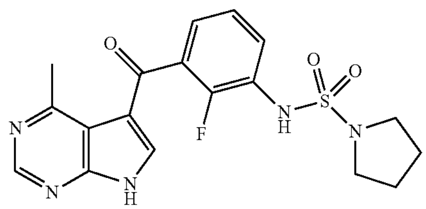 [SMILES: Cc1ncnc2[nH]cc(C(=O)c3cccc(NS(=O)(=O)N4CCCC4)c3F)c12] | 402.0* |
| P-2077 | N-[2-fluoro-3-[4-(2,2,2-trifluoroethylamino)-7H-pyrrolo[2,3-d]pyrimidine-5-carbonyl]phenyl]pyrrolidine-1-sulfonamide | 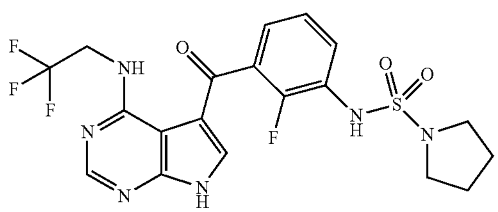 [SMILES: O=C(c1cccc(NS(=O)(=O)N2CCCC2)c1F)c1c[nH]c2ncnc(NCC(F)(F)F)c12] | 487.2 |
| P-2078 | N-[3-(4-cyclopropyl-7H-pyrrolo[2,3-d]pyrimidine-5-carbonyl)-2-fluoro-phenyl]pyrrolidine-1-sulfonamide | 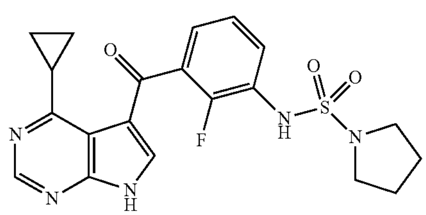 [SMILES: O=C(c1cccc(NS(=O)(=O)N2CCCC2)c1F)c1c[nH]c2ncnc(C3CC3)c12] | 428.1* |
| P-2079 | 4-[[(1R)-1-cyclopropylethyl]amino]-5-[3-[[ethyl(methyl)sulfamoyl]amino]-2-fluoro-benzoyl]-7H-pyrrolo[2,3-d]pyrimidine | 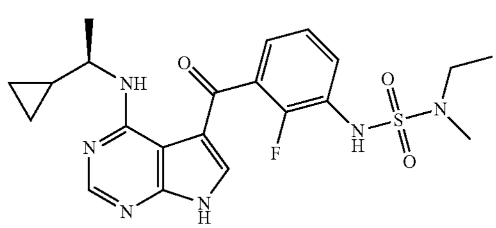 [SMILES: CCN(C)S(=O)(=O)Nc1cccc(C(=O)c2c[nH]c3ncnc(N[C@H](C)C4CC4)c23)c1F] | 461.1 |

TABLE 1-continued

| Compound No. | Name | Structure | (MS (ESI) [M + H⁺]⁺) |
|---|---|---|---|
| P-2080 | 4-[[(1S)-1-cyclopropylethyl]amino]-5-[3-[[ethyl(methyl)sulfamoyl]amino]-2-fluoro-benzoyl]-7H-pyrrolo[2,3-d]pyrimidine | 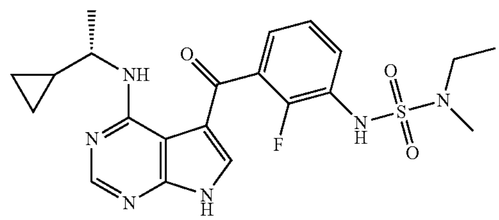 [SMILES: CCN(C)S(=O)(=O)Nc1cccc(C(=O)c2c[nH]c3ncnc(N[C@@H](C)C4CC4)c23)c1F] | 461.5 |
| P-2081 | N-[3-[4-(cyclobutylamino)-7H-pyrrolo[2,3-d]pyrimidine-5-carbonyl]-2-fluoro-phenyl]pyrrolidine-1-sulfonamide | 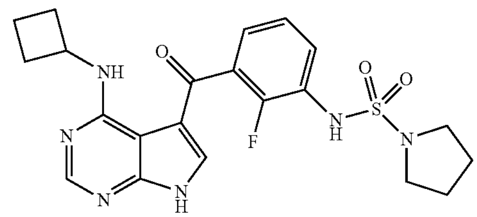 [SMILES: O=C(c1cccc(NS(=O)(=O)N2CCCC2)c1F)c1c[nH]c2ncnc(NC3CCC3)c12] | 459.4 |
| P-2082 | N-[2-fluoro-3-[4-[[(2S)-tetrahydrofuran-2-yl]methylamino]-7H-pyrrolo[2,3-d]pyrimidine-5-carbonyl]phenyl]pyrrolidine-1-sulfonamide | 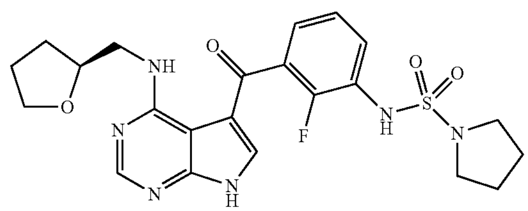 [SMILES: O=C(c1cccc(NS(=O)(=O)N2CCCC2)c1F)c1c[nH]c2ncnc(NC[C@@H]3CCCO3)c12] | 489.4 |
| P-2083 | N-[2-fluoro-3-[4-(tetrahydropyran-4-ylamino)-7H-pyrrolo[2,3-d]pyrimidine-5-carbonyl]phenyl]pyrrolidine-1-sulfonamide | 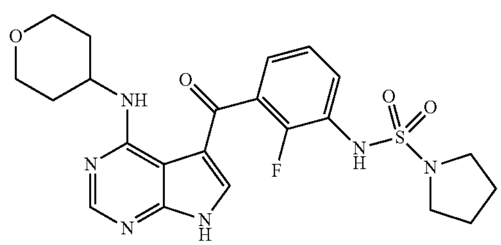 [SMILES: O=C(c1cccc(NS(=O)(=O)N2CCCC2)c1F)c1c[nH]c2ncnc(NC3CCOCC3)c12] | 489.1 |
| P-2084 | N-[2-fluoro-3-(4-methoxy-7H-pyrrolo[2,3-d]pyrimidine-5-carbonyl)phenyl]pyrrolidine-1-sulfonamide | 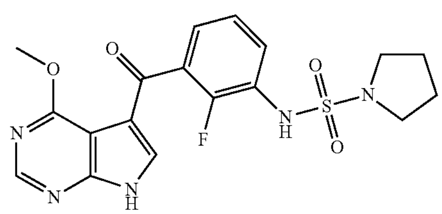 [SMILES: COc1ncnc2[nH]cc(C(=O)c3cccc(NS(=O)(=O)N4CCCC4)c3F)c12] | 419.9 |
| P-2085 | 2-tert-butyl-5-(2-chloropyrimidin-4-yl)-4-[3-[[ethyl(methyl)sulfamoyl]amino]-2-fluoro-phenyl]thiazole | 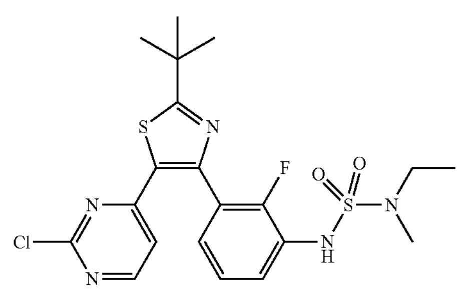 [SMILES: CCN(C)S(=O)(=O)Nc1cccc(-c2nc(C(C)(C)C)sc2-c2ccnc(Cl)n2)c1F] | |

TABLE 1-continued

| Compound No. | Name | Structure | (MS (ESI) [M + H⁺]⁺) |
|---|---|---|---|
| P-2086 | 5-[2-fluoro-3-[[methyl(propyl)sulfamoyl]amino]benzoyl]-4-methyl-7H-pyrrolo[2,3-d]pyrimidine | 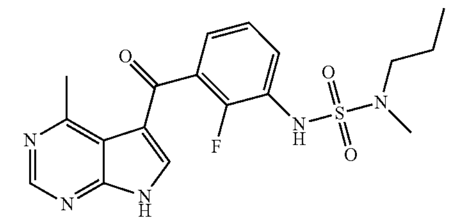 [SMILES: CCCN(C)S(=O)(=O)Nc1cccc(C(=O)c2c[nH]c3ncnc(C)c23)c1F] | |
| P-2087 | 4-cyclopropyl-5-[2-fluoro-3-[[methyl(propyl)sulfamoyl]amino]benzoyl]-7H-pyrrolo[2,3-d]pyrimidine | 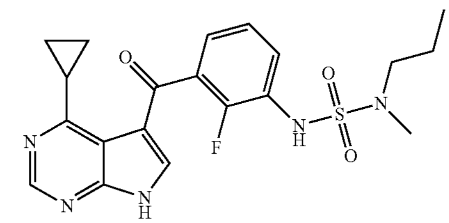 [SMILES: CCCN(C)S(=O)(=O)Nc1cccc(C(=O)c2c[nH]c3ncnc(C4CC4)c23)c1F] | |
| P-2088 | 2-tert-butyl-4-[3-[[ethyl(methyl)sulfamoyl]amino]-2-fluoro-phenyl]-5-(2-methoxypyrimidin-4-yl)thiazole | 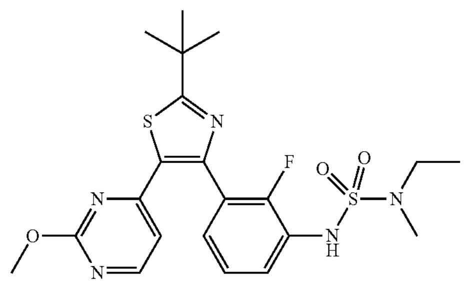 [SMILES: CCN(C)S(=O)(=O)Nc1cccc(-c2nc(C(C)(C)C)sc2-c2ccnc(OC)n2)c1F] | |
| P-2089 | 5-(2-aminopyrimidin-4-yl)-2-tert-butyl-4-[3-[[ethyl(methyl)sulfamoyl]amino]-2-fluoro-phenyl]thiazole | 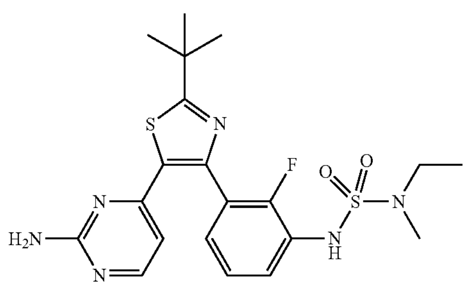 [SMILES: CCN(C)S(=O)(=O)Nc1cccc(-c2nc(C(C)(C)C)sc2-c2ccnc(N)n2)c1F] | |
| P-2090 | 5-[3-[[ethyl(methyl)sulfamoyl]amino]-2-fluoro-benzoyl]-4-methyl-7H-pyrrolo[2,3-d]pyrimidine | 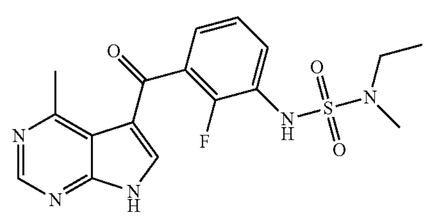 [SMILES: CCN(C)S(=O)(=O)Nc1cccc(C(=O)c2c[nH]c3ncnc(C)c23)c1F] | |
| P-2091 | 4-cyclopropyl-5-[3-[[ethyl(methyl)sulfamoyl]amino]-2-fluoro-benzoyl]-7H-pyrrolo[2,3-d]pyrimidine | 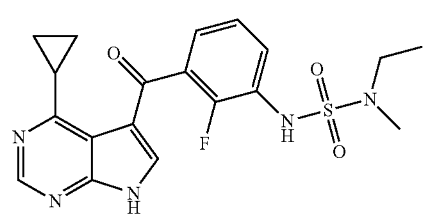 [SMILES: CCN(C)S(=O)(=O)Nc1cccc(C(=O)c2c[nH]c3ncnc(C4CC4)c23)c1F] | |

TABLE 1-continued

| Compound No. | Name | Structure | (MS (ESI) [M + H+]+) |
|---|---|---|---|
| P-2092 | 5-[3-[[ethyl(methyl)sulfamoyl]amino]-2-fluoro-benzoyl]-4-methoxy-7H-pyrrolo[2,3-d]pyrimidine | 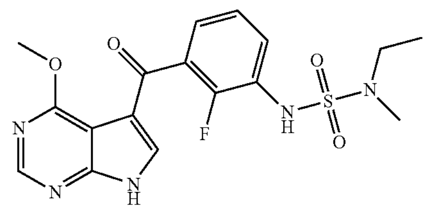 [SMILES: CCN(C)S(=O)(=O)Nc1cccc(C(=O)c2c[nH]c3ncnc(OC)c23)c1F] | 406.1* |
| P-2093 | 5-(2-aminopyrimidin-4-yl)-2-tert-butyl-4-[3-(dimethylsulfamoylamino)-2-fluoro-phenyl]thiazole | 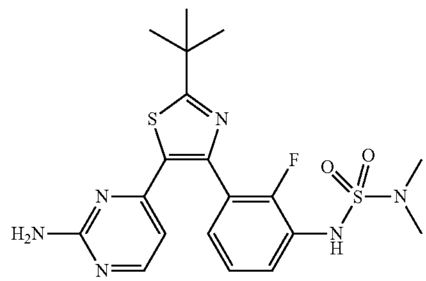 [SMILES: CN(C)S(=O)(=O)Nc1cccc(-c2nc(C(C)(C)C)sc2-c2ccnc(N)n2)c1F] | |
| P-2094 | N-[3-[4-[[(1R)-1-cyclopropylethyl]amino]-7H-pyrrolo[2,3-d]pyrimidine-5-carbonyl]-2-fluoro-phenyl]pyrrolidine-1-sulfonamide | 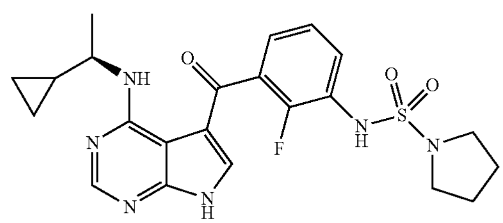 [SMILES: C[C@@H](Nc1ncnc2[nH]cc(C(=O)c3cccc(NS(=O)(=O)N4CCCC4)c3F)c12)C1CC1] | 473.4 |
| P-2095 | N-[3-[4-[(2,2-dimethyl-1,3-dioxolan-4-yl)methylamino]-7H-pyrrolo[2,3-d]pyrimidine-5-carbonyl]-2-fluoro-phenyl]pyrrolidine-1-sulfonamide | 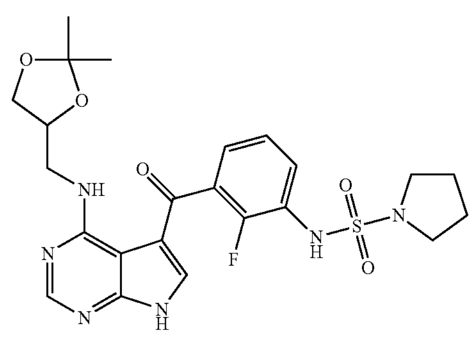 [SMILES: CC1(C)OCC(CNc2ncnc3[nH]cc(C(=O)c4cccc(NS(=O)(=O)N5CCCC5)c4F)c23)O1] | 519.1 |
| P-2096 | N-[3-[4-(2,3-dihydroxypropylamino)-7H-pyrrolo[2,3-d]pyrimidine-5-carbonyl]-2-fluoro-phenyl]pyrrolidine-1-sulfonamide | 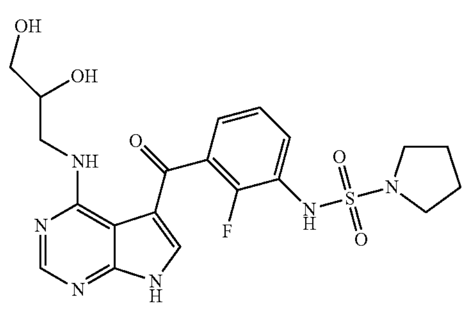 [SMILES: O=C(c1cccc(NS(=O)(=O)N2CCCC2)c1F)c1c[nH]c2ncnc(NCC(O)CO)c12] | 479.1 |

TABLE 1-continued

| Compound No. | Name | Structure | (MS (ESI) [M + H+]+) |
|---|---|---|---|
| P-2097 | 1-[[5-[2-fluoro-3-(pyrrolidin-1-ylsulfonylamino)benzoyl]-7H-pyrrolo[2,3-d]pyrimidin-4-yl]amino]cyclopropanecarboxylic acid | 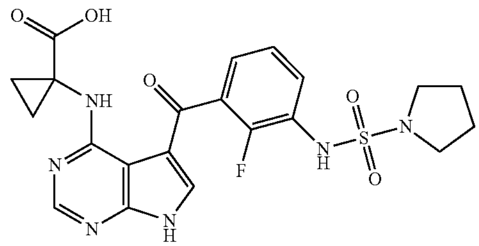 [SMILES: O=C(c1cccc(NS(=O)(=O)N2CCCC2)c1F)c1c[nH]c2ncnc(NC3(C(=O)O)CC3)c12] | 489.0 |
| P-2098 | N-[2-fluoro-3-[4-[(3-hydroxycyclobutyl)methylamino]-7H-pyrrolo[2,3-d]pyrimidine-5-carbonyl]phenyl]pyrrolidine-1-sulfonamide | 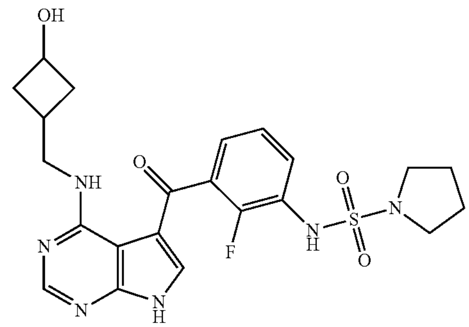 [SMILES: O=C(c1cccc(NS(=O)(=O)N2CCCC2)c1F)c1c[nH]c2ncnc(NCC3CC(O)C3)c12] | 489.1 |
| P-2099 | 5-[3-[[ethyl(methyl)sulfamoyl]amino]-2,6-difluoro-benzoyl]-4-(propylamino)-7H-pyrrolo[2,3-d]pyrimidine | 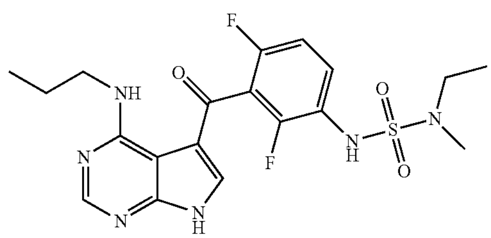 [SMILES: CCCNc1ncnc2[nH]cc(C(=O)c3c(F)ccc(NS(=O)(=O)N(C)CC)c3F)c12] | 453.2 |
| P-2100 | 5-[3-[[ethyl(methyl)sulfamoyl]amino]-2,6-difluoro-benzoyl]-4-(2-methoxyethylamino)-7H-pyrrolo[2,3-d]pyrimidine | 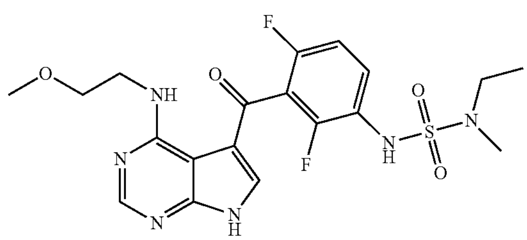 [SMILES: CCN(C)S(=O)(=O)Nc1ccc(F)c(C(=O)c2c[nH]c3ncnc(NCCOC)c23)c1F] | 469.1 |
| P-2101 | 4-(cyclobutylamino)-5-[3-[[ethyl(methyl)sulfamoyl]amino]-2,6-difluoro-benzoyl]-7H-pyrrolo[2,3-d]pyrimidine | 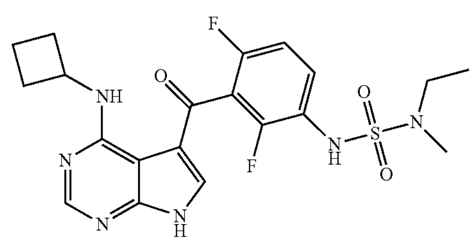 [SMILES: CCN(C)S(=O)(=O)Nc1ccc(F)c(C(=O)c2c[nH]c3ncnc(NC4CCC4)c23)c1F] | 465.0 |
| P-2102 | N-[3-[4-(2-aminoethylamino)-7H-pyrrolo[2,3-d]pyrimidine-5-carbonyl]-2-fluoro-phenyl]pyrrolidine-1-sulfonamide | 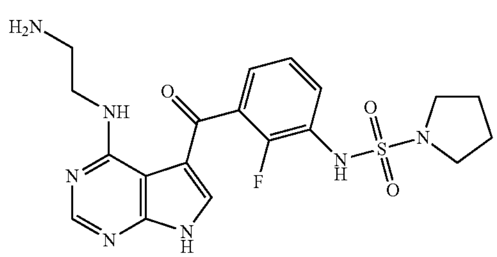 [SMILES: NCCNc1ncnc2[nH]cc(C(=O)c3cccc(NS(=O)(=O)N4CCCC4)c3F)c12] | 448.0 |

TABLE 1-continued

| Compound No. | Name | Structure | (MS (ESI) [M + H⁺]⁺) |
|---|---|---|---|
| P-2103 | ethyl 2-[[5-[2-fluoro-3-(pyrrolidin-1-ylsulfonylamino)benzoyl]-7H-pyrrolo[2,3-d]pyrimidin-4-yl]amino]acetate | 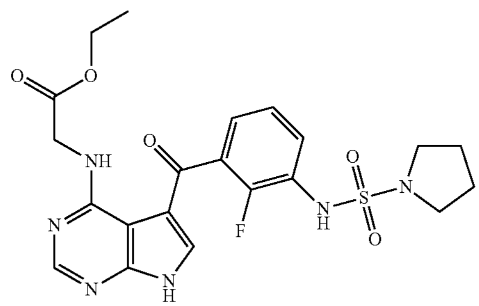 [SMILES: CCOC(=O)CNc1ncnc2[nH]cc(C(=O)c3cccc(NS(=O)(=O)N4CCCC4)c3F)c12] | 491.2 |
| P-2104 | N-[2-fluoro-3-[4-(2-methoxyethylamino)-7H-pyrrolo[2,3-d]pyrimidine-5-carbonyl]phenyl]pyrrolidine-1-sulfonamide | 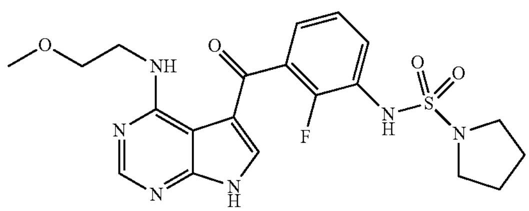 [SMILES: COCCNc1ncnc2[nH]cc(C(=O)c3cccc(NS(=O)(=O)N4CCCC4)c3F)c12] | 463.2 |
| P-2105 | N-[2-fluoro-3-[4-(3-methoxypropylamino)-7H-pyrrolo[2,3-d]pyrimidine-5-carbonyl]phenyl]pyrrolidine-1-sulfonamide | 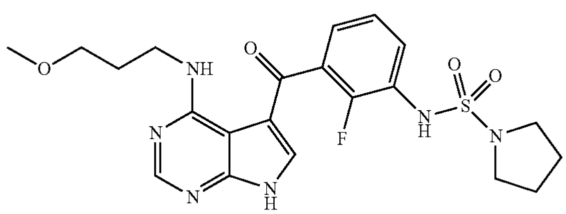 [SMILES: COCCCNc1ncnc2[nH]cc(C(=O)c3cccc(NS(=O)(=O)N4CCCC4)c3F)c12] | 477.1 |
| P-2106 | N-[3-[5-(2-aminopyrimidin-4-yl)-2-tert-butyl-thiazol-4-yl]-2-fluoro-phenyl]butane-2-sulfonamide | 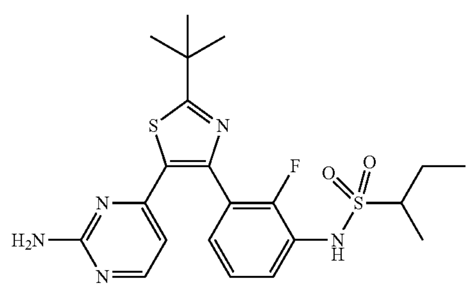 [SMILES: CCC(C)S(=O)(=O)Nc1cccc(-c2nc(C(C)(C)C)sc2-c2ccnc(N)n2)c1F] | |
| P-2107 | methyl 2-[[5-[2-fluoro-3-(pyrrolidin-1-ylsulfonylamino)benzoyl]-7H-pyrrolo[2,3-d]pyrimidin-4-yl]amino]-4-methyl-pentanoate | 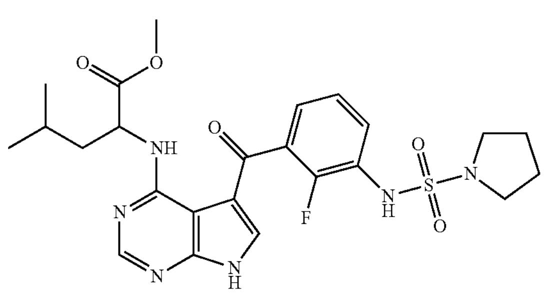 [SMILES: COC(=O)C(CC(C)C)Nc1ncnc2[nH]cc(C(=O)c3cccc(NS(=O)(=O)N4CCCC4)c3F)c12] | 533.2 |

TABLE 1-continued

| Compound No. | Name | Structure | (MS (ESI) [M + H+]+) |
|---|---|---|---|
| P-2108 | N-[2-fluoro-3-[4-[(3-hydroxy-3-methylbutyl)amino]-7H-pyrrolo[2,3-d]pyrimidine 5-carbonyl]phenyl]pyrrolidine-1-sulfonamide | 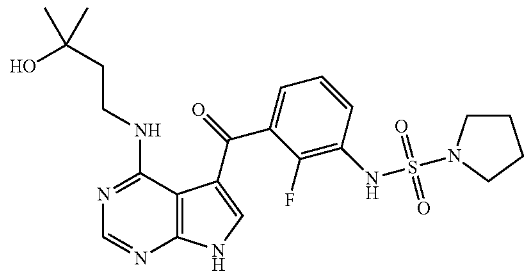 [SMILES: CC(C)(O)CCNc1ncnc2[nH]cc(C(=O)c3cccc(NS(=O)(=O)N4CCCC4)c3F)c12] | 491.2 |
| P-2109 | 2-[[5-[2-fluoro-3-(pyrrolidin-1-ylsulfonylamino)benzoyl]-7H-pyrrolo[2,3-d]pyrimidin-4-yl]amino]acetic acid | 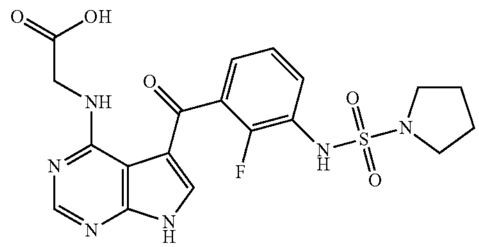 [SMILES: O=C(O)CNc1ncnc2[nH]cc(C(=O)c3cccc(NS(=O)(=O)N4CCCC4)c3F)c12] | 463.0 |
| P-2110 | N-[2-fluoro-3-[4-(2-morpholinoethylamino)-7H-pyrrolo[2,3-d]pyrimidine-5-carbonyl]phenyl]pyrrolidine-1-sulfonamide | 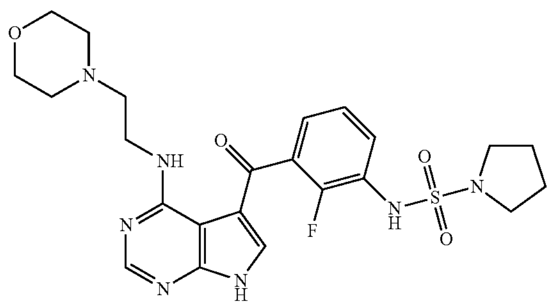 [SMILES: O=C(c1cccc(NS(=O)(=O)N2CCCC2)c1F)c1c[nH]c2ncnc(NCCN3CCOCC3)c12] | 518.1 |
| P-2111 | N-[2-fluoro-3-[4-(3-morpholinopropylamino)-7H-pyrrolo[2,3-d]pyrimidine-5-carbonyl]phenyl]pyrrolidine-1-sulfonamide | 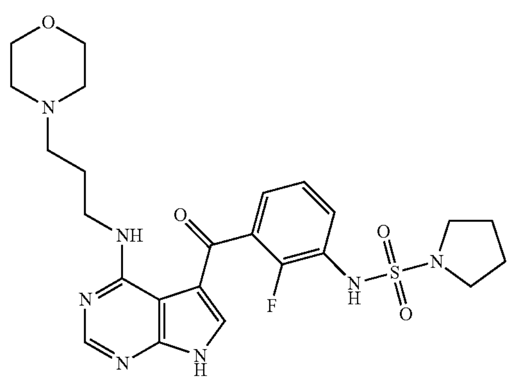 [SMILES: O=C(c1cccc(NS(=O)(=O)N2CCCC2)c1F)c1c[nH]c2ncnc(NCCCN3CCOCC3)c12] | 532.1 |
| P-2112 | N-[2-fluoro-3-[4-(3,3,3-trifluoropropylamino)-7H-pyrrolo[2,3-d]pyrimidine-5-carbonyl]phenyl]pyrrolidine-1-sulfonamide | 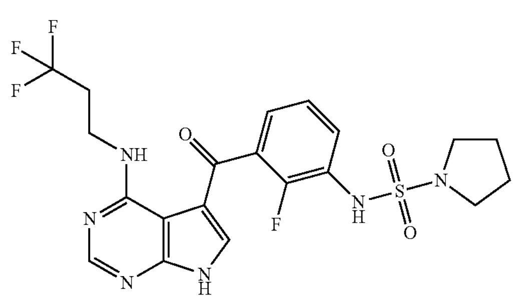 [SMILES: O=C(c1cccc(NS(=O)(=O)N2CCCC2)c1F)c1c[nH]c2ncnc(NCCC(F)(F)F)c12] | 501.0 |

TABLE 1-continued

| Compound No. | Name | Structure | (MS (ESI) [M + H⁺]⁺) |
|---|---|---|---|
| P-2113 | N-[3-[4-[[3-(dimethylamino)-2,2-dimethyl-propyl]amino]-7H-pyrrolo[2,3-d]pyrimidine-5-carbonyl]-2-fluoro-phenyl]pyrrolidine-1-sulfonamide | 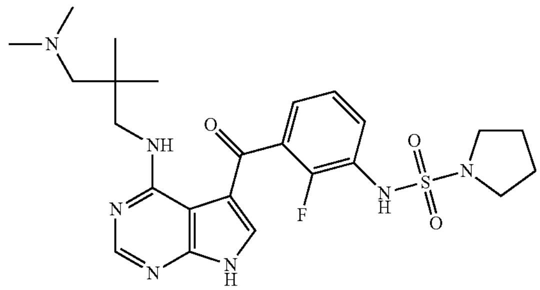 [SMILES: CN(C)CC(C)(C)CNc1ncnc2[nH]cc(C(=O)c3cccc(NS(=O)(=O)N4CCCC4)c3F)c12] | 518.1 |
| P-2114 | N-[3-[5-(2-aminopyrimidin-4-yl)-2-tert-butyl-thiazol-4-yl]-2-fluoro-phenyl]pyrrolidine-1-sulfonamide | 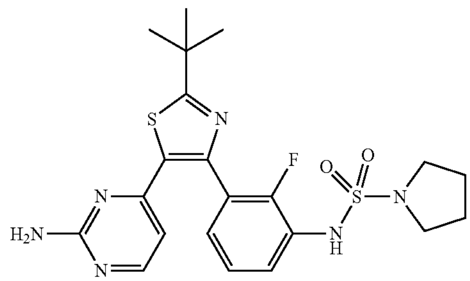 [SMILES: CC(C)(C)c1nc(-c2cccc(NS(=O)(=O)N3CCCC3)c2F)c(-c2ccnc(N)n2)s1] | |
| P-2115 | 5-[3-[[ethyl(methyl)sulfamoyl]amino]-2-fluoro-benzoyl]-4-(3-methoxypropylamino)-7H-pyrrolo[2,3-d]pyrimidine | 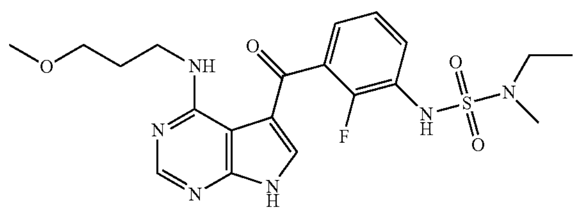 [SMILES: CCN(C)S(=O)(=O)Nc1cccc(C(=O)c2c[nH]c3ncnc(NCCCOC)c23)c1F] | 465.1 |
| P-2116 | 5-[3-[[ethyl(methyl)sulfamoyl]amino]-2,6-difluoro-benzoyl]-4-(3-methoxypropylamino)-7H-pyrrolo[2,3-d]pyrimidine | 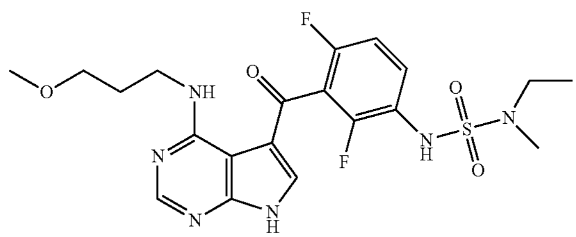 [SMILES: CCN(C)S(=O)(=O)Nc1ccc(F)c(C(=O)c2c[nH]c3ncnc(NCCCOC)c23)c1F] | 483.1 |
| P-2117 | 5-[3-[[ethyl(methyl)sulfamoyl]amino]-2,6-difluoro-benzoyl]-4-(isopropylamino)-7H-pyrrolo[2,3-d]pyrimidine | 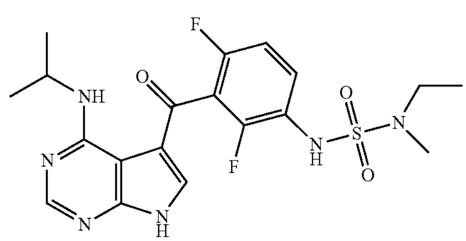 [SMILES: CCN(C)S(=O)(=O)Nc1ccc(F)c(C(=O)c2c[nH]c3ncnc(NC(C)C)c23)c1F] | 453.0 |
| P-2118 | 4-[[(1R)-1-cyclopropylethyl]amino]-5-[3-[[ethyl(methyl(sulfamoyl]amino]-2,6-d]fluoro-benzoyl]-7H-pyrrolo[2,3-d]pyrimidine | 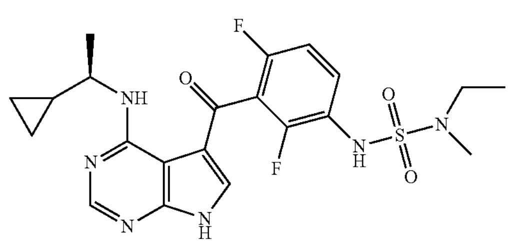 [SMILES: CCN(C)S(=O)(=O)Nc1ccc(F)c(C(=O)c2c[nH]c3ncnc(N[C@H](C)C4CC4)c23)c1F] | 479.0 |

TABLE 1-continued

| Compound No. | Name | Structure | (MS (ESI) [M + H+]+) |
|---|---|---|---|
| P-2119 | 5-[3-[[ethyl(methyl)sulfamoyl]amino]-2,6-difluoro-benzoyl]-4-(tetrahydropyran-4-ylamino)-7H-pyrrolo[2,3-d]pyrimidine | 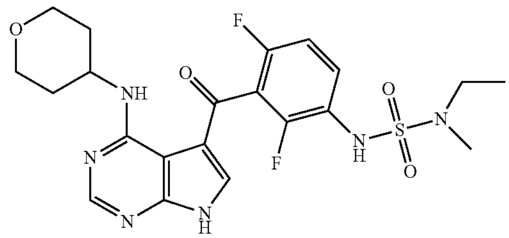 [SMILES: CCN(C)S(=O)(=O)Nc1ccc(F)c(C(=O)c2c[nH]c3ncnc(NC4CCOCC4)c23)c1F] | 495.3 |
| P-2120 | N-[3-[2-tert-butyl-5-(1H-pyrrolo[2,3-b]pyridin-4-yl)thiazol-4-yl]-2-fluoro-phenyl]pyrrolidine-1-sulfonamide | 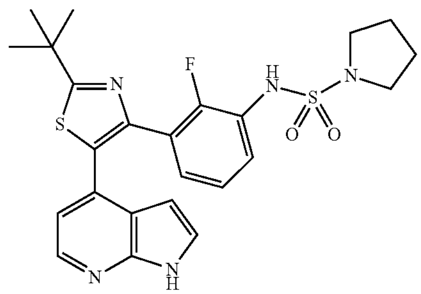 [SMILES: CC(C)(C)c1nc(-c2cccc(NS(=O)(=O)N3CCCC3)c2F)c(-c2ccnc3[nH]ccc23)s1] | 500.0 |
| P-2121 | N-[3-[2-tert-butyl-5-(2-methyl-1H-pyrrolo[2,3-b]pyridin-4-yl)thiazol-4-yl]-2-fluoro-phenyl]pyrrolidine-1-sulfonamide | 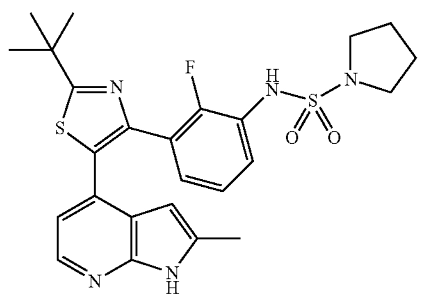 | |
| P-2122 | N-[3-[2-tert-butyl-5-(7H-pyrrolo[2,3-d]pyrimidin-4-yl)thiazol-4-yl]-2-fluoro-phenyl]pyrrolidine-1-sulfonamide | 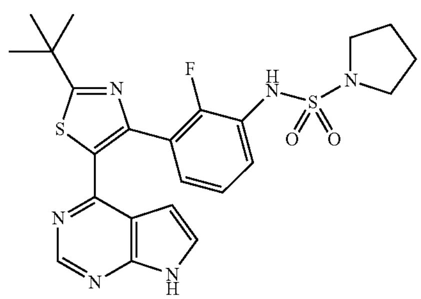 [SMILES: CC(C)(C)c1nc(-c2cccc(NS(=O)(=O)N3CCCC3)c2F)c(-c2ncnc3[nH]ccc23)s1] | |
| P-2123 | N-[3-[2-tert-butyl-5-(6-methyl-7H-pyrrolo[2,3-d]pyrimidin-4-yl)thiazol-4-yl]-2-fluoro-phenyl]pyrrolidine-1-sulfonamide | 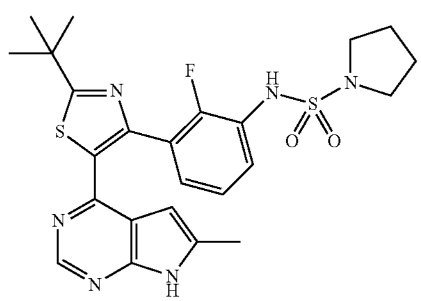 [SMILES: Cc1cc2c(-c3sc(C(C)(C)C)nc3-c3cccc(NS(=O)(=O)N4CCCC4)c3F)ncnc2[nH]1] | 515.1 |

TABLE 1-continued

| Compound No. | Name | Structure | (MS (ESI) [M + H+]+) |
|---|---|---|---|
| P-2124 | N-[3-[2-tert-butyl-5-(8-methyl-9H-purin-6-yl)thiazol-4-yl]-2-fluoro-phenyl]pyrrolidine-1-sulfonamide | 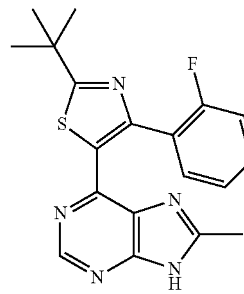 | 516.3 |
| P-2125 | N-[3-[2-tert-buty]-5-(9H-purin-6-yl)thiazol-4-yl]-2-fluoro-phenyl]pyrrolidine-1-sulfonamide | 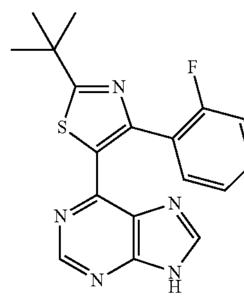 | 502.2 |
| P-2126 | N-[3-[2-tert-butyl-5-(2-methyl-3H-imidazo[4,5-b]pyridin-7-yl)thiazol-4-yl]-2-fluoro-phenyl]pyrrolidine-1-sulfonamide | 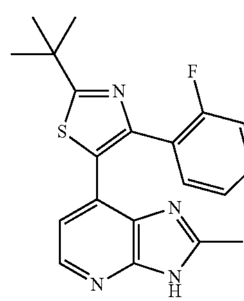 | 515.1 |
| P-2127 | N-[3-(5-bromo-2-tert-butyl-thiazol-4-yl)-2-fluoro-phenyl]pyrrolidine-1-sulfonamide | 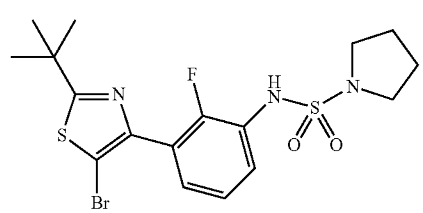 [SMILES: CC(C)(C)c1nc(-c2cccc(NS(=O)(=O)N3CCCC3)c2F)c(Br)s1] | |
| P-2128 | N-(6-acetamido-3-pyridyl)-2,6-difluoro-3-(morpholinosulfonylamino)benzamide | 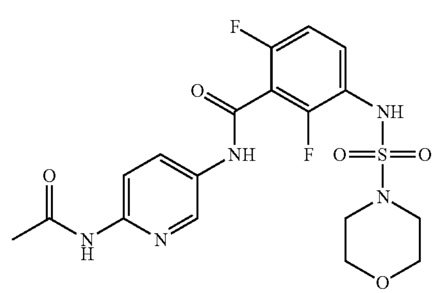 [SMILES: CC(=O)Nc1ccc(NC(=O)c2c(F)ccc(NS(=O)(=O)N3CCOCC3)c2F)cn1] | 456.3 |

TABLE 1-continued

| Compound No. | Name | Structure | (MS (ESI) [M + H⁺]⁺) |
|---|---|---|---|
| P-2129 | (3R)-N-[3-[5-(2-aminopyrimidin-4-yl)-2-tert-butyl-thiazol-4-yl]-2-fluoro-phenyl]-3-fluoro-pyrrolidine-1-sulfonamide | 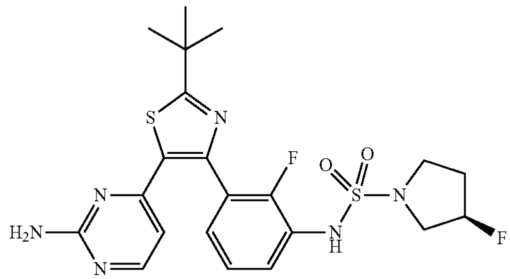 [SMILES: CC(C)(C)c1nc(-c2cccc(NS(=O)(=O)N3CC[C@@H](F)C3)c2F)c(-c2ccnc(N)n2)s1] | 495.3 |
| P-2130 | (3S)-N-[3-[5-(2-aminopyrimidin-4-yl)-2-tert-butyl-thiazol-4-yl]-2-fluoro-phenyl]-3-fluoro-pyrrolidine-1-sulfonamide | 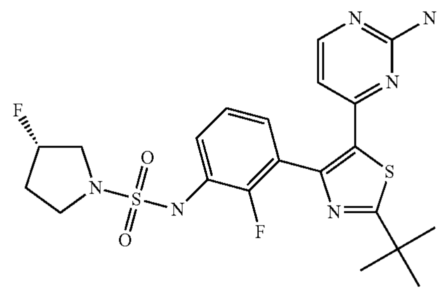 [SMILES: CC(C)(C)c1nc(-c2cccc(NS(=O)(=O)N3CC[C@H](F)C3)c2F)c(-c2ccnc(N)n2)s1] | 494.6 |
| P-2131 | N-[3-[5-(2-aminopyrimidin-4-yl)-2-tert-butyl-thiazol-4-yl]-2-fluoro-phenyl]azetidine-1-sulfonamide | 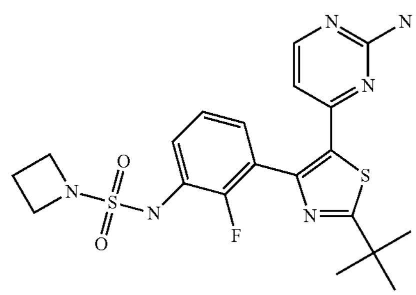 [SMILES: CC(C)(C)c1nc(-c2cccc(NS(=O)(=O)N3CCC3)c2F)c(-c2ccnc(N)n2)s1] | |
| P-2132 | N-[3-[5-(2-aminopyrimidin-4-yl)-2-tert-butyl-thiazol-4-yl]-2-fluoro-phenyl]piperidine-1-sulfonamide | 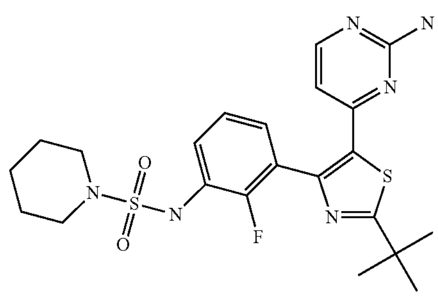 [SMILES: CC(C)(C)c1nc(-c2cccc(NS(=O)(=O)N3CCCCC3)c2F)c(-c2ccnc(N)n2)s1] | |
| P-2133 | N-[3-[5-(2-aminopyrimidin-4-yl)-2-tert-butyl-thiazol-4-yl]-2-fluoro-phenyl]cyclopropanesulfonamide | 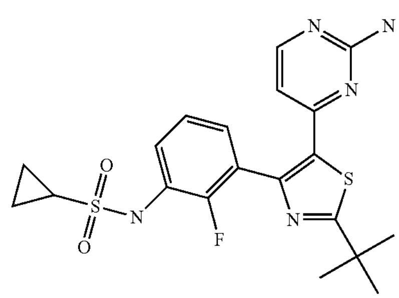 [SMILES: CC(C)(C)c1nc(-c2cccc(NS(=O)(=O)C3CC3)c2F)c(-c2ccnc(N)n2)s1] | |

TABLE 1-continued

| Compound No. | Name | Structure | (MS (ESI) [M + H+]+) |
|---|---|---|---|
| P-2134 | N-[3-[5-(2-aminopyrimidin-4-yl)-2-tert-butyl-thiazol-4-yl]-2-fluoro-phenyl]cyclobutanesulfonamide | 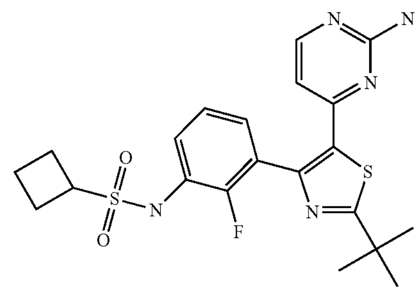 [SMILES: CC(C)(C)c1nc(-c2cccc(NS(=O)(=O)C3CCC3)c2F)c(-c2ccnc(N)n2)s1] | |
| P-2135 | N-[3-[5-(2-aminopyrimidin-4-yl)-2-tert-butyl-thiazol-4-yl]-2-fluoro-phenyl]cyclopentanesulfonamide | 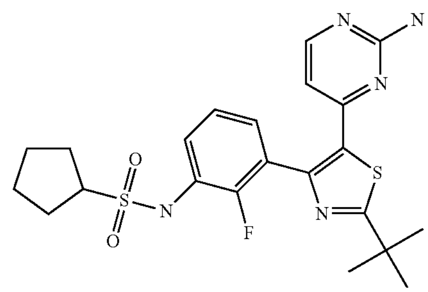 [SMILES: CC(C)(C)c1nc(-c2cccc(NS(=O)(=O)C3CCCC3)c2F)c(-c2ccnc(N)n2)s1] | |
| P-2136 | N-[3-[5-(2-aminopyrimidin-4-yl)-2-tert-butyl-thiazol-4-yl]-2-fluoro-phenyl]cyclohexanesulfonamide | 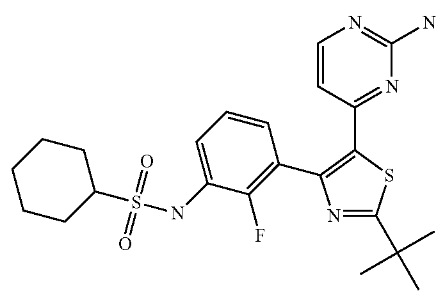 | |
| P-2137 | methyl N-[(1S)-2-[[4-[4-[3-(azetidin-1-ylsulfonylamino)-2-fluoro-phenyl]-2-tert-butyl-thiazol-5-yl]pyrimidin-2-yl]amino]-1-methyl-ethyl]carbamate | 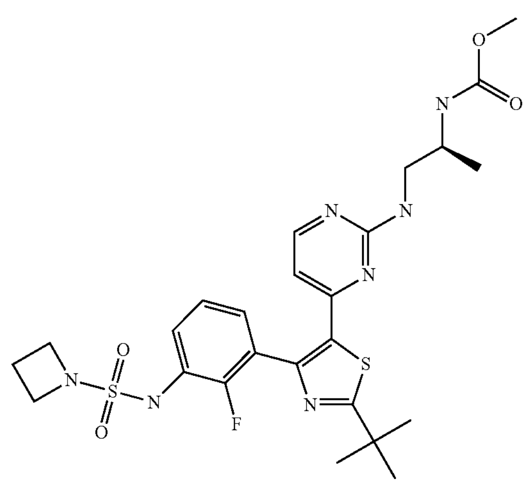 [SMILES: COC(=O)N[C@@H](C)CNc1nccc(-c2sc(C(C)(C)C)nc2-c2cccc(NS(=O)(=O)N3CCC3)c2F)n1] | |

TABLE 1-continued

| Compound No. | Name | Structure | (MS (ESI) [M + H⁺]⁺) |
|---|---|---|---|
| P-2138 | methyl N-[(1S)-2-[[4-[2-tert-butyl-4-[2-fluoro-3-[[(3R)-3-fluoropyrrolidin-1-yl]sulfonylamino]phenyl]thiazol-5-yl]pyrimidin-2-yl]amino]-1-methyl-ethyl]carbamate | 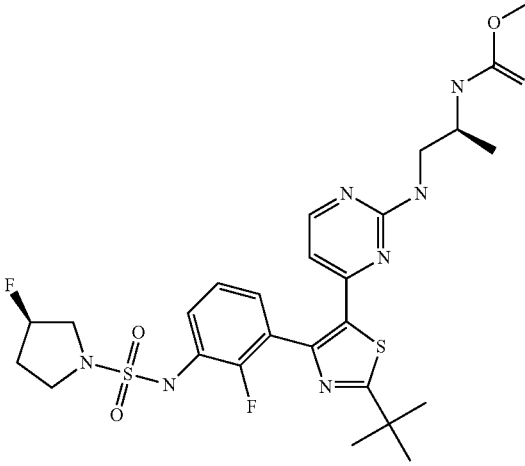 | 609.7 |
| P-2139 | methyl N-[(1S)-2-[[4-[2-tert-butyl-4-[2-fluoro-3-[[(3S)-3-fluoropyrrolidin-1-yl]sulfonylamino]phenyl]thiazol-5-yl]pyrimidin-2-yl]amino]-1-methyl-ethyl]carbamate | 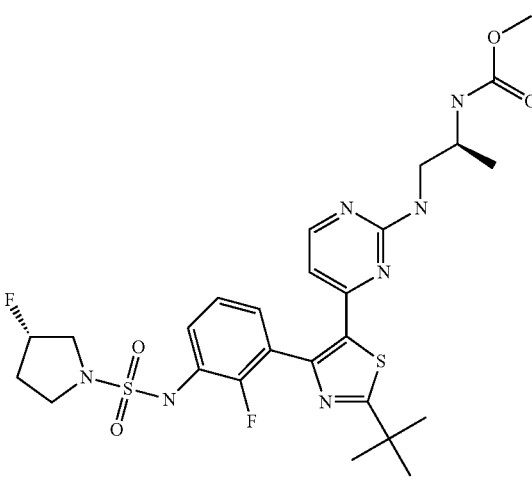 [SMILES: COC(=O)N[C@@H](C)CNc1nccc(-c2sc(C(C)(C)C)nc2-c2cccc(NS(=O)(=O)N3CC[C@H](F)C3)c2F)n1] | |
| P-2140 | methyl N-[(1S)-2-[[4-[2-tert-butyl-4-[2-fluoro-3-(1-piperidylsulfonylamino)phenyl]thiazol-5-yl]pyrimidin-2-yl]amino]-1-methyl-ethyl]carbamate | 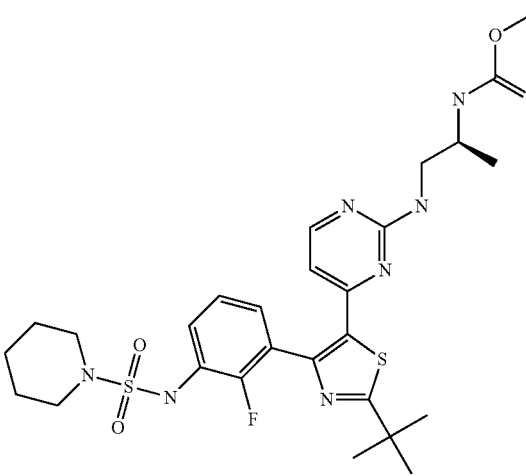 | |

| Compound No. | Name | Structure | (MS (ESI) [M + H⁺]⁺) |
|---|---|---|---|
| P-2141 | methyl N-[(1S)-2-[[4-[2-tert-butyl-4-[3-[[ethyl(methyl)sulfamoyl]amino]-2-fluoro-phenyl]thiazol-5-yl]pyrimidin-2-yl]amino]-1-methyl-ethyl]carbamate | 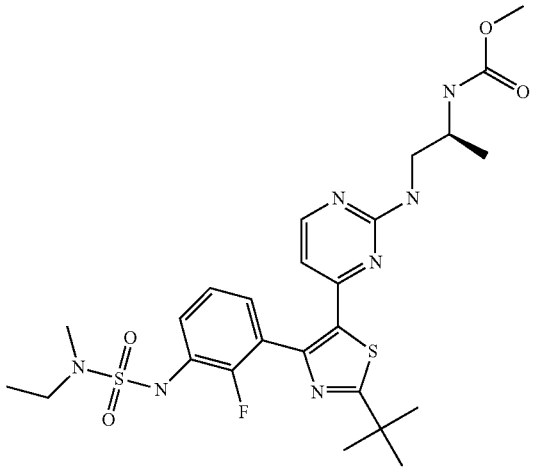 [SMILES: CCN(C)S(=O)(=O)Nc1cccc(-c2nc(C(C)(C)C)sc2-c2ccnc(NC[C@H](C)NC(=O)OC)n2)c1F] | |
| P-2142 | methyl N-[(1S)-2-[[4-[2-tert-butyl-4-[3-(cyclopropylsulfonylamino)-2-fluoro-phenyl]thiazol-5-yl]pyrimidin-2-yl]amino]-1-methyl-ethyl]carbamate | 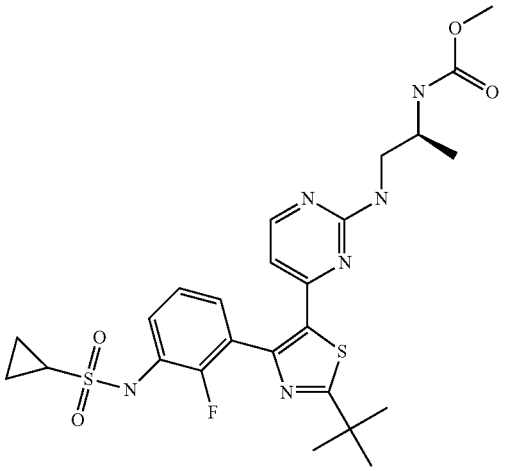 [SMILES: COC(=O)N[C@@H](C)CNc1nccc(-c2sc(C(C)(C)C)nc2-c2cccc(NS(=O)(=O)C3CC3)c2F)n1] | |
| P-2143 | methyl N-[(1S)-2-[[4-[2-tert-butyl-4-[3-(cyclobutylsulfonylamino)-2-fluoro-phenyl]thiazol-5-yl]pyrimidin-2-yl]amino]-1-methyl-ethyl]carbamate | 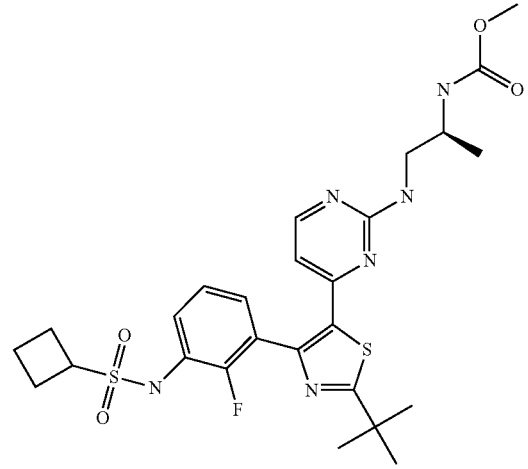 [SMILES: COC(=O)N[C@@H](C)CNc1nccc(-c2sc(C(C)(C)C)nc2-c2cccc(NS(=O)(=O)C3CCC3)c2F)n1] | |

TABLE 1-continued

| Compound No. | Name | Structure | (MS (ESI) [M + H+]+) |
|---|---|---|---|
| P-2144 | methyl N-[(1S)-2-[[4-[2-tert-butyl-4-[3-(cyclopentylsulfonylamino)-2-fluoro-phenyl]thiazol-5-yl]pyrimidin-2-yl]amino]-1-methyl-ethyl]carbamate | 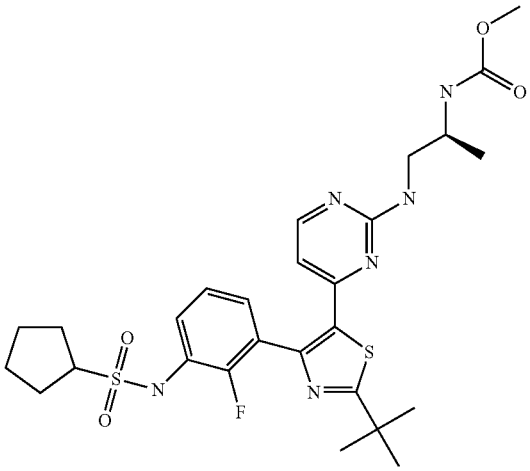 [SMILES: COC(=O)N[C@@H](C)CNc1nccc(-c2sc(C(C)(C)C)nc2-c2cccc(NS(=O)(=O)C3CCCC3)c2F)n1] | |
| P-2145 | methyl N-[(1S)-2-[[4-[2-tert-butyl-4-[3-(cyclohexylsulfonylamino)-2-fluoro-phenyl]thiazol-5-yl]pyrimidin-2-yl]amino]-1-methyl-ethyl]carbamate | 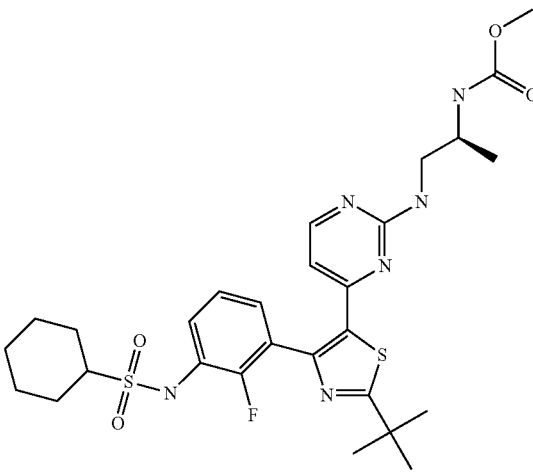 | |
| P-2146 | N-[3-[5-(2-aminopyrimidin-4-yl)-2-phenyl-thiazol-4-yl]-2-fluoro-phenyl]pyrrolidine-1-sulfonamide | 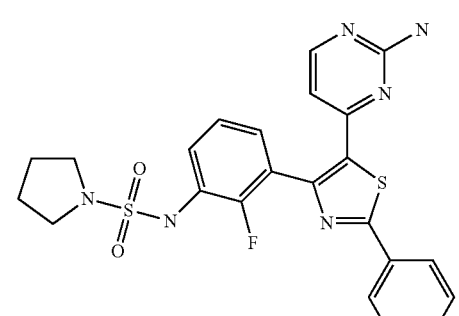 | |

TABLE 1-continued

| Compound No. | Name | Structure | (MS (ESI) [M + H+]+) |
|---|---|---|---|
| P-2147 | (3S)-N-[3-[5-(2-aminopyrimidin-4-yl)-2-phenyl-thiazol-4-yl]-2-fluoro-phenyl]-3-fluoro-pyrrolidine-1-sulfonamide | 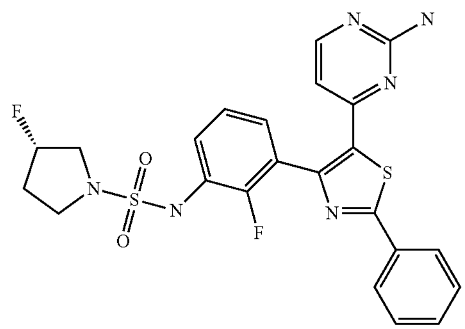 [SMILES: Nc1nccc(-c2sc(-c3ccccc3)nc2-c2cccc(NS(=O)(=O)N3CC[C@H](F)C3)c2F)n1] | |
| P-2148 | N-[3-[5-(2-aminopyrimidin-4-yl)-2-phenyl-thiazol-4-yl]-2-fluoro-phenyl]piperidine-1-sulfonamide | 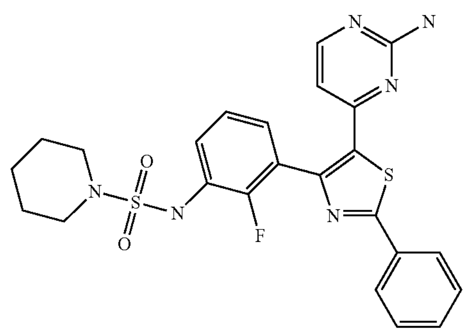 [SMILES: Nc1nccc(-c2sc(-c3ccccc3)nc2-c2cccc(NS(=O)(=O)N3CCCCC3)c2F)n1] | |
| P-2149 | N-[3-[5-(2-aminopyrimidin-4-yl)-2-phenyl-thiazol-4-yl]-2-fluoro-phenyl]cyclopentanesulfonamide | 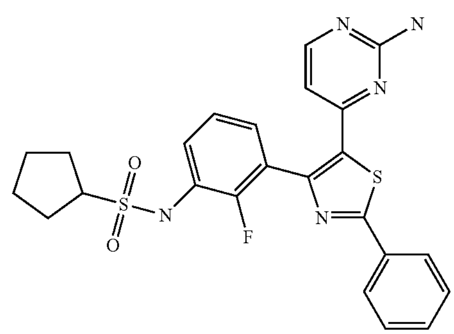 [SMILES: Nc1nccc(-c2sc(-c3ccccc3)nc2-c2cccc(NS(=O)(=O)C3CCCC3)c2F)n1] | |
| P-2150 | N-[3-[5-(2-aminopyrimidin-4-yl)-2-phenyl-thiazol-4-yl]-2-fluoro-phenyl]cyclohexanesulfonamide | 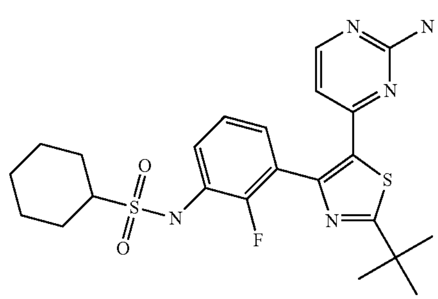 [SMILES: CC(C)(C)c1nc(-c2cccc(NS(=O)(=O)C3CCCCC3)c2F)c(-c2ccnc(N)n2)s1] | |

TABLE 1-continued

| Compound No. | Name | Structure | (MS (ESI) [M + H+]+) |
|---|---|---|---|
| P-2151 | methyl N-[(1S)-2-[[4-[4-[3-(azetidin-1-ylsulfonylamino)-2-fluoro-phenyl]-2-phenyl-thiazol-5-yl]pyrimidin-2-yl]amino]-1-methyl-ethyl]carbamate | 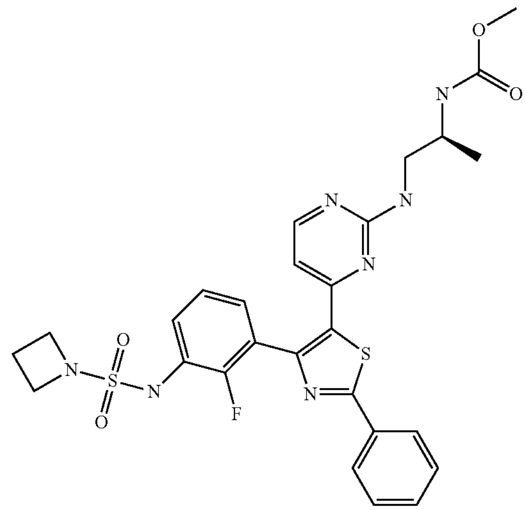 | |
| P-2152 | methyl N-[(1S)-2-[[4-[4-[2-fluoro-3-[[(3R)-3-fluoropyrrolidin-1-yl]sulfonylamino]phenyl]-2-phenyl-thiazol-5-yl]pyrimidin-2-yl]amino]-1-methyl-ethyl]carbamate | 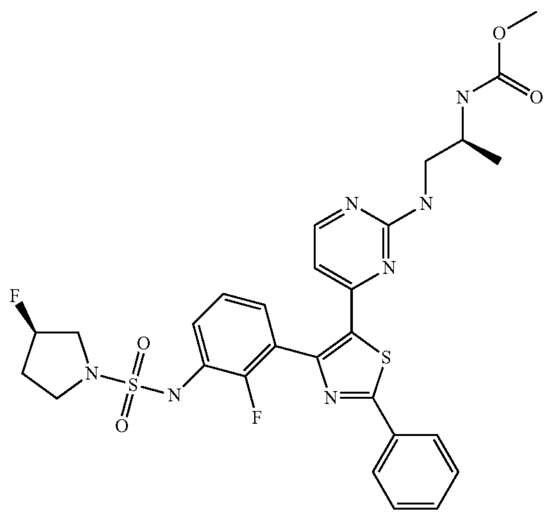 [SMILES: COC(=O)N[C@@H](C)CNc1nccc(-c2sc(-c3ccccc3)nc2-c2cccc(NS(=O)(=O)N3CC[C@@H](F)C3)c2F)n1] | 629.7 |
| P-2153 | methyl N-[(1S)-2-[[4-[4-[2-fluoro-3-[[(3S)-3-fluoropyrrolidin-1-yl]sulfonylamino]phenyl]-2-phenyl-thiazol-5-yl]pyrimidin-2-yl]amino]-1-methyl-ethyl]carbamate | 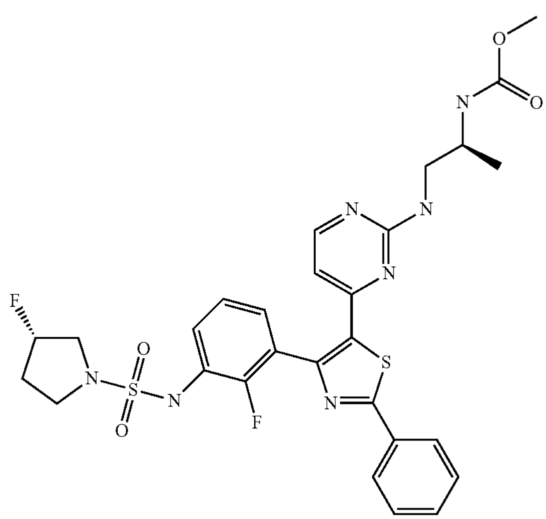 [SMILES: COC(=O)N[C@@H](C)CNc1nccc(-c2sc(-c3ccccc3)nc2-c2cccc(NS(=O)(=O)N3CC[C@H](F)C3)c2F)n1] | 629.7 |

TABLE 1-continued

| Compound No. | Name | Structure | (MS (ESI) [M + H+]+) |
|---|---|---|---|
| P-2154 | methyl N-[(1S)-2-[[4-[4-[2-fluoro-3-(1-piperidylsulfonylamino)phenyl]-2-phenyl-thiazol-5-yl]pyrimidin-2-yl]amino]-1-methyl-ethyl]carbamate | 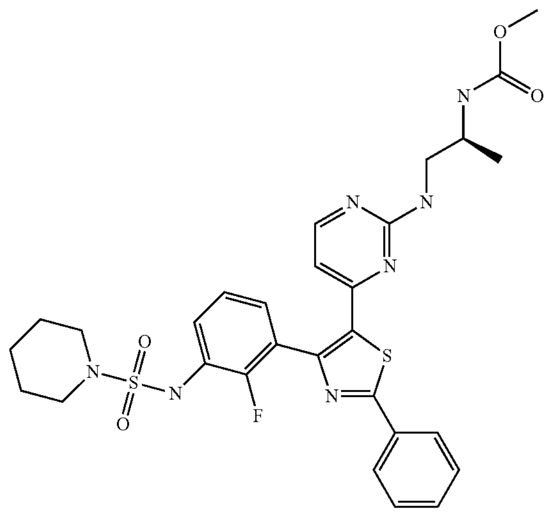 | |
| P-2155 | methyl N-[(1S)-2-[[4-[4-[3-[[ethyl(methyl)sulfamoyl]amino]-2-fluoro-phenyl]-2-phenyl-thiazol-5-yl]pyrimidin-2-yl]amino]-1-methyl-ethyl]carbamate | 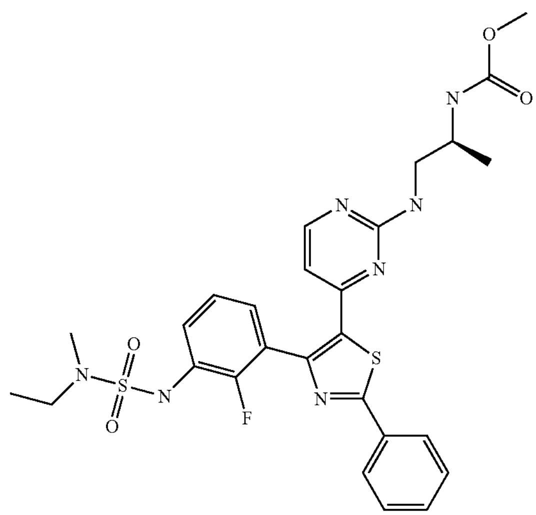 [SMILES: CCN(C)S(=O)(=O)Nc1cccc(-c2nc(-c3ccccc3)sc2-c2ccnc(NC[C@H](C)NC(=O)OC)n2)c1F] | |
| P-2156 | methyl N-[(1S)-2-[[4-[4-[3-(cyclopropylsulfonylamino)-2-fluoro-phenyl]-2-phenyl-thiazol-5-yl]pyrimidin-2-yl]amino]-1-methyl-ethyl]carbamate | 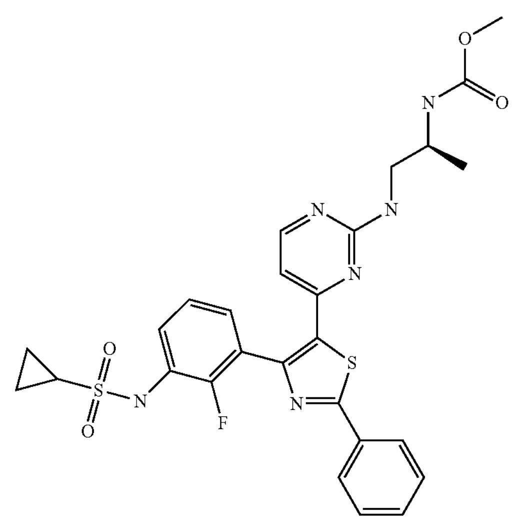 [SMILES: COC(=O)N[C@@H](C)CNc1nccc(-c2sc(-c3ccccc3)nc2-c2cccc(NS(=O)(=O)C3CC3)c2F)n1] | |

TABLE 1-continued

| Compound No. | Name | Structure | (MS (ESI) [M + H+]+) |
|---|---|---|---|
| P-2157 | methyl N-[(1S)-2-[[4-[4-[3-(cyclobutylsulfonylamino)-2-fluorophenyl]-2-phenyl-thiazol-5-yl]pyrimidin-2-yl]amino]-1-methyl-ethyl]carbamate | 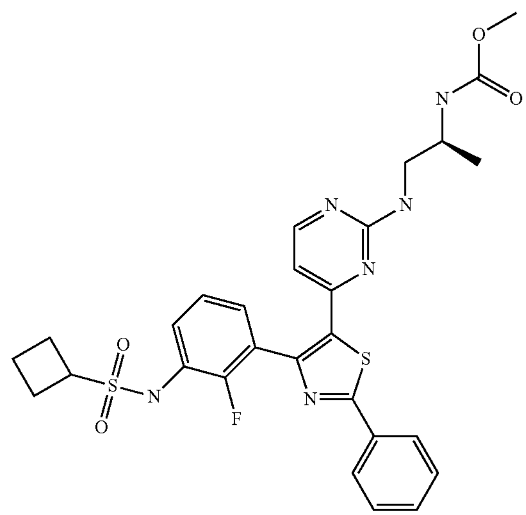 [SMILES: COC(=O)N[C@@H](C)CNc1nccc(-c2sc(-c3ccccc3)nc2-c2cccc(NS(=O)(=O)C3CCC3)c2F)n1] | |
| P-2158 | methyl N-[(1S)-2-[[4-[4-[3-(cyclopentylsulfonylamino)-2-fluorophenyl]-2-phenyl-thiazol-5-yl]pyrimidin-2-yl]amino]-1-methyl-ethyl]carbamate | 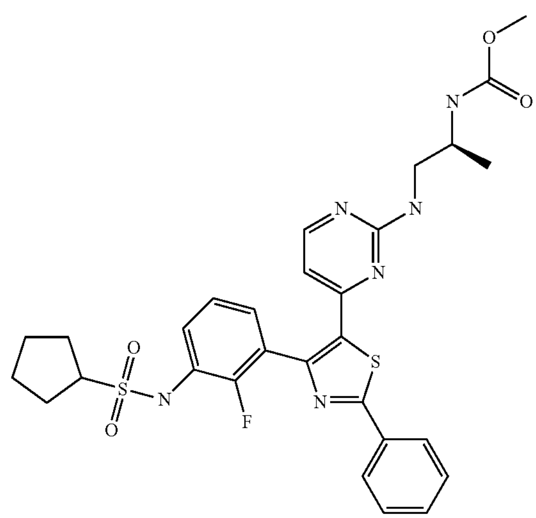 [SMILES: COC(=O)N[C@@H](C)CNc1nccc(-c2sc(-c3ccccc3)nc2-c2cccc(NS(=O)(=O)C3CCCC3)c2F)n1] | |
| P-2159 | methyl N-[(1S)-2-[[4-[4-[3-(cyclohexylsulfonylamino)-2-fluorophenyl]-2-phenyl-thiazol-5-yl]pyrimidin-2-yl]amino]-1-methyl-ethyl]carbamate | 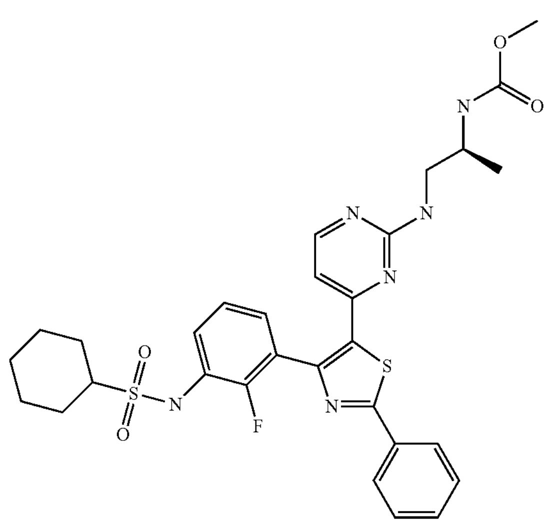 | |

TABLE 1-continued

| Compound No. | Name | Structure | (MS (ESI) [M + H+]+) |
|---|---|---|---|
| P-2160 | methyl N-[(1S)-2-[[4-[4-[5-chloro-2-fluoro-3-(pyrrolidin-1-ylsulfonylamino)phenyl]-1-isopropyl-pyrazol-3-yl]pyrimidin-2-yl]amino]-1-methyl-ethyl]carbamate | 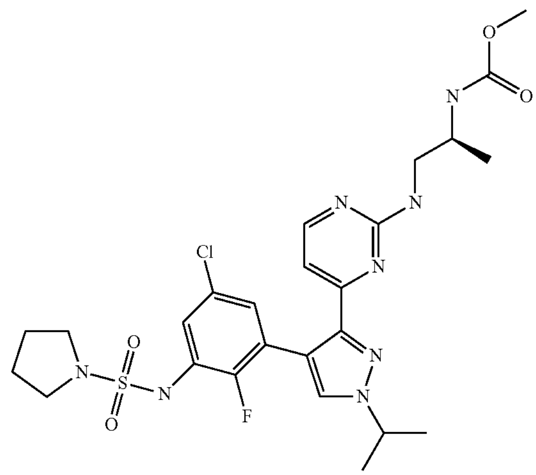 [SMILES: COC(=O)N[C@@H](C)CNc1nccc(-c2nn(C(C)C)cc2-c2cc(Cl)cc(NS(=O)(=O)N3CCCC3)c2F)n1] | 595.1 |
| P-2161 | methyl N-[(1S)-2-[[4-[4-[5-chloro-2-fluoro-3-[[(3R)-3-fluoropyrrolidin-1-yl]sulfonylamino]phenyl]-1-isopropyl-pyrazol-3-yl]pyrimidin-2-yl]amino]-1-methyl-ethyl]carbamate | 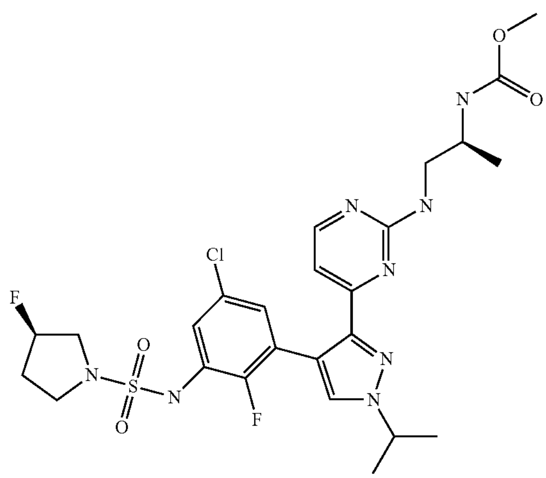 [SMILES: COC(=O)N[C@@H](C)CNc1nccc(-c2nn(C(C)C)cc2-c2cc(Cl)cc(NS(=O)(=O)N3CC[C@@H](F)C3)c2F)n1] | 613.1 |
| P-2162 | methyl N-[(1S)-2-[[4-[4-[5-chloro-2-fluoro-3-[[(3S)-3-fluoropyrrolidin-1-yl]sulfonylamino]phenyl]-1-isopropyl-pyrazol-3-yl]pyrimidin-2-yl]amino]-1-methyl-ethyl]carbamate | 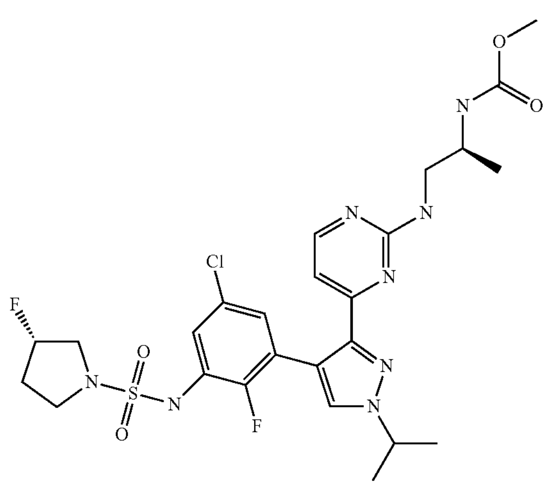 [SMILES: COC(=O)N[C@@H](C)CNc1nccc(-c2nn(C(C)C)cc2-c2cc(Cl)cc(NS(=O)(=O)N3CC[C@H](F)C3)c2F)n1] | |

TABLE 1-continued

| Compound No. | Name | Structure | (MS (ESI) [M + H⁺]⁺) |
|---|---|---|---|
| P-2163 | methyl N-[(1S)-2-[[4-[4-[3-(azetidin-1-ylsulfonylamino)-5-chloro-2-fluoro-phenyl]-1-isopropyl-pyrazol-3-yl]pyrimidin-2-yl]amino]-1-methyl-ethyl]carbamate | 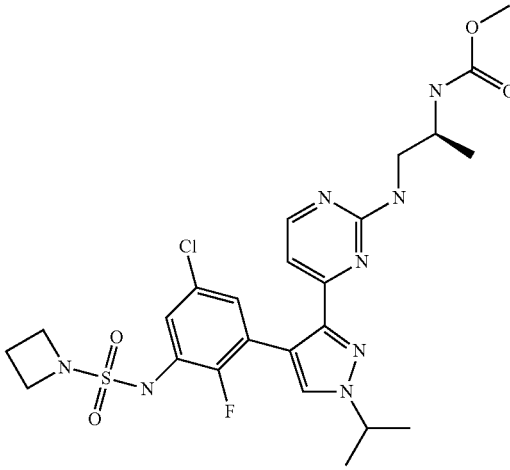 | 581.1 |
| P-2164 | methyl N-[(1S)-2-[[4-[4-[5-chloro-3-[[ethyl(methyl)sulfamoyl]amino]-2-fluoro-phenyl]-1-isopropyl-pyrazol-3-yl]pyrimidin-2-yl]amino]-1-methyl-ethyl]carbamate | 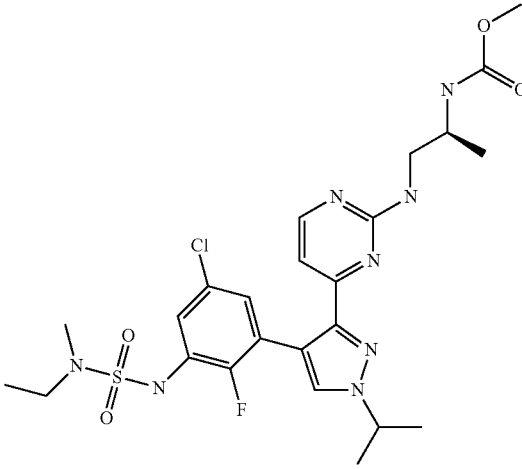 [SMILES: CCN(C)S(=O)(=O)Nc1cc(Cl)cc(-c2cn(C(C)C)nc2-c2ccnc(NC[C@H](C)NC(=O)OC)n2)c1F] | 583.1 |
| P-2165 | methyl N-[(1S)-2-[[4-[4-[5-chloro-3-(diethylsulfamoylamino)-2-fluoro-phenyl]-1-isopropyl-pyrazol-3-yl]pyrimidin-2-yl]amino]-1-methyl-ethyl]carbamate | 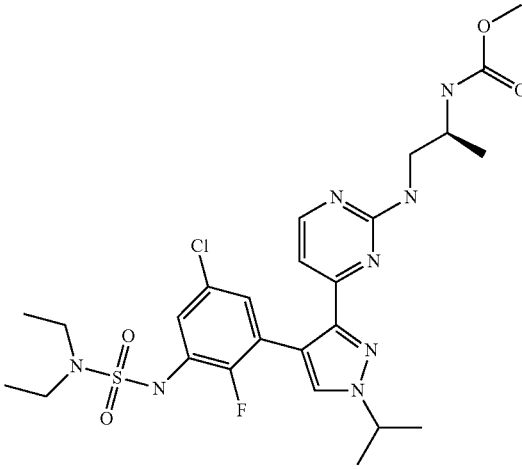 [SMILES: CCN(CC)S(=O)(=O)Nc1cc(Cl)cc(-c2cn(C(C)C)nc2-c2ccnc(NC[C@H](C)NC(=O)OC)n2)c1F] | 597.1 |

US 9,873,700 B2

123                                                                124

TABLE 1-continued

| Compound No. | Name | Structure | (MS (ESI) [M + H⁺]⁺) |
|---|---|---|---|
| P-2166 | methyl N-[(1S)-2-[[4-[4-[5-chloro-3-(dimethylsulfamoylamino)-2-fluorophenyl]-1-isopropyl-pyrazol-3-yl]pyrimidin-2-yl]amino]-1-methylethyl]carbamate | 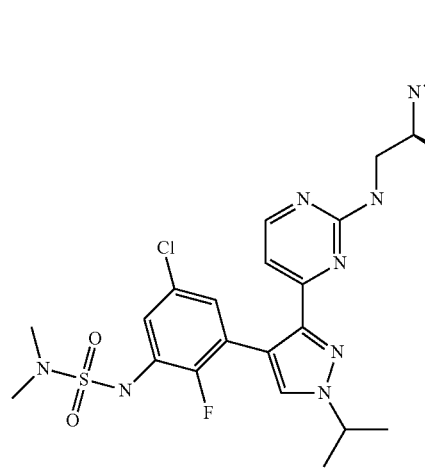 | 569.1 |
| P-2167 | methyl N-[(1S)-2-[[4-[4-[5-chloro-3-(cyclohexylsulfonylamino)-2-fluorophenyl]-1-isopropyl-pyrazol-3-yl]pyrimidin-2-yl]amino]-1-methylethyl]carbamate | 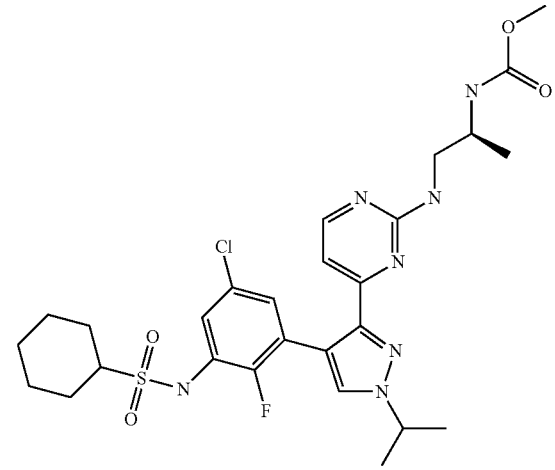 [SMILES: COC(=O)N[C@@H](C)CNc1nccc(-c2nn(C(C)C)cc2-c2cc(Cl)cc(NS(=O)(=O)C3CCCCC3)c2F)n1] | |
| P-2168 | methyl N-[(1S)-2-[[4-[4-[5-chloro-3-(cyclopentylsulfonylamino)-2-fluorophenyl]-1-isopropyl-pyrazol-3-yl]pyrimidin-2-yl]amino]-1-methylethyl]carbamate | 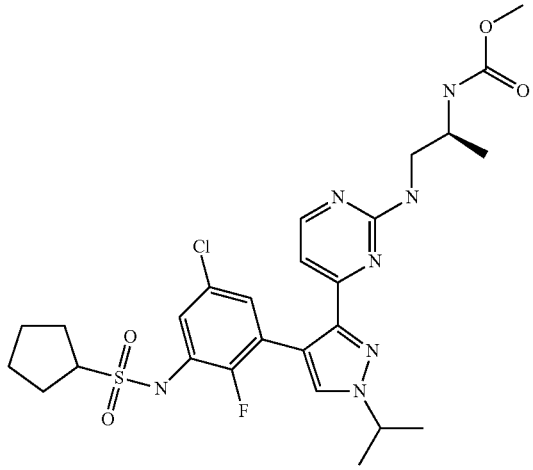 [SMILES: COC(=O)N[C@@H](C)CNc1nccc(-c2nn(C(C)C)cc2-c2cc(Cl)cc(NS(=O)(=O)C3CCCC3)c2F)n1] | |

TABLE 1-continued

| Compound No. | Name | Structure | (MS (ESI) [M + H⁺]⁺) |
|---|---|---|---|
| P-2169 | methyl N-[(1S)-2-[[4-[4-[5-chloro-3-(cyclobutylsulfonylamino)-2-fluorophenyl]-1-isopropyl-pyrazol-3-yl]pyrimidin-2-yl]amino]-1-methyl-ethyl]carbamate | 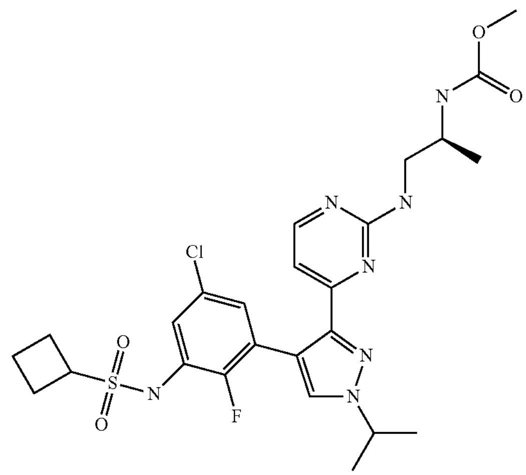 [SMILES: COC(=O)N[C@@H](C)CNc1nccc(-c2nn(C(C)C)cc2-c2cc(Cl)cc(NS(=O)(=O)C3CCC3)c2F)n1] | 580.1 |
| P-2170 | methyl N-[(1S)-2-[[4-[4-[5-chloro-3-(cyclopropylsulfonylamino)-2-fluorophenyl]-1-isopropyl-pyrazol-3-yl]pyrimidin-2-yl]amino]-1-methyl-ethyl]carbamate | 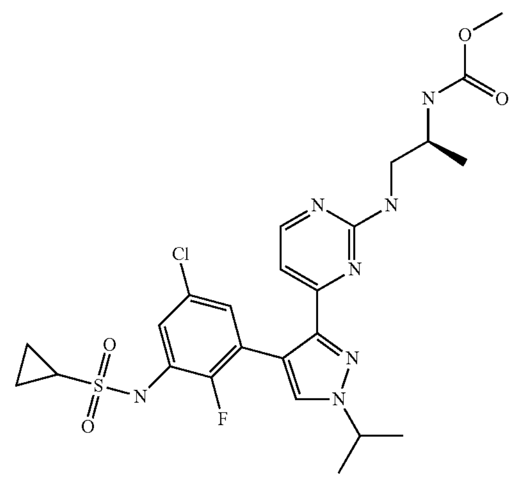 [SMILES: COC(=O)N[C@@H](C)CNc1nccc(-c2nn(C(C)C)cc2-c2cc(Cl)cc(NS(=O)(=O)C3CC3)c2F)n1] | 566.0 |
| P-2181 | methyl N-[(1S)-2-[[4-[3-[5-chloro-2-fluoro-3-(1-piperidylsulfonylamino)phenyl]-1-isopropyl-pyrazol-4-yl]pyrimidin-2-yl]amino]-1-methyl-ethyl]carbamate | 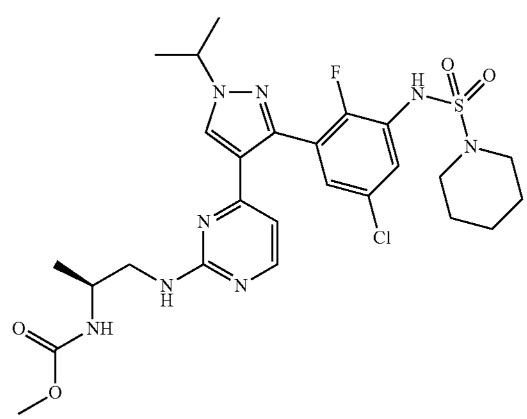 [SMILES: COC(=O)N[C@@H](C)CNc1nccc(-c2cn(C(C)C)nc2-c2cc(Cl)cc(NS(=O)(=O)N3CCCCC3)c2F)n1] | 609.1 |

The asterisk * in Table 1 indicates the observed MS (ESI) [M − H⁺]⁻molecular weights.

Some embodiments described herein provide a compound as set forth in Table 2 or a pharmaceutically acceptable salt, hydrate, solvate, isomers, tautomers or deuterated analogs thereof.

TABLE 2

| Compound No. | Name | Structure | MS(ESI) [M + H⁺]⁺ observed |
|---|---|---|---|
| P-2171 | N-[3-[5-(2-cyclopropylpyrimidin-5-yl)-1H-pyrrolo[2,3-b]pyridine-3-carbonyl]-2,5-difluoro-phenyl]pyrrolidine-1-sulfonamide | 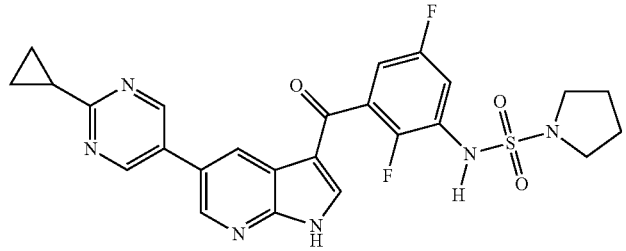 [SMILES: O=C(c1cc(F)cc(NS(=O)(=O)N2CCCC2)c1F)c1c[nH]c2ncc(-c3cnc(C4CC4)nc3)cc12] | 525.3 |
| P-2172 | (3R)-N-[3-[5-(2-cyclopropylpyrimidin-5-yl)-1H-pyrrolo[2,3-b]pyridine-3-carbonyl]-2,5-difluoro-phenyl]-3-fluoro-pyrrolidine-1-sulfonamide | 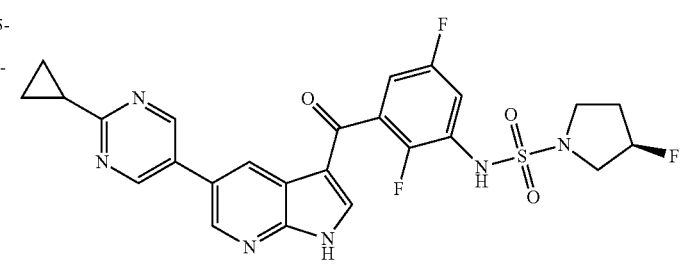 | 543.3 |
| P-2173 | 5-(2-cyclopropylpyrimidin-5-yl)-3-[3-(dimethylsulfamoylamino)-2,5-difluoro-benzoyl]-1H-pyrrolo[2,3-b]pyridine | 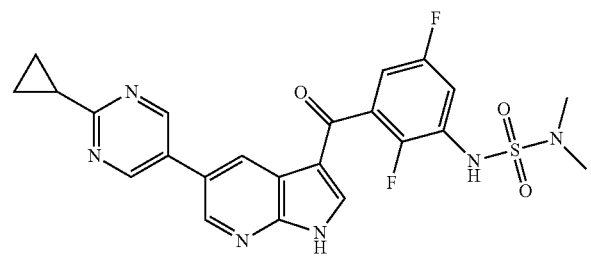 [SMILES: CN(C)S(=O)(=O)Nc1cc(F)cc(C(=O)c2c[nH]c3ncc(-c4cnc(C5CC5)nc4)cc23)c1F] | 499.3 |
| P-2174 | (3R)-N-[5-chloro-3-[5-(2-cyclopropylpyrimidin-5-yl)-1H-pyrrolo[2,3-b]pyridine-3-carbonyl]-2-fluoro-phenyl]-3-fluoro-pyrrolidine-1-sulfonamide | 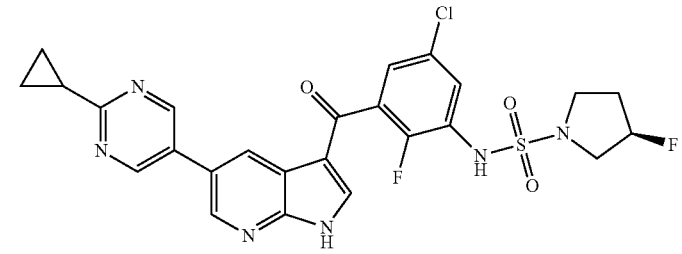 [SMILES: O=C(c1cc(Cl)cc(NS(=O)(=O)N2CC[C@@H](F)C2)c1F)c1c[nH]c2ncc(-c3cnc(C4CC4)nc3)cc12] | 559.2 |
| P-2175 | 3-[5-chloro-3-(dimethylsulfamoylamino)-2-fluoro-benzoyl]-5-(2-cyclopropylpyrimidin-5-yl)-1H-pyrrolo[2,3-b]pyridine | 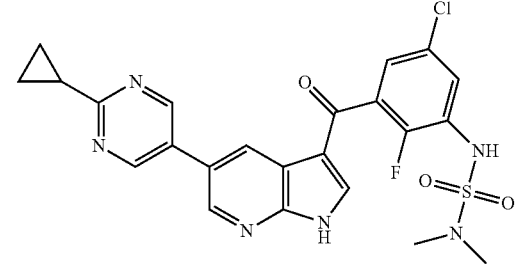 [SMILES: CN(C)S(=O)(=O)Nc1cc(Cl)cc(C(=O)c2c[nH]c3ncc(-c4cnc(C5CC5)nc4)cc23)c1F] | 515.2 |
| P-2176 | N-[5-chloro-3-[5-(2-cyclopropylpyrimidin-5-yl)-1H-pyrrolo[2,3-b]pyridine-3-carbonyl]-2-fluoro-phenyl]-2,2,5,5-tetradeuterio-pyrrolidine-1-sulfonamide | 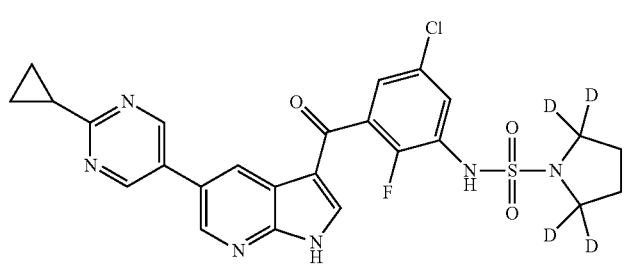 [SMILES: [2H]C1([2H])CCC([2H])([2H])N1S(=O)(=O)Nc1cc(Cl)cc(C(=O)c2c[nH]c3ncc(-c4cnc(C5CC5)nc4)cc23)c1F] | 545.1 |

TABLE 2-continued

| Compound No. | Name | Structure | MS(ESI) [M + H+]+ observed |
|---|---|---|---|
| P-2177 | N-[5-chloro-3-[5-(2-cyclopropylpyrimidin-5-yl)-1H-pyrrolo[2,3-b]pyridine-3-carbonyl]-2-fluoro-phenyl]-2,2,3,3,4,4,5,5-octadeuterio-pyrrolidine-1-sulfonamide | 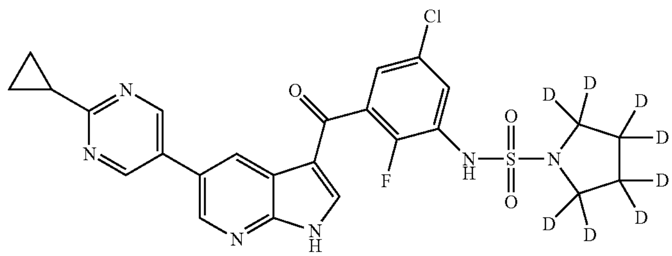 [SMILES: [2H]C1([2H])N(S(=O)(=O)Nc2cc(Cl)cc(C(=O)c3c[nH]c4ncc(-c5cnc(C6CC6)nc5)cc34)c2F)C([2H])([2H])C([2H])([2H])C1([2H])[2H]] | 549.0 |
| P-2178 | (3R)-N-[3-[5-(2-cyclopropylpyrimidin-5-yl)-1H-pyrrolo[2,3-b]pyridine-3-carbonyl]-2-fluoro-5-(trifluoromethyl)phenyl]-3-fluoro-pyrrolidine-1-sulfonamide | 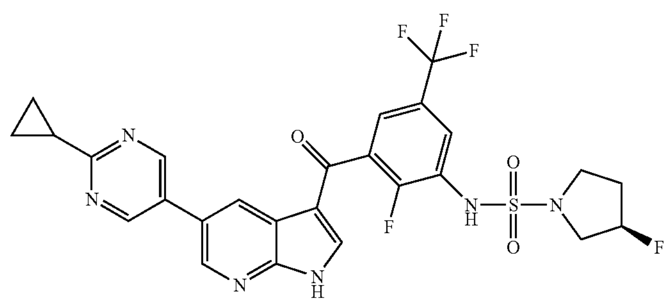 [SMILES: O=C(c1cc(C(F)(F)F)cc(NS(=O)(=O)N2CC[C@@H](F)C2)c1F)c1c[nH]c2ncc(-c3cnc(C4CC4)nc3)cc12] | 593.1 |
| P-2179 | N-[3-[5-(2-cyclopropylpyrimidin-5-yl)-1H-pyrrolo[2,3-b]pyridine-3-carbonyl]-2-fluoro-5-(trifluoromethyl)phenyl]pyrrolidine-1-sulfonamide | 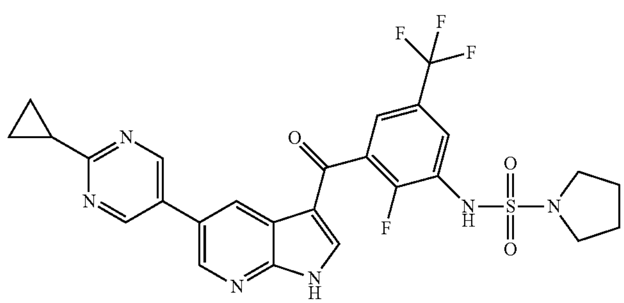 [SMILES: O=C(c1cc(C(F)(F)F)cc(NS(=O)(=O)N2CCCC2)c1F)c1c[nH]c2ncc(-c3cnc(C4CC4)nc3)cc12] | 575.1 |
| P-2180 | N-(5-chloro-3-(5-(2-cyclopropylpyrimidin-5-yl)-1H-pyrrolo[2,3-b]pyridine-3-carbonyl)-2-fluorophenyl)pyrrolidine-1-sulfonamide | 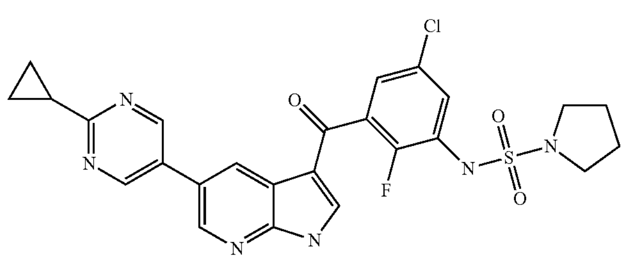 [SMILES: O=C(c1cc(Cl)cc(NS(=O)(=O)N2CCCC2)c1F)c1c[nH]c2ncc(-c3cnc(C4CC4)nc3)cc12] | 540.9 |
| P-2182 | (3R)-N-[3-[5-(2-cyclopropylpyrimidin-5-yl)-1H-pyrrolo[2,3-b]pyridine-3-carbonyl]-2-fluoro-5-methyl-phenyl]-3-fluoro-pyrrolidine-1-sulfonamide | 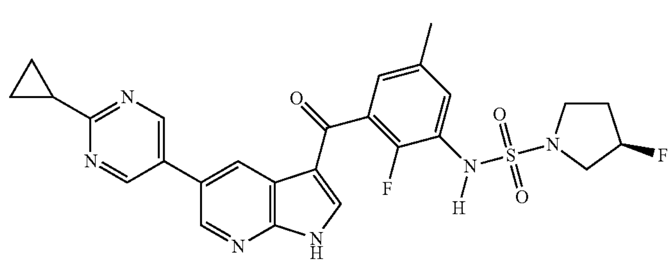 [SMILES: Cc1cc(NS(=O)(=O)N2CC[C@@H](F)C2)c(F)c(C(=O)c2c[nH]c3ncc(-c4cnc(C5CC5)nc4)cc23)c1] | 538.6 |

TABLE 2-continued

| Compound No. | Name | Structure | MS(ESI) [M + H⁺]⁺ observed |
|---|---|---|---|
| P-2183 | N-[3-[5-(2-cyclopropylpyrimidin-5-yl)-1H-pyrrolo[2,3-b]pyridine-3-carbonyl]-2-fluoro-5-methyl-phenyl]pyrrolidine-2-sulfonamide | 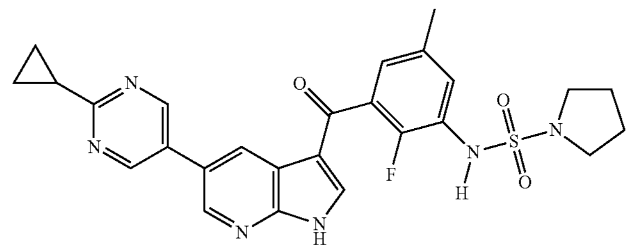 [SMILES: Cc1cc(NS(=O)(=O)N2CCCC2)c(F)c(C(=O)c2c[nH]c3ncc(-c4cnc(C5CC5)nc4)cc23)c1] | 520.6 |

IV. Methods

In another aspect, the present disclosure provides a method for regulating or modulating a MAPK pathway signaling. The method includes selectively inhibiting the MAPK pathway in a first cell having a mutant RAF kinase with a compound of formula (I) or a compound of any of the subgeneric formulas of formula (I), or a compound as described herein, or a pharmaceutically acceptable salt or a solvate or hydrate thereof, or a composition comprising a compound of formula (I') or (I) or a compound of any of the subgeneric formulas of formula (I), for example, formulas (Ia), (Ia-1), (Ia-2), (Ib), (Ib-1), (Ib-2), (Ib-1a), (Ib-1b), (Ic), (Ic-1), (Ic-1a), (Ic-2), (Ic-2a), (Id), (Id-1), (Id-1a), (Id-2), (Id-2a), (Ie), (Ie-1), (Ie-1a), (Ie-2), (Ie-2a), (If), (If-1), (If-2), (If-3), (If-4), (Ig), (Ig-1), (Ig-2), (Ig-3), (Ig-4), (Ih), (Ih-1), (Ih-2), (Ih-3), (Ih-4), (Ij), (Ij-1) or (Ij-2), or any of the compounds described herein, or a pharmaceutically acceptable salt or a solvate or hydrate thereof, wherein the compound does not induce the activation of the MAPK pathway in a second cell. In some embodiments, the selectively inhibiting comprises selectively inhibiting a mutant Raf kinase in a first cell. In some embodiments, the mutant RAF kinase is a mutant A-raf kinase, a mutant BRAF kinase, a mutant c-Raf kinase or combinations thereof. In one embodiment, the mutant RAD kinase is a mutant BRAF kinase. In certain embodiments, the mutant Raf kinase is mutant BRAF kinase. In one embodiment, the regulating, modulating or inhibiting of a MAPK pathway signaling can be achieved through regulating the interaction of a BRAF kinase inhibitor as described herein with the Leucine 505 amino acid residue in the C-terminal end of an αC helix, such that there is no activation of MAPK pathway in a second cell as determined by monitoring the levels of pERK and/or pMEK. In one instance, the BRAF inhibitor is in direct contact with the Leucine 505 amino acid residue in the C-terminal end of an αC helix. In some embodiments, the second cell has RAS mutation or upstream receptor tyrosine kinase activation. In some embodiments, the disclosure provides contacting a cell having a mutant BRAF kinase with a BRAF inhibitor. In one embodiment, the regulating, modulating or inhibiting of a MAPK pathway signaling can be achieved through regulating the interaction of a BRAF kinase inhibitor as described herein with the Leucine 505 amino acid residue in the C-terminal end of an αC helix, such that there is no activation of pERK kinase.

In some embodiments of the methods provided herein, the RAF inhibitor, e.g., a BRAF inhibitor is a molecule/compound containing a sulfamoylamino group having the formula:

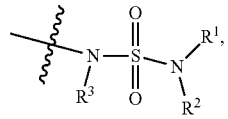

wherein $R^1$, $R^2$ and $R^3$ are as defined in any embodiments of compounds of formula (I) or any subgeneric formulas of formula (I). In certain embodiments, $R^1$ and $R^2$ are each independently optionally substituted alkyl, aryl, heteroaryl, cycloalkyl or $R^1$ and $R^2$ taken together to form a optionally substituted 5- or 6-membered heterocycloalkyl ring having from 0-1 heteroatoms selected from O, N or S; $R^3$ is H or $C_{1-6}$alkyl; and the wavy line indicates the point of attachment to the rest of the molecule. In certain embodiments, the BRAF inhibitor is a compound having formula (I'):

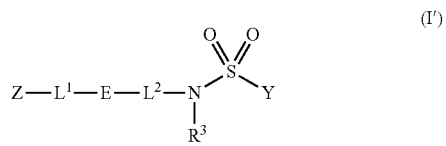

where the variables Z, $L^1$, E, $L^2$, $R^3$ and Y are as defined in any embodiments of compounds of formula (I) and subgeneric formulas of formula (I) as described herein. In one embodiment, Y is —N($R^1$)($R^2$). In another embodiment, Y is —C($R^8$)($R^9$)($R^{10}$). In one embodiment, $R^3$ is H. In another embodiment, $R^1$ is methyl and $R^2$ is ethyl. In other embodiments, $R^1$ and $R^2$ taken together with the nitrogen atom to which they are attached form an optionally substituted 5-membered heterocycloalkyl ring.

In some embodiments of the methods provided herein, the BRAF inhibitor is a compound of formula (I') or (I) or a compound of any of the subgeneric formulas of formula (I), or a compound as described herein, or a pharmaceutically acceptable salt or a solvate or hydrate thereof, or a composition comprising a compound of formula (I) or (I') or a compound of any of the subgeneric formulas of formula (I), for example, formulas (Ia), (Ia-1), (Ia-2), (Ib), (Ib-1), (Ib-2), (Ib-1a), (Ib-1b), (Ic), (Ic-1), (Ic-1a), (Ic-2), (Ic-2a), (Id), (Id-1), (Id-1a), (Id-2), (Id-2a), (Ie), (Ie-1), (Ie-1a), (Ie-2), (Ie-2a), (If), (If-1), (If-2), (If-3), (If-4), (Ig), (Ig-1), (Ig-2), (Ig-3), (Ig-4), (Ih), (Ih-1), (Ih-2), (Ih-3), (Ih-4), (Ij), (Ij-1) or (Ij-2) or any of the compounds described herein, or a pharmaceutically acceptable salt or a solvate or hydrate thereof.

In some embodiments of the methods provided herein, the inhibition involves regulating the interaction of the —N($R^1$)($R^2$) or —C($R^8$)($R^9$)($R^{10}$) group of the BRAF kinase inhibitor with the Leucine 505 amino acid residue in the C-terminal end of an αC helix, wherein the wavy line indicates the point of attachment to the rest of the molecule. In one embodiment, the BRAF inhibitor is in direct contact with the Leucine 505 amino acid residue in the C-terminal end of an αC helix.

The cell can have RAS mutation or upstream receptor tyrosine kinase activation. In the methods provided herein, the inhibition of the mutant BRAF kinase does not activate the MAPK pathway in cells having RAS mutation or upstream receptor tyrosine kinase activation.

In some embodiments of the methods provided herein, the BRAF inhibitor is a compound listed in Table A.

TABLE A

N-[3-[5-(4-chlorophenyl)-1H-pyrrolo[2,3-b]pyridine-3-carbonyl]-2-fluoro-phenyl]pyrrolidine-1-sulfonamide (P-0012);
5-chloro-3-[3-[[ethyl(methyl)sulfamoyl]amino]-2,6-difluoro-benzoyl]-1H-pyrrolo[2,3-b]pyridine (P-0013);
5-(4-chlorophenyl)-3-[3-[[ethyl(methyl)sulfamoyl]amino]-2,6-difluoro-benzoyl]-1H-pyrrolo[2,3-b]pyridine (P-0014);
3-[3-[[ethyl(methyl)sulfamoyl]amino]-2,6-difluoro-benzoyl]-5-(2-methoxypyrimidin-5-yl)-1H-pyrrolo[2,3-b]pyridine (P-0015);
N-[2,4-difluoro-3-(5-fluoro-4-iodo-1H-pyrrolo[2,3-b]pyridine-3-carbonyl)phenyl]pyrrolidine-1-sulfonamide (P-0016);
N-[3-[4-(cyclopropylmethylamino)-5-fluoro-1H-pyrrolo[2,3-b]pyridine-3-carbonyl]-2,4-difluoro-phenyl]pyrrolidine-1-sulfonamide (P-0017);
5-cyano-3-[3-[[ethyl(methyl)sulfamoyl]amino]-2,6-difluoro-benzoyl]-1H-pyrrolo[2,3-b]pyridine (P-0018);
5-chloro-3-[3-[[ethyl(methyl)sulfamoyl]amino]-2-fluoro-benzoyl]-1H-pyrrolo[2,3-b]pyridine (P-0019);
5-(4-chlorophenyl)-3-[3-[[ethyl(methyl)sulfamoyl]amino]-2-fluoro-benzoyl]-1H-pyrrolo[2,3-b]pyridine (P-0020);
3-[3-[[ethyl(methyl)sulfamoyl]amino]-2-fluoro-benzoyl]-5-(2-methoxypyrimidin-5-yl)-1H-pyrrolo[2,3-b]pyridine (P-0021);
N-[3-[5-(4-chlorophenyl)-1H-pyrrolo[2,3-b]pyridine-3-carbonyl]-2,4-difluoro-phenyl]pyrrolidine-1-sulfonamide (P-0022);
N-[3-[5-[2-(dimethylamino)pyrimidin-5-yl]-1H-pyrrolo[2,3-b]pyridine-3-carbonyl]-2,4-difluoro-phenyl]pyrrolidine-1-sulfonamide (P-0023);
N-[2-fluoro-3-(5-methyl-1H-pyrrolo[2,3-b]pyridine-3-carbonyl)phenyl]pyrrolidine-1-sulfonamide (P-0024);
N-[2,4-difluoro-3-(5-iodo-1H-pyrrolo[2,3-b]pyridine-3-carbonyl)phenyl]pyrrolidine-1-sulfonamide (P-0025);
3-[3-[[cyclopropyl(methyl)sulfamoyl]amino]-2-fluoro-benzoyl]-5-(2-methoxypyrimidin-5-yl)-1H-pyrrolo[2,3-b]pyridine (P-0026);
[2-fluoro-3-(methylsulfamoylamino)phenyl]-[5-(2-methoxypyrimidin-5-yl)-1H-pyrrolo[2,3-b]pyridin-3-yl]methanone (P-0027);
5-(4-cyanophenyl)-3-[3-(dimethylsulfamoylamino)-2-fluoro-benzoyl]-1H-pyrrolo[2,3-b]pyridine (P-0028);
3-[3-(dimethylsulfamoylamino)-2-fluoro-benzoyl]-5-(3-pyridyl)-1H-pyrrolo[2,3-b]pyridine (P-0029);
3-[3-(dimethylsulfamoylamino)-2-fluoro-benzoyl]-5-(6-methyl-3-pyridyl)-1H-pyrrolo[2,3-b]pyridine (P-0030);
5-[6-(dimethylamino)-3-pyridyl]-3-[3-(dimethylsulfamoylamino)-2-fluoro-benzoyl]-1H-pyrrolo[2,3-b]pyridine (P-0031);
5-(4-cyanophenyl)-3-[3-[[ethyl(methyl)sulfamoyl]amino]-2-fluoro-benzoyl]-1H-pyrrolo[2,3-b]pyridine (P-0032);
3-[3-[[ethyl(methyl)sulfamoyl]amino]-2-fluoro-benzoyl]-5-(3-pyridyl)-1H-pyrrolo[2,3-b]pyridine (P-0033);
3-[3-[[ethyl(methyl)sulfamoyl]amino]-2-fluoro-benzoyl]-5-(6-methyl-3-pyridyl)-1H-pyrrolo[2,3-b]pyridine (P-0034);
3-[3-[[ethyl(methyl)sulfamoyl]amino]-2-fluoro-benzoyl]-5-(4-fluorophenyl)-1H-pyrrolo[2,3-b]pyridine (P-0035);
3-[3-(dimethylsulfamoylamino)-2-fluoro-benzoyl]-5-(4-fluorophenyl)-1H-pyrrolo[2,3-b]pyridine;
3-[3-[[ethyl(methyl)sulfamoyl]amino]-2-fluoro-benzoyl]-5-phenyl-1H-pyrrolo[2,3-b]pyridine (P-0036);
3-[3-(dimethylsulfamoylamino)-2-fluoro-benzoyl]-5-phenyl-1H-pyrrolo[2,3-b]pyridine (P-0037);
5-bromo-3-[3-[[ethyl(methyl)sulfamoyl]amino]-2-fluoro-benzoyl]-1H-pyrrolo[2,3-b]pyridine (P-0038);
5-cyano-3-[3-[[ethyl(methyl)sulfamoyl]amino]-2-fluoro-benzoyl]-1H-pyrrolo[2,3-b]pyridine (P-0039);
3-[2-fluoro-3-[[methyl(propyl)sulfamoyl]amino]benzoyl]-5-(2-methoxypyrimidin-5-yl)-1H-pyrrolo[2,3-b]pyridine (P-0040);
3-benzyloxy-N-[2-fluoro-3-[5-(2-methoxypyrimidin-5-yl)-1H-pyrrolo[2,3-b]pyridine-3-carbonyl]phenyl]pyrrolidine-1-sulfonamide (P-0041);
1-cyclopropyl-N-[2-fluoro-3-[5-(1-methylpyrazol-4-yl)-1H-pyrrolo[2,3-b]pyridine-3-carbonyl]phenyl]methanesulfonamide (P-0042);
N-[2-fluoro-3-[5-(3-pyridyl)-1H-pyrrolo[2,3-b]pyridine-3-carbonyl]phenyl]pyrrolidine-1-sulfonamide (P-0043);
N-[3-[5-(2,4-dimethoxypyrimidin-5-yl)-1H-pyrrolo[2,3-b]pyridine-3-carbonyl]-2-fluoro-phenyl]pyrrolidine-1-sulfonamide (P-0044);
N-[2-fluoro-3-[5-(6-methyl-3-pyridyl)-1H-pyrrolo[2,3-b]pyridine-3-carbonyl]phenyl]pyrrolidine-1-sulfonamide (P-0045);
N-[3-[5-[6-(dimethylamino)-3-pyridyl]-1H-pyrrolo[2,3-b]pyridine-3-carbonyl]-2-fluoro-phenyl]pyrrolidine-1-sulfonamide (P-0046);
N-[2-fluoro-3-[5-(2-isopropylpyrimidin-5-yl)-1H-pyrrolo[2,3-b]pyridine-3-carbonyl]phenyl]pyrrolidine-1-sulfonamide (P-0047);
N-[3-[5-(2-cyclopropylpyrimidin-5-yl)-1H-pyrrolo[2,3-b]pyridine-3-carbonyl]-2-fluoro-phenyl]pyrrolidine-1-sulfonamide (P-0048);
N-[3-[5-(4-cyano-3-methoxy-phenyl)-1H-pyrrolo[2,3-b]pyridine-3-carbonyl]-2-fluoro-phenyl]pyrrolidine-1-sulfonamide (P-0049);
N-[3-[5-[4-(1-cyanocyclopropyl)phenyl]-1H-pyrrolo[2,3-b]pyridine-3-carbonyl]-2-fluoro-phenyl]pyrrolidine-1-sulfonamide (P-0050);
3-[3-(dimethylsulfamoylamino)-2-fluoro-benzoyl]-5-(2-isopropylpyrimidin-5-yl)-1H-pyrrolo[2,3-b]pyridine (P-0051);
5-(2-cyclopropylpyrimidin-5-yl)-3-[3-(dimethylsulfamoylamino)-2-fluoro-benzoyl]-1H-pyrrolo[2,3-b]pyridine (P-0052);
3-[3-(dimethylsulfamoylamino)-2-fluoro-benzoyl]-5-[6-(trifluoromethyl)-3-pyridyl]-1H-pyrrolo[2,3-b]pyridine (P-0053);

TABLE A-continued 5-(4-cyano-3-methoxy-phenyl)-3-[3-(dimethylsulfamoylamino)-2-fluoro-benzoyl]-1H-pyrrolo[2,3-b]pyridine (P-0054);
5-[4-(1-cyanocyclopropyl)phenyl]-3-[3-(dimethylsulfamoylamino)-2-fluoro-benzoyl]-1H-pyrrolo[2,3-b]pyridine (P-0055);
3-[3-[[ethyl(methyl)sulfamoyl]amino]-2-fluoro-benzoyl]-5-(2-methylpyrimidin-5-yl)-1H-pyrrolo[2,3-b]pyridine (P-0056);
3-[3-[[ethyl(methyl)sulfamoyl]amino]-2-fluoro-benzoyl]-5-(2-isopropylpyrimidin-5-yl)-1H-pyrrolo[2,3-b]pyridine (P-0057);
5-(2-cyclopropylpyrimidin-5-yl)-3-[3-[[ethyl(methyl)sulfamoyl]amino]-2-fluoro-benzoyl]-1H-pyrrolo[2,3-b]pyridine (P-0058);
3-[3-[[ethyl(methyl)sulfamoyl]amino]-2-fluoro-benzoyl]-5-[6-(trifluoromethyl)-3-pyridyl]-1H-pyrrolo[2,3-b]pyridine (P-0059);
5-(4-cyano-3-methoxy-phenyl)-3-[3-[[ethyl(methyl)sulfamoyl] amino]-2-fluoro-benzoyl]-1H-pyrrolo[2,3-b]pyridine (P-0060);
5-[4-(1-cyanocyclopropyl)phenyl]-3-[3-[[ethyl(methyl)sulfamoyl]amino]-2-fluoro-benzoyl]-1H-pyrrolo[2,3-b]pyridine (P-0061);
N-[2-fluoro-3-[5-(4-fluorophenyl)-1H-pyrrolo[2,3-b]pyridine-3-carbonyl]phenyl]pyrrolidine-1-sulfonamide (P-0062);
N-[2-fluoro-3-(5-phenyl-1H-pyrrolo[2,3-b]pyridine-3-carbonyl)phenyl]pyrrolidine-1-sulfonamide (P-0063);
5-[2-(cyclopropylamino)pyrimidin-5-yl]-3-[3-(dimethylsulfamoylamino)-2-fluoro-benzoyl]-1H-pyrrolo[2,3-b]pyridine (P-0064);
N-[2-fluoro-3-[5-(2-methoxypyrimidin-5-yl)-1H-pyrrolo[2,3-b]pyridine-3-carbonyl]phenyl]-2-methoxy-ethanesulfonamide (P-0065);
methyl 3-[[2-fluoro-3-[5-(2-methoxypyrimidin-5-yl)-1H-pyrrolo[2,3-b]pyridine-3-carbonyl]phenyl]sulfamoyl]propanoate (P-0066);
N-[2-fluoro-3-[5-(2-methoxypyrimidin-5-yl)-1H-pyrrolo[2,3-b]pyridine-3-carbonyl]phenyl]cyclopropanesulfonamide (P-0067);
[3-(ethylsulfamoylamino)-2-fluoro-phenyl]-[5-(2-methoxypyrimidin-5-yl)-1H-pyrrolo[2,3-b]pyridin-3-yl]methanone (P-0068);
[3-(ethylsulfamoylamino)-2-fluoro-phenyl]-(5-iodo-1H-pyrrolo[2,3-b]pyridin-3-yl)methanone (P-0069);
3-[2-fluoro-3-[[isobutyl(methyl)sulfamoyl]amino]benzoyl]-5-iodo-1H-pyrrolo[2,3-b]pyridine (P-0070);
[2-fluoro-3-(isopropylsulfamoylamino)phenyl]-(5-iodo-1H-pyrrolo[2,3-b]pyridin-3-yl)methanone (P-0071);
3-[2-fluoro-3-[[isobutyl(methyl)sulfamoyl]amino]benzoyl]-5-(2-methoxypyrimidin-5-yl)-1H-pyrrolo[2,3-b]pyridine (P-0072);
3-[2-fluoro-3-[[2-methoxyethyl(methyl)sulfamoyl]amino]benzoyl]-5-(2-methoxypyrimidin-5-yl)-1H-pyrrolo[2,3-b]pyridine (P-0073);
N-[2-fluoro-3-[5-(2-methoxypyrimidin-5-yl)-1H-pyrrolo[2,3-b]pyridine-3-carbonyl]phenyl]-2-methyl-pyrrolidine-1-sulfonamide (P-0074);
3-[2-fluoro-3-[[isopropyl(methyl)sulfamoyl]amino]benzoyl]-5-(2-methoxypyrimidin-5-yl)-1H-pyrrolo[2,3-b]pyridine (P-0075);
5-[6-(dimethylamino)-3-pyridyl]-3-[3-[[ethyl(methyl)sulfamoyl]amino]-2-fluoro-benzoyl]-1H-pyrrolo[2,3-b]pyridine (P-0076);
5-[2-(cyclopropylamino)pyrimidin-5-yl]-3-[3-[[ethyl(methyl)sulfamoyl]amino]-2-fluoro-benzoyl]-1H-pyrrolo[2,3-b]pyridine (P-0077);
5-(2-cyclopropylpyrimidin-5-yl)-3-[2,6-difluoro-3-[[methyl(propyl)sulfamoyl]amino]benzoyl]-1H-pyrrolo[2,3-b]pyridine (P-0078);
5-[4-(1-cyanocyclopropyl)phenyl]-3-[2,6-difluoro-3-[[methyl(propyl)sulfamoyl]amino]benzoyl]-1H-pyrrolo[2,3-b]pyridine (P-0079);
5-[4-(1-cyanocyclopropyl)phenyl]-3-[2-fluoro-3-[[2-methoxyethyl(methyl)sulfamoyl]amino]benzoyl]-1H-pyrrolo[2,3-b]pyridine (P-0080);
5-[2-(cyclopropylamino)pyrimidin-5-yl]-3-[2-fluoro-3-[[2-methoxyethyl(methyl)sulfamoyl]amino]benzoyl]-1H-pyrrolo[2,3-b]pyridine (P-0081);
5-[2-(cyclopropylamino)pyrimidin-5-yl]-3-[2-fluoro-3-[[methyl(propyl)sulfamoyl]amino]benzoyl]-1H-pyrrolo[2,3-b]pyridine (P-0082);
3-[3-[[cyclopropylmethyl(methyl)sulfamoyl]amino]-2-fluoro-benzoyl]-5-(2-methoxypyrimidin-5-yl)-1H-pyrrolo[2,3-b]pyridine (P-0083);
3-[3-[[cyclopropylmethyl(methyl)sulfamoyl]amino]-2-fluoro-benzoyl]-5-(2-cyclopropylpyrimidin-5-yl)-1H-pyrrolo[2,3-b]pyridine (P-0084);
5-(2-cyclopropylpyrimidin-5-yl)-3-[2-fluoro-3-[[2-methoxyethyl(methyl)sulfamoyl]amino]benzoyl]-1H-pyrrolo[2,3-b]pyridine (P-0085);
5-(2-cyclopropylpyrimidin-5-yl)-3-[2-fluoro-3-[[methyl(propyl)sulfamoyl]amino]benzoyl]-1H-pyrrolo[2,3-b]pyridine (P-0086);
5-(6-cyclopropyl-3-pyridyl)-3-[3-[[ethyl(methyl)sulfamoyl]amino]-2-fluoro-benzoyl]-1H-pyrrolo[2,3-b]pyridine (P-0087);
3,3-difluoro-N-[2-fluoro-3-[5-(2-methoxypyrimidin-5-yl)-1H-pyrrolo[2,3-b]pyridine-3-carbonyl]phenyl]azetidine-1-sulfonamide (P-0088);
4-[[(1S)-1-cyclopropylethyl]amino]-5-[3-[[ethyl(methyl)sulfamoyl]amino]-2-fluoro-benzoyl]-7H-pyrrolo[2,3-d]pyrimidine (P-0089);
N-[3-[5-(4-cyanophenyl)-1H-pyrrolo[2,3-b]pyridine-3-carbonyl]-2-fluoro-phenyl]pyrrolidine-1-sulfonamide (P-0090);
N-[3-[5-(2-cyanopyrimidin-5-yl)-1H-pyrrolo[2,3-b]pyridine-3-carbonyl]-2-fluoro-phenyl]pyrrolidine-1-sulfonamide (P-0091);
N-[2-fluoro-3-[5-(2-methylpyrimidin-5-yl)-1H-pyrrolo[2,3-b]pyridine-3-carbonyl]phenyl]pyrrolidine-1-sulfonamide (P-0092);
N-[3-[5-(5-cyano-3-pyridyl)-1H-pyrrolo[2,3-b]pyridine-3-carbonyl]-2-fluoro-phenyl]pyrrolidine-1-sulfonamide (P-0093);
N-[2-fluoro-3-[5-[6-(trifluoromethyl)-3-pyridyl]-1H-pyrrolo[2,3-b]pyridine-3-carbonyl]phenyl]pyrrolidine-1-sulfonamide (P-0095);
5-(2-cyanopyrimidin-5-yl)-3-[3-(dimethylsulfamoylamino)-2-fluoro-benzoyl]-1H-pyrrolo[2,3-b]pyridine (P-0096);

TABLE A-continued

3-[3-(dimethylsulfamoylamino)-2-fluoro-benzoyl]-5-(2-methylpyrimidin-5-yl)-1H-pyrrolo[2,3-b]pyridine (P-0097);
5-(5-cyano-3-pyridyl)-3-[3-(dimethylsulfamoylamino)-2-fluoro-benzoyl]-1H-pyrrolo[2,3-b]pyridine (P-0098);
5-(6-cyano-3-pyridyl)-3-[3-(dimethylsulfamoylamino)-2-fluoro-benzoyl]-1H-pyrrolo[2,3-b]pyridine (P-0099);
5-(2-cyanopyrimidin-5-yl)-3-[3-[[ethyl(methyl)sulfamoyl]amino]-2-fluoro-benzoyl]-1H-pyrrolo[2,3-b]pyridine (P-0100);
5-(5-cyano-3-pyridyl)-3-[3-[[ethyl(methyl)sulfamoyl]amino]-2-fluoro-benzoyl]-1H-pyrrolo[2,3-b]pyridine (P-0101);
5-(6-cyano-3-pyridyl)-3-[3-[[ethyl(methyl)sulfamoyl]amino]-2-fluoro-benzoyl]-1H-pyrrolo[2,3-b]pyridine (P-0102);
3-[3-(dimethylsulfamoylamino)-2-fluoro-benzoyl]-5-[4-(1-hydroxy-1-methyl-ethyl)phenyl]-1H-pyrrolo[2,3-b]pyridine (P-0103);
3-[3-[[ethyl(methyl)sulfamoyl]amino]-2-fluoro-benzoyl]-5-[4-(1-hydroxy-1-methyl-ethyl)phenyl]-1H-pyrrolo[2,3-b]pyridine (P-0104);
N-[2-fluoro-3-[5-[4-(1-hydroxy-1-methyl-ethyl)phenyl]-1H-pyrrolo[2,3-b]pyridine-3-carbonyl]phenyl]pyrrolidine-1-sulfonamide (P-0105);
5-[2-(dimethylamino)pyrimidin-5-yl]-3-[3-(dimethylsulfamoylamino)-2-fluoro-benzoyl]-1H-pyrrolo[2,3-b]pyridine (P-0106);
3-[3-(dimethylsulfamoylamino)-2-fluoro-benzoyl]-5-(2-pyrrolidin-1-ylpyrimidin-5-yl)-1H-pyrrolo[2,3-b]pyridine (P-0107);
3-[3-[[ethyl(methyl)sulfamoyl]amino]-2-fluoro-benzoyl]-5-(2-pyrrolidin-1-ylpyrimidin-5-yl)-1H-pyrrolo[2,3-b]pyridine (P-0108);
N-[2-fluoro-3-[5-(2-pyrrolidin-1-ylpyrimidin-5-yl)-1H-pyrrolo[2,3-b]pyridine-3-carbonyl]phenyl]pyrrolidine-1-sulfonamide (P-0109);
3-[3-(dimethylsulfamoylamino)-2-fluoro-benzoyl]-5-iodo-1H-pyrrolo[2,3-b]pyridine (P-0110);
3-[2-fluoro-3-[[methyl(propyl)sulfamoyl]amino]benzoyl]-5-(2-methylpyrimidin-5-yl)-1H-pyrrolo[2,3-b]pyridine (P-0111);
3-[3-[[cyclopropylmethyl(methyl)sulfamoyl]amino]-2-fluoro-benzoyl]-5-(2-methylpyrimidin-5-yl)-1H-pyrrolo[2,3-b]pyridine (P-0112);
5-(6-cyclopropyl-3-pyridyl)-3-[3-(dimethylsulfamoylamino)-2-fluoro-benzoyl]-1H-pyrrolo[2,3-b]pyridine (P-0113);
5-(6-cyclopropyl-3-pyridyl)-3-[2-fluoro-3-[[methyl(propyl)sulfamoyl]amino]benzoyl]-1H-pyrrolo[2,3-b]pyridine (P-0114);
3-[3-[[cyclopropylmethyl(methyl)sulfamoyl]amino]-2-fluoro-benzoyl]-5-(6-cyclopropyl-3-pyridyl)-1H-pyrrolo[2,3-b]pyridine (P-0115);
3-[2,6-difluoro-3-[[methyl(propyl)sulfamoyl]amino]benzoyl]-5-(2-methoxypyrimidin-5-yl)-1H-pyrrolo[2,3-b]pyridine (P-0116);
[2-fluoro-3-(propylsulfamoylamino)phenyl]-(5-iodo-1H-pyrrolo[2,3-b]pyridin-3-yl)methanone (P-0117);
[2-fluoro-3-(propylsulfamoylamino)phenyl]-(5-methyl-1H-pyrrolo[2,3-b]pyridin-3-yl)methanone (P-0223);
N-[2-fluoro-3-[5-(2-methoxypyrimidin-5-yl)-1H-pyrrolo[2,3-b]pyridine-3-carbonyl]phenyl]butane-2-sulfonamide (P-0024);
N-[2-fluoro-3-[5-(2-pyrrolidin-1-ylpyrimidin-5-yl)-1H-pyrrolo[2,3-b]pyridine-3-carbonyl]phenyl]butane-2-sulfonamide (P-0225);
N-[3-[5-[2-(cyclopropylamino)pyrimidin-5-yl]-1H-pyrrolo[2,3-b]pyridine-3-carbonyl]-2-fluoro-phenyl]butane-2-sulfonamide (P-0226);
N-[3-[5-[4-(1-cyanocyclopropyl)phenyl]-1H-pyrrolo[2,3-b]pyridine-3-carbonyl]-2-fluoro-phenyl]butane-2-sulfonamide (P-00227);
N-[3-[5-(2-cyclopropylpyrimidin-5-yl)-1H-pyrrolo[2,3-b]pyridine-3-carbonyl]-2-fluoro-phenyl]butane-2-sulfonamide (P-0228);
N-[2-fluoro-3-[5-(2-isopropylpyrimidin-5-yl)-1H-pyrrolo[2,3-b]pyridine-3-carbonyl]phenyl]butane-2-sulfonamide (P-0229);
N-[3-[5-[6-(dimethylamino)-3-pyridyl]-1H-pyrrolo[2,3-b]pyridine-3-carbonyl]-2-fluoro-phenyl]butane-2-sulfonamide (P-0230);
N-[2-fluoro-3-[5-(2-methylpyrimidin-5-yl)-1H-pyrrolo[2,3-b]pyridine-3-carbonyl]phenyl]butane-2-sulfonamide (P-0231);
N-[3-[5-[2-(cyclopropylamino)pyrimidin-5-yl]-1H-pyrrolo[2,3-b]pyridine-3-carbonyl]-2-fluoro-phenyl]pyrrolidine-1-sulfonamide (P-0232);
5-(2-cyclopropylpyrimidin-5-yl)-3-[2-fluoro-3-[[isopropyl(methyl)sulfamoyl]amino]benzoyl]-1H-pyrrolo[2,3-b]pyridine (P-0233);
N-[2-fluoro-3-[5-(2-morpholinopyrimidin-5-yl)-1H-pyrrolo[2,3-b]pyridine-3-carbonyl]phenyl]pyrrolidine-1-sulfonamide; (P-0235);
N-[2-fluoro-3-[5-(2-morpholinopyrimidin-5-yl)-1H-pyrrolo[2,3-b]pyridine-3-carbonyl]phenyl]butane-2-sulfonamide (P-0236);
5-[4-(1-cyanocyclopropyl)phenyl]-3-[3-(dimethylsulfamoylamino)-2,6-difluoro-benzoyl]-1H-pyrrolo[2,3-b]pyridine (P-0237);
5-(2-cyclopropylpyrimidin-5-yl)-3-[3-(dimethylsulfamoylamino)-2,6-difluoro-benzoyl]-1H-pyrrolo[2,3-b]pyridine (P-0238);
5-[4-(1-cyanocyclopropyl)phenyl]-3-[3-[[ethyl(methyl)sulfamoyl]amino]-2,6-difluoro-benzoyl]-1H-pyrrolo[2,3-b]pyridine (P-0239);
5-(2-cyclopropylpyrimidin-5-yl)-3-[3-[[ethyl(methyl)sulfamoyl]amino]-2,6-difluoro-benzoyl]-1H-pyrrolo[2,3-b]pyridine (P-0240);
N-[3-[5-(2-cyclopropylpyrimidin-5-yl)-1H-pyrrolo[2,3-b]pyridine-3-carbonyl]-2,4-difluoro-phenyl]pyrrolidine-1-sulfonamide (P-0241);
[2-fluoro-3-(propylsulfamoylamino)phenyl]-[5-(1-methylpyrazol-4-yl)-1H-pyrrolo[2,3-b]pyridin-3-yl]methanone (P-0242);
1-[4-[3-[2-fluoro-3-(pyrrolidin-1-ylsulfonylamino)benzoyl]-1H-pyrrolo[2,3-b]pyridin-5-yl]phenyl]cyclopropanecarboxylic acid (P-0243);
3-[3-(dimethylsulfamoylamino)-2,6-difluoro-benzoyl]-5-(5-ethoxypyrazin-2-yl)-1H-pyrrolo[2,3-b]pyridine (P-0244);

TABLE A-continued

5-[4-(1-cyano-1-methyl-ethyl)phenyl]-3-[3-(dimethylsulfamoylamino)-2-fluoro-benzoyl]-1H-pyrrolo[2,3-b]pyridine (P-0245);
N-[3-[5-(2-cyclopropylpyrimidin-5-yl)-1H-pyrrolo[2,3-b]pyridine-3-carbonyl]-2-fluoro-phenyl]-3,3-dimethyl-pyrrolidine-1-sulfonamide (P-0246);
N-[3-[5-(2-cyclopropylpyrimidin-5-yl)-1H-pyrrolo[2,3-b]pyridine-3-carbonyl]-2-fluoro-phenyl]-3-methyl-pyrrolidine-1-sulfonamide (P-0247);
N-[3-[5-[4-(1-cyanocyclopropyl)phenyl]-1H-pyrrolo[2,3-b]pyridine-3-carbonyl]-2,4-difluoro-phenyl]pyrrolidine-1-sulfonamide (P-0248);
3-[3-[[cyclopropyl(methyl)sulfamoyl]amino]-2-fluoro-benzoyl]-5-(2-cyclopropylpyrimidin-5-yl)-1H-pyrrolo[2,3-b]pyridine (P-0249);
[5-(2-cyclopropylpyrimidin-5-yl)-1H-pyrrolo[2,3-b]pyridin-3-yl]-[2-fluoro-3-(propylsulfamoylamino)phenyl]methanone (P-0251);
3-[3-[[cyclopropyl(methyl)sulfamoyl]amino]-2,6-difluoro-benzoyl]-5-(2-cyclopropylpyrimidin-5-yl)-1H-pyrrolo[2,3-b]pyridine (P-0252);
1-[4-[3-[2-fluoro-3-(pyrrolidin-1-ylsulfonylamino)benzoyl]-1H-pyrrolo[2,3-b]pyridin-5-yl]phenyl]cyclopropanecarboxamide (P-0253);
methyl 1-[4-[3-[2-fluoro-3-(pyrrolidin-1-ylsulfonylamino)benzoyl]-1H-pyrrolo[2,3-b]pyridin-5-yl]phenyl]cyclopropanecarboxylate (P-0254);
5-[4-(1-cyano-1-methyl-ethyl)phenyl]-3-[3-(dimethylsulfamoylamino)-2,6-difluoro-benzoyl]-1H-pyrrolo[2,3-b]pyridine (P-0255);
5-(2-ethoxypyrimidin-5-yl)-3-[3-[[ethyl(methyl)sulfamoyl]amino]-2,6-difluoro-benzoyl]-1H-pyrrolo[2,3-b]pyridine (P-0256);
ethyl 1-[[2-fluoro-3-[5-(2-methoxypyrimidin-5-yl)-1H-pyrrolo[2,3-b]pyridine-3-carbonyl]phenyl]sulfamoyl]pyrrolidine-2-carboxylate (P-0257);
4-[5-[3-[3-[[ethyl(methyl)sulfamoyl]amino]-2,6-difluoro-benzoyl]-1H-pyrrolo[2,3-b]pyridin-5-yl]pyrimidin-2-yl]morpholine (P-0258);
4-[3-[3-[[ethyl(methyl)sulfamoyl]amino]-2,6-difluoro-benzoyl]-1H-pyrrolo[2,3-b]pyridin-5-yl]phenyl]morpholine (P-0259);
N-[2,4-difluoro-3-[5-[2-(4-methylpiperazin-1-yl)pyrimidin-5-yl]-1H-pyrrolo[2,3-b]pyridine-3-carbonyl]phenyl]pyrrolidine-1-sulfonamide (P-0260);
N-[2,4-difluoro-3-[5-(2-piperazin-1-ylpyrimidin-5-yl)-1H-pyrrolo[2,3-b]pyridine-3-carbonyl]phenyl]pyrrolidine-1-sulfonamide (P-0261);
N-[2,4-difluoro-3-[5-[2-(4-hydroxy-1-piperidyl)pyrimidin-5-yl]-1H-pyrrolo[2,3-b]pyridine-3-carbonyl]phenyl]pyrrolidine-1-sulfonamide (P-0262);
3-[3-[[ethyl(methyl)sulfamoyl]amino]-2,6-difluoro-benzoyl]-5-[2-(4-methylpiperazin-1-yl)pyrimidin-5-yl]-1H-pyrrolo[2,3-b]pyridine (P-0263);
tert-butyl 4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazine-1-carboxylate (P-0264);
N-[2,4-difluoro-3-[5-[2-(1-hydroxy-1-methyl-ethyl)thiazol-4-yl]-1H-pyrrolo[2,3-b]pyridine-3-carbonyl]phenyl]pyrrolidine-1-sulfonamide (P-0265);
N-[2,4-difluoro-3-[5-(2-morpholinopyrimidin-5-yl)-1H-pyrrolo[2,3-b]pyridine-3-carbonyl]phenyl]pyrrolidine-1-sulfonamide (P-0266);
N-[1-[[3-[5-(2-cyclopropylpyrimidin-5-yl)-1H-pyrrolo[2,3-b]pyridine-3-carbonyl]-2-fluoro-phenyl]sulfamoyl]pyrrolidin-3-yl]-N-methyl-acetamide (P-0267);
3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (P-0268);
N-[3-[5-[2-(azetidin-1-yl)pyrimidin-5-yl]-1H-pyrrolo[2,3-b]pyridine-3-carbonyl]-2,4-difluoro-phenyl]pyrrolidine-1-sulfonamide (P-0269);
N-[2,4-difluoro-3-[5-(2-methoxythiazol-5-yl)-1H-pyrrolo[2,3-b]pyridine-3-carbonyl]phenyl]pyrrolidine-1-sulfonamide (P-0270);
(3R)-N-[3-[5-(2-cyclopropylpyrimidin-5-yl)-1H-pyrrolo[2,3-b]pyridine-3-carbonyl]-2-fluoro-phenyl]-3-methyl-pyrrolidine-1-sulfonamide (P-0271);
N-[3-[5-(2-cyclopropylpyrimidin-5-yl)-1H-pyrrolo[2,3-b]pyridine-3-carbonyl]-2-fluoro-phenyl]-3-(methylamino)pyrrolidine-1-sulfonamide (P-0272);
N-[2,4-difluoro-3-[5-(4-pyridyl)-1H-pyrrolo[2,3-b]pyridine-3-carbonyl]phenyl]pyrrolidine-1-sulfonamide (P-0273);
N-[3-(5-cyclopropyl-1H-pyrrolo[2,3-b]pyridine-3-carbonyl)-2-fluoro-phenyl]pyrrolidine-1-sulfonamide (P-0274);
3-[3-[[ethyl(methyl)sulfamoyl]amino]-2,6-difluoro-benzoyl]-5-[2-(4-hydroxy-1-piperidyl)pyrimidin-5-yl]-1H-pyrrolo[2,3-b]pyridine (P-0275);
5-[3-(1-cyanocyclopropyl)phenyl]-3-[3-[[ethyl(methyl)sulfamoyl]amino]-2,6-difluoro-benzoyl]-1H-pyrrolo[2,3-b]pyridine (P-0276);
5-[2-(azetidin-1-yl)pyrimidin-5-yl]-3-[3-[[ethyl(methyl)sulfamoyl]amino]-2,6-difluoro-benzoyl]-1H-pyrrolo[2,3-b]pyridine (P-0277);
N-[3-[5-(2-aminopyrimidin-5-yl)-1H-pyrrolo[2,3-b]pyridine-3-carbonyl]-2,4-difluoro-phenyl]pyrrolidine-1-sulfonamide (P-0279);
N-[3-[5-(2-aminopyrimidin-4-yl)-1H-pyrrolo[2,3-b]pyridine-3-carbonyl]-2,4-difluoro-phenyl]pyrrolidine-1-sulfonamide (P-0280);
N-[2-fluoro-3-[5-(4-pyridyl)-1H-pyrrolo[2,3-b]pyridine-3-carbonyl]phenyl]pyrrolidine-1-sulfonamide (P-0281);
N-[2,4-difluoro-3-[5-(2-morpholinopyrimidin-4-yl)-1H-pyrrolo[2,3-b]pyridine-3-carbonyl]phenyl]pyrrolidine-1-sulfonamide (P-0282);
3-[3-[[ethyl(methyl)sulfamoyl]amino]-2,6-difluoro-benzoyl]-5-(2-fluoro-4-pyridyl)-1H-pyrrolo[2,3-b]pyridine (P-0283);
N-[2,4-difluoro-3-[5-(2-morpholino-4-pyridyl)-1H-pyrrolo[2,3-b]pyridine-3-carbonyl]phenyl]pyrrolidine-1-sulfonamide (P-0284);
N-[2,4-difluoro-3-[5-[2-(4-methylpiperazin-1-yl)-4-pyridyl]-1H-pyrrolo[2,3-b]pyridine-3-carbonyl]phenyl]pyrrolidine-1-sulfonamide (P-0285);
N-[3-[5-[2-(cyclobutoxy)-4-pyridyl]-1H-pyrrolo[2,3-b]pyridine-3-carbonyl]-2,4-difluoro-phenyl]pyrrolidine-1-sulfonamide (P-0286);

TABLE A-continued

N-[2,4-difluoro-3-[5-(2-methoxy-4-pyridyl)-1H-pyrrolo[2,3-b]pyridine-3-carbonyl]phenyl]pyrrolidine-1-sulfonamide (P-0287);
N-[3-[5-(2-cyclopropylpyrimidin-5-yl)-1H-pyrrolo[2,3-b]pyridine-3-carbonyl]-2,4-difluoro-phenyl]-3,3-difluoro-pyrrolidine-1-sulfonamide (P-0288);
(3S)-N-[3-[5-(2-cyclopropylpyrimidin-5-yl)-1H-pyrrolo[2,3-b]pyridine-3-carbonyl]-2,4-difluoro-phenyl]-3-fluoro-pyrrolidine-1-sulfonamide (P-0289);
methyl 2-[[3-[5-(2-cyclopropylpyrimidin-5-yl)-1H-pyrrolo[2,3-b]pyridine-3-carbonyl]-2-fluoro-phenyl]sulfamoyl]propanoate (P-0291);
5-[2-(dimethylamino)pyrimidin-5-yl]-3-[3-[[ethyl(methyl)sulfamoyl]amino]-2,6-difluoro-benzoyl]-1H-pyrrolo[2,3-b]pyridine (P-0292);
3-[3-[[ethyl(methyl)sulfamoyl]amino]-2,6-difluoro-benzoyl]-5-(2-pyrrolidin-1-ylpyrimidin-5-yl)-1H-pyrrolo[2,3-b]pyridine (P-0293);
N-[2,4-difluoro-3-[5-[6-(trifluoromethyl)pyrimidin-4-yl]-1H-pyrrolo[2,3-b]pyridine-3-carbonyl]phenyl]pyrrolidine-1-sulfonamide (P-0294);
N-[3-[5-(2-cyclopropyl-4-pyridyl)-1H-pyrrolo[2,3-b]pyridine-3-carbonyl]-2,4-difluoro-phenyl]pyrrolidine-1-sulfonamide (P-0295);
5-cyclobutyl-3-[3-[[ethyl(methyl)sulfamoyl]amino]-2-fluoro-benzoyl]-1H-pyrrolo[2,3-b]pyridine (P-0297);
5-cyclopropyl-3-[3-[[ethyl(methyl)sulfamoyl]amino]-2-fluoro-benzoyl]-1H-pyrrolo[2,3-b]pyridine (P-0298);
N-[3-[5-(6-aminopyrimidin-4-yl)-1H-pyrrolo[2,3-b]pyridine-3-carbonyl]-2-fluoro-phenyl]pyrrolidine-1-sulfonamide (P-0299);
5-(4-cyanophenyl)-3-[3-[[ethyl(methyl)sulfamoyl]amino]-2,6-difluoro-benzoyl]-1H-pyrrolo[2,3-b]pyridine (P-0300);
3-[3-[[ethyl(methyl)sulfamoyl]amino]-2,6-difluoro-benzoyl]-5-[4-(trifluoromethyl)phenyl]-1H-pyrrolo[2,3-b]pyridine (P-0301);
5-[3-(dimethylamino)phenyl]-3-[3-[[ethyl(methyl)sulfamoyl]amino]-2,6-difluoro-benzoyl]-1H-pyrrolo[2,3-b]pyridine (P-0302);
3-[3-[[ethyl(methyl)sulfamoyl]amino]-2,6-difluoro-benzoyl]-5-(4-pyrrolidin-1-ylphenyl)-1H-pyrrolo[2,3-b]pyridine (P-0303);
2-[4-[3-[3-[[ethyl(methyl)sulfamoyl]amino]-2,6-difluoro-benzoyl]-1H-pyrrolo[2,3-b]pyridin-5-yl]phenyl]-5-methyl-1,3,4-oxadiazole (P-0304);
2-[4-[3-[3-[[ethyl(methyl)sulfamoyl]amino]-2,6-difluoro-benzoyl]-1H-pyrrolo[2,3-b]pyridin-5-yl]phenyl]-5-(methylamino)-1,3,4-thiadiazole (P-0305);
3-[3-[[ethyl(methyl)sulfamoyl]amino]-2,6-difluoro-benzoyl]-5-[5-(1-hydroxy-1-methyl-ethyl)-3-pyridyl]-1H-pyrrolo[2,3-b]pyridine (P-0306);
3-[3-[[ethyl(methyl)sulfamoyl]amino]-2,6-difluoro-benzoyl]-5-[6-(1-hydroxy-1-methyl-ethyl)-3-pyridyl]-1H-pyrrolo[2,3-b]pyridine (P-0307);
5-[4-(diethylamino)phenyl]-3-[3-[[ethyl(methyl)sulfamoyl]amino]-2,6-difluoro-benzoyl]-1H-pyrrolo[2,3-b]pyridine (P-0308);
3-[3-[[ethyl(methyl)sulfamoyl]amino]-2,6-difluoro-benzoyl]-5-(2-oxoindolin-6-yl)-1H-pyrrolo[2,3-b]pyridine (P-0309);
3-[5-[3-[[ethyl(methyl)sulfamoyl]amino]-2,6-difluoro-benzoyl]-1H-pyrrolo[2,3-b]pyridin-5-yl]-2-thienyl]-5-methyl-1,2,4-oxadiazole (P-0310);
2-amino-6-[3-[3-[[ethyl(methyl)sulfamoyl]amino]-2,6-difluoro-benzoyl]-1H-pyrrolo[2,3-b]pyridin-5-yl]quinazoline (P-0311);
N-cyclopropyl-5-[3-[3-[[ethyl(methyl)sulfamoyl]amino]-2,6-difluoro-benzoyl]-1H-pyrrolo[2,3-b]pyridin-5-yl]pyridine-2-carboxamide (P-0312);
2-(dimethylamino)-6-[3-[3-[[ethyl(methyl)sulfamoyl]amino]-2,6-difluoro-benzoyl]-1H-pyrrolo[2,3-b]pyridin-5-yl]quinazoline (P-0313);
3-[3-[[ethyl(methyl)sulfamoyl]amino]-2,6-difluoro-benzoyl]-5-[4-(1-hydroxycyclopropyl)phenyl]-1H-pyrrolo[2,3-b]pyridine (P-0314);
5-[3-[3-[[ethyl(methyl)sulfamoyl]amino]-2,6-difluoro-benzoyl]-1H-pyrrolo[2,3-b]pyridin-5-yl]thiazole (P-0315);
4-[3-[3-[[ethyl(methyl)sulfamoyl]amino]-2,6-difluoro-benzoyl]-1H-pyrrolo[2,3-b]pyridin-5-yl]-2-(1-hydroxy-1-methyl-ethyl)thiazole (P-0316);
3-[3-[[ethyl(methyl)sulfamoyl]amino]-2,6-difluoro-benzoyl]-5-(6-methoxypyridazin-3-yl)-1H-pyrrolo[2,3-b]pyridine (P-0317);
N-[2,4-difluoro-3-[5-(6-morpholinopyrimidin-4-yl)-1H-pyrrolo[2,3-b]pyridine-3-carbonyl]phenyl]pyrrolidine-1-sulfonamide (P-0318);
N-[2,4-difluoro-3-[5-[6-(4-methylpiperazin-1-yl)pyrimidin-4-yl]-1H-pyrrolo[2,3-b]pyridine-3-carbonyl]phenyl]pyrrolidine-1-sulfonamide (P-0319);
(3S)-N-[3-[5-(2-cyclopropylpyrimidin-5-yl)-1H-pyrrolo[2,3-b]pyridine-3-carbonyl]-2,4-difluoro-phenyl]-3-methyl-pyrrolidine-1-sulfonamide (P-0320);
N-[2-fluoro-3-[5-(6-morpholinopyrimidin-4-yl)-1H-pyrrolo[2,3-b]pyridine-3-carbonyl]phenyl]pyrrolidine-1-sulfonamide (P-0321);
N-[2-fluoro-3-[5-[6-(4-methylpiperazin-1-yl)pyrimidin-4-yl]-1H-pyrrolo[2,3-b]pyridine-3-carbonyl]phenyl]pyrrolidine-1-sulfonamide (P-0322);
N-[2-fluoro-3-[5-[6-(4-methylpiperazin-1-yl)-2-pyridyl]-1H-pyrrolo[2,3-b]pyridine-3-carbonyl]phenyl]pyrrolidine-1-sulfonamide (P-0324);
N-[2-fluoro-3-[5-(4-methoxypyrimidin-2-yl)-1H-pyrrolo[2,3-b]pyridine-3-carbonyl]phenyl]pyrrolidine-1-sulfonamide (P-0325);
N-[2-fluoro-3-[5-(4-methylpyrimidin-2-yl)-1H-pyrrolo[2,3-b]pyridine-3-carbonyl]phenyl]pyrrolidine-1-sulfonamide (P-0326);
(3R)-N-[3-[5-(2-cyclopropylpyrimidin-5-yl)-1H-pyrrolo[2,3-b]pyridine-3-carbonyl]-2-fluoro-phenyl]-3-fluoro-pyrrolidine-1-sulfonamide (P-0327);
[5-(2-cyclopropylpyrimidin-5-yl)-1H-pyrrolo[2,3-b]pyridin-3-yl]-[2,6-difluoro-3-(methylsulfamoylamino)phenyl]methanone (P-0334);
[5-(2-cyclopropylpyrimidin-5-yl)-1H-pyrrolo[2,3-b]pyridin-3-yl]-[3-(ethylsulfamoylamino)-2,6-difluoro-phenyl]methanone (P-0335);
5-(2-cyclopropylpyrimidin-5-yl)-3-[2,6-difluoro-3-(sulfamoylamino)benzoyl]-1H-pyrrolo[2,3-b]pyridine (P-0336);

TABLE A-continued

N-[3-[5-(4-chlorophenyl)-1H-pyrrolo[2,3-b]pyridine-3-carbonyl]-2,4-difluoro-phenyl]butane-2-sulfonamide (P-0337);
(3R)-N-[3-[5-(2-cyclopropylpyrimidin-5-yl)-1H-pyrrolo[2,3-b]pyridine-3-carbonyl]-2,4-difluoro-phenyl]-3-fluoro-pyrrolidine-1-sulfonamide (P-0338);
N-[3-[5-(2-cyclopropylpyrimidin-5-yl)-1H-pyrrolo[2,3-b]pyridine-3-carbonyl]-2,4-difluoro-phenyl]-3-fluoro-pyrrolidine-1-sulfonamide (P-0339);
5-(2-cyclopropylpyrimidin-5-yl)-3-[2,6-difluoro-3-[[methyl(2,2,2-trifluoroethyl)sulfamoyl]amino]benzoyl]-1H-pyrrolo[2,3-b]pyridine (P-0340);
N-[3-[5-(2-cyclopropylpyrimidin-5-yl)-1H-pyrrolo[2,3-b]pyridine-3-carbonyl]-2,4-difluoro-phenyl]butane-2-sulfonamide (P-0342);
5-[3-[[ethyl(methyl)sulfamoyl]amino]-2,6-difluoro-benzoyl]-1H-pyrrolo[2,3-b]pyridin-5-yl]-2-methoxy-thiazole (P-0343);
3-[3-[[ethyl(methyl)sulfamoyl]amino]-2,6-difluoro-benzoyl]-5-(1H-indazol-6-yl)-1H-pyrrolo[2,3-b]pyridine (P-0344);
N-[2,4-difluoro-3-[5-(2-pyrrolidin-1-ylpyrimidin-5-yl)-1H-pyrrolo[2,3-b]pyridine-3-carbonyl]phenyl]pyrrolidine-1-sulfonamide (P-0345);
N-[3-(5-cyclobutyl-1H-pyrrolo[2,3-b]pyridine-3-carbonyl)-2-fluoro-phenyl]pyrrolidine-1-sulfonamide (P-0346);
N-[2-fluoro-3-[5-(2-methoxypyrimidin-5-yl)-1H-pyrrolo[2,3-b]pyridine-3-carbonyl]phenyl]cyclopropanesulfonamide (P-0347);
1-allyl-N-[3-(5-cyano-1H-pyrrolo[2,3-b]pyridine-3-carbonyl)-2,4-difluoro-phenyl]cyclopropanesulfonamide (P-0348);
N-[2,4-difluoro-3-[5-(2-methoxypyrimidin-5-yl)-1H-pyrrolo[2,3-b]pyridine-3-carbonyl]phenyl]cyclopropanesulfonamide (P-0349);
N-[2,4-difluoro-3-[5-(5-methoxy-3-pyridyl)-1H-pyrrolo[2,3-b]pyridine-3-carbonyl]phenyl]cyclopropanesulfonamide (P-0350); and
N-[3-(5-cyano-1H-pyrrolo[2,3-b]pyridine-3-carbonyl)-2,4-difluoro-phenyl]cyclopropanesulfonamide (P-0351);
5-(2-aminopyrimidin-4-yl)-2-tert-butyl-4-[3-[[ethyl(methyl)sulfamoyl]amino]-2-fluoro-phenyl]thiazole (P-0352);

or pharmaceutically acceptable salts, hydrates, solvates, tautomers or isomers thereof. In some embodiments, the methods provide the above selected compounds and pharmaceutically acceptable salts thereof. In other embodiments, the methods provide the above selected compounds and pharmaceutically acceptable salts and tautomers and isomers thereof.

In some embodiments of the methods provided herein, the BRAF inhibitor is a compound listed in Table B.

TABLE B

| Compound No. | Name (MS(ESI) [M + H$^+$]$^+$) |
|---|---|
| P-0118 | [2-fluoro-3-(phenylsulfamoylamino)phenyl]-[5-(2-methoxypyrimidin-5-yl)-1H-pyrrolo[2,3-b]pyridin-3-yl]methanone (519.1) |
| P-0119 | 3-[2-fluoro-3-[[methyl(phenyl)sulfamoyl]amino]benzoyl]-5-(2-methoxypyrimidin-5-yl)-1H-pyrrolo[2,3-b]pyridine (533.1) |
| P-0120 | [2-fluoro-3-(3-pyridylsulfamoylamino)phenyl]-[5-(2-methoxypyrimidin-5-yl)-1H-pyrrolo[2,3-b]pyridin-3-yl]methanone (520.1) |
| P-0121 | 3-[2-fluoro-3-[[methyl(3-pyridyl)sulfamoyl]amino]benzoyl]-5-(2-methoxypyrimidin-5-yl)-1H-pyrrolo[2,3-b]pyridine (534.1) |
| P-0122 | [2-fluoro-3-(thiazol-5-ylsulfamoylamino)phenyl]-[5-(2-methoxypyrimidin-5-yl)-1H-pyrrolo[2,3-b]pyridin-3-yl]methanone (526.1) |
| P-0123 | 5-[[2-fluoro-3-[5-(2-methoxypyrimidin-5-yl)-1H-pyrrolo[2,3-b]pyridine-3-carbonyl]phenyl]sulfamoyl-methyl-amino]thiazole (540.1) |
| P-0124 | [3-(cyclopentylsulfamoylamino)-2-fluoro-phenyl]-[5-(2-methoxypyrimidin-5-yl)-1H-pyrrolo[2,3-b]pyridin-3-yl]methanone (511.1) |
| P-0125 | 3-[3-[[cyclopentyl(methyl)sulfamoyl]amino]-2-fluoro-benzoyl]-5-(2-methoxypyrimidin-5-yl)-1H-pyrrolo[2,3-b]pyridine (525.2) |
| P-0126 | [3-(cyclopropylsulfamoylamino)-2-fluoro-phenyl]-[5-(2-methoxypyrimidin-5-yl)-1H-pyrrolo[2,3-b]pyridin-3-yl]methanone (483.1) |
| P-0127 | [2-fluoro-3-(tetrahydropyran-4-ylsulfamoylamino)phenyl]-[5-(2-methoxypyrimidin-5-yl)-1H-pyrrolo[2,3-b]pyridin-3-yl]methanone (527.1) |
| P-0128 | 3-[2-fluoro-3-[[methyl(tetrahydropyran-4-yl)sulfamoyl]amino]benzoyl]-5-(2-methoxypyrimidin-5-yl)-1H-pyrrolo[2,3-b]pyridine (541.2) |
| P-0129 | 3-[2-fluoro-3-[[2-fluoroethyl(methyl)sulfamoyl]amino]benzoyl]-5-(2-methoxypyrimidin-5-yl)-1H-pyrrolo[2,3-b]pyridine (503.1) |
| P-0130 | 3-[2-fluoro-3-[[methyl(2,2,2-trifluoroethyl)sulfamoyl]amino]benzoyl]-5-(2-methoxypyrimidin-5-yl)-1H-pyrrolo[2,3-b]pyridine (539.1) |

TABLE B-continued

| Compound No. | Name (MS(ESI) [M + H$^+$]$^+$) |
|---|---|
| P-0131 | 3-[2-fluoro-3-[[3-fluoropropyl(methyl)sulfamoyl]amino]benzoyl]-5-(2-methoxypyrimidin-5-yl)-1H-pyrrolo[2,3-b]pyridine (517.1) |
| P-0132 | 5-chloro-3-[2-fluoro-3-[[2-methoxyethyl(methyl)sulfamoyl]amino]benzoyl]-1H-pyrrolo[2,3-b]pyridine (441.1) |
| P-0133 | 5-chloro-3-[2-fluoro-3-[[3-fluoropropyl(methyl)sulfamoyl]amino]benzoyl]-1H-pyrrolo[2,3-b]pyridine (443.1) |
| P-0134 | 3-[2-fluoro-3-[[3-fluoropropyl(methyl)sulfamoyl]amino]benzoyl]-5-(2-isopropylpyrimidin-5-yl)-1H-pyrrolo[2,3-b]pyridine (529.2) |
| P-0135 | 3-[2-fluoro-3-[[[1-(methoxymethyl)cyclopropyl]-methyl-sulfamoyl]amino]benzoyl]-5-(2-isopropylpyrimidin-5-yl)-1H-pyrrolo[2,3-b]pyridine (553.2) |
| P-0136 | 5-chloro-3-[2-fluoro-3-[[[1-(methoxymethyl)cyclopropyl]-methyl-sulfamoyl]amino]benzoyl]-1H-pyrrolo[2,3-b]pyridine (467.1) |
| P-0137 | 5-chloro-3-[3-[[2-cyclopropylethyl(methyl)sulfamoyl]amino]-2-fluoro-benzoyl]-1H-pyrrolo[2,3-b]pyridine (451.1) |
| P-0138 | 3-[3-[[2-cyclopropylethyl(methyl)sulfamoyl]amino]-2-fluoro-benzoyl]-5-(2-isopropylpyrimidin-5-yl)-1H-pyrrolo[2,3-b]pyridine (537.2) |
| P-0139 | 5-chloro-3-[2-fluoro-3-[[[1-(hydroxymethyl)cyclopropyl]methyl-methyl-sulfamoyl]amino]benzoyl]-1H-pyrrolo[2,3-b]pyridine (467.1) |
| P-0140 | methyl 1-[[[[3-(5-chloro-1H-pyrrolo[2,3-b]pyridine-3-carbonyl)-2-fluoro-phenyl]sulfamoyl-methyl-amino]methyl]cyclopropanecarboxylate (495.1) |
| P-0141 | 5-chloro-3-[3-[[2-cyanoethyl(methyl)sulfamoyl]amino]-2-fluoro-benzoyl]-1H-pyrrolo[2,3-b]pyridine (436.1) |
| P-0142 | (5-chloro-1H-pyrrolo[2,3-b]pyridin-3-yl)-[2-fluoro-3-(3-methoxypropylsulfamoylamino)phenyl]methanone (441.1) |
| P-0143 | N-[3-(5-chloro-1H-pyrrolo[2,3-b]pyridine-3-carbonyl)-2-fluoro-phenyl]-4-methyl-piperazine-1-sulfonamide (452.1) |
| P-0144 | 5-chloro-3-[2-fluoro-3-[[(2-hydroxy-2-methyl-propyl)-methyl-sulfamoyl]amino]benzoyl]-1H-pyrrolo[2,3-b]pyridine (455.1) |
| P-0145 | 5-chloro-3-[2-fluoro-3-[[(2-hydroxy-1,1-dimethyl-ethyl)-methyl-sulfamoyl]amino]benzoyl]-1H-pyrrolo[2,3-b]pyridine (455.1) |
| P-0146 | N-[3-[5-(2-cyclopropylpyrimidin-5-yl)-1H-pyrrolo[2,3-b]pyridine-3-carbonyl]-2-fluoro-phenyl]azetidine-1-sulfonamide (493.1) |
| P-0147 | N-[3-[5-(2-cyclopropylpyrimidin-5-yl)-1H-pyrrolo[2,3-b]pyridine-3-carbonyl]-2-fluoro-phenyl]-3-fluoro-azetidine-1-sulfonamide (511.1) |
| P-0148 | 5-(2-cyclopropylpyrimidin-5-yl)-3-[2-fluoro-3-[[methyl(oxetan-3-yl)sulfamoyl]amino]benzoyl]-1H-pyrrolo[2,3-b]pyridine (523.1) |
| P-0149 | 3-[3-[[cyclobutyl(methyl)sulfamoyl]amino]-2-fluoro-benzoyl]-5-(2-cyclopropylpyrimidin-5-yl)-1H-pyrrolo[2,3-b]pyridine (521.2) |
| P-0150 | 5-chloro-3-[2-fluoro-3-[[methyl(tetrahydrofuran-3-yl)sulfamoyl]amino]benzoyl]-1H-pyrrolo[2,3-b]pyridine (453.1) |
| P-0151 | N-[3-(5-chloro-1H-pyrrolo[2,3-b]pyridine-3-carbonyl)-2-fluoro-phenyl]-3-methoxy-pyrrolidine-1-sulfonamide (453.1) |
| P-0152 | N-[3-(5-chloro-1H-pyrrolo[2,3-b]pyridine-3-carbonyl)-2-fluoro-phenyl]-3-(methylamino)pyrrolidine-1-sulfonamide (452.1) |
| P-0153 | N-[3-(5-chloro-1H-pyrrolo[2,3-b]pyridine-3-carbonyl)-2-fluoro-phenyl]-3-(dimethylamino)pyrrolidine-1-sulfonamide (466.1) |
| P-0154 | N-[3-[5-[6-(1-cyanocyclopropyl)-3-pyridyl]-1H-pyrrolo[2,3-b]pyridine-3-carbonyl]-2-fluoro-phenyl]pyrrolidine-1-sulfonamide (531.2) |
| P-0155 | 1-[5-[3-[2-fluoro-3-(pyrrolidin-1-ylsulfonylamino)benzoyl]-1H-pyrrolo[2,3-b]pyridin-5-yl]-2-pyridyl]cyclopropanecarboxamide (549.2) |
| P-0156 | 1-[5-[3-[2-fluoro-3-(pyrrolidin-1-ylsulfonylamino)benzoyl]-1H-pyrrolo[2,3-b]pyridin-5-yl]-2-pyridyl]cyclopropanecarboxylic acid (550.2) |
| P-0157 | 1-[4-[3-[2-fluoro-3-(pyrrolidin-1-ylsulfonylamino)benzoyl]-1H-pyrrolo[2,3-b]pyridin-5-yl]phenyl]cyclopropanecarboxamide (548.2) |
| P-0158 | 1-[4-[3-[2-fluoro-3-(pyrrolidin-1-ylsulfonylamino)benzoyl]-1H-pyrrolo[2,3-b]pyridin-5-yl]phenyl]cyclopropanecarboxylic acid (548.2) |

TABLE B-continued

| Compound No. | Name (MS(ESI) [M + H⁺]⁺) |
|---|---|
| P-0159 | 3-[3-(dimethylsulfamoylamino)-2-fluoro-benzoyl]-5-(5-methoxypyrazin-2-yl)-1H-pyrrolo[2,3-b]pyridine (471.1) |
| P-0160 | 5-[5-(dimethylamino)pyrazin-2-yl]-3-[3-(dimethylsulfamoylamino)-2-fluoro-benzoyl]-1H-pyrrolo[2,3-b]pyridine (484.2) |
| P-0161 | 3-[3-(dimethylsulfamoylamino)-2-fluoro-benzoyl]-5-(6-methoxypyridazin-3-yl)-1H-pyrrolo[2,3-b]pyridine (471.1) |
| P-0162 | 4-[5-[3-[3-[[ethyl(methyl)sulfamoyl]amino]-2-fluoro-benzoyl]-1H-pyrrolo[2,3-b]pyridin-5-yl]pyrimidin-2-yl]morpholine (540.2) |
| P-0163 | 5-chloro-3-[2-fluoro-3-[[(4-fluorophenyl)-methyl-sulfamoyl]amino]benzoyl]-1H-pyrrolo[2,3-b]pyridine (477.1) |
| P-0164 | 3-[3-[[ethyl(methyl)sulfamoyl]amino]-2-fluoro-benzoyl]-5-(1-methylpyrrol-3-yl)-1H-pyrrolo[2,3-b]pyridine (442.1) |
| P-0165 | 3-[2-fluoro-3-[[methyl(propyl)sulfamoyl]amino]benzoyl]-5-(1-methylpyrazol-4-yl)-1H-pyrrolo[2,3-b]pyridine (471.2) |
| P-0166 | 5-[3-[3-[[ethyl(methyl)sulfamoyl]amino]-2-fluoro-benzoyl]-1H-pyrrolo[2,3-b]pyridin-5-yl]thiazole (460.1) |
| P-0167 | 3-[3-[[ethyl(methyl)sulfamoyl]amino]-2-fluoro-benzoyl]-5-(1-methylimidazol-4-yl)-1H-pyrrolo[2,3-b]pyridine (457.1) |
| P-0168 | 4-[3-[3-[[ethyl(methyl)sulfamoyl]amino]-2-fluoro-benzoyl]-1H-pyrrolo[2,3-b]pyridin-5-yl]oxazole (444.1) |
| P-0169 | [2,6-difluoro-3-(phenylsulfamoylamino)phenyl]-[5-(2-methoxypyrimidin-5-yl)-1H-pyrrolo[2,3-b]pyridin-3-yl]methanone (537.1) |
| P-0170 | 3-[2,6-difluoro-3-[[methyl(phenyl)sulfamoyl]amino]benzoyl]-5-(2-methoxypyrimidin-5-yl)-1H-pyrrolo[2,3-b]pyridine (551.1) |
| P-0171 | [2,6-difluoro-3-(3-pyridylsulfamoylamino)phenyl]-[5-(2-methoxypyrimidin-5-yl)-1H-pyrrolo[2,3-b]pyridin-3-yl]methanone (538.1) |
| P-0172 | 3-[2,6-difluoro-3-[[methyl(3-pyridyl)sulfamoyl]amino]benzoyl]-5-(2-methoxypyrimidin-5-yl)-1H-pyrrolo[2,3-b]pyridine (552.1) |
| P-0173 | [2,6-difluoro-3-(thiazol-5-ylsulfamoylamino)phenyl]-[5-(2-methoxypyrimidin-5-yl)-1H-pyrrolo[2,3-b]pyridin-3-yl]methanone (544.1) |
| P-0174 | 5-[[2,4-difluoro-3-[5-(2-methoxypyrimidin-5-yl)-1H-pyrrolo[2,3-b]pyridine-3-carbonyl]phenyl]sulfamoyl-methyl-amino]thiazole (558.1) |
| P-0175 | [3-(cyclopentylsulfamoylamino)-2,6-difluoro-phenyl]-[5-(2-methoxypyrimidin-5-yl)-1H-pyrrolo[2,3-b]pyridin-3-yl]methanone (529.1) |
| P-0176 | 3-[3-[[cyclopentyl(methyl)sulfamoyl]amino]-2,6-difluoro-benzoyl]-5-(2-methoxypyrimidin-5-yl)-1H-pyrrolo[2,3-b]pyridine (543.2) |
| P-0177 | [3-(cyclopropylsulfamoylamino)-2,6-difluoro-phenyl]-[5-(2-methoxypyrimidin-5-yl)-1H-pyrrolo[2,3-b]pyridin-3-yl]methanone (501.1) |
| P-0178 | [2,6-difluoro-3-(tetrahydropyran-4-ylsulfamoylamino)phenyl]-[5-(2-methoxypyrimidin-5-yl)-1H-pyrrolo[2,3-b]pyridin-3-yl]methanone (545.1) |
| P-0179 | 3-[2,6-difluoro-3-[[methyl(tetrahydropyran-4-yl)sulfamoyl]amino]benzoyl]-5-(2-methoxypyrimidin-5-yl)-1H-pyrrolo[2,3-b]pyridine (559.1) |
| P-0180 | 3-[2,6-difluoro-3-[[2-fluoroethyl(methyl)sulfamoyl]amino]benzoyl]-5-(2-methoxypyrimidin-5-yl)-1H-pyrrolo[2,3-b]pyridine (521.1) |
| P-0181 | 3-[2,6-difluoro-3-[[methyl(2,2,2-trifluoroethyl)sulfamoyl]amino]benzoyl]-5-(2-methoxypyrimidin-5-yl)-1H-pyrrolo[2,3-b]pyridine (556.1) |
| P-0182 | 3-[2,6-difluoro-3-[[3-fluoropropyl(methyl)sulfamoyl]amino]benzoyl]-5-(2-methoxypyrimidin-5-yl)-1H-pyrrolo[2,3-b]pyridine (534.1) |
| P-0183 | 5-chloro-3-[2,6-difluoro-3-[[2-methoxyethyl(methyl)sulfamoyl]amino]benzoyl]-1H-pyrrolo[2,3-b]pyridine (458.1) |
| P-0184 | 5-chloro-3-[2,6-difluoro-3-[[3-fluoropropyl(methyl)sulfamoyl]amino]benzoyl]-1H-pyrrolo[2,3-b]pyridine (561.1) |

TABLE B-continued

| Compound No. | Name (MS(ESI) [M + H+]+) |
|---|---|
| P-0185 | 3-[2,6-difluoro-3-[[3-fluoropropyl(methyl)sulfamoyl]amino]benzoyl]-5-(2-isopropylpyrimidin-5-yl)-1H-pyrrolo[2,3-b]pyridine (547.2) |
| P-0186 | 3-[2,6-difluoro-3-[[[1-(methoxymethyl)cyclopropyl]-methyl-sulfamoyl]amino]benzoyl]-5-(2-isopropylpyrimidin-5-yl)-1H-pyrrolo[2,3-b]pyridine (571.2) |
| P-0187 | 5-chloro-3-[2,6-difluoro-3-[[[1-(methoxymethyl)cyclopropyl]-methyl-sulfamoyl]amino]benzoyl]-1H-pyrrolo[2,3-b]pyridine (485.1) |
| P-0188 | 5-chloro-3-[3-[[2-cyclopropylethyl(methyl)sulfamoyl]amino]-2,6-difluoro-benzoyl]-1H-pyrrolo[2,3-b]pyridine (469.1) |
| P-0189 | 3-[3-[[2-cyclopropylethyl(methyl)sulfamoyl]amino]-2,6-difluoro-benzoyl]-5-(2-isopropylpyrimidin-5-yl)-1H-pyrrolo[2,3-b]pyridine (555.2) |
| P-0190 | 5-chloro-3-[2,6-difluoro-3-[[[1-(hydroxymethyl)cyclopropyl]methyl-methyl-sulfamoyl]amino]benzoyl]-1H-pyrrolo[2,3-b]pyridine (485.1) |
| P-0191 | methyl 1-[[[[3-(5-chloro-1H-pyrrolo[2,3-b]pyridine-3-carbonyl)-2,4-difluoro-phenyl]sulfamoyl-methyl-amino]methyl]cyclopropanecarboxylate (513.1) |
| P-0192 | 5-chloro-3-[3-[[2-cyanoethyl(methyl)sulfamoyl]amino]-2,6-difluoro-benzoyl]-1H-pyrrolo[2,3-b]pyridine (454.0) |
| P-0193 | (5-chloro-1H-pyrrolo[2,3-b]pyridin-3-yl)-[2,6-difluoro-3-(3-methoxypropylsulfamoylamino)phenyl]methanone (459.1) |
| P-0194 | N-[3-(5-chloro-1H-pyrrolo[2,3-b]pyridine-3-carbonyl)-2,4-difluoro-phenyl]-4-methyl-piperazine-1-sulfonamide (470.1) |
| P-0195 | 5-chloro-3-[2,6-difluoro-3-[[(2-hydroxy-2-methyl-propyl)-methyl-sulfamoyl]amino]benzoyl]-1H-pyrrolo[2,3-b]pyridine (473.1) |
| P-0196 | 5-chloro-3-[2,6-difluoro-3-[[(2-hydroxy-1,1-dimethyl-ethyl)-methyl-sulfamoyl]amino]benzoyl]-1H-pyrrolo[2,3-b]pyridine (473.1) |
| P-0197 | N-[3-[5-(2-cyclopropylpyrimidin-5-yl)-1H-pyrrolo[2,3-b]pyridine-3-carbonyl]-2,4-difluoro-phenyl]azetidine-1-sulfonamide (511.1) |
| P-0198 | N-[3-[5-(2-cyclopropylpyrimidin-5-yl)-1H-pyrrolo[2,3-b]pyridine-3-carbonyl]-2,4-difluoro-phenyl]-3-fluoro-azetidine-1-sulfonamide (529.1) |
| P-0199 | 5-(2-cyclopropylpyrimidin-5-yl)-3-[2,6-difluoro-3-[[methyl(oxetan-3-yl)sulfamoyl]amino]benzoyl]-1H-pyrrolo[2,3-b]pyridine (541.1) |
| P-0200 | 3-[3-[[cyclobutyl(methyl)sulfamoyl]amino]-2,6-difluoro-benzoyl]-5-(2-cyclopropylpyrimidin-5-yl)-1H-pyrrolo[2,3-b]pyridine (539.2) |
| P-0201 | 5-chloro-3-[2,6-difluoro-3-[[methyl(tetrahydrofuran-3-yl)sulfamoyl]amino]benzoyl]-1H-pyrrolo[2,3-b]pyridine (471.1) |
| P-0202 | N-[3-(5-chloro-1H-pyrrolo[2,3-b]pyridine-3-carbonyl)-2,4-difluoro-phenyl]-3-methoxy-pyrrolidine-1-sulfonamide (471.1) |
| P-0203 | N-[3-(5-chloro-1H-pyrrolo[2,3-b]pyridine-3-carbonyl)-2,4-difluoro-phenyl]-3-(methylamino)pyrrolidine-1-sulfonamide (470.1) |
| P-0204 | N-[3-(5-chloro-1H-pyrrolo[2,3-b]pyridine-3-carbonyl)-2,4-difluoro-phenyl]-3-(dimethylamino)pyrrolidine-1-sulfonamide (484.1) |
| P-0205 | N-[3-[5-[6-(1-cyanocyclopropyl)-3-pyridyl]-1H-pyrrolo[2,3-b]pyridine-3-carbonyl]-2,4-difluoro-phenyl]pyrrolidine-1-sulfonamide (549.1) |
| P-0206 | 1-[5-[3-[2,6-difluoro-3-(pyrrolidin-1-ylsulfonylamino)benzoyl]-1H-pyrrolo[2,3-b]pyridin-5-yl]-2-pyridyl]cyclopropanecarboxamide (567.2) |
| P-0207 | 1-[5-[3-[2,6-difluoro-3-(pyrrolidin-1-ylsulfonylamino)benzoyl]-1H-pyrrolo[2,3-b]pyridin-5-yl]-2-pyridyl]cyclopropanecarboxylic acid (568.1) |
| P-0208 | 1-[4-[3-[2,6-difluoro-3-(pyrrolidin-1-ylsulfonylamino)benzoyl]-1H-pyrrolo[2,3-b]pyridin-5-yl]phenyl]cyclopropanecarboxamide (566.2) |
| P-0209 | 1-[4-[3-[2,6-difluoro-3-(pyrrolidin-1-ylsulfonylamino)benzoyl]-1H-pyrrolo[2,3-b]pyridin-5-yl]phenyl]cyclopropanecarboxylic acid (567.1) |
| P-0210 | 3-[3-(dimethylsulfamoylamino)-2,6-difluoro-benzoyl]-5-(5-methoxypyrazin-2-yl)-1H-pyrrolo[2,3-b]pyridine (489.1) |

TABLE B-continued

| Compound No. | Name (MS(ESI) [M + H+]+) |
|---|---|
| P-0211 | 5-[5-(dimethylamino)pyrazin-2-yl]-3-[3-(dimethylsulfamoylamino)-2,6-difluoro-benzoyl]-1H-pyrrolo[2,3-b]pyridine (502.1) |
| P-0212 | 3-[3-(dimethylsulfamoylamino)-2,6-difluoro-benzoyl]-5-(6-methoxypyridazin-3-yl)-1H-pyrrolo[2,3-b]pyridine (489.1) |
| P-0213 | 4-[5-[3-[3-[[ethyl(methyl)sulfamoyl]amino]-2,6-difluoro-benzoyl]-1H-pyrrolo[2,3-b]pyridin-5-yl]pyrimidin-2-yl]morpholine (558.2) |
| P-0214 | 5-chloro-3-[2,6-difluoro-3-[[(4-fluorophenyl)-methyl-sulfamoyl]amino]benzoyl]-1H-pyrrolo[2,3-b]pyridine (495.0) |
| P-0215 | 3-[3-(dimethylsulfamoylamino)-2,6-difluoro-benzoyl]-5-(1-methylpyrrol-3-yl)-1H-pyrrolo[2,3-b]pyridine (460.1) |
| P-0216 | 3-[2,6-difluoro-3-[[methyl(propyl)sulfamoyl]amino]benzoyl]-5-(1-methylpyrazol-4-yl)-1H-pyrrolo[2,3-b]pyridine (489.1) |
| P-0217 | 5-[3-[3-[[ethyl(methyl)sulfamoyl]amino]-2,6-difluoro-benzoyl]-1H-pyrrolo[2,3-b]pyridin-5-yl]thiazole (478.1) |
| P-0218 | 3-[3-[[ethyl(methyl)sulfamoyl]amino]-2,6-difluoro-benzoyl]-5-(1-methylimidazol-4-yl)-1H-pyrrolo[2,3-b]pyridine (475.1) |
| P-0219 | 4-[3-[3-[[ethyl(methyl)sulfamoyl]amino]-2,6-difluoro-benzoyl]-1H-pyrrolo[2,3-b]pyridin-5-yl]oxazole (462.1) |
| P-0220 | 6-[3-[3-(dimethylsulfamoylamino)-2,6-difluoro-benzoyl]-1H-pyrrolo[2,3-b]pyridin-5-yl]quinoline (508.1) |
| P-0221 | 6-[3-[3-(dimethylsulfamoylamino)-2,6-difluoro-benzoyl]-1H-pyrrolo[2,3-b]pyridin-5-yl]quinazoline (509.1) |
| P-0222 | 6-[3-[3-(dimethylsulfamoylamino)-2,6-difluoro-benzoyl]-1H-pyrrolo[2,3-b]pyridin-5-yl]-1,3-benzothiazole (514.1) | or pharmaceutically acceptable salts, hydrates, solvates, tautomers or isomers thereof. In some embodiments, the methods provide the above selected compounds and pharmaceutically acceptable salts thereof. In other embodiments, the methods provide the above selected compounds and pharmaceutically acceptable salts and tautomers and isomers thereof.

In another aspect, provided herewith is a method for suppressing or preventing a MAPK pathway signaling. The method includes contacting a mutant BRAF protein kinase in a cell with a BRAF inhibitor; and regulating/modulating the interaction of the BRAF inhibitor Leucine 505 amino acid residue in the C-terminal end of an αC helix in the mutant BRAF protein kinase, thereby suppressing or preventing the activation of MAPK pathway signaling. The activation of MAPK pathway or activation of pERk can also be suppressed or prevented in cells that have RAS mutation or upstream receptor tyrosine kinase activation.

In some embodiments of methods for suppressing/preventing a MAPK pathway signaling provided herein, the BRAF inhibitor is a molecule containing a sulfamoylamino group having the formula:

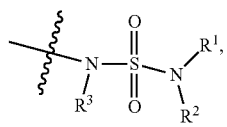

wherein $R^1$ and $R^2$ are each independently optionally substituted alkyl, aryl, heteroaryl, cycloalkyl or $R^1$ and $R^2$ taken together to form a optionally substituted 5- or 6-membered heterocycloalkyl ring having from 0-1 heteroatoms selected from O, N or S; and $R^3$ is H or $C_{1-6}$alkyl. In some embodiments, $R^1$, $R^2$ and $R^3$ are as defined in any of the embodiments described herein. In certain embodiments of methods for suppressing/preventing a MAPK pathway signaling provided herein, the BRAF inhibitor is a compound of formula (I') or (I) or a compound of any of the subgeneric formulas of formula (I), or a compound as described herein, or a pharmaceutically acceptable salt or a solvate or hydrate thereof, or a composition comprising a compound of formula (I) or (I') a compound of any of the subgeneric formulas of formula (I), for example, formulas (Ia), (Ia-1), (Ia-2), (Ib), (Ib-1), (Ib-2), (Ib-1a), (Ib-1b), (Ic), (Ic-1), (Ic-1a), (Ic-2), (Ic-2a), (Id), (Id-1), (Id-1a), (Id-2), (Id-2a), (Ie), (Ie-1), (Ie-1a), (Ie-2), (Ie-2a), (If), (If-1), (If-2), (If-3), (If-4), (Ig), (Ig-1), (Ig-2), (Ig-3), (Ig-4), (Ih), (Ih-1), (Ih-2), (Ih-3), (Ih-4), (Ij), (Ij-1) or (Ij-2), or any of the compounds described herein, or a pharmaceutically acceptable salt or a solvate or hydrate thereof.

In some embodiments of methods for suppressing/preventing a MAPK pathway signaling provided herein, the BRAF-inhibitor is a compound of formula (I') or (I) or a compound of any of the subgeneric formulas of formula (I), or a compound as described herein, or a pharmaceutically acceptable salt or a solvate or hydrate thereof, or a composition comprising a compound of formula (I) or (I') or a compound of any of the subgeneric formulas of formula (I), for example, formulas (Ia), (Ia-1), (Ia-2), (Ib), (Ib-1), (Ib-2), (Ib-1a), (Ib-1b), (Ic), (Ic-1), (Ic-1a), (Ic-2), (Ic-2a), (Id), (Id-1), (Id-1a), (Id-2), (Id-2a), (Ie), (Ie-1), (Ie-1a), (Ie-2), (Ie-2a), (If), (If-1), (If-2), (If-3), (If-4), (Ig), (Ig-1), (Ig-2), (Ig-3), (Ig-4), (Ih), (Ih-1), (Ih-2), (Ih-3), (Ih-4), (Ij), (Ij-1) or (Ij-2), or any of the compounds described herein, or a pharmaceutically acceptable salt or a solvate or hydrate thereof.

In another aspect, provided herewith is a method for suppressing the induction of expression of EGFR ligands in cells. The method includes contacting the mutant BRAF kinase in a cell with a compound of formula (I') or (I) or a compound of any of the subgeneric formulas of formula (I), or a compound as described herein, or a pharmaceutically acceptable salt or a solvate or hydrate thereof, or a composition comprising a compound of formula (I) or (I') or a compound of any of the subgeneric formulas of formula (I), for example, formulas (Ia), (Ia-1), (Ia-2), (Ib), (Ib-1), (Ib-2), (Ib-1a), (Ib-1b), (Ic), (Ic-1), (Ic-1a), (Ic-2), (Ic-2a), (Id), (Id-1), (Id-1a), (Id-2), (Id-2a), (Ie), (Ie-1), (Ie-1a), (Ie-2), (Ie-2a), (If), (If-1), (If-2), (If-3), (If-4), (Ig), (Ig-1), (Ig-2), (Ig-3), (Ig-4), (Ih), (Ih-1), (Ih-2), (Ih-3), (Ih-4), (Ij), (Ij-1) or (Ij-2), or any of the compounds described herein, or a pharmaceutically acceptable salt or a solvate or hydrate thereof, under condition sufficient to inhibit the mutant BRAF kinase, wherein the inhibition of BRAF kinase does not induce the expression of EGFR ligands. In some embodiments, the method includes administering to a subject an effective amount of a compound of formula (I) to suppress the induction of expression of EGFR ligands. The variables Y, $R^3$, $R^4$, L and Z are as defined in any of the embodiments of formula (I) or subgeneric formulas of formula (I) as described herein.

In another aspect, provided herewith is a method for inhibiting a mutant BRAF kinase. The method includes contacting the mutant BRAF kinase in a cell with a compound of formula (I') or (I) or a compound of any of the subgeneric formulas of formula (I), or a compound as described herein, or a pharmaceutically acceptable salt or a solvate or hydrate thereof, or a composition comprising a compound of formula (I) or (I') or a compound of any of the subgeneric formulas of formula (I), for example, formulas (Ia), (Ia-1), (Ia-2), (Ib), (Ib-1), (Ib-2), (Ib-1a), (Ib-1b), (Ic), (Ic-1), (Ic-1a), (Ic-2), (Ic-2a), (Id), (Id-1), (Id-1a), (Id-2), (Id-2a), (Ie), (Ie-1), (Ie-1a), (Ie-2), (Ie-2a), (If), (If-1), (If-2), (If-3), (If-4), (Ig), (Ig-1), (Ig-2), (Ig-3), (Ig-4), (Ih), (Ih-1), (Ih-2), (Ih-3), (Ih-4), (Ij), (Ij-1) or (Ij-2), or any of the compounds described herein, or a pharmaceutically acceptable salt or a solvate or hydrate thereof, under condition sufficient to inhibit the mutant BRAF kinase, wherein the inhibition of BRAF kinase does not cause or induce an activation of a pERK kinase. There is no reactivation of pERK kinase even in cells having RAS mutation or upstream receptor tyrosine kinase activation. In some embodiments of the methods provided herein, in formula (I), Y is —N($R^1$)($R^2$) $R^1$ and $R^2$ are each independently optionally substituted alkyl, aryl, heteroaryl, cycloalkyl or $R^1$ and $R^2$ taken together to form a optionally substituted 5- or 6-membered heterocycloalkyl ring having from 0-1 heteroatoms selected from O, N or S; $R^3$ is H or $C_{1-6}$alkyl; $R^4$ is halogen or hydrogen; L is a bond, —C(O)—, —C(S)— or —C[=C($R^5$)($R^6$)]—, wherein $R^5$ and $R^6$ are each independently a member selected from H, $R^7$, $R^a$, $R^b$, $R^c$, $R^d$, $R^e$, $R^f$ or $R^g$; or $R^5$ and $R^6$ are taken together to form an optionally substituted 5- or 6-membered ring having from 0-4 heteroatoms selected from O, N or S, where N and S are optionally oxidized; and Z is an optionally substituted aryl or optionally substituted heteroaryl. In some embodiments, Z is other than an optionally substituted

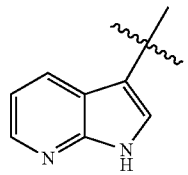 [SMILES: *c1c[nH]c2ncccc12]

core, wherein the wavy line indicates point of attachment to the rest of the molecule. In some instances, the variables $R^1$, $R^2$, $R^3$, $R^4$, L and Z are as defined in any of the embodiments described herein. In some instances, the BRAF inhibitor interact with the Leucine 505 amino acid residue in the C-terminal end of an αC helix results in inhibition of pERK activation. In some instances, the BRAF inhibitor is in direct contact with the Leucine 505 amino acid residue in the C-terminal end of an αC helix, for example, through the —N($R^1$)($R^2$) moiety.

In another aspect, provided herewith is a method for inhibiting a mutant BRAF kinase in a subject. The method includes administering to the subject an effective amount of a compound of formula (I') or (I) or a compound of any of the subgeneric formulas of formula (I), or a compound as described herein, or a pharmaceutically acceptable salt or a solvate or hydrate thereof, or a composition comprising a compound of formula (I) or (I') or a compound of any of the subgeneric formulas of formula (I), for example, formulas (Ia), (Ia-1), (Ia-2), (Ib), (Ib-1), (Ib-2), (Ib-1a), (Ib-1b), (Ic), (Ic-1), (Ic-1a), (Ic-2), (Ic-2a), (Id), (Id-1), (Id-1a), (Id-2), (Id-2a), (Ie), (Ie-1), (Ie-1a), (Ie-2), (Ie-2a), (If), (If-1), (If-2), (If-3), (If-4), (Ig), (Ig-1), (Ig-2), (Ig-3), (Ig-4), (Ih), (Ih-1), (Ih-2), (Ih-3), (Ih-4), (Ij), (Ij-1) or (Ij-2), or any of the compounds described herein, or a pharmaceutically acceptable salt or a solvate or hydrate thereof. In some embodiments of the methods provided herein, in formula (I), Y is —N($R^1$)($R^2$), wherein $R^1$ and $R^2$ are each independently optionally substituted alkyl, aryl, heteroaryl, cycloalkyl or $R^1$ and $R^2$ taken together to form a optionally substituted 5- or 6-membered heterocycloalkyl ring having from 0-1 heteroatoms selected from O, N or S; $R^3$ is H or $C_{1-6}$alkyl; $R^4$ is halogen or hydrogen; L is a bond, —C(O)—, —C(S)— or —C[=C($R^5$)($R^6$)]—, wherein $R^5$ and $R^6$ are each independently a member selected from H, $R^7$, $R^a$, $R^b$, $R^c$, $R^d$, $R^e$, $R^f$ or $R^g$; or $R^5$ and $R^6$ are taken together to form an optionally substituted 5- or 6-membered ring having from 0-4 heteroatoms selected from O, N or S, where N and S are optionally oxidized; and Z is an optionally substituted aryl or optionally substituted heteroaryl and wherein the inhibition of BRAF kinase does not cause the activation of a pERK kinase. There is no reactivation of pERK kinase even in cells having RAS mutation or upstream receptor tyrosine kinase activation. In some embodiments, Z is other than an optionally substituted

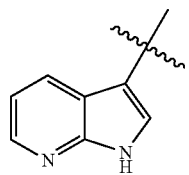 [SMILES: *c1c[nH]c2ncccc12]

core, wherein the wavy line indicates point of attachment to the rest of the molecule. In some instances, the variables $R^1$, $R^2$, $R^3$, $R^4$, L and Z are as defined in any of the embodiments described herein. In some instances, the BRAF inhibitors interact with the Leucine 505 amino acid residue in the C-terminal end of an αC helix results in inhibition of pERK activation. In some instances, the BRAF inhibitor is in direct contact with the Leucine 505 amino acid residue in the C-terminal end of an αC helix, for example, through the —N(R¹)(R²) or —C(R⁸)(R⁹)(R¹⁰) moiety.

In another aspect, provided herewith is a method for inhibiting the activity of a mutant BRAF$^{V600}$ protein kinase, for example, in a MPAK pathway. The method includes contacting the BRAF$^{V600}$ mutant with a BRAF inhibitor of formula (I') or (I) or a compound of any of the subgeneric formulas of formula (I), or a compound as described herein, or a pharmaceutically acceptable salt or a solvate or hydrate thereof, or a composition comprising a compound of formula (I) or (I') a compound of any of the subgeneric formulas of formula (I), for example, formulas (Ia), (Ia-1), (Ia-2), (Ib), (Ib-1), (Ib-2), (Ib-1a), (Ib-1b), (Ic), (Ic-1), (Ic-1a), (Ic-2), (Ic-2a), (Id), (Id-1), (Id-1a), (Id-2), (Id-2a), (Ie), (Ie-1), (Ie-1a), (Ie-2), (Ie-2a), (If), (If-1), (If-2), (If-3), (If-4), (Ig), (Ig-1), (Ig-2), (Ig-3), (Ig-4), (Ih), (Ih-1), (Ih-2), (Ih-3), (Ih-4), (Ij), (Ij-1) or (Ij-2), or any of the compounds described herein, or a pharmaceutically acceptable salt or a solvate or hydrate thereof, wherein the inhibition of mutant BRAF$^{V600}$ kinase does not cause or induce the activation of pERK. In some embodiments, the inhibiting the activity of a mutant BRAF$^{V600}$ protein kinase can be achieved by regulating the interaction of the —N(R¹)(R²) or —C(R⁸)(R⁹)(R¹⁰) group of the BRAF kinase inhibitor with the Leucine 505 amino acid residue in the C-terminal end of an αC helix. For example, the BRAF inhibitor can be in direct contact with the Leucine 505 amino acid residue in the C-terminal end of an αC helix, for example, via the —N(R¹)(R²) or —C(R⁸)(R⁹)(R¹⁰) group. The cells containing RAF kinase can have RAS mutation or upstream receptor tyrosine kinase activation. In some embodiments, the method includes contacting a BRAF$^{V600}$ protein kinase with a compound of formula (I):

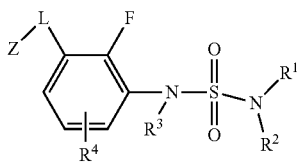

(I)

wherein R¹ and R² are each independently optionally substituted alkyl, aryl, heteroaryl, cycloalkyl or R' and R² taken together to form a optionally substituted 5- or 6-membered heterocycloalkyl ring having from 0-1 heteroatoms selected from O, N or S; R³ is H or C$_{1-6}$alkyl; R⁴ is halogen or hydrogen; L is a bond, —C(O)—, —C(S)— or —C[=C(R⁵)(R⁶)]—, wherein R⁵ and R⁶ are each independently a member selected from H, R⁷, R$^a$, R$^b$, R$^c$, R$^d$, R$^e$, R$^f$ or R$^g$; or R⁵ and R⁶ are taken together to form an optionally substituted 5- or 6-membered ring having from 0-4 heteroatoms selected from O, N or S, where N and S are optionally oxidized; Z is an optionally substituted aryl or optionally substituted heteroaryl. In some embodiments, Z is other than an optionally substituted

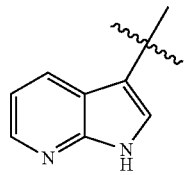 [SMILES: *c1c[nH]c2ncccc12]

core, wherein the wavy line indicates point of attachment to the rest of the molecule. In some instances, the variables R¹, R², R³, R⁴, L and Z are as defined in any of the embodiments described herein.

In another aspect, provided herewith is a method for inhibiting the activity of a mutant BRAF$^{V600}$ in a subject. The method includes administering to the subject in need thereof an effective amount of a BRAF inhibitor of formula (I') or (I) or a compound of any of the subgeneric formulas of formula (I), or a compound as described herein, or a pharmaceutically acceptable salt or a solvate or hydrate thereof, or a composition comprising a compound of formula (I) or (I') or a compound of any of the subgeneric formulas of formula (I), for example, formulas (Ia), (Ia-1), (Ia-2), (Ib), (Ib-1), (Ib-2), (Ib-1a), (Ib-1b), (Ic), (Ic-1), (Ic-1a), (Ic-2), (Ic-2a), (Id), (Id-1), (Id-1a), (Id-2), (Id-2a), (Ie), (Ie-1), (Ie-1a), (Ie-2), (Ie-2a), (If), (If-1), (If-2), (If-3), (If-4), (Ig), (Ig-1), (Ig-2), (Ig-3), (Ig-4), (Ih), (Ih-1), (Ih-2), (Ih-3), (Ih-4), (Ij), (Ij-1) or (Ij-2), or any of the compounds described herein, or a pharmaceutically acceptable salt or a solvate or hydrate thereof, wherein the inhibition of mutant BRAF$^{V600}$ kinase does not cause or induce the activation of pERK. In some embodiments, the method includes administering to the subject an effective amount of a compound of formula (I):

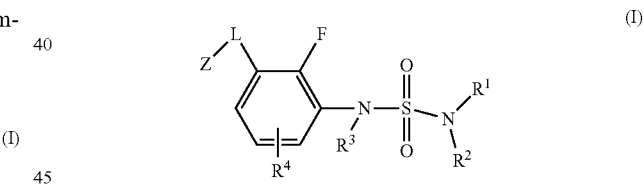

(I)

wherein R¹ and R² are each independently optionally substituted alkyl, aryl, heteroaryl, cycloalkyl or R' and R² taken together to form a optionally substituted 5- or 6-membered heterocycloalkyl ring having from 0-1 heteroatoms selected from O, N or S; R³ is H or C$_{1-6}$alkyl; R⁴ is halogen or hydrogen; L is a bond, —C(O)—, —C(S)— or —C[=C(R⁵)(R⁶)]—, wherein R⁵ and R⁶ are each independently a member selected from H, R⁷, R$^a$, R$^b$, R$^c$, R$^d$, R$^e$, R$^f$ or R$^g$; or R⁵ and R⁶ are taken together to form an optionally substituted 5- or 6-membered ring having from 0-4 heteroatoms selected from O, N or S, where N and S are optionally oxidized; and Z is an optionally substituted aryl or optionally substituted heteroaryl and wherein the inhibition of BRAF kinase does not cause the activation of a pERK kinase. There is no reactivation of pERK kinase even in cells having RAS mutation or upstream receptor tyrosine kinase activation. In some embodiments, Z is other than an optionally substituted

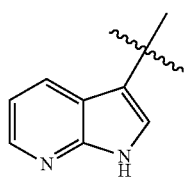 [SMILES: *c1c[nH]c2ncccc12]

core, wherein the wavy line indicates point of attachment to the rest of the molecule. In some instances, the variables $R^1$, $R^2$, $R^3$, $R^4$, L and Z are as defined in any of the embodiments described herein. In some instances, the BRAF inhibitors interact with the Leucine 505 amino acid residue in the C-terminal end of an αC helix results in inhibition of pERK activation. In some instances, the BRAF inhibitor can be in direct contact with the Leucine 505 amino acid residue in the C-terminal end of an αC helix, for example, through the —N($R^1$)($R^2$) or —C($R^8$)($R^9$)($R^{10}$) moiety.

In another aspect, provided herewith is a method for treating a subject suffering from a disease or condition as described herein. In some embodiments, diseases or conditions include a metastatic melanoma, a thyroid cancer, a colorectal cancer, a lung cancer or an ovarian cancer. The method includes administering to the subject in need there of an effective amount of a BRAF inhibitor of formula (I') or (I) or a compound of any of the subgeneric formulas of formula (I), or a compound as described herein, or a pharmaceutically acceptable salt or a solvate or hydrate thereof, or a composition comprising a compound of formula (I) or (I') or a compound of any of the subgeneric formulas of formula (I), for example, formulas (Ia), (Ia-1), (Ia-2), (Ib), (Ib-1), (Ib-2), (Ib-1a), (Ib-1b), (Ic), (Ic-1), (Ic-1a), (Ic-2), (Ic-2a), (Id), (Id-1), (Id-1a), (Id-2), (Id-2a), (Ie), (Ie-1), (Ie-1a), (Ie-2), (Ie-2a), (If), (If-1), (If-2), (If-3), (If-4), (Ig), (Ig-1), (Ig-2), (Ig-3), (Ig-4), (Ih), (Ih-1), (Ih-2), (Ih-3), (Ih-4), (Ij), (Ij-1) or (Ij-2), or any of the compounds described herein, or a pharmaceutically acceptable salt or a solvate or hydrate thereof, wherein the inhibition of mutant BRAF$^{V600}$ kinase does not cause or induce the activation of pERK. In some embodiments, the method includes administering to the subject an effective amount of a compound of formula (I):

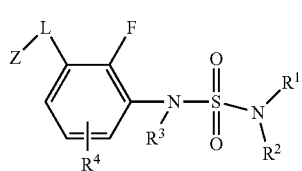

(I)

wherein $R^1$ and $R^2$ are each independently optionally substituted alkyl, aryl, heteroaryl, cycloalkyl or $R^1$ and $R^2$ taken together to form a optionally substituted 5- or 6-membered heterocycloalkyl ring having from 0-1 heteroatoms selected from O, N or S; $R^3$ is H or $C_{1-6}$alkyl; $R^4$ is halogen or hydrogen; L is a bond, —C(O)—, —C(S)— or —C[=C($R^5$)($R^6$)]—, wherein $R^5$ and $R^6$ are each independently a member selected from H, $R^7$, $R^a$, $R^b$, $R^c$, $R^d$, $R^e$, $R^f$ or $R^g$; or $R^5$ and $R^6$ are taken together to form an optionally substituted 5- or 6-membered ring having from 0-4 heteroatoms selected from O, N or S, where N and S are optionally oxidized; and Z is an optionally substituted aryl or optionally substituted heteroaryl and wherein the inhibition of BRAF kinase does not cause the activation of a pERK kinase. There is no reactivation of pERK kinase even in cells having RAS mutation or upstream receptor tyrosine kinase activation. In some embodiments, Z is other than an optionally substituted

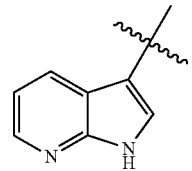 [SMILES: *c1c[nH]c2ncccc12]

core, wherein the wavy line indicates point of attachment to the rest of the molecule. In some instances, the variables $R^1$, $R^2$, $R^3$, $R^4$, L and Z are as defined in any of the embodiments described herein. In some instances, the BRAF inhibitors interact with the Leucine 505 amino acid residue in the C-terminal end of an αC helix results in inhibition of pERK activation. In some instances, the BRAF inhibitor can be in direct contact with the Leucine 505 amino acid residue in the C-terminal end of an αC helix, for example, through the —N($R^1$)($R^2$) or —C($R^8$)($R^9$)($R^{10}$) moiety.

In any of the methods provided herein, the mutant BRAF protein kinases can have a mutation encoding a V600 amino acid substitution, a L505 amino acid substitution or a combination thereof. Exemplary mutant BRAF kinases include BRAF$^{V600A}$, BRAF$^{V600M}$, BRAF$^{V600R}$, BRAF$^{V600E}$, BRAF$^{V600K}$, BRAF$^{V600G}$ or BRAF$^{L505H}$ or combinations thereof. In one instance, the mutant BRAF kinase has a V600E amino acid substitution. In another instance, the mutant BRAF kinase has a V600K amino acid substitution. In another instance, the mutant BRAF kinase has a V600 amino acid substitution. In another instance, the mutant BRAF kinase has V600 and L505 substitutions. In another instance, the mutant BRAF kinase has BRAF$^{V600E}$ and BRAF$^{L505H}$ mutations. In another instance, the mutant BRAF kinase has BRAF$^{V600K}$ and BRAF$^{L505H}$ mutations. In another instance, the mutant BRAF kinase has BRAF$^{V600A}$ and BRAF$^{L505H}$ mutations. In another instance, the mutant BRAF kinase has BRAF$^{V600M}$ and BRAF$^{L505H}$ mutations. In another instance, the mutant BRAF kinase has BRAF$^{V600R}$ and BRAF$^{L505H}$ mutations. In another instance, the mutant BRAF kinase has BRAF$^{V600G}$ and BRAF$^{L505H}$ mutations.

A compound of formula (I') or (I) or a compound of any of the subgeneric formulas of formula (I), or a compound as described herein, or a pharmaceutically acceptable salt or a solvate or hydrate thereof, or a composition comprising a compound of formula (I) or (I') or a compound of any of the subgeneric formulas of formula (I), for example, formulas (Ia), (Ia-1), (Ia-2), (Ib), (Ib-1), (Ib-2), (Ib-1a), (Ib-1b), (Ic), (Ic-1), (Ic-1a), (Ic-2), (Ic-2a), (Id), (Id-1), (Id-1a), (Id-2), (Id-2a), (Ie), (Ie-1), (Ie-1a), (Ie-2), (Ie-2a), (If), (If-1), (If-2), (If-3), (If-4), (Ig), (Ig-1), (Ig-2), (Ig-3), (Ig-4), (Ih), (Ih-1), (Ih-2), (Ih-3), (Ih-4), (Ij), (Ij-1) or (Ij-2), or any of the compounds described herein, or a pharmaceutically acceptable salt or a solvate or hydrate thereof, can have an $IC_{50}$ of less than 500 nm, less than 100 nM, less than 50 nM, less than 20 nM, less than 10 nM, less than 5 nM, or less than 1 nM as determined in a generally accepted RAF kinase activity assay. In some embodiments, a compound as described herein is selective relative to other protein kinases, such that the ratio of $IC_{ED}$ for another kinase assessed comparably, divided by the $IC_{ED}$ for RAF kinase is >20, also >30, also >40, also >50, also >60, also >70, also >80, also >90, also >100, wherein the other protein kinase includes, but is not limited to, wild type BRAF and C-raf kinases.

In some embodiments, a compound of formula (I') or (I) or a compound of any of the subgeneric formulas of formula (I), or a compound as described herein, or a pharmaceutically acceptable salt or a solvate or hydrate thereof, or a composition comprising a compound of formula (I) or (I') or a compound of any of the subgeneric formulas of formula (I), for example, formulas (Ia), (Ia-1), (Ia-2), (Ib), (Ib-1), (Ib-2), (Ib-1a), (Ib-1b), (Ic), (Ic-1), (Ic-1a), (Ic-2), (Ic-2a), (Id), (Id-1), (Id-1a), (Id-2), (Id-2a), (Ie), (Ie-1), (Ie-1a), (Ie-2), (Ie-2a), (If), (If-1), (If-2), (If-3), (If-4), (Ig), (Ig-1), (Ig-2), (Ig-3), (Ig-4), (Ih), (Ih-1), (Ih-2), (Ih-3), (Ih-4), (Ij), (Ij-1) or (Ij-2), or any of the compounds described herein, or a pharmaceutically acceptable salt or a solvate or hydrate thereof, is a potent inhibitor of mutant $BRAF^{V600K/L505H}$ or $BRAF^{V600E/L505H}$ with an $IC_{50}$ of less than 1 µM, less than 500 nm, less than 100 nM, less than 50 nM, less than 20 nM, less than 10 nM, less than 5 nM, or less than 1 nM as determined in a generally accepted RAF kinase activity assay.

Organic Synthetic Techniques

A wide array of organic synthetic techniques exist in the art to facilitate the construction of potential modulators. Many of these organic synthetic methods are described in detail in standard reference sources utilized by those skilled in the art. One example of such a reference is March, 1994, *Advanced Organic Chemistry; Reactions, Mechanisms and Structure*, New York, McGraw Hill. Thus, the techniques useful to synthesize a potential modulator of kinase function are readily available to those skilled in the art of organic chemical synthesis.

Alternative Compound Forms or Derivatives

Compounds contemplated herein are described with reference to both generic formulae and specific compounds. In addition, compounds disclosed herein may exist in a number of different forms or derivatives, all within the scope of the disclosure. Alternative forms or derivatives, include, for example, (a) prodrugs, and active metabolites (b) tautomers, isomers (including stereoisomers and regioisomers), and racemic mixtures (c) pharmaceutically acceptable salts and (d) solid forms, including different crystal forms, polymorphic or amorphous solids, including hydrates and solvates thereof, and other forms.

(a) Prodrugs and Metabolites

In addition to the present formulae and compounds described herein, the disclosure also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolism, the ester group is cleaved to yield the active drug. Esters include, for example, esters of a carboxylic acid group, or S-acyl or O-acyl derivatives of thiol, alcohol, or phenol groups. In this context, a common example is an alkyl ester of a carboxylic acid. Prodrugs may also include variants wherein an —NH group of the compound has undergone acylation, such as the 1-position of the 1H-pyr-rolo[2,3-b]pyridine ring, or the nitrogen of the sulfonamide group of compounds as described herein, where cleavage of the acyl group provides the free —NH group of the active drug. Some prodrugs are activated enzymatically to yield the active compound, or a compound may undergo further chemical reaction to yield the active compound. Prodrugs may proceed from prodrug form to active form in a single step or may have one or more intermediate forms which may themselves have activity or may be inactive.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative reactions: Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation by reactions such as reduction of carbonyl functionalities, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation by reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, incorporated herein by reference.) Such carrier prodrugs are often advantageous for orally administered drugs. In some instances, the transport moiety provides targeted delivery of the drug, for example the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

Metabolites of a compound may be identified using routine techniques known in the art, and their activities determined using tests such as those described herein. See, e.g., Bertolini et al., 1997, *J. Med. Chem.*, 40:2011-2016; Shan et al., 1997, *J Pharm Sci* 86(7):756-757; Bagshawe, 1995, *Drug Dev. Res.*, 34:220-230; Wermuth, supra.

(b) Tautomers, Stereoisomers, and Regioisomers

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds disclosed herein may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the disclosure. Unless specified to the contrary, all such stereoisomeric forms are included within the formulae provided herein.

In some embodiments, a chiral compound disclosed herein is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form, such optically pure form being prepared and/or isolated by methods known in the art (e.g. by recrystallization techniques, chiral synthetic techniques (including synthesis from optically pure starting materials), and chromatographic separation using a chiral column.

(c) Pharmaceutically Acceptable Salts

Unless specified to the contrary, specification of a compound herein includes pharmaceutically acceptable salts of such compound. Thus, compounds described herein and recited in any of the claims can be in the form of pharmaceutically acceptable salts, or can be formulated as pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. A compound described herein may possess a sufficiently acidic, a sufficiently basic, or both functional groups, and accordingly can react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, phenylacetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1, 6-dioate, caproate, caprylate, chlorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4-aminosalicylate, sebacate, stearate, suberate, succinate, sulfate, pyrosulfate, bisulfate, sulfite, bisulfite, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine. For example, see Remington's Pharmaceutical Sciences, 19$^{th}$ ed., Mack Publishing Co., Easton, Pa., Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

(d) Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the disclosure and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds described herein are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound disclosed herein with the acid or base, an amorphous complex is preferably formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, dimethyl sulfoxide, ethyl acetate, acetic acid, or ethanolamine.

IV. Formulations and Administration

In another aspect, some embodiments provide for pharmaceutical compositions comprising/including a pharmaceutically acceptable carrier or excipient and a compound described herein or a pharmaceutically acceptable salt or solvate thereof. An exemplary embodiment provides a pharmaceutical formulation comprising/including a compound as described herein. In one embodiment, the compound has any of formulas I, and Ia to In.

The methods and compounds will typically be used in therapy for human subjects. However, they may also be used to treat similar or identical indications in other animal subjects. Compounds described herein can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in Remington: *The Science and Practice of Pharmacy*, 21$^{st}$ edition, Lippincott, Williams and Wilkins, Philadelphia, Pa., 2005 (hereby incorporated by reference herein).

In some embodiments, compositions will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, difatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound described herein (as a free-base, solvate (including hydrate) or salt, in any form), depending on the condition being treated, the route of administration, and the age, weight and condition of the patient. Preferred unit dosage formulations are those containing a daily dose, weekly dose, monthly dose, a sub-dose or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including capsules, tablets, liquid-filled capsules, disintegrating tablets, immediate, delayed and controlled release tablets, oral strips, solutions, syrups, buccal and sublingual), rectal, nasal, inhalation, topical (including transdermal), vaginal or parenteral (including subcutaneous, intramuscular, intravenous or intradermal) route. Such formulations may be prepared by any method known in the art of pharmacy, for example by bringing into association the active ingredient with the carrier(s), excipient(s) or diluent. Generally, the carrier, excipient or diluent employed in the pharmaceutical formulation is "non-toxic," meaning that it/they is/are deemed safe for consumption in the amount delivered in the pharmaceutical composition, and "inert" meaning that it/they does/do not appreciably react with or result in an undesired effect on the therapeutic activity of the active ingredient.

In some embodiments, oral administration may be used. Pharmaceutical preparations for oral use can be formulated into conventional oral dosage forms such as discreet units capsules, tablets, and liquid preparations such as syrups, elixirs, and concentrated drops. Compounds described herein may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethylcellulose, sodium carboxymethylcellulose (CMC), and/or polyvinylpyrrolidone (PVP: povidone); oily excipients, including vegetable and animal oils, such as sunflower oil, olive oil, or cod-liver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations, such as unit dosages. Also provided are dragee cores with suitable coatings. For this purpose, concentrated sugar solutions may be used, which may optionally contain, for example, gum arabic, talc, poly-vinylpyrrolidone, carbopol gel, polyethylene glycol, and/or titanium dioxide, lacquer solutions, and suitable organic solvents or solvent mixtures. Oral fluids such as solutions, syrups and elixirs can be prepared in dosage unit form so that a given quantity contains a predetermined amount of the compound.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds described herein for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use. The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use.

In some embodiments, transmucosal, topical or transdermal administration may be used. In such formulations of compounds described herein, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds described herein for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, compounds are administered as inhalants. Compounds described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds described herein may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

The compounds described herein may also be used in combination with other therapies for treating the same disease. Such combination use includes administration of the compounds and one or more other therapeutics at different times, or co-administration of the compound and one or more other therapies. In some embodiments, dosage may be modified for one or more of the compounds described herein or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound described herein, or at the same time as a compound described herein. Use in combination also includes use with a therapy or medical procedure that is administered once or infrequently, such as surgery, along with a compound described herein administered within a short time or longer time before or after the other therapy or procedure. In some embodiments, the disclosure provides for delivery of a compound described herein and one or more other drug therapeutics delivered by a different route of administration or by the same route of administration. The use in combination for any route of administration includes delivery of a compound described herein and one or more other drug therapeutics delivered by the same route of administration together in any formulation, including formulations where the two compounds are chemically linked in such a way that they maintain their therapeutic activity when administered. In one aspect, the other drug therapy may be co-administered with a compound described herein. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound described herein and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

V. Kinase Targets and Indications

Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Specific target protein kinases contemplated by the disclosure are described in the art, including, without limitation, protein kinases as described in U.S. patent application Ser. No. 11/473,347 (see also, PCT publication WO2007002433), the disclosure of which is hereby incorporated by reference as it relates to such kinase targets, as well as the following:

A-Raf:

Target kinase A-Raf (i.e., v-raf murine sarcoma 3611 viral oncogene homolog 1) is a 67.6 kDa serine/threonine kinase encoded by chromosome Xp11.4-p11.2 (symbol: ARAF). The mature protein comprises RBD (i.e., Ras binding domain) and phorbol-ester/DAG-type zinc finger domain and is involved in the transduction of mitogenic signals from the cell membrane to the nucleus. A-Raf inhibitors may be useful in treating neurologic diseases such as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myelodysplastic syndrome, leukemia, tumor angiogenesis; pain of neuropathic or inflammatory origin, including acute pain, chronic pain, cancer-related pain and migraine; and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

BRAF:

Target kinase BRAF (i.e., v-raf murine sarcoma viral oncogene homolog B1) is a 84.4 kDa serine/threonine kinase encoded by chromosome 7q34 (symbol: BRAF). The mature protein comprises RBD (i.e., Ras binding domain), C1 (i.e., protein kinase C conserved region 1) and STK (i.e., serine/threonine kinase) domains.

Target kinase BRAF is involved in the transduction of mitogenic signals from the cell membrane to the nucleus and may play a role in the postsynaptic responses of hippocampal neurons. As such, genes of the RAF family encode kinases that are regulated by Ras and mediate cellular responses to growth signals. Indeed, BRAF kinase is a key component of the RAS→Raf→MEK→ERK/MAP kinase signaling pathway, which plays a fundamental role in the regulation of cell growth, division and proliferation, and, when constitutively activated, causes tumorigenesis. Among several isoforms of Raf kinase, the B-type, or BRAF, is the strongest activator of the downstream MAP kinase signaling.

The BRAF gene is frequently mutated in a variety of human tumors, especially in malignant melanoma and colon carcinoma. The most common reported mutation was a missense thymine (T) to adenine (A) transversion at nucleotide 1796 (T1796A; amino acid change in the BRAF protein is Val<600> to Glu<600>) observed in 80% of malignant melanoma tumors. Functional analysis reveals that this transversion is the only detected mutation that causes constitutive activation of BRAF kinase activity, independent of RAS activation, by converting BRAF into a dominant transforming protein. Based on precedents, human tumors develop resistance to kinase inhibitors by mutating a specific amino acid in the catalytic domain as the "gatekeeper". (Balak, et. al., Clin Cancer Res. 2006, 12:6494-501). Mutation of Thr-529 in BRAF to Ile is thus anticipated as a mechanism of resistance to BRAF inhibitors, and this can be envisioned as a transition in codon 529 from ACC to ATC.

Niihori et al., report that in 43 individuals with cardio-facio-cutaneous (CFC) syndrome, they identified two heterozygous KRAS mutations in three individuals and eight BRAF mutations in 16 individuals, suggesting that dysregulation of the RAS-RAF-ERK pathway is a common molecular basis for the three related disorders (Niihori et al., Nat Genet. 2006, 38(3):294-6).

Many cancers associated with dysregulation of the RAS-RAF-ERK pathway, such as cancers having BRAF V600, such as V600E mutations or NRAS mutations, may be treated with Raf kinase inhibitors, such as the Pan Raf kinase inhibitors as described herein. The ability of these compounds to inhibit multiple Raf kinase targets, including c-Raf-1, BRAF, and BRAF V600, such as V600E, provides additional benefits for inhibiting activating mutations in this pathway, with such cancers less likely to develop resistance to such inhibitors as they are targeting several points in the pathway. Pan Raf kinase inhibitors as described herein may be useful in treating a variety of cancers, including, but not limited to, melanoma, glioma, glioblastoma mulitforme, pilocytic astrocytoma, carcinoma (e.g. gastrointestinal, liver, biliary tract, bile duct (cholangiocarcinoma), colorectal, lung, brain, bladder, gallbladder, breast, pancreatic, thyroid, kidney, ovarian, adrenocortical, prostate), gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma. See McDermott et al., PNAS, 2007, 104(50): 19936-19941; and Jaiswal et al., PLoS One, 2009, 4(5):e5717.

c-Raf-1:

Target kinase c-Raf-1 (i.e., v-raf murine sarcoma viral oncogene homolog 1) is a 73.0 kDa STK encoded by chromosome 3p25 (symbol: RAF1). c-Raf-1 can be targeted to the mitochondria by BCL2 (i.e., oncogene B-cell leukemia 2) which is a regulator of apoptotic cell death. Active c-Raf-1 improves BCL2-mediated resistance to apoptosis, and c-Raf-1 phosphorylates BAD (i.e., BCL2-binding protein). c-Raf-1 is implicated in carcinomas, including colorectal, ovarian, lung and renal cell carcinoma. c-Raf-1 is also implicated as an important mediator of tumor angiogenesis (Hood, J. D. et al., 2002, Science 296, 2404). c-Raf-1 inhibitors may also be useful for the treatment of acute myeloid leukemia and myelodysplastic syndromes (Crump, Curr Pharm Des 2002, 8(25):2243-8). c-Raf-1 activators may be useful as treatment for neuroendocrine tumors, such as medullary thyroid cancer, carcinoid, small cell lung cancer and pheochromocytoma (Kunnimalaiyaan et al., Anticancer Drugs 2006, 17(2): 139-42).

Raf inhibitors (A-Raf and/or BRAF and/or c-Raf-1) may be useful in treating A-Raf-mediated, BRAF-mediated or c-Raf-1-mediated diseases or conditions selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract, bile duct (cholangiocarcinoma), colorectal, lung, brain, bladder, gallbladder, breast, pancreatic, thyroid, renal, ovarian, adrenocortical, prostate), lymphoma (e.g. histiocytic lymphoma) neurofibromatosis, acute myeloid leukemia, myelodysplastic syndrome, leukemia, chronic myelomonocytic leukemia, childhood, acute lymphoblastic leukemia, plasma cell leukemia, multiple myeloma, tumor angiogenesis, gastrointestinal stromal tumors, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, *Hepatitis* and *Influenza* viruses, fever, HIV, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

Erk2:

Target kinase Erk2 (i.e., extracellular signal-regulated kinase 2) is a 41.4 kDa dual function serine/threonine-tyrosine kinase encoded by chromosome 22q11.2 (symbol: MAPK1). Erk2 is a member of the mitogen-activated protein (MAP) kinase family and is alternatively known as mitogen-activated protein kinase 1 (i.e., MAPK1). MAP kinases act as an integration point for multiple biochemical signals, and are involved in a wide variety of cellular processes such as proliferation, differentiation, transcription regulation and development.

The activation of Erk2 requires phosphorylation by upstream kinases. Upon activation, Erk2 translocates to the nucleus of the stimulated cells, where it phosphorylates nuclear targets, in addition to other targets including microtubule associated protein 2, myelin basic protein and ELK1. MacKenzie et al. state that the cAMP-specific phosphodiesterase family 4, subfamily D, isoform 3 (i.e., PDE4D3) is shown to have FQF (i.e., Phe-Gln-Phe) and KIM (i.e., Kinase Interaction Motif) docking sites for Erk2. These sites straddle the Ser(579) target residue for Erk2 phosphorylation of PDE4D3. Mutation of either or both of these docking sites prevent Erk2 from being co-immunoprecipitated with PDE4D3, ablate the ability of epidermal growth factor (EGF) to inhibit PDE4D3 through Erk2 action in transfected COS cells, and attenuate the ability of Erk2 to phosphorylate PDE4D3 in vitro. The two conserved NH(2)-terminal blocks of sequence, called upstream conserved regions 1 and 2 (i.e., UCR1 and UCR2), that characterize PDE4 long isoforms, are proposed to amplify the small, inherent inhibitory effect that Erk2 phosphorylation exerts on the PDE4D catalytic unit. In contrast to this, the lone intact UCR2 region found in PDE4D1 directs COOH-terminal Erk2 phosphorylation to cause the activation of this short isoform. From the analysis of PDE4D3 truncates, it is suggested that UCR1 and UCR2 provide a regulatory signal integration module that serves to orchestrate the functional consequences of Erk2 phosphorylation. The PDE4D gene thus encodes a series of isoenzymes that are either inhibited or activated by Erk2 phosphorylation and thereby offers the potential for ERK2 activation either to increase or decrease cAMP levels in cellular compartments (MacKenzie et al., J Biol Chem 2000, 275(22):16609-17).

According to OMIM, Pleschka et al. (Nature Cell Biol., 2001, 3: 301-305) proposed that Erk2 regulates a cellular factor involved in the viral nuclear export protein function. They suggested that local application of MEK inhibitors may have only minor toxic effects on the host while inhibiting viral replication without giving rise to drug-resistant virus variants (OMIM MIM Number: 176948: Oct. 27, 2005). Erk2 is involved in cytokine signaling and is a target for treating inflammation. Ramesh and Philipp state that lipoproteins are the key inflammatory molecule type of *Borrelia burgdorferi*, the spirochete that causes Lyme disease. They investigated whether specific inhibition of p38 and Erk1/2 MAPK would inhibit TNF-alpha and IL-6 production and thus astrocyte apoptosis, and proliferation, respectively. Lipoprotein-stimulated IL-6 production was unaffected by the MAPK inhibitors. In contrast, inhibition of both p38 and Erk1/2 significantly diminished TNF-alpha production, and totally abrogated production of this cytokine when both MAPK pathways were inhibited simultaneously. MAPK inhibition thus may be considered as a strategy to control inflammation and apoptosis in Lyme neuroborreliosis (Ramesh and Philipp, Neurosci Lett 2005, 384(1-2):112-6). The role of Erk2 in signaling of cell differentiation, proliferation and survival suggests that inhibition of Erk2 may be therapeutic for several types of cancer. Husain et al. studied the effect of NSAIDs on MAPK activity and phosphorylation in gastric cancer. They conclude that NS-398 (a selective COX-2 inhibitor) and indomethacin (a non-selective NSAID) significantly inhibit proliferation and growth of human gastric cancer cell line MKN28. This effect is mediated by NSAID-induced inhibition of MAPK (ERK2) kinase signaling pathway, essential for cell proliferation (Husain et al., Life Sci 2001, 69(25-6):3045-54). Erk2 inhibitors may be useful in treating cancer, including gastric cancer, and in treating inflammation, including control of inflammation and apoptosis in Lyme neuroborreliosis.

Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases describe assays that can be used.

In certain embodiments, compounds as disclosed herein are active in an assay measuring BRAF protein kinase activity. In some embodiments, a compound as described herein has an $IC_{50}$ of less than 1,000 nM, less than 500 nM, less than 100 nM, less than 50 nM, less than 20 nM, less than 10 nM, less than 5 nM, or less than 1 nM as determined in a generally accepted BRAF kinase activity assay. In some embodiments, a compound as described herein has an $IC_{50}$ of less than 1,000 nM, less than 500 nM, less than 100 nM, less than 50 nM, less than 20 nM, less than 10 nM, less than 5 nM, or less than 1 nM as determined in a generally accepted mutant BRAF kinase (such as V600A, V600M, V600R, V600E, V600K or V600G) activity assay. In some embodiments the assay for measuring BRAF kinase activity and/or mutant BRAF kinase (such as V600A, V600M, V600R, V600E, V600K or V600G) activity includes an assay (e.g., biochemical or cell-bases assays) such as described in Example 13 or an assay well known in the art similar to those described in Example 13.

In some embodiments, compounds as described herein have little or no activity in an assay measuring activation of the ERK pathway (i.e., in stimulating the phosphorylation of ERK 1/2). In some embodiments, compounds as described herein have an $EC_{50}$ in an ERK activation assay that is greater than 1 μM; or greater than 2 μM; or greater than 3 μM; or greater than 4 μM; or greater than 5 μM; or greater than 8 μM; or greater than 10 μM. In certain embodiments, the assay for measuring activation of the ERK pathway includes an assay (e.g., biochemical or cell-bases assays) such as described in Example 13 or one or more assays well known in the art for measuring ERK activity similar to that described in Example 13.

In some embodiments, compounds as described herein are active in an assay measuring BRAF protein kinase activity and/or an assay for measuring mutant BRAF (such as V600A, V600M, V600R, V600E, V600K or V600G) protein kinase activity, and have little or no activity in an assay measuring activation of the ERK pathway. In some embodiments a compound as described herein has an $IC_{50}$ of less than 1,000 nM, less than 500 nM, less than 100 nM, less than 50 nM, less than 20 nM, less than 10 nM, less than 5 nM, or less than 1 nM as determined in a generally accepted BRAF kinase activity assay (including a mutant BRAF kinase activity assay) and an $EC_{50}$ in an ERK activation assay that is greater than 1 μM; or greater than 2 μM; or greater than 3 μM; or greater than 4 μM; or greater than 5 μM; or greater than 8 μM; or greater than 10 μM. In some embodiments, a compound as described herein has an $IC_{50}$ of less than 100 nM in a V600A, V600M, V600R, V600E, V600K or V600G mutant BRAF activity assay and an $EC_{50}$ of greater than 10 in an ERK activation assay.

Figure 5:
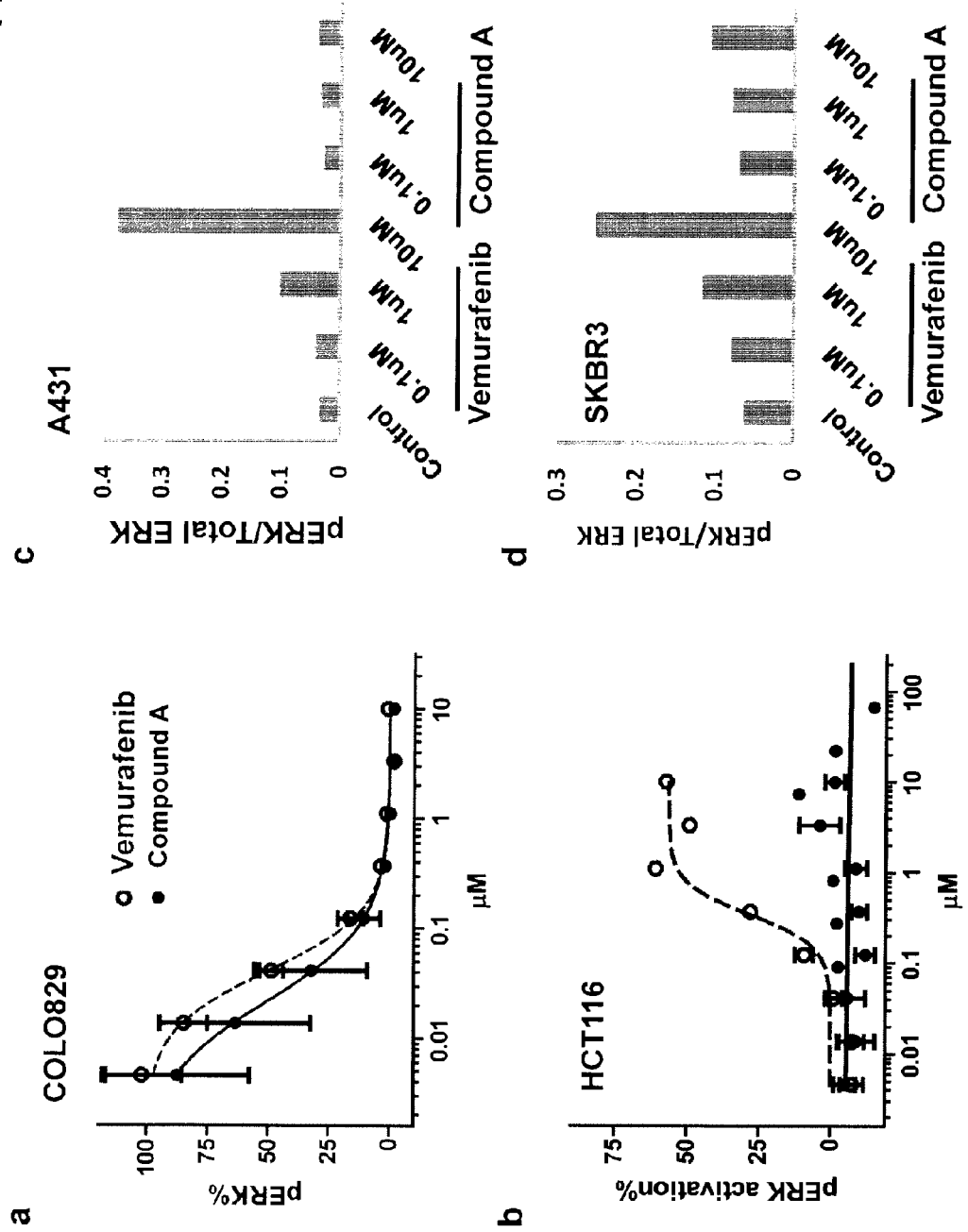
FIG. 5. Compounds containing sulfamoylamino moiety, for example, compounds of formula (I), such as compound A, and vemurafenib show similar potency in blocking pERK signaling in (a) human BRAF$^{V600E}$ melanoma cell COLO829 but in (b) RAS activated human colorectal carcinoma cell line HCT116 (KRAS$^{G13D}$), (c) EGFR-overexpressed human SCC cell line A431 or (d) HER2-overexpressed human breast carcinoma cell line SKBR3, vemurafenib paradoxically activates MAPK signaling whereas compound A causes negligible pERK increase. The pERK curves in COLO829 and HCT116 were generated using AlphaScreen® assay. (c) and (d) Quantification of the immunoblots in FIG. 1c.

Compounds as described herein or compounds of formula (I) or any subgeneric formulas, or a pharmaceutically acceptable salt, a solvate, a tautomer or an isomer thereof, or a composition comprising a compound as described herein or a compound of formula (I) or any subgeneric formulas, or a pharmaceutically acceptable salt, a solvate, a tautomer or an isomer thereof are effective in pERK inhibition and show essentially no pERK activation in RAS mutant cell line. The degree of separation between pERK inhibition and activation (dubbed "phospho-selectivity") is expressed as the ratio between the mean pERK activation $EC_{50}$ of a compound in three RAS mutant cell lines (murine cuSCC cell line B9, human melanoma cell line IPC-298, and human colorectal carcinoma cell line HCT116) and its mean pERK inhibition $IC_{50}$ in two $BRAF^{V600E}$ melanoma cell lines (A375 and COLO829). FIG. 1a and FIG. 5 demonstrate that a compound of formula (I), for example, compound A exhibits essentially no pERK activation in RAS mutant cell lines at up to the highest concentration tested.

Compounds as described herein or compounds of formula (I) or any subgeneric formulas, or a pharmaceutically acceptable salt, a solvate, a tautomer or an isomer thereof, or a composition comprising a compound as described herein or a compound of formula (I) or any subgeneric formulas, or a pharmaceutically acceptable salt, a solvate, a tautomer or an isomer thereof do not increase pERk level in cells. For example, a compound of formula (I) such as compound A was evaluated in the human SCC cell line A431 and the human breast carcinoma cell line SKBR3 as these cells express active MAPK pathway by upstream signals feeding into RAS (though overexpression of EGFR and HER2, respectively). Unlike vemurafenib, compound A did not increase pERK levels in these cells (FIG. 1b). As used herein, Paradox Breakers refer to a class of BRAF inhibitory compounds that selectively inhibit mutant BRAF protein kinase, but does not increase pERK levels in cells.

Compounds as described herein or compounds of formula (I) or any subgeneric formulas, or a pharmaceutically acceptable salt, a solvate, a tautomer or an isomer thereof, or a composition comprising a compound as described herein or a compound of formula (I) or any subgeneric formulas, or a pharmaceutically acceptable salt, a solvate, a tautomer or an isomer thereof are effective in inhibit the in vitro growth of colorectal cancer cell line COLO205 that expresses $BRAF^{V600E}$ For example, compound A inhibited the in vitro growth of two aforementioned melanoma cell lines (A375 and COLO829) and an additional human colorectal cancer cell line COLO205 that expresses $BRAF^{V600E}$ The growth inhibition $IC_{50}$'s of compound A in the three cell lines are less than 1 μM. Consistent with this in vitro result, a compound of formula (I), for example, compound A and vemurafenib produced similar antitumor effects in a subcutaneous COLO205 xenograft model (FIG. 1c) with matching doses (25 mg/kg twice daily) and plasma exposures (steady state AUC=~200,000 hr*ng/mL). In soft agar, both vemurafenib and its sister compound N-[3-(5-chloro-1H-pyrrolo[2,3-b]pyridine-3-carbonyl)-2,4-difluoro-phenyl]propane-1-sulfonamide (P-1000) stimulated B9 colony formation at concentrations similar to the growth inhibitory $IC_{50}$'s in A375, COLO829 and COLO205 cells whereas compounds of formula (I) do not (FIG. 1d). When tested in vivo, subcutaneous B9-tumor growth was accelerated by vemurafenib but not by compounds of formula (I), for example, compound A administered at the same dose (FIG. 1e).

Figure 2:
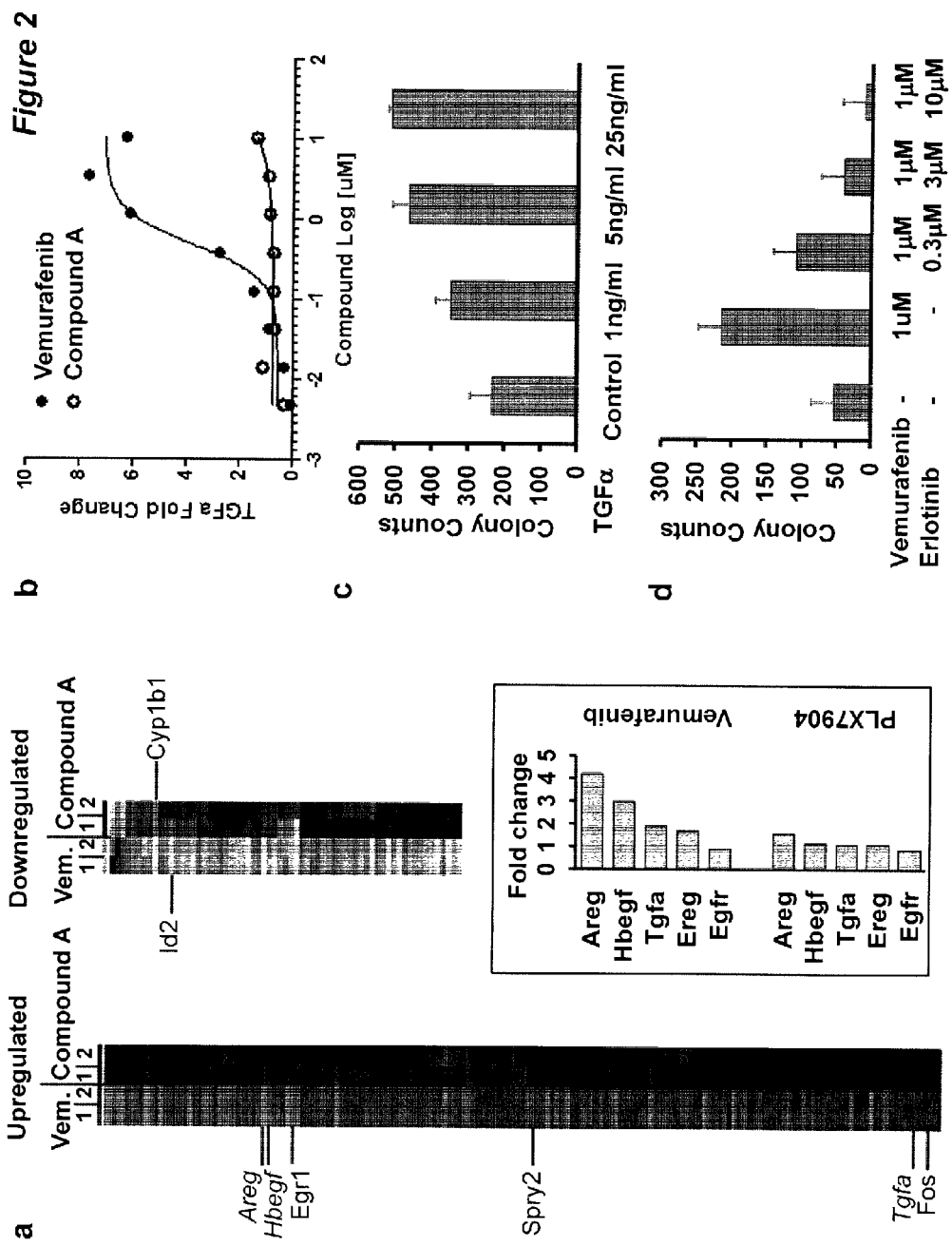
FIG. 2. A link between EGFR signaling and vemurafenib-induced cuSCC. (a) Hierarchical clustering of the 239 Affymetrix gene probes (see Table 4 for a complete list) that showed altered expression in B9 cells in response to either vemurafenib (233 probes) or a compound of formula (I), e.g. compound A (4 probes) treatment. The single overlap, Cyp1b1, and four representative MAPK pathway-responsive genes as well as three genes that encode EGFR ligands are marked. The inset shows the fold change in the expression of four EGFR ligands along with EGFR itself. (b) vemurafenib, but not compound A, induced TGFα protein expression in B9 cells. (c) Exogenous TGFα stimulated the anchorage-independent growth of B9 cells. (d) Erlotinib inhibited vemurafenib-induced growth of B9 cells.
Figure 6:
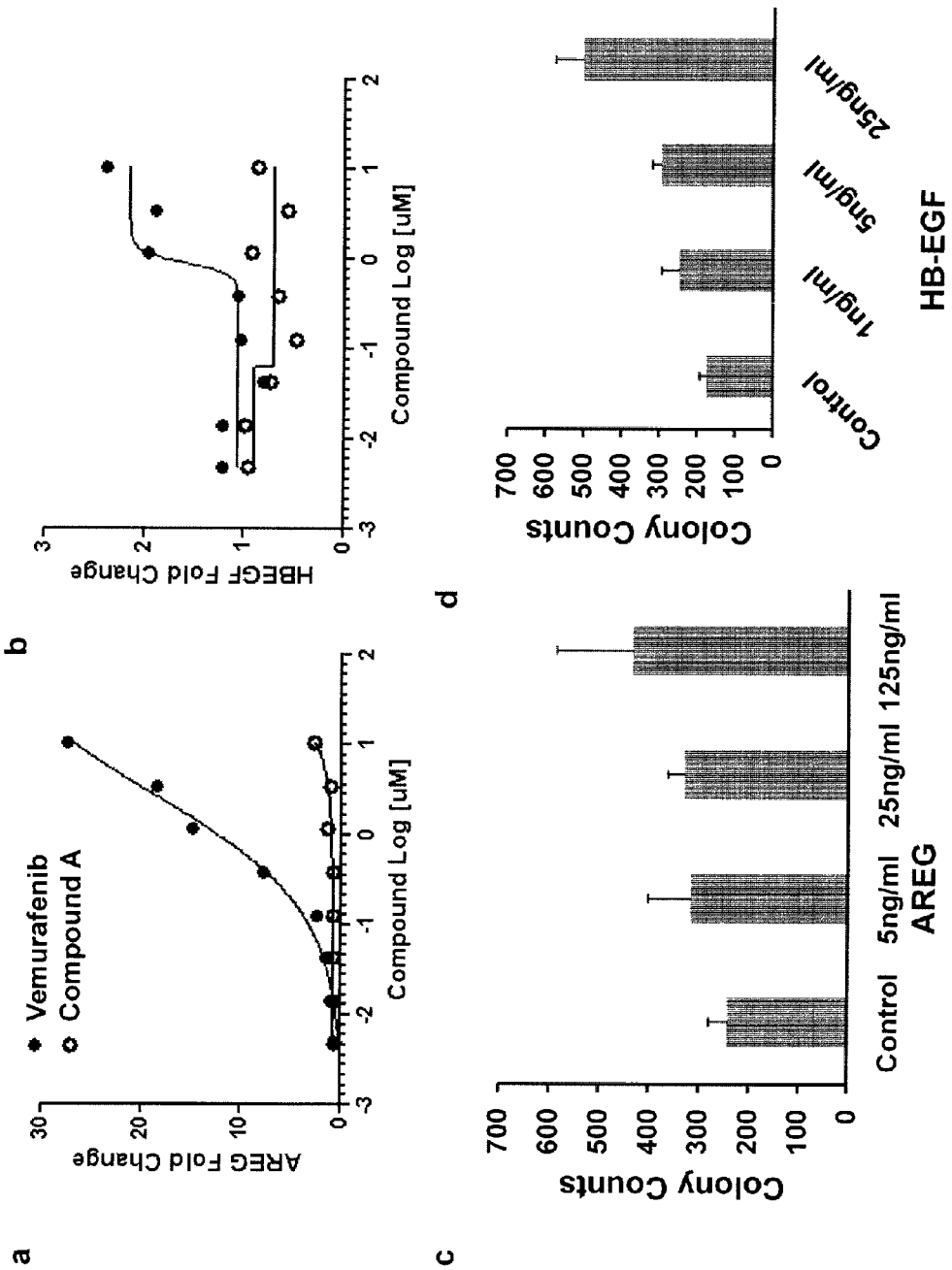
FIG. 6. Vemurafenib significantly induces the expression of EGFR ligands in transformed keratinocytes. (a) vemurafenib's upregulation of AREG protein in B9 cell supernatant and (b) its upregulation of HB-EGF in B9 cell lysates were confirmed by ELISA assay. Compounds containing sulfamoylamino moiety, for example, compounds of formula (I), don't induce the expression of EGFR ligands. (c) and (d) Exogenous EGFR ligands AREG and HB-EGF recapitulate the growth stimulating effect of vemurafenib.

Gene expression changes in B9 cells after exposure to vemurafenib and a compound of formula (I), e.g. compound A were compared. After sorting by differential expression scores, a total of 233 Affymetrix Mouse430_2 probes (representing 191 uniquely annotated mouse genes) showed more than 1.9 fold changes in response to overnight incubation of 1 μM vemurafenib (FIG. 2a and Table 4). Several of the best-characterized markers of the MAPK pathway response genes, including Spry2, Fos, and Egr1, were upregulated by vemurafenib. The corresponding human genes are known to be suppressed by vemurafenib in $BRAF^{V600E}$ mutant human melanoma[20]. Therefore, BRAF inhibitor-stimulated growth of B9 cells results from paradoxically increased MAPK signaling and associated transcriptional effects in cells with mutant HRAS. In contrast, compounds of formula (I), e.g. compound A had a minimal effect on B9 cells: affecting the expression of only a few genes (FIG. 2a and Table 4). Of the genes significantly induced by vemurafenib in B9 cells, three (AREG, HB-EGF and TGFα) code for EGFR ligands (amphiregulin, heparin-binding EGF-like growth factor, and transforming growth factor α, respectively) (FIG. 2a). The upregulation of AREG, HB-EGF and TGFα proteins in B9 cells were confirmed by ELISA (FIG. 2b and FIG. 6). All three ligands have been shown to promote SCC (Oshima, G. et al. *J Cancer Res Clin Oncol* 138, 491-499 (2012)). The fourth EGFR ligand that was abundantly expressed in B9 cells, EREG/epiregulin, was also moderately induced, although the expression of EGFR and other ERBB family members remained unchanged (FIG. 2a). not being bound by the theory, the overexpression of these autocrine growth factors may synergize with the transforming potential of activated HRAS. In the soft agar assay, exogenous AREG, HB-EGF and TGFα stimulated B9 cell colony formation (FIG. 2c and FIG. 6) whereas the EGFR inhibitor erlotinib antagonizes vemurafenib-induced B9 colony formation (FIG. 2d). Not being bound by the theory, these data implicate EGFR signaling as a potential molecular link between BRAF inhibition and squamous cell carcinogenesis. In contrast to vemurafenib and consistent with its Paradox Breaker profile, expression of the EGFR ligands was largely unaffected by compounds as described herein, e.g. compounds of formula (I) (FIG. 2a).

Compounds as described herein or compounds of formula (I') or (I) or any subgeneric formulas, or a pharmaceutically acceptable salt, a solvate, a tautomer or an isomer thereof, or a composition comprising a compound as described herein or a compound of formula (I) or any subgeneric formulas, or a pharmaceutically acceptable salt, a solvate, a tautomer or an isomer thereof effective in modulating RAF dimerization. Based on the crystal structures of compounds of formula (I') or (I) in complex with $BRAF^{V600E}$, the terminal

Figure 3:
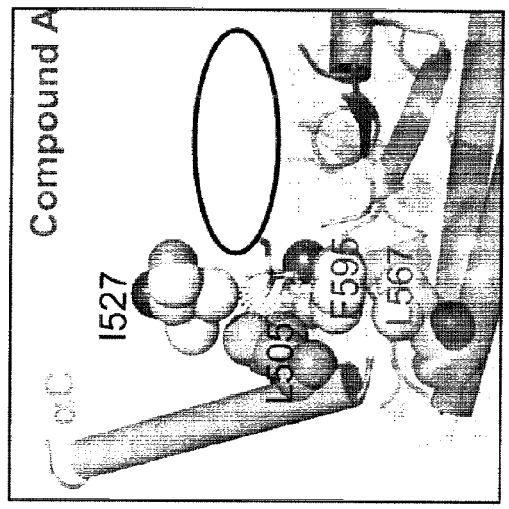
FIG. 3. Illustration of the differentiating molecular mechanism of Paradox Breakers, e.g. compounds containing a sulfamoylamino moiety or compounds of formula (I') or (I). (a) Comparative binding of the N-ethylmethyl-sulfamoid tail in compound A (with carbon atoms in green) and that of the propyl-sulfonamide tail of vemurafenib (with carbon atoms in cyan). The complexes are viewed from the dimer interfaces. The N-lobe is removed to show the inhibitor and its interaction with the four-residue R-spine (Leu505, Ile527, Leu567 and Phe595) and αC helix (orange). A dotted surface around the N-methyl group in compound A illustrates its close contact with the R-spine residue Leu505. Phe595 of the DFG motif is depicted as spheres to indicate the DFG-in conformation of the activation loop (Type 1 binding mode). Other pocket residues are rendered in sticks; (b) BRAF-CRAF heterodimers in B9 and IPC-298 cells after one hour treatment with increasing concentrations of compound A or vemurafenib, (c) pMEK and growth IC50 curves for vemurafenib and compound A in the SKMEL-239 parental cell line and a representative vemurafenib-resistant clone (C3) that expresses a spliced variant of BRAF$^{V600E}$. Vemurafenib-resistant cells remain relatively sensitive to Paradox Breakers.
Figure 3:
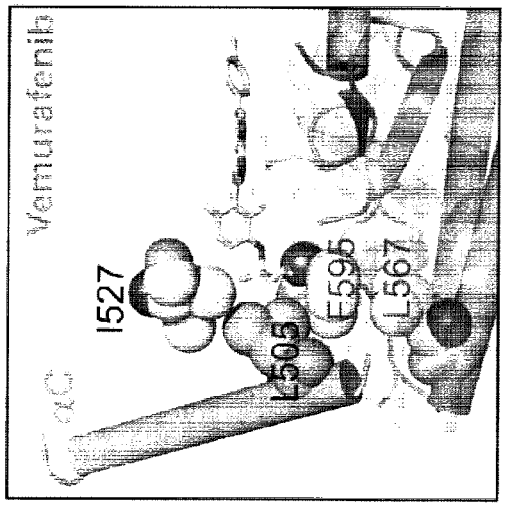
Figure 3:
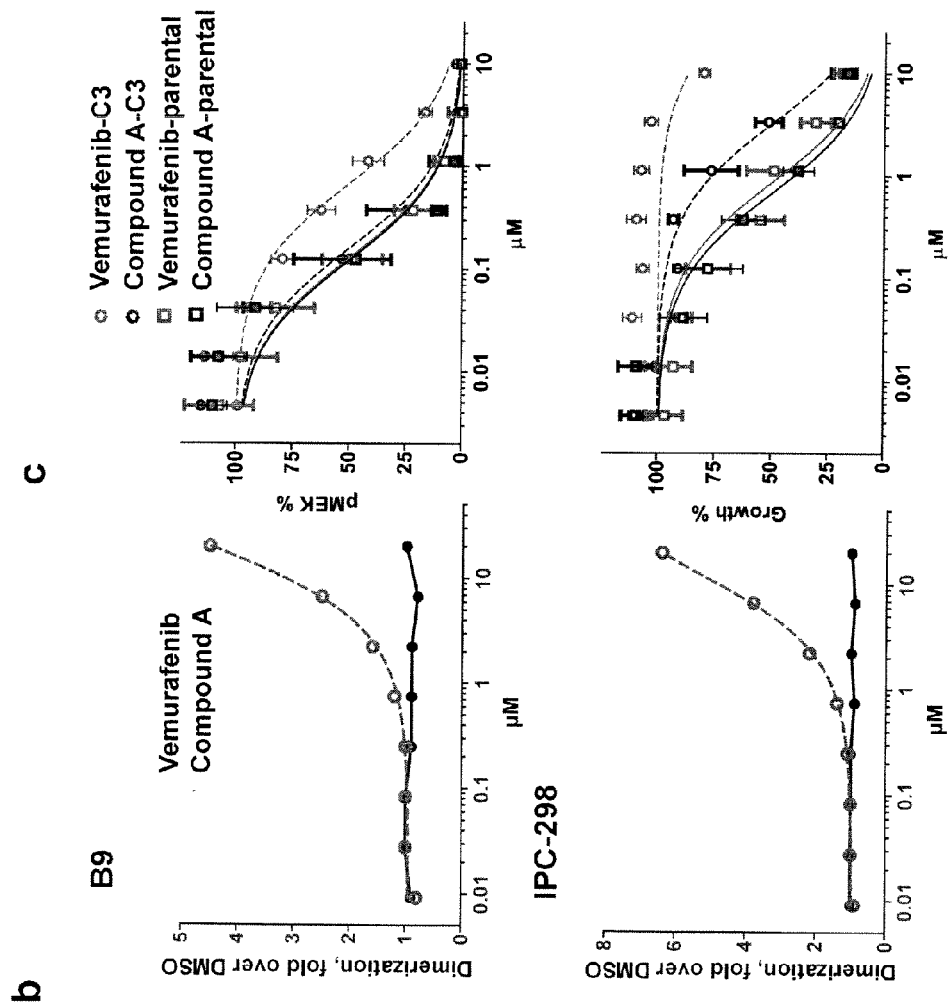
Figure 7:
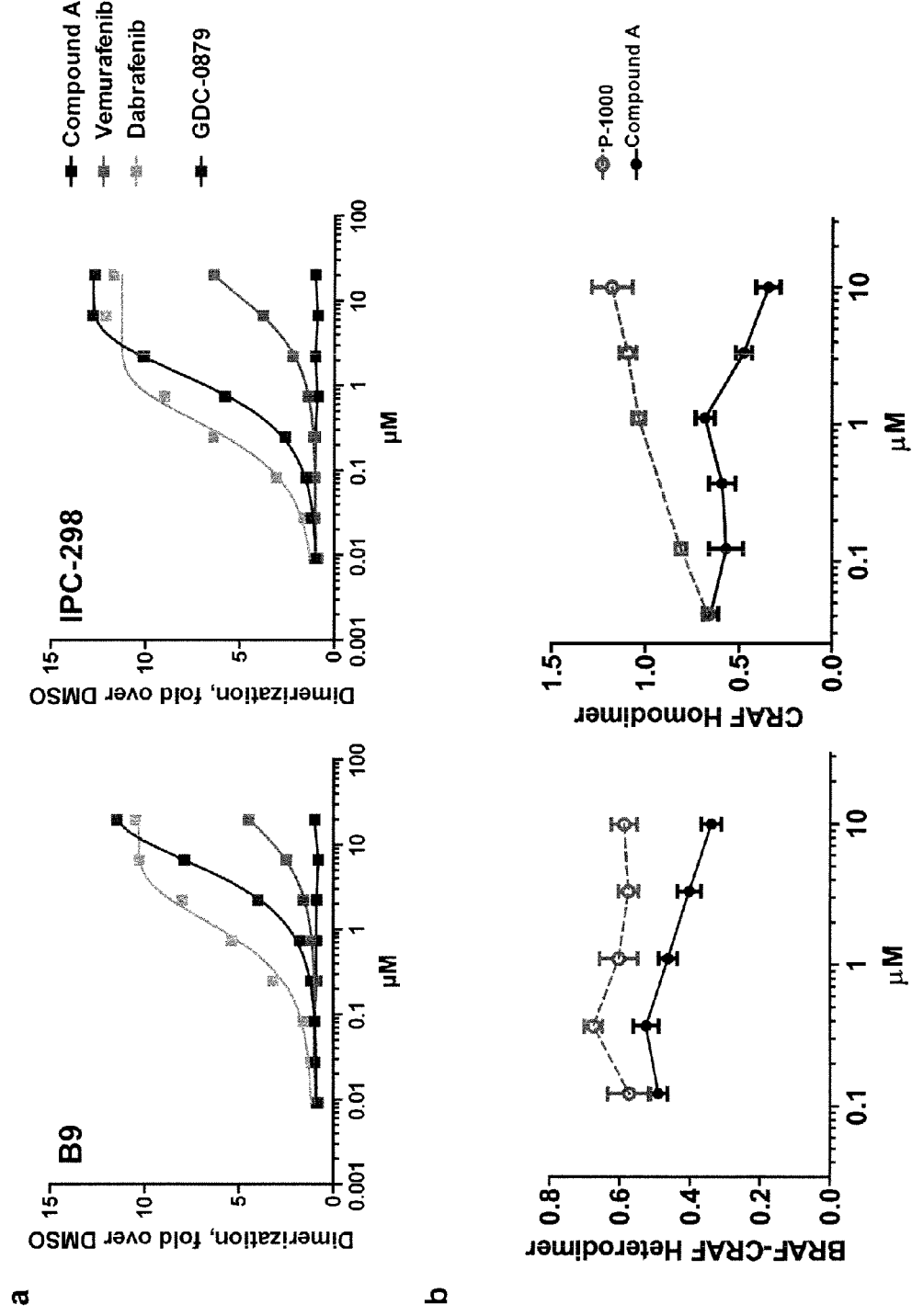
FIG. 7. Modulation of RAF dimerization by RAF inhibitors. (a) Immunoblots of lysates detecting endogenous BRAF-CRAF heterodimer With the exception of Paradox Breaker, for example, e.g. compounds containing a sulfamoylamino moiety or compounds of formula (I), all known RAF inhibitors induce BRAF-CRAF dimer formation. (b) Biochemical dimerization assays using recombinant kinase domains show that a compound of formula (I), e.g. compound A interrupts the formation of BRAF-CRAF heterodimer and CRAF homodimer.

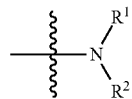

group occupying the small interior pocket forms closer contact with Leu505 in the pocket. Leu505 is part of the four residues that comprise the so called regulatory spine of kinases (Taylor, S. S. & Kornev, A. P. *Trends Biochem Sci* 36, 65-77 (2011). Situated close to the C-terminal end of αC helix, Leu505 is the only residue from the αC helix that makes a direct contact with the inhibitor. FIG. 3a shows N-ethylmethyl moiety forms closer contact with Leu505 in the pocket. Paradoxical MAPK pathway activation relies on binding of the RAF inhibitor to one protomer of a RAF homodimer or heterodimer, leading to transactivation of the other protomer of the dimer in a RAS-dependent manner (Hatzivassiliou, G. et al. *Nature* 464, 431-435 (2010); Heidorn, S. J. et al. *Cell* 140, 209-221 (2010); and Poulikakos, P. I., Zhang, C., Bollag, G., Shokat, K. M. & Rosen, N. *Nature* 464, 427-430 (2010)). The C-terminus of αC helix plays a critical role in RAF dimer formation (Wan, P. T. et al. *Cell* 116, 855-867 (2004); Hatzivassiliou, G. et al. *Nature* 464, 431-435 (2010); Heidorn, S. J. et al. *Cell* 140, 209-221 (2010); and Tsai, J. et al. *Proc Natl Acad Sci USA* 105, 3041-3046 (2008)) and mutations that disrupt the dimer contacts involving the αC helix counteract RAF activation by inhibitors. Without being bound by the theory, the close interaction of a compound of formula (I), e.g. compound A with Leu505 of the αC helix suggests the possibility that compounds of formula (I) might modulate RAF dimerization through an allosteric mechanism. In the co-immunoprecipitation-Western blot dimerization assay using cell lysates, vemurafenib promoted endogenous BRAF-CRAF heterodimer formation in both B9 and IPC-298 cells whereas the dimer formation was indifferent to the presence of a compound of formula (I), e.g. compound A (FIG. 3b). In two-component biochemical dimerization assays using recombinant RAF kinase domains, a compound of formula (I), e.g. compound A appeared to disrupt the formation of both BRAF-CRAF heterodimers and CRAF homodimers at mid to high concentration (FIG. 7).

Compounds as described herein or compounds of formula (I) or any subgeneric formulas, or a pharmaceutically acceptable salt, a solvate, a tautomer or an isomer thereof, or a composition comprising a compound as described herein or a compound of formula (I) or any subgeneric formulas, or a pharmaceutically acceptable salt, a solvate, a tautomer or an isomer thereof are effective in combating dimerization-mediated resistance and overcome RAF inhibitor resistance in BRAF fusions characterizing pediatric astrocytomas. FIG. 3c shows that compound A demonstrates minimal shift in pMEK $IC_{50}$ and modest increase (5 fold) in growth inhibition $IC_{50}$ in C3 cell line.

Figure 4:
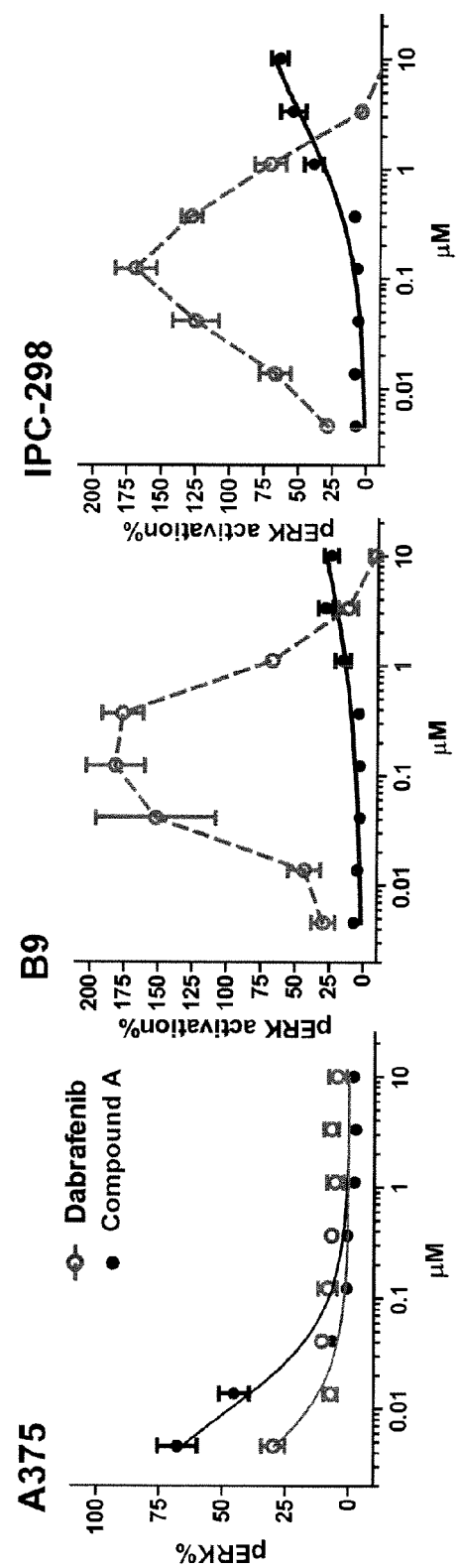
FIG. 4. The structural determinant of Paradox Breakers, the N-ethylmethyl-sulfamoyl group, can be transferred to another chemical series to drastically change its biological profile. Dabrafenib, a highly potent inhibitor of pERK in BRAF$^{V600E}$ cell lines, exhibited an unusual bell-shaped pERK activation curve in mutant NRAS cell lines (B9 and IPC-298). Substituting the 2,6-difluoro-phenylsulfonamide with N-ethylmethylsulfamoid resulted in a compound (P-0352) that shows markedly reduced pERK activation in mutant RAS cells with only a moderate decrease in pERK IC$_{50}$ in BRAF$^{V600E}$ cell line (A375).

FIG. 4 demonstrates

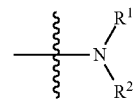

group in compounds of formula (I) is critical in reducing pERk activation. For example, compound P-0352 showed significantly reduced pERK activation in mutant RAS cell lines while preserving the potent inhibitory activity against $BRAF^{V600E}$ cells.

VI. Methods for Treating Conditions Mediated by Kinases

Some embodiments described herein provide a method for treating a subject suffering from or at risk of a protein kinase mediated diseases or conditions. The method includes administering to the subject an effective amount of a compound of formula (I) or (I'), or a compound of any of the subgeneric formulas of formula (I), or a compound as described herein, or a pharmaceutically acceptable salt or a solvate or hydrate thereof, or a composition comprising a compound of formula (I) or a compound of any of the subgeneric formulas of formula (I) or any of the compounds described herein, or a pharmaceutically acceptable salt or a solvate or hydrate thereof. In certain embodiments, the method involves administering to the subject an effective amount of any one or more compound(s) as described herein in combination with one or more other therapies for the disease or condition. In some embodiments, the protein kinase is a mutant RAF protein kinase. In some embodiments, the mutant RAF protein kinase is a mutant BRAF kinase. In certain instances, the mutant BRAF kinase has a $BRAF^{V600}$ mutation. In one instance, the mutant BRAF has a $BRAF^{V600E}$ mutation.

In some embodiments, the diseases or conditions treatable with the compounds described herein include, but are not limited to, multi-infarct dementia, head injury, brain trauma, brain injury, cognition impairment, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract, bile duct (cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori, Hepatitis* and *Influenza* viruses, fever, HIV, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardiofaciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency). In one embodiment, the disease or condition is selected from the group consisting of melanoma, glioma, glioblastoma multiforme, pilocytic astrocytoma, sarcoma, liver cancer, biliary tract cancer, cholangiocarcinoma, colorectal cancer, lung cancer, gallbladder cancer, breast cancer, pancreatic cancer, thyroid cancer, renal cancer, ovarian cancer, adrenocortical cancer, prostate cancer, histiocytic lymphoma, neurofibromatosis, gastrointestinal stromal tumors, acute myeloid leukemia, myelodysplastic syndrome, leukemia, tumor angiogenesis, medullary thyroid cancer, carcinoid, small cell lung cancer, Kaposi's sarcoma, pheochromocytoma, acute pain, chronic pain, and polycystic kidney disease. In a preferred embodiment, the disease or condition is selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, cholangiocarcinoma, acute pain, chronic pain, and polycystic kidney disease.

In other embodiments, the diseases or conditions treatable with the compounds described herein include, but are not limited to, ischemic stroke, brain injury, brain trauma, cerebrovascular ischemia, multi-infarct dementia, head injury, spinal cord injury, Alzheimer's disease, Parkinson's disease, amyotrophic lateral sclerosis, dementia, senile chorea, Huntington's disease, neoplastic disease, complications with neoplastic disease, chemotherapy-induced hypoxia, gastrointestinal stromal tumors, prostate tumors, mast cell tumors, canine mast cell tumors, acute myeloid leukemia, acute lymphocytic leukemia, chronic myeloid leukemia, chronic lymphocytic leukemia, multiple myeloma, melanoma, mastocytosis, glioma, glioblastoma, astrocytoma, neuroblastoma, sarcomas, sarcomas of neuroectodermal origin, leiomyosarcoma, lung carcinoma, breast carcinoma, pancreatic carcinoma, colon carcinoma, hepatocellular carcinoma, renal carcinoma, carcinoma of the female genital tract, squamous cell carcinoma, carcinoma in situ, lymphoma, histiocytic lymphoma, non-Hodgkin's lymphoma, MEN2 syndromes, neurofibromatosis, Schwann cell neoplasia, myelodysplastic syndrome, leukemia, tumor angiogenesis, thyroid cancer, liver cancer, bone cancer, skin cancer, brain cancer, cancer of the central nervous system, pancreatic cancer, lung cancer, small cell lung cancer, non small cell lung cancer, breast cancer, colon cancer, bladder cancer, prostate cancer, gastrointestinal tract cancer, cancer of the endometrium, fallopian tube cancer, testicular cancer, ovarian cancer, bone pain, pain of prostate cancer origin, pain of neuropathic origin, pain of inflammatory origin, acute pain, chronic pain, migraine, cardiovascular disease, heart failure, cardiac hypertrophy, thrombosis, thrombotic microangiopathy syndromes, atherosclerosis, reperfusion injury, ischemia, cerebrovascular ischemia, liver ischemia, inflammation, polycystic kidney disease, age-related macular degeneration, rheumatoid arthritis, allergic rhinitis, inflammatory bowel disease, ulcerative colitis, Crohn's disease, systemic lupus erythematosis, Sjogren's Syndrome, Wegener's granulomatosis, psoriasis, scleroderma, chronic thyroiditis, Grave's disease, myasthenia gravis, multiple sclerosis, osteoarthritis, endometriosis, dermal scarring, tissue scarring, vascular restenosis, fibrotic disorders, hypereosinophilia, CNS inflammation, pancreatitis, nephritis, atopic dermatitis, hepatitis, immunodeficiency diseases, severe combined immunodeficiency, organ transplant rejection, graft versus host disease, renal disease, prostatic disease, diabetic nephropathy, nephrosclerosis, glomerulonephritis, interstitial nephritis, Lupus nephritis, prostate hyperplasia, chronic renal failure, tubular necrosis, diabetes-associated renal complication, associated renal hypertrophy, type 1 diabetes, type 2 diabetes, metabolic syndrome, obesity, hepatic steatosis, insulin resistance, hyperglycemia, lipolysis obesity, infection, *Helicobacter pylori* infection, *Influenza* virus infection, fever, sepsis, pulmonary diseases, chronic obstructive pulmonary disease, acute respiratory distress syndrome, asthma, allergy, bronchitis, emphysema, pulmonary fibrosis, genetic developmental diseases, Noonan's syndrome, Crouzon syndrome, acrocephalo-syndactyly type I, Pfeiffer's syndrome, Jackson-Weiss syndrome, Costello syndrome, faciocutaneoskeletal syndrome, leopard syndrome, cardio-faciocutaneous syndrome, neural crest syndrome abnormalities causing cardiovascular, skeletal, intestinal, skin, hair or endocrine diseases, disorders of bone structure or mineralization, osteoporosis, increased risk of fracture, hypercalcemia, bone metastases, pigmented villonodular synovitis (PVNS), Grave's disease, Hirschsprung's disease, lymphoedema, selective T-cell defect, X-linked agammaglobulinemia, diabetic retinopathy, alopecia, erectile dysfunction, and tuberous sclerosis.

In some embodiments, the disease is a cancer selected from the group consisting of melanoma, glioma, glioblastoma, pilocytic astrocytoma, liver cancer, biliary tract cancer, cholangiocarcinoma, colorectal cancer, lung cancer, bladder cancer, gallbladder cancer, breast cancer, pancreatic cancer, thyroid cancer, kidney cancer, ovarian cancer, adrenocortical cancer, prostate cancer, gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma. In certain instances, the disease is mediated, regulated or modulated by a BRAF V600 mutant, such as V600A, V600E, V600G, V600K, V600M or V600R mutant. In other instances, the diseases are mediated, regulated or modulated by BRAF$^{V600/L505H}$ mutant. In one embodiment, the disease is a BRAF$^{V600E}$ mutant mediated disease. In another embodiment, the disease is a BRAF$^{V600E/L505H}$ mutant mediated disease. In one embodiment, the disease is a cancer, preferably selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, and cholangiocarcinoma. In one embodiment, the cancer is melanoma, colorectal cancer, thyroid cancer or lung cancer.

In some embodiments, the disclosure provides methods for treating any BRAF protein kinase mediated disease or condition, including any BRAF mutant kinase mediated disease or condition in an animal subject in need thereof, wherein the method involves administering to the subject in need thereof an effective amount of any one or more compound(s) as described herein. In certain embodiments, the method involves administering to the subject an effective amount of any one or more compound(s) as described herein in combination with one or more other therapies for the disease or condition.

In some embodiments, the disclosure provides methods for treating any BRAF V600 mutant protein kinase, such as V600A, V600E, V600G, V600K, V600M or V600R mutant protein kinase mediated disease or condition in an animal subject in need thereof, wherein the method involves administering to the subject in need thereof an effective amount of any one or more compound(s) as described herein. In certain embodiments, the method involves administering to the subject an effective amount of any one or more compound(s) as described herein in combination with one or more other therapies for the disease or condition.

In some embodiments, a compound as described herein is a Raf kinase inhibitor and has an $IC_{50}$ of less than 500 nM, less than 100 nM, less than 50 nM, less than 20 nM, less than 10 nM, less than 5 nM, or less than 1 nM as determined in a generally accepted Raf kinase activity assay. In some embodiments, a compound as described herein will have an $IC_{50}$ of less than 500 nM, less than 100 nM, less than 50 nM, less than 20 nM, less than 10 nM, less than 5 nM, or less than 1 nM with respect to BRAF, c-Raf-1, or BRAF V600 mutant. In some embodiments, a compound as described herein will selectively inhibit one or more Raf kinases relative to one or more other Raf kinases.

In some embodiments, the disclosure provides a method for inhibiting a BRAF V600 mutant protein kinase, such as V600A, V600E, V600G, V600K, V600M or V600R mutant protein kinase. The method includes contacting a compound of formula (I) or a compound of any of the subgeneric formulas of formula (I), or a compound as described herein, or a pharmaceutically acceptable salt or a solvate or hydrate thereof, or a composition comprising a compound of formula (I) or a compound of any of the subgeneric formulas of formula (I) or any of the compounds described herein, or a pharmaceutically acceptable salt or a solvate or hydrate thereof with a cell or a BRAF V600 mutant protein kinase either in vitro or in vivo.

In certain embodiments, the disclosure provides use of a compound of formula (I) or a compound of any of the subgeneric formulas of formula (I), or a compound as described herein, or a pharmaceutically acceptable salt or a solvate or hydrate thereof, or a composition comprising a compound of formula (I) or a compound of any of the subgeneric formulas of formula (I) or any of the compounds described herein, or a pharmaceutically acceptable salt or a solvate or hydrate thereof in the manufacture of a medicament for the treatment of a disease or condition as described herein. In other embodiments, the invention provides a compound of formula (I) or a compound of any of the subgeneric formulas of formula (I), or a compound as described herein, or a pharmaceutically acceptable salt or a solvate or hydrate thereof, or a composition comprising a compound of formula (I) or a compound of any of the subgeneric formulas of formula (I) or any of the compounds described herein, or a pharmaceutically acceptable salt or a solvate or hydrate thereof for use in treating a disease or condition as described herein.

In some embodiments, the disclosure provides a method for suppressing UV induced cell apoptosis. The method includes contacting a cell with a compound of formula (I) or a compound of any of the subgeneric formulas of formula (I), or a compound as described herein, or a pharmaceutically acceptable salt or a solvate or hydrate thereof, or a composition comprising a compound of formula (I) or a compound of any of the subgeneric formulas of formula (I) or any of the compounds described herein, or a pharmaceutically acceptable salt or a solvate or hydrate thereof prior to subject the cell to UV exposure or radiation.

In another aspect, the disclosure provides a method for inhibiting a mutant BRAF kinase. The method includes contacting the mutant BRAF kinase in a cell with a compound of formula (I) or a compound of any of the subgeneric formulas of formula (I), or a compound as described herein, or a pharmaceutically acceptable salt or a solvate or hydrate thereof, or a composition comprising a compound of formula (I) or a compound of any of the subgeneric formulas of formula (I) or any of the compounds described herein, or a pharmaceutically acceptable salt or a solvate or hydrate thereof. The contacting can be carried out either in vitro or in vivo. In certain embodiments, the mutant BRAF kinase is a BRAF V600 mutant protein kinase, such as V600A, V600E, V600G, V600K, V600M or V600R mutant protein kinase.

In another aspect, the disclosure provides a method for inhibiting a mutant BRAF kinase in a subject. The method includes administering to the subject an effective amount of a compound of formula (I) or a compound of any of the subgeneric formulas of formula (I), or a compound as described herein, or a pharmaceutically acceptable salt or a solvate or hydrate thereof, or a composition comprising a compound of formula (I) or a compound of any of the subgeneric formulas of formula (I) or any of the compounds as described herein, or a pharmaceutically acceptable salt or a solvate or hydrate thereof. In some embodiments, the mutant BRAF is a $BRAF^{V600}$ mutant.

In another aspect, the disclosure provides a method for treating a subject suffering from a melanoma, a thyroid cancer or a colorectal cancer. The method includes administering to the subject in need thereof an effective amount of a compound of formula (I) or a compound of any of the subgeneric formulas of formula (I), or a compound as described herein, or a pharmaceutically acceptable salt or a solvate or hydrate thereof, or a composition comprising a compound of formula (I) or a compound of any of the subgeneric formulas of formula (I) or any of the compounds as described herein, or a pharmaceutically acceptable salt or a solvate or hydrate thereof. In some embodiment, the melanoma is a metastatic melanoma.

Combination Therapy

Protein kinase modulators may be usefully combined with another pharmacologically active compound, or with two or more other pharmacologically active compounds, particularly in the treatment of cancer. In one embodiment, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer.

In some embodiments, the disclosure provides a composition comprising a compound of any of formulas (I') or (I) or a compound of any of the subgeneric formulas of formula (I), or a compound as described herein, or a pharmaceutically acceptable salt or a solvate or hydrate thereof, or a composition comprising a compound of formula (I) or (I') or a compound of any of the subgeneric formulas of formula (I), for example, formulas (Ia), (Ia-1), (Ia-2), (Ib), (Ib-1), (Ib-2), (Ib-1a), (Ib-1b), (Ic), (Ic-1), (Ic-1a), (Ic-2), (Ic-2a), (Id), (Id-1), (Id-1a), (Id-2), (Id-2a), (Ie), (Ie-1), (Ie-1a), (Ie-2), (Ie-2a), (If), (If-1), (If-2), (If-3), (If-4), (Ig), (Ig-1), (Ig-2), (Ig-3), (Ig-4), (Ih), (Ih-1), (Ih-2), (Ih-3), (Ih-4), (Ij), (Ij-1) or (Ij-2) or any of the compounds described herein, or a pharmaceutically acceptable salt or a solvate or hydrate thereof, and one or more therapeutic agents. In some embodiments, the one or more therapeutic agents are selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, azathioprine, raltitrexed, tegafur-uracil, thioguanine, trimethoprim, trimetrexate, and vidarabine; an immunotherapy, including, but not limited to, alemtuzumab, bevacizumab, cetuximab, galiximab, gemtuzumab, panitumumab, pertuzumab, rituximab, tositumomab, trastuzumab, 90 Y ibritumomab tiuxetan, ipilimumab, and tremelimumab; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, vemurafenib, BeiGene-283 (or BGB-283), dabrafenib, LGX818, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-beta, and interleukin-2; and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. tanespimycin) and farnesyltransferase inhibitors (e.g. tipifarnib); MEK inhibitors (e.g., AS703026, AZD6244 (selumetinib), AZD8330, BIX02188, CI1040 (PD184352), D-87503, GSK1120212 (JTP-74057), GDC0973, PD0325901, PD318088, PD98059, PDEA119 (BAY 869766), TAK-733). Preferably, the method of treating a cancer involves administering to the subject an effective amount of a composition including any one or more compound(s) as described herein in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-beta, interleukin-2, or erlotinib. In some embodiments, a protein kinase modulator, particularly a compound of any of formula (I) to formula In, or a compound described herein, or a pharmaceutically acceptable salt or solvate thereof, as defined above, may be administered simultaneously, sequentially or separately in combination with one or more agents as described above.

In some embodiments, the therapeutic agent is chlorambucil, melphalan, cyclophosphamide, ifosfamide, busulfan, carmustine, lomustine, streptozocin, cisplatin, carboplatin, oxaliplatin, dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, topotecan, irinotecan, etoposide, trabectedin, dactinomycin, doxorubicin, epirubicin, daunorubicin, mitoxantrone, bleomycin, mitomycin, ixabepilone, tamoxifen, fiutamide, gonadorelin analogues, megestrol, prednisone, dexamethasone, methylprednisolone, thalidomide, interferon alfa, leucovorin, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, vemurafenib, vismodegib, volasertib, alemtuzumab, bevacizumab, brentuximabvedotin, catumaxomab, cetuximab, denosumab, gemtuzumab, ipilimumab, nimotuzumab, ofatumumab, panitumumab, ramucirumab, rituximab, tositumomab, trastuzumab, or a combination thereof.

In one embodiment, the disclosure provides methods for treating a disease or condition mediated by BRAF kinase, including mutations thereof, by administering to the subject an effective amount of a composition including any one or more compound(s) as described herein in combination with one or more other suitable therapies for treating the disease.

In one embodiment, the disclosure provides methods for treating a disease or condition mediated by BRAF V600 mutant kinases, such as V600A, V600E, V600G, V600K, V600M or V600R mutant kinase, by administering to the subject an effective amount of a composition including any one or more compound(s) as described herein in combination with one or more other suitable therapies for treating the disease. In one embodiment, the disclosure provides methods for treating a cancer mediated by BRAF mutant kinases, such as V600A, V600E, V600G, V600M or V600R mutant by administering to the subject an effective amount of a composition including any one or more compound(s) as described herein. In one embodiment, the disclosure provides methods for treating a cancer mediated by BRAF mutant kinases, such as V600A, V600E, V600G, V600K, V600M or V600R mutant by administering to the subject an effective amount of a composition including any one or more compound(s) as described herein in combination with one or more suitable anticancer therapies, such as one or more chemotherapeutic drugs. In one instance, the BRAF mutant kinase is V600A. In another instance, the BRAF mutant kinase is V600E. In yet another instance, the BRAF mutant kinase is V600G. In another instance, the BRAF mutant kinase is V600K. In another instance, the BRAF mutant kinase is V600M. In another instance, the BRAF mutant kinase is V600R.

In one embodiment, the disclosure provides a method of treating a cancer in a subject in need thereof by administering to the subject an effective amount of a composition including any one or more compound(s) as described herein in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, or bone marrow and stem cell transplantation.

Kit

In another aspect, the disclosure provides kits that include a compound of any of formulas (I) to (In) or a compound as described herein or composition thereof as described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a protein kinase mediated disease or condition; the disclosure kit may include written instructions for use and/or other indication that the compound or composition is suitable or approved for administration to a mammal, e.g., a human, for a Raf protein kinase-mediated disease or condition; and the compound or composition may be packaged in unit dose or single dose form, e.g., single dose pills, capsules, or the like.

VII. Examples

The following examples are offered to illustrate, but not to limit the disclosure.

The synthesis for the compounds described herein and those set forth in Tables 1 and 2 may be performed according to methods known in the art, such as in PCT patent publication No. WO 2012/109075, which is incorporated by reference in its entirety. A person of skill in the art is readily capable of preparing all the compounds described herein and those encompassed by generic formula (I') or (I) and its sub-generic formulas using the procedures described in the above-mentioned patent application and the processes described herein. In addition, abbreviations as used herein have respective meanings as follows:

| | |
|---|---|
| ATP | Adenosine triphosphate |
| BSA | Bovine serum albumin |
| cc | Cubic centimeter |
| cm | centimeter |
| DMAP | 4-Dimethylaminopyridine |
| DCM | Dichloromethane |
| DIPEA | Diisopropylethylamine |
| DMEM | Dulbecco's Modified Eagle Medium |
| DMF | Dimethylformamide |
| DMSO | Dimethylsulfoxide |
| EDTA | Ethylenediaminetetraacetic acid |
| eq./equiv. | Equivalent |
| ESI | Electrospray ionization |
| EtOAc | Ethyl acetate |
| EtOH | Ethanol |
| FBS | Fetal bovine serum |
| g | Gram |
| h/hrs | Hour |
| HPLC | High-pressure liquid chromatography |
| Hz | Hertz |
| i-Pr | isopropyl |
| J | Joule |
| kg | killigram |
| L | Liter |
| LCMS | Liquid chromatography-mass spectrometry |
| M | Molar |
| MeOH | Methanol |
| m/z | Mass to charge |
| mg | Milligram |
| MHz | Mega hertz |
| mins | minutes |
| mL/ml | Milliliter |
| mol | mole |
| mm | millimeter |
| mM | Millimolar |
| mmol | Millimole |
| MS | Mass spectrometry |
| MTBE | Methyl tert-butyl ether |
| mW | Milliwatts |
| nM | Nanomolar |
| nm | nanometer |
| NMR | Nuclear magnetic resonance |
| PBS | Phosphate buffered saline |
| PSI/psi | Pound-force per square inch |
| $R_f$ | Retention factor |
| TBAF | Tetra-n-butylammonium fluoride |
| THF | Tetrahydrofuran |
| TLC | Thin layer chromatography |
| μL | Microliter |
| μM | Micromolar |

Example 1: Preparation of 5-(2-aminopyrimidin-4-yl)-2-tert-butyl-4-[3-[[ethyl(methyl)sulfamoyl]amino]-2-fluoro-phenyl]thiazole (P-0352)

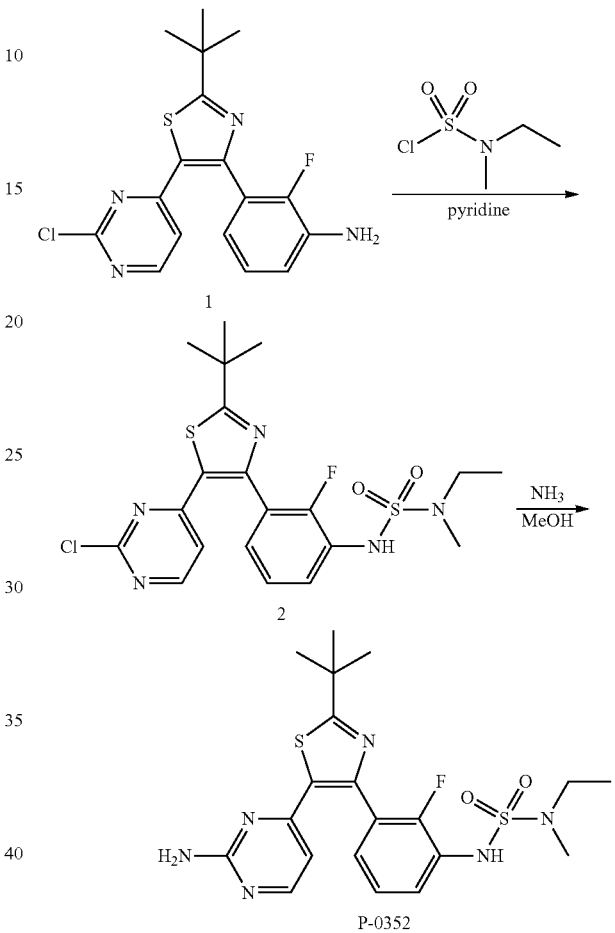

Scheme 1.

Step 1: Synthesis of 2-tert-butyl-5-(2-chloropyrimidin-4-yl)-4-[3-[[ethyl(methyl)sulfamoyl]amino]-2-fluoro-phenyl]thiazole (2)

Compound 1 was prepared according to the procedure described in U.S. Pat. No. 7,994,185. To a solution of 3-[2-tert-butyl-5-(2-chloropyrimidin-4-yl)thiazol-4-yl]-2-fluoro-aniline (1, 102 mg, 0.28 mmol) in dichloromethane (1 mL) was added pyridine (500 μL, 6.2 mmol) followed by N-ethyl-N-methyl-sulfamoyl chloride (265 mg, 1.68 mmol). The reaction was allowed to stir at 50° C. for 96 hours. The reaction was worked up by extraction with ethyl acetate and 0.1 M HCl(aq). The product was purified by flash chromatography (5-30% ethyl acetate in hexanes) which gave impure material. This material was again purified by flash chromatography (0.5-6% methanol in DCM). This provided 55 mg of 2-tert-butyl-5-(2-chloropyrimidin-4-yl)-4-[3-[[ethyl(methyl)sulfamoyl]amino]-2-fluoro-phenyl]thiazole (2) that was ~90% pure and was used in the next step. MS (ESI) [M+H$^+$]$^+$=484.2. MS (ESI) [M−H$^+$]$^−$=482.10.

Step 2: Synthesis of 5-(2-aminopyrimidin-4-yl)-2-tert-butyl-4-[3-[[ethyl(methyl)sulfamoyl]amino]-2-fluoro-phenyl]thiazole (P-0352)

2-tert-butyl-5-(2-chloropyrimidin-4-yl)-4-[3-[[ethyl(methyl)sulfamoyl]amino]-2-fluoro-phenyl]thiazole (7, 51 mg, 0.11 mmol) was dissolved in 5 mL of 7 M ammonia in methanol in a sealed reaction vial. The reaction was placed in an oil bath at 80° C. and allowed to stir for 48 hours. All of the volatiles were removed by rotary evaporation. The resulting residue was purified by reverse phase HPLC (Buffer A: 5% $CH_3CN$, 95% water, 0.01% formic acid. Buffer B: 95% $CH_3CN$, 5% water, 0.01% formic acid) to provide 31 mg of 5-(2-aminopyrimidin-4-yl)-2-tert-butyl-4-[3-[[ethyl(methyl)sulfamoyl]amino]-2-fluoro-phenyl]thiazole (P-0352) MS (ESI) $[M+H+]^+=465.20$.

$^1$H-NMR Chemical Shift Assignments for P-0352 (DMSO-$d_6$, 400 MHz)

| Hydrogen | Chemical Shift (ppm) | Splitting Pattern | Integration | Coupling (Hz) |
|---|---|---|---|---|
| $NH_2$ | 6.77 | br s | 2 | — |
| $NH-SO_2-$ | 9.71 | br s | 1 | — |
| Pyrimidine ring | 8.04 | d | 1 | 5.1 |
| Benzene ring | 7.54 | m | 1 | — |
| Benzene ring | 7.30 | m | 2 | — |
| Pyrimidine ring | 6.03 | d | 1 | 5.1 |
| $N-CH_2CH_3$ | 3.06 | q | 2 | 7.0 |
| $N-CH_3$ | 2.67 | s | 3 | — |
| $-(CH_3)_3$ | 1.41 | s | 9 | — |
| $N-CH_2CH_3$ | 0.99 | t | 3 | 7.0 | br s: broad singlet
s: singlet
d: doublet
t: triplet
dd: doublet of doublets
ddd: doublet of doublet of doublets
m: multiplet Example 2: Preparation of N-(6-acetamido-3-pyridyl)-2,6-difluoro-3-(pyrrolidin-1-ylsulfonylamino)benzamide (P-2036)

Scheme 1.

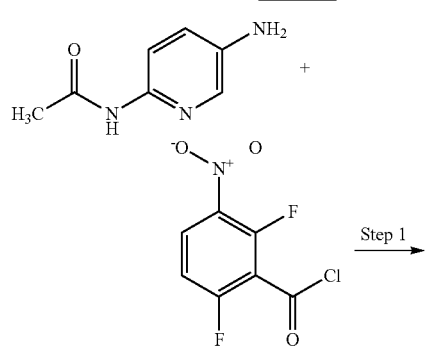

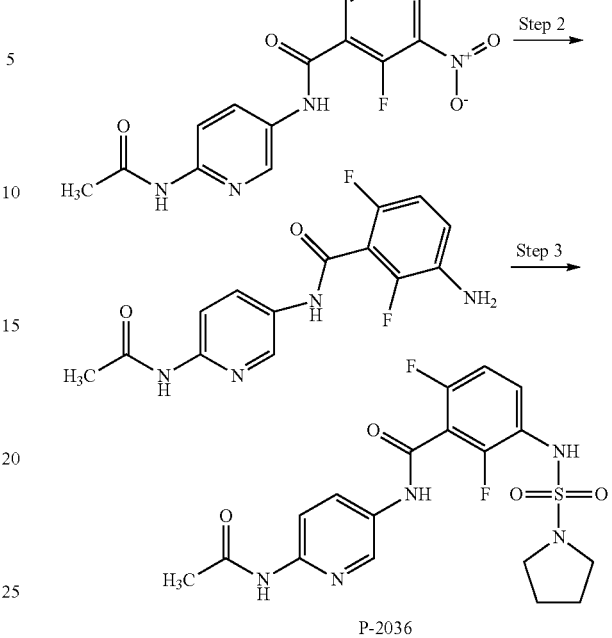

P-2036

Step 1. Synthesis of N-(6-acetamido-3-pyridyl)-2,6-difluoro-3-nitro-benzamide. To N-(5-Amino-pyridin-2-yl)-acetamide (1.53 g, 0.0101 mol) was added tetrahydrofuran (20 mL, 0.2 mol) followed by pyridine (0.900 mL, 0.0111 mol). To this suspension was added a solution of 2,6-difluoro-3-nitrobenzoyl chloride (2.24 g, 0.0101 mol) in tetrahydrofuran (10 mL, 0.1 mol). After stirring at room temperature overnight, the reaction was extracted with ethyl acetate and water (with added HCl). The organic layer was washed with brine, and the combined aqueous layers were extracted with ethyl acetate. The combined organic layers were dried over anhydrous magnesium sulfate, filtered and volatiles removed to give 1.91 g of crude product. This material was purified by silica gel column chromatography eluting with a gradient of 1 to 6% methanol in DCM to give 1.527 g of N-(6-acetamido-3-pyridyl)-2,6-difluoro-3-nitro-benzamide. MS(ESI)$[M+H^+]^+=336.9$.

Step 2. Synthesis of N-(6-acetamido-3-pyridyl)-3-amino-2,6-difluoro-benzamide. To N-(6-acetylamido-pyridin-3-yl)-2,6-difluoro-3-nitro-benzamide (0.500 g, 0.00149 mol) in ethanol (30 mL, 0.5 mol) and tetrahydrofuran (85 mL, 1.0 mol) was added ~3 cc of Raney nickel slurry in water (2800). Then, the reaction was placed in a parr hydrogenator under hydrogen at 35 psi. After 2 hours, TLC indicated all starting material consumed, but two new spots observed. The reaction was allowed to continue. After a total of 6.5 hrs, TLC shows only one new spot. The reaction was filtered through celite and all volatiles removed to give crude material that was purified by silica gel column chromatography eluting with a gradient from 1 to 6% methanol in DCM to give 345 mg of N-(6-acetamido-3-pyridyl)-3-amino-2,6-difluoro-benzamide. MS(ESI)$[M+H^+]^+=306.9$.

Step 3. Synthesis of N-(6-acetamido-3-pyridyl)-2,6-difluoro-3-(pyrrolidin-1-ylsulfonylamino)benzamide. To 9.6 mg (0.03 mmol, 1 eq.) of N-(6-acetamido-3-pyridyl)-3-amino-2,6-difluoro-benzamide was weighed into a 4 mL vial and combined with 5.1 mg (0.03 mmol, 1 eq.) of pyrrolidine-1-sulfonyl chloride. This mixture was dissolved in 300 μL of THF. To this solution, 25 μL of pyridine was added. The reaction mixture was shaken at 65° C. for 2 days. All solvents were removed under reduced atmosphere. The crude material was dissolved in 400 μL of dimethyl sulfoxide and purified by RP-LCMS to provide 5.3 mg of N-(6-acetamido-3-pyridyl)-2,6-difluoro-3-(pyrrolidin-1-ylsulfonylamino)benzamide. MS(ESI)$[M+H^+]^+=440.3$.

The following compounds were made in a manner as set forth in Scheme 1.

| Compound No. | Name | MH(+) |
|---|---|---|
| P-2033 | N-(6-acetamido-3-pyridyl)-2,6-difluoro-3-(1-piperidylsulfonylamino)benzamide | 454.3 |
| P-2034 | N-(6-acetamido-3-pyridyl)-3-(dimethylsulfamoylamino)-2,6-difluoro-benzamide | 414.3 |
| P-2035 | N-(6-acetamido-3-pyridyl)-3-(cyclopentylsulfonylamino)-2,6-difluoro-benzamide | 439.1 |
| P-2128 | N-(6-acetamido-3-pyridyl)-2,6-difluoro-3-(morpholinosulfonylamino)benzamide | 456.3 |

Example 3: Preparation of 5-(2-aminopyrimidin-4-yl)-4-[3-[[ethyl(methyl)sulfamoyl]amino]-2-fluoro-phenyl]-2-isopropyl-thiazole and 2-tert-butyl-4-[3-[[ethyl(methyl)sulfamoyl]amino]-2-fluoro-phenyl]-5-(2-methoxypyrimidin-4-yl)thiazole (P-2089) and 2-tert-butyl-4-[3-[[ethyl(methyl)sulfamoyl]amino]-2-fluoro-phenyl]-5-(2-methoxypyrimidin-4-yl)thiazole (P-2088)

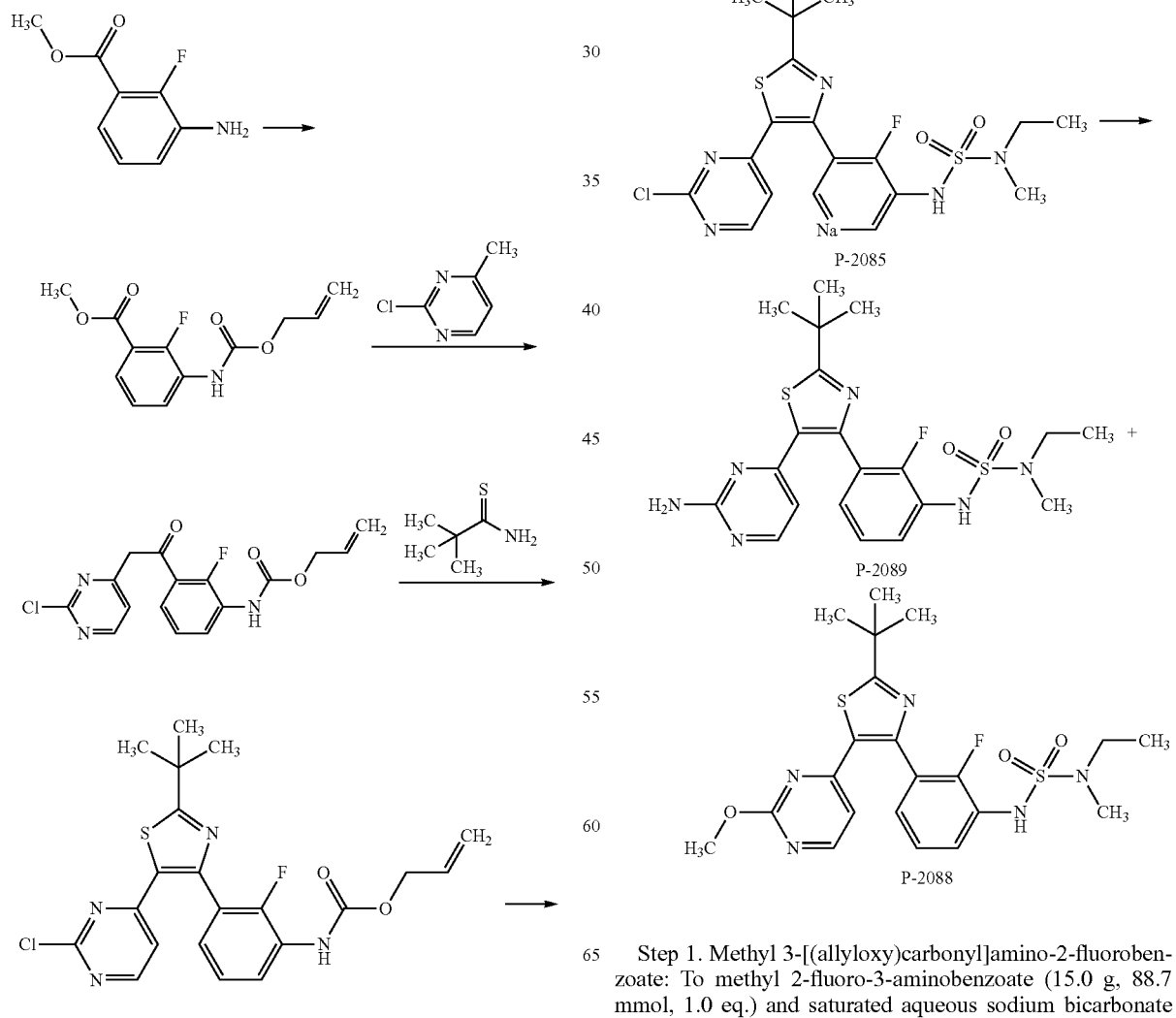

Step 1. Methyl 3-[(allyloxy)carbonyl]amino-2-fluorobenzoate: To methyl 2-fluoro-3-aminobenzoate (15.0 g, 88.7 mmol, 1.0 eq.) and saturated aqueous sodium bicarbonate (120 mL) in tetrahydrofuran (37.5 mL) at 0° C. was added allyl chloroformate (12.75 g, 106 mmol, 1.19 eq.) dropwise. The reaction was allowed to warm to room temperature slowly. When the reaction was complete as indicated by TLC, it was poured into water (800 mL) and extracted with ethyl acetate. The extracts were dried sodium sulfate, filtered, and concentrated under reduced pressure to provide methyl 3-[(allyloxy)carbonyl]amino-2-fluorobenzoate (24.8 g, 100% yield) as an amber liquid.

Step 2. Synthesis of allyl(3-(2-(tert-butyl)-5-(2-chloropyrimidin-4-yl)thiazol-4-yl)-2-fluorophenyl) carbamate: To methyl 3-[(allyloxy)carbonyl]amino-2-fluorobenzoate (10.0 g, 39 mmol, 1.0 eq.) in tetrahydrofuran (100 mL) at 0° C. was added a 1.0 M solution of lithium bis(trimethylsilyl) amide in tetrahydrofuran (138 mL, 138 mmol, 3.5 eq.) dropwise. After stirring for 1 hour at 0° C., a solution of 2-chloro-4-methylpyrimidine (6.09 g, 47 mmol, 1.2 eq.) in tetrahydrofuran (100 mL) was added over 20 minutes. The reaction was allowed to warm to room temperature slowly. When the reaction was complete as indicated by LCMS, it was poured into water (1 L). The pH was adjusted to 7 by the addition of 1N HCl and then NaHCO$_3$. The contents were extracted with ethyl acetate, and the extracts were dried over sodium sulfate, filtered, and concentrated under reduced pressure to provide allyl(3-(2-(tert-butyl)-5-(2-chloropyrimidin-4-yl)thiazol-4-yl)-2-fluorophenyl) carbamate (12.5 g, 92% yield) as an orange solid.

Step 3. Synthesis of Allyl(3-(2-(tert-butyl)-5-(2-chloropyrimidin-4-yl)thiazol-4-yl)-2-fluorophenyl)carbamate: To ally(3-(2-(tert-butyl)-5-(2-chloropyrimidin-4-yl)thiazol-4-yl)-2-fluorophenyl) carbamate (3.21 g, 9.18 mmol, 1.0 eq.) in dimethylacetamide (35 mL) at room temperature was added N-bromosuccinimide (1.64 g, 9.21 mmol, 1.0 eq.). When the disappearance of starting material was complete as indicated by LCMS, 2,2,2-trimethylthioacetamide (1.3 g, 11.1 mmol, 1.2 eq.) was added and the reaction heated at 60° C. overnight. LCMS indicated the reaction was complete. The reaction was poured into water (250 mL) and the contents were extracted with ethyl acetate. The extracts were dried sodium sulfate, filtered, and concentrated under reduced pressure. The crude product was purified by silica gel chromatography (300 g, 3" diameter column) eluting with 20% ethyl acetate/heptanes to provide allyl(3-(2-(tert-butyl)-5-(2-chloropyrimidin-4-yl)thiazol-4-yl)-2-fluorophenyl)carbamate as an oil (2.92 g, 70% yield).

Step 4. Synthesis of 3-[2-tert-butyl-5-(2-chloropyrimidin-4-yl)thiazol-4-yl]-2-fluoro-aniline: To ally(3-(2-(tert-butyl)-5-(2-chloropyrimidin-4-yl)thiazol-4-yl)-2-fluorophenyl)carbamate (2.67 g, 5.97 mmol, 1.0 eq.) in dichloromethane (130 mL) and water (2 mL) at room temperature was added tri-n-butyltin hydride (1.6 mL, 5.97 mmol, 1.0 eq.) then tetrakis(triphenylphoshine)palladium(0) (347 mg, 0.3 mmol, 0.05 eq.). After 1.5 hours, the reaction was complete as indicated by LCMS. Sodium sulfate was added to the reaction. Filtration followed by concentrating under reduced pressure of the filtrate provided the crude product which was purified by column chromatography (275 g silica gel; 3" diameter column) eluting with 25% ethyl acetate/heptanes to provide 3-[2-tert-butyl-5-(2-chloropyrimidin-4-yl)thiazol-4-yl]-2-fluoro-aniline (1.04 g, 48% yield) as a yellow solid.

Step 5. Synthesis of 2-tert-butyl-5-(2-chloropyrimidin-4-yl)-4-[3-[[ethyl(methyl)sulfamoyl]amino]-2-fluoro-phenyl]thiazole. To a solution of 3-[2-tert-butyl-5-(2-chloropyrimidin-4-yl)thiazol-4-yl]-2-fluoro-aniline (102 mg, 0.281 mmol) in dichloromethane (1 mL) was added pyridine (254 ul, 3.2 mmol) followed by N-ethyl-N-methyl-sulfamoyl chloride (326 mg, 2.1 mmol) and dimethylaminopyridine (4 mg, 33 umol). The reaction was allowed to stir at 40° C. for 72 hours. The reaction was worked up by extraction with ethyl acetate and 0.1 M HCl (aq). The product was purified by flash chromatography (5-30% ethyl acetate in hexanes) which gave impure material. This material was again purified by flash chromatography (0.5-6% methanol in DCM) to give 18 mg of 2-tert-butyl-5-(2-chloropyrimidin-4-yl)-4-[3-[[ethyl(methyl)sulfamoyl]amino]-2-fluoro-phenyl]thiazole as a white solid. MS (ESI) [M+H+]+=484.2.

Step 6. Synthesis of 5-(2-aminopyrimidin-4-yl)-4-[3-[[ethyl(methyl)sulfamoyl]amino]-2-fluoro-phenyl]-2-isopropyl-thiazole and 2-tert-butyl-4-[3-[[ethyl(methyl)sulfamoyl]amino]-2-fluoro-phenyl]-5-(2-methoxypyrimidin-4-yl)thiazole. To 2-tert-butyl-5-(2-chloropyrimidin-4-yl)-4-[3-[[ethyl(methyl)sulfamoyl]amino]-2-fluoro-phenyl]thiazole (51 mg, 0.11 mmol) in a vial was added 5 mL of 7M ammonia in methanol and the reaction vial was sealed. The reaction was placed in an oil bath at 80° C. and allowed to stir for 48 hours. All of the volatiles were removed by rotary evaporation. The resulting residue was purified by RP-HPLC to provide 31 mg of 5-(2-aminopyrimidin-4-yl)-4-[3-[[ethyl(methyl)sulfamoyl]amino]-2-fluoro-phenyl]-2-isopropyl-thiazole as a white solid (MS (ESI) [M+H$^+$]$^+$=465.20) and 7 mg of 2-tert-butyl-4-[3-[[ethyl(methyl)sulfamoyl]amino]-2-fluoro-phenyl]-5-(2-methoxypyrimidin-4-yl)thiazole as a white solid. MS (ESI) [M+H$^+$]$^+$=480.20.

The following compounds were made according to the procedures set forth in Example 3 and Scheme 2.

| Compound No. | Name |
| --- | --- |
| P-2093 | 5-(2-aminopyrimidin-4-yl)-2-tert-butyl-4-[3-(dimethylsulfamoylamino)-2-fluoro-phenyl]thiazole |
| P-2106 | N-[3-[5-(2-aminopyrimidin-4-yl)-2-tert-butyl-thiazol-4-yl]-2-fluoro-phenyl]butane-2-sulfonamide |
| P-2114 | N-[3-[5-(2-aminopyrimidin-4-yl)-2-tert-butyl-thiazol-4-yl]-2-fluoro-phenyl]pyrrolidine-1-sulfonamide |
| P-2129 | (3R)-N-[3-[5-(2-aminopyrimidin-4-yl)-2-tert-butyl-thiazol-4-yl]-2-fluoro-phenyl]-3-fluoro-pyrrolidine-1-sulfonamide |
| P-2130 | (3S)-N-[3-[5-(2-aminopyrimidin-4-yl)-2-tert-butyl-thiazol-4-yl]-2-fluoro-phenyl]-3-fluoro-pyrrolidine-1-sulfonamide |
| P-2131 | N-[3-[5-(2-aminopyrimidin-4-yl)-2-tert-butyl-thiazol-4-yl]-2-fluoro-phenyl]azetidine-1-sulfonamide |
| P-2132 | N-[3-[5-(2-aminopyrimidin-4-yl)-2-tert-butyl-thiazol-4-yl]-2-fluoro-phenyl]piperidine-1-sulfonamide |
| P-2133 | N-[3-[5-(2-aminopyrimidin-4-yl)-2-tert-butyl-thiazol-4-yl]-2-fluoro-phenyl]cyclopropanesulfonamide |

-continued

| Compound No. | Name |
|---|---|
| P-2134 | N-[3-[5-(2-aminopyrimidin-4-yl)-2-tert-butyl-thiazol-4-yl]-2-fluoro-phenyl]cyclobutanesulfonamide |
| P-2135 | N-[3-[5-(2-aminopyrimidin-4-yl)-2-tert-butyl-thiazol-4-yl]-2-fluoro-phenyl]cyclopentanesulfonamide |
| P-2136 | N-[3-[5-(2-aminopyrimidin-4-yl)-2-tert-butyl-thiazol-4-yl]-2-fluoro-phenyl]cyclohexanesulfonamide |

Example 3: Synthesis of methyl N-[(1S)-2-[[4-[2-tert-butyl-4-[2-fluoro-3-(pyrrolidin-1-ylsulfonylamino)phenyl]thiazol-5-yl]pyrimidin-2-yl]amino]-1-methyl-ethyl]carbamate Scheme 2b.

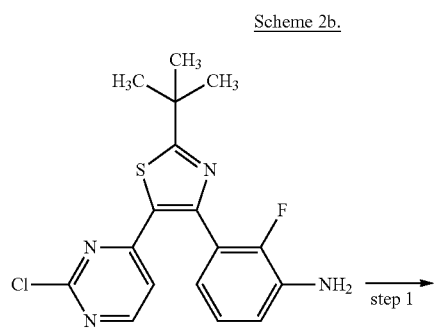

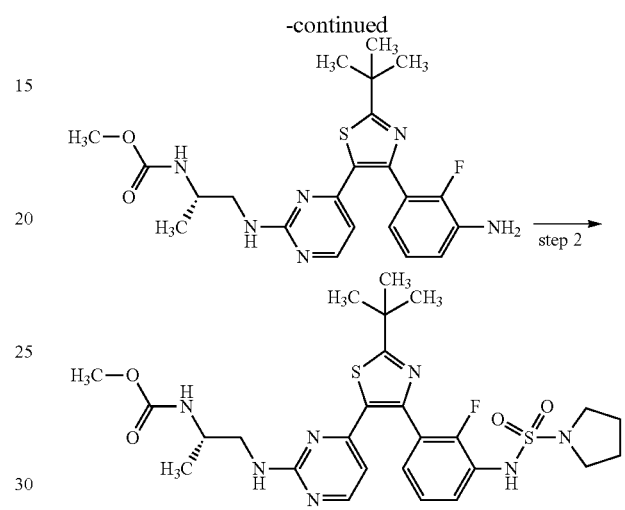

The following compounds were made according to the protocol set forth in Scheme 2b.

| Compound No. | Name |
|---|---|
| P-2137 | methyl N-[(1S)-2-[[4-[4-[3-(azetidin-1-ylsulfonylamino)-2-fluoro-phenyl]-2-tert-butyl-thiazol-5-yl]pyrimidin-2-yl]amino]-1-methyl-ethyl]carbamate |
| P-2138 | methyl N-[(1S)-2-[[4-[2-tert-butyl-4-[2-fluoro-3-[[(3R)-3-fluoropyrrolidin-1-yl]sulfonylamino]phenyl]thiazol-5-yl]pyrimidin-2-yl]amino]-1-methyl-ethyl]carbamate |
| P-2139 | methyl N-[(1S)-2-[[4-[2-tert-butyl-4-[2-fluoro-3-[[(3S)-3-fluoropyrrolidin-1-yl]sulfonylamino]phenyl]thiazol-5-yl]pyrimidin-2-yl]amino]-1-methyl-ethyl]carbamate |
| P-2140 | methyl N-[(1S)-2-[[4-[2-tert-butyl-4-[2-fluoro-3-(1-piperidylsulfonylamino)phenyl]thiazol-5-yl]pyrimidin-2-yl]amino]-1-methyl-ethyl]carbamate |
| P-2141 | methyl N-[(1S)-2-[[4-[2-tert-butyl-4-[3-[[ethyl(methyl)sulfamoyl]amino]-2-fluoro-phenyl]thiazol-5-yl]pyrimidin-2-yl]amino]-1-methyl-ethyl]carbamate |
| P-2142 | methyl N-[(1S)-2-[[4-[2-tert-butyl-4-[3-(cyclopropylsulfonylamino)-2-fluoro-phenyl]thiazol-5-yl]pyrimidin-2-yl]amino]-1-methyl-ethyl]carbamate |
| P-2143 | methyl N-[(1S)-2-[[4-[2-tert-butyl-4-[3-(cyclobutylsulfonylamino)-2-fluoro-phenyl]thiazol-5-yl]pyrimidin-2-yl]amino]-1-methyl-ethyl]carbamate |
| P-2144 | methyl N-[(1S)-2-[[4-[2-tert-butyl-4-[3-(cyclopentylsulfonylamino)-2-fluoro-phenyl]thiazol-5-yl]pyrimidin-2-yl]amino]-1-methyl-ethyl]carbamate |
| P-2145 | methyl N-[(1S)-2-[[4-[2-tert-butyl-4-[3-(cyclohexylsulfonylamino)-2-fluoro-phenyl]thiazol-5-yl]pyrimidin-2-yl]amino]-1-methyl-ethyl]carbamate |

Example 4: Synthesis of (3R)—N-[3-[5-(2-aminopyrimidin-4-yl)-2-phenyl-thiazol-4-yl]-2-fluoro-phenyl]-3-fluoro-pyrrolidine-1-sulfonamide Scheme 3a.

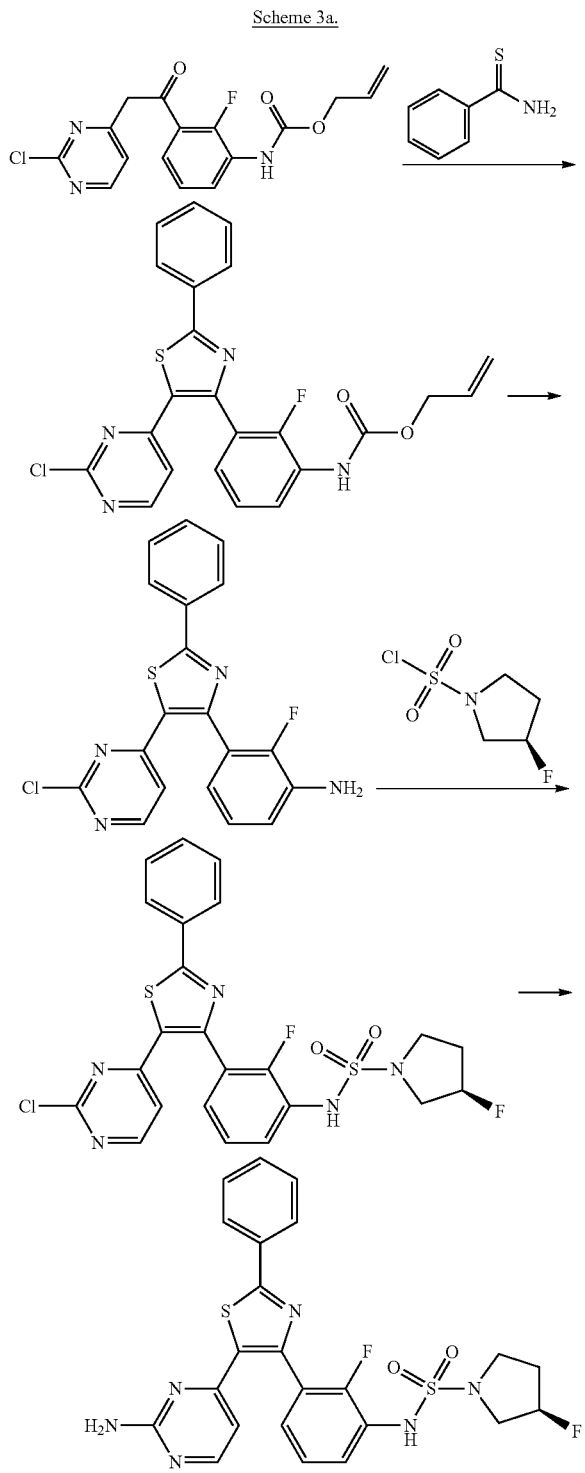

Step 1. Allyl(3-(2-phenyl)-5-(2-chloropyrimidin-4-yl)thiazol-4-yl)-2-fluorophenyl)carbamate: To ally(3-(2-(2-chloropyrimidin-4-yl)acetyl)-2-fluorophenyl)carbamate (4.0 g, 11.4 mmol, 1.0 eq.) in dimethylacetamide (40 mL) at room temperature was added NBS (2.04 g, 11.4 mmol, 1.0 eq.). When the disappearance of starting material was complete as indicated by LCMS, thiobenzamide (1.88 g, 13.7 mmol, 1.2 eq.) was added and the reaction heated at 60° C. for 2.5 hours. The reaction was poured into water (350 mL) and the contents were extracted with ethyl acetate/THF. The extracts were dried sodium sulfate, filtered, and concentrated under reduced pressure. The crude product was purified via silica gel chromatography (300 g, 3" diameter column) eluting with 25-50% ethyl acetate/heptane to provide allyl(3-(2-phenyl)-5-(2-chloropyrimidin-4-yl)thiazol-4-yl)-2-fluorophenyl)carbamate as a yellow-orange solid (3.3 g, 62% yield).

Step 2. 3-[2-Phenyl-5-(2-chloropyrimidin-4-yl)thiazol-4-yl]-2-fluoroaniline: To ally(3-(2-phenyl)-5-(2-chloropyrimidin-4-yl)thiazol-4-yl)-2-fluorophenyl)carbamate (3.3 g, 7.07 mmol, 1.0 eq.) in dichloromethane (100 mL) and water (2.5 mL) at room temperature was added tri-n-butyltin hydride (1.9 mL, 7.07 mmol, 1.0 eq.) then tetrakis(triphenylphosphine)palladium(0) (408 mg, 0.35 mmol, 0.05 eq.). After 6.25 hours, the reaction was complete by LCMS. Sodium sulfate was added to the reaction. Filtration followed by concentration under reduced pressure of the filtrate provided the crude product which was purified via column chromatography (250 g silica gel; 3" diameter column) eluting with 20-30% ethyl acetate/heptane then DCM to provide 5 (470 mg, 17% yield) as a yellow solid.

The following compounds were made according to the protocol set forth in Scheme 3a.

| Compound No. | Name |
| --- | --- |
| P-2146 | N-[3-[5-(2-aminopyrimidin-4-yl)-2-phenyl-thiazol-4-yl]-2-fluoro-phenyl]pyrrolidine-1-sulfonamide |
| P-2147 | (3S)-N-[3-[5-(2-aminopyrimidin-4-yl)-2-phenyl-thiazol-4-yl]-2-fluoro-phenyl]-3-fluoro-pyrrolidine-1-sulfonamide |
| P-2148 | N-[3-[5-(2-aminopyrimidin-4-yl)-2-phenyl-thiazol-4-yl]-2-fluoro-phenyl]piperidine-1-sulfonamide |
| P-2149 | N-[3-[5-(2-aminopyrimidin-4-yl)-2-phenyl-thiazol-4-yl]-2-fluoro-phenyl]cyclopentanesulfonamide |
| P-2150 | N-[3-[5-(2-aminopyrimidin-4-yl)-2-phenyl-thiazol-4-yl]-2-fluoro-phenyl]cyclohexanesulfonamide |

Example 5: Synthesis of methyl N-[(1S)-2-[[4-[4-[2-fluoro-3-(pyrrolidin-1-ylsulfonylamino)phenyl]-2-phenyl-thiazol-5-yl]pyrimidin-2-yl]amino]-1-methyl-ethyl]carbamate Scheme 3b

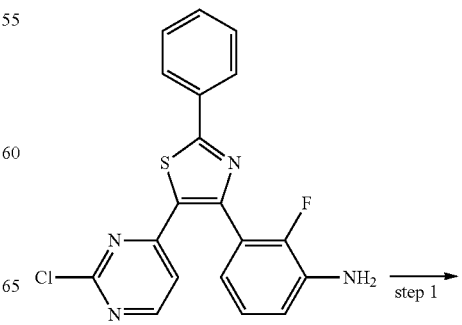

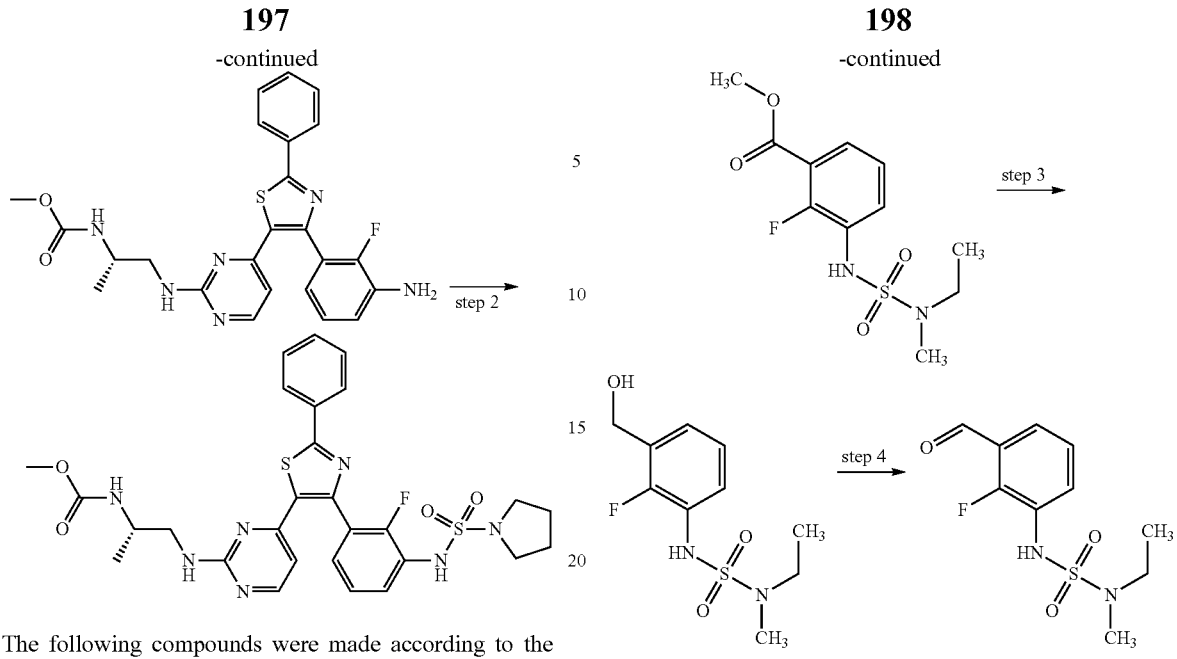

The following compounds were made according to the protocol set forth in Scheme 3b.

| Compound No. | Name |
| --- | --- |
| P-2151 | methyl N-[(1S)-2-[[4-[4-[3-(azetidin-1-ylsulfonylamino)-2-fluoro-phenyl]-2-phenyl-thiazol-5-yl]pyrimidin-2-yl]amino]-1-methyl-ethyl]carbamate |
| P-2152 | methyl N-[(1S)-2-[[4-[4-[2-fluoro-3-[[(3R)-3-fluoropyrrolidin-1-yl]sulfonylamino]phenyl]-2-phenyl-thiazol-5-yl]pyrimidin-2-yl]amino]-1-methyl-ethyl]carbamate |
| P-2153 | methyl N-[(1S)-2-[[4-[4-[2-fluoro-3-[[(3S)-3-fluoropyrrolidin-1-yl]sulfonylamino]phenyl]-2-phenyl-thiazol-5-yl]pyrimidin-2-yl]amino]-1-methyl-ethyl]carbamate |
| P-2154 | methyl N-[(1S)-2-[[4-[4-[2-fluoro-3-(1-piperidylsulfonylamino)phenyl]-2-phenyl-thiazol-5-yl]pyrimidin-2-yl]amino]-1-methyl-ethyl]carbamate |
| P-2155 | methyl N-[(1S)-2-[[4-[4-[3-[[ethyl(methyl)sulfamoyl]amino]-2-fluoro-phenyl]-2-phenyl-thiazol-5-yl]pyrimidin-2-yl]amino]-1-methyl-ethyl]carbamate |
| P-2156 | methyl N-[(1S)-2-[[4-[4-[3-(cyclopropylsulfonylamino)-2-fluoro-phenyl]-2-phenyl-thiazol-5-yl]pyrimidin-2-yl]amino]-1-methyl-ethyl]carbamate |
| P-2157 | methyl N-[(1S)-2-[[4-[4-[3-(cyclobutylsulfonylamino)-2-fluoro-phenyl]-2-phenyl-thiazol-5-yl]pyrimidin-2-yl]amino]-1-methyl-ethyl]carbamate |
| P-2158 | methyl N-[(1S)-2-[[4-[4-[3-(cyclopentylsulfonylamino)-2-fluoro-phenyl]-2-phenyl-thiazol-5-yl]pyrimidin-2-yl]amino]-1-methyl-ethyl]carbamate |
| P-2159 | methyl N-[(1S)-2-[[4-[4-[3-(cyclohexylsulfonylamino)-2-fluoro-phenyl]-2-phenyl-thiazol-5-yl]pyrimidin-2-yl]amino]-1-methyl-ethyl]carbamate |

Example 6: Preparation of 5-[3-[[ethyl(methyl)sulfamoyl]amino]-2-fluoro-benzoyl]-4-methyl-7H-pyrrolo[2,3-d]pyrimidine (P-2090)

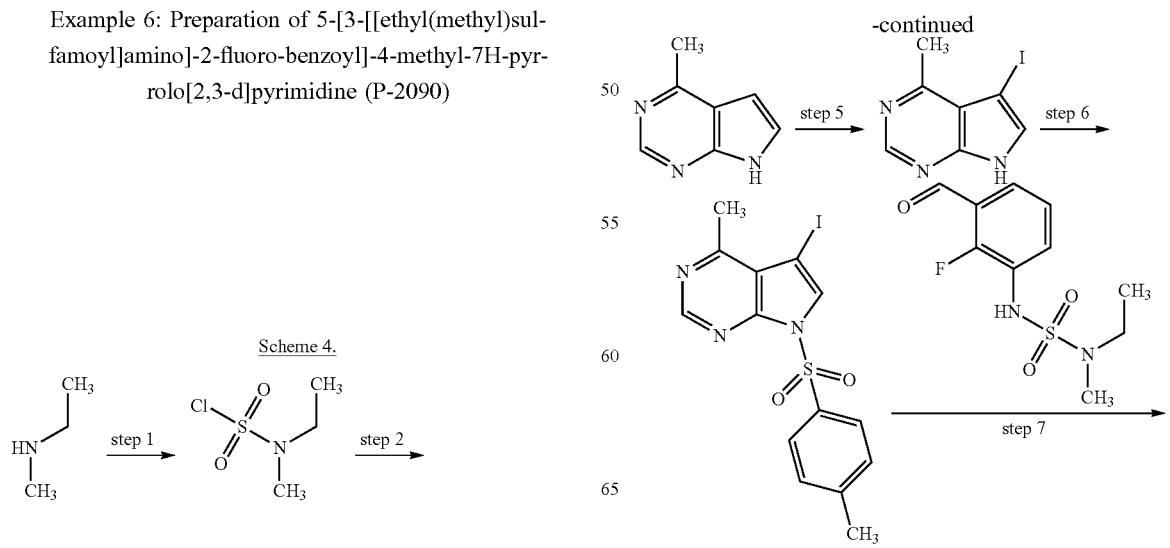

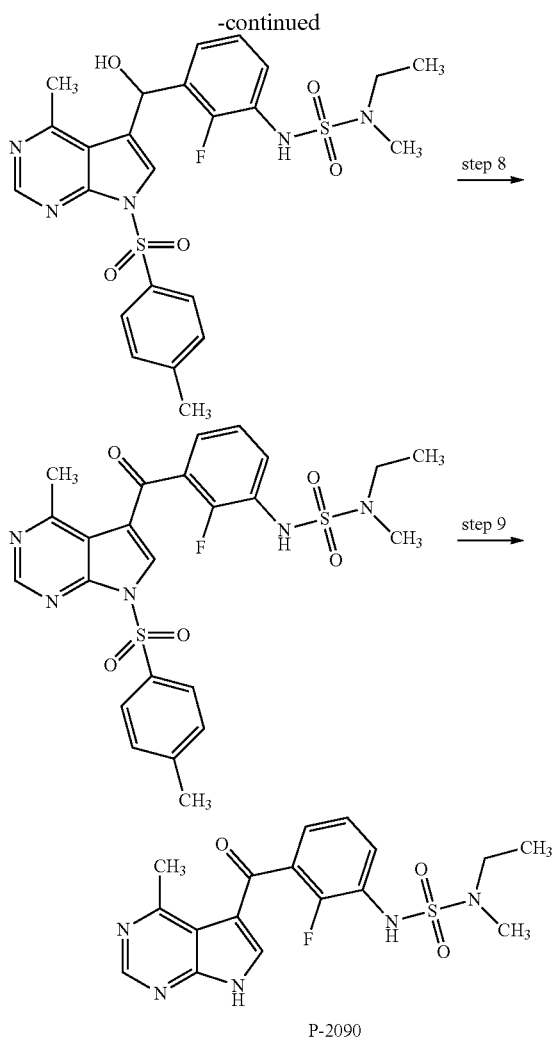

Step 1.

N-ethyl-N-methyl-sulfamoyl chloride: To sulfuryl chloride (20.63 ml, 253.76 mmol) in dichloromethane (500 mL), cooled with ice water, were added N-methylethanamine (21.76 ml, 253.76 mmol) and triethylamine (35.39 ml, 253.76 mmol) in dichloromethane (150 mL) over 3 hours. After complete addition, the reaction was allowed to continue for 1 hour. The reaction was poured into cold 1 N HCl (50 mL). The organic layer was separated and washed with brine and 1N HCl twice, dried over anhydrous sodium sulfate, and filtered. The filtrate was concentrated to give N-ethyl-N-methyl-sulfamoyl chloride 29.5 g (74%) as a light yellow oil.

Step 2.

methyl 3-[[ethyl(methyl)sulfamoyl]amino]-2-fluoro-benzoate: To methyl 3-amino-2-fluoro-benzoate (1.5 g, 8.87 mmol) in pyridine (5 ml, 61.82 mmol) was added DMAP (0.11 g, 0.89 mmol) and N-ethyl-N-methyl-sulfamoyl chloride (2.8 g, 17.74 mmol). The reaction mixture was stirred at room temperature for 4 days. The reaction mixture was diluted with water (+1 N citric acid) and extracted with ethyl acetate. The organic layer was washed with water and brine, dried (MgSO$_4$) and filtered. The volatiles were removed under vacuum. The crude material was purified by silica gel flash column chromatography using EtOAc/Hexane (0-35% gradient). The pure fractions were combined and concentrated under vacuum. This provided 1.53 g of methyl 3-[[ethyl(methyl)sulfamoyl]amino]-2-fluoro-benzoate. MS (ESI) [M+H]$^+$=291.0.

Step 3.

1-[[ethyl(methyl)sulfamoyl]amino]-2-fluoro-3-(hydroxymethyl)benzene. To methyl 3-[[ethyl(methyl)sulfamoyl]amino]-2-fluoro-benzoate (2.03 g, 0.01 mol) dissolved in 50 mL of THF and cooled to −20° C. was added 1 M LiAlH$_4$ in THF (15.03 mL). The reaction mixture became cloudy and slowly warmed to −10° C. for 2 hrs and was kept between −20° C. and −10° C. for 5 hrs. The reaction mixture was quenched with 25 grams Na$_2$SO$_4$-10H$_2$O and allowed to stir for 1 hour. The solid material was removed by filtration. The filtrate was concentrated under vacuum extracted with EtOAc and water. The organic layer was washed with water and brine, dried (MgSO$_4$), and filtered. The volatiles were removed under vacuum. The product was purified by silica gel column chromatography using EtOAc/Hexane (0-80% gradient). The pure fractions were combined and concentrated under vacuum to provide 1-[[ethyl(methyl)sulfamoyl]amino]-2-fluoro-3-(hydroxymethyl)benzene (1.72 g). MS (ESI) [M+H]$^+$=262.8.

Step 4.

1-[[ethyl(methyl)sulfamoyl]amino]-2-fluoro-3-formyl-benzene. To 1-[[ethyl(methyl)sulfamoyl]amino]-2-fluoro-3-(hydroxymethyl)benzene (1.72 g, 6.56 mmol) was added tetrahydrofuran (80 mL, 1221.54 mmol) and 2-iodoxybenzoic acid (45%, 5.3 g, 8.52 mmol). The reaction mixture was stirred at room temperature overnight. The precipitate was removed by filtration. The filtrate was collected and concentrated under vacuum. The product was purified by silica gel column chromatography using EtOAc/Hexane (0-60% gradient). The pure fractions were combined and concentrated under vacuum to provide 1-[[ethyl(methyl)sulfamoyl]amino]-2-fluoro-3-formyl-benzene (950 mg). MS(ESI) [M+H]$^+$=260.8.

Step 5.

5-iodo-4-methyl-7H-pyrrolo[2,3-d]pyrimidine. To 4-methyl-7H-pyrrolo[2,3-d]pyrimidine (1 g, 7.51 mmol) suspended in 30 mL of DCM was added N-iodosuccinimide (1.86 g, 8.26 mmol). The reaction mixture was stirred at room temperature for 2 hrs. The volatiles were removed under vacuum. The resulting residue was extracted with ethyl acetate and 50% aqueous saturated NaHCO$_3$. The organic layer was washed with water and brine, dried (MgSO$_4$), filtered and the volatiles were removed under vacuum. The residue was suspended in acetonitrile and sonicated for 45 mins. The solid material was collected by filtration to provide 5-iodo-4-methyl-7H-pyrrolo[2,3-d]pyrimidine (1.69 gram).

Step 6.

5-iodo-4-methyl-7-(p-tolylsulfonyl)pyrrolo[2,3-d]pyrimidine. To 5-iodo-4-methyl-7H-pyrrolo[2,3-d]pyrimidine (14.17 g, 54.7 mmol) suspended in 250 mL of THF and 10 mL of DMF was added NaH (60%, 3.56 g, 82.05 mmol) portion wise. The reaction mixture was stirred at room temperature for 30 minutes followed by the addition of 4-methylbenzenesulfonyl chloride (15.64 g, 82.05 mmol). The reaction mixture was stirred at room temperature overnight. TLC showed there is no the starting material left along with a new higher R$_f$ spot. The reaction mixture was quenched with 6 N HCl to pH ~3 followed by the addition of water and extraction with dichloromethane. The organic layer was washed with water and brine, dried (MgSO$_4$) and filtered. The volatiles were removed under vacuum and the residue was suspended in acetonitrile and sonicated for 45 mins. The solid material was collected by filtration and washed with acetonitrile. This provided 5-iodo-4-methyl-7-(p-tolylsulfonyl)pyrrolo[2,3-d]pyrimidine (12.99 gram). MS (ESI) [M+H]$^+$=413.8.

Step 7.

5-[[3-[[ethyl(methyl)sulfamoyl]amino]-2-fluoro-phenyl]-hydroxy-methyl]-4-methyl-7-(p-tolylsulfonyl)pyrrolo[2,3-d]pyrimidine. To 5-iodo-4-methyl-7-(p-tolylsulfonyl)pyrrolo[2,3-d]pyrimidine (0.63 g, 1.51 mmol) in THF (5 mL), under an atmosphere of itrogen at −40° C., was added a solution of 2 M i-PrMgCl in THF (0.75 ml). The reaction was allowed to stir at 5° C. in 1 hour. The reaction was cooled to −40° C., and then 1-[[ethyl(methyl)sulfamoyl]amino]-2-fluoro-3-formyl-benzene (0.15 g, 0.58 mmol) was added. The reaction was allowed to warm to room temperature over 1 hour. The reaction was poured into water and extracted with ethyl acetate. The organic layer was washed with brine, dried over sodium sulfate, and filtered. The filtrate was concentrated and purified by silica gel column chromatography eluting with a gradient of 20% to 100% ethyl acetate in hexane to give 5-[[3-[[ethyl(methyl)sulfamoyl]amino]-2-fluoro-phenyl]-hydroxy-methyl]-4-methyl-7-(p-tolylsulfonyl)pyrrolo[2,3-d]pyrimidine (0.28 g). MS (ESI) [M+H$^+$]$^+$=548.2.

Step 8.

5-[3-[[ethyl(methyl)sulfamoyl]amino]-2-fluoro-benzoyl]-4-methyl-7-(p-tolylsulfonyl)pyrrolo[2,3-d]pyrimidine. To 5-[[3-[[ethyl(methyl)sulfamoyl]amino]-2-fluoro-phenyl]-hydroxy-methyl]-4-methyl-7-(p-tolylsulfonyl)pyrrolo[2,3-d]pyrimidine (0.28 g, 0.51 mmol) in dichloromethane (40 mL) was added Dess-Martin periodinane (0.26 g, 0.61 mmol). The reaction was allowed to stir for 10 minutes at room temperature. The reaction was concentrated and purified using silica gel column chromatography eluting with 20% to 100% ethyl acetate in hexane to give the product 5-[3-[[ethyl(methyl)sulfamoyl]amino]-2-fluoro-benzoyl]-4-methyl-7-(p-tolylsulfonyl)pyrrolo[2,3-d]pyrimidine (0.23 g).

Step 9.

5-[3-[[ethyl(methyl)sulfamoyl]amino]-2-fluoro-benzoyl]-4-methyl-7H-pyrrolo[2,3-d]pyrimidine. To 5-[3-[[ethyl(methyl)sulfamoyl]amino]-2-fluoro-benzoyl]-4-methyl-7-(p-tolylsulfonyl)pyrrolo[2,3-d]pyrimidine (0.23 g, 0.42 mmol) in methanol (50 ml) was added potassium hydroxide (0.2 g, 3.56 mmol). The reaction was allowed to stir for 60 minutes at room temperature. The reaction was concentrated and purified using silica gel column chromatography eluting with 2% to 15% methanol in methylene chloride to give 5-[3-[[ethyl(methyl)sulfamoyl]amino]-2-fluoro-benzoyl]-4-methyl-7H-pyrrolo[2,3-d]pyrimidine (P-2090) (71.8 mg). MS (ESI) [M+H+]+=392.1.

The following compounds were made according to the synthetic protocol set forth in Scheme 4.

| Compound No. | Name | MH(+) |
| --- | --- | --- |
| P-2026 | 5-[3-(dimethylsulfamoylamino)-2,6-difluoro-benzoyl]-7H-pyrrolo[2,3-d]pyrimidine | 381.9 |
| P-2027 | N-[2,4-difluoro-3-(7H-pyrrolo[2,3-d]pyrimidine-5-carbonyl)phenyl]cyclohexanesulfonamide | 421.1 |
| P-2028 | N-[2,4-difluoro-3-(7H-pyrrolo[2,3-d]pyrimidine-5-carbonyl)phenyl]cyclopentanesulfonamide | 407.1 |
| P-2029 | N-[2,4-difluoro-3-(7H-pyrrolo[2,3-d]pyrimidine-5-carbonyl)phenyl]pyrrolidine-1-sulfonamide | 408.3 |
| P-2030 | N-[2,4-difluoro-3-(7H-pyrrolo[2,3-d]pyrimidine-5-carbonyl)phenyl]cyclobutanesulfonamide | 393.1 |
| P-2031 | N-[2,4-difluoro-3-(7H-pyrrolo[2,3-d]pyrimidine-5-carbonyl)phenyl]morpholine-4-sulfonamide | 424.3 |
| P-2032 | N-[2-fluoro-3-(7H-pyrrolo[2,3-d]pyrimidine-5-carbonyl)phenyl]pyrrolidine-1-sulfonamide | 390.3 |
| P-2076 | N-[2-fluoro-3-(4-methyl-7H-pyrrolo[2,3-d]pyrimidine-5-carbonyl)phenyl]pyrrolidine-1-sulfonamide | 402.0 (MH−) |
| P-2078 | N-[3-(4-cyclopropyl-7H-pyrrolo[2,3-d]pyrimidine-5-carbonyl)-2-fluoro-phenyl]pyrrolidine-1-sulfonamide | 428.1 (MH−) |
| P-2086 | 5-[2-fluoro-3-[[methyl(propyl)sulfamoyl]amino]benzoyl]-4-methyl-7H-pyrrolo[2,3-d]pyrimidine | 406.2 |
| P-2087 | 4-cyclopropyl-5-[2-fluoro-3-[[methyl(propyl)sulfamoyl]amino]benzoyl]-7H-pyrrolo[2,3-d]pyrimidine | 432.2 |
| P-2091 | 4-cyclopropyl-5-[3-[[ethyl(methyl)sulfamoyl]amino]-2-fluoro-benzoyl]-7H-pyrrolo[2,3-d]pyrimidine | 418.2 |

Example 7: Preparation of 4-(cyclopropylmethyl-amino)-5-[3-(dimethylsulfamoylamino)-2,6-difluoro-benzoyl]-7H-pyrrolo[2,3-d]pyrimidine (P-2048)

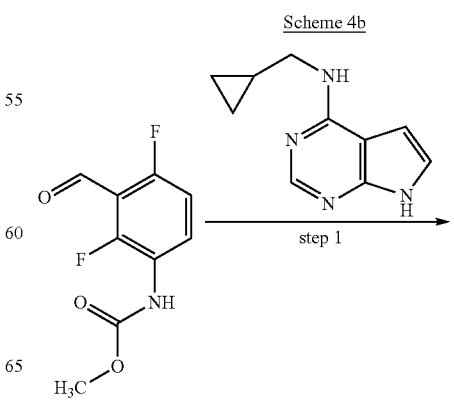

Scheme 4b

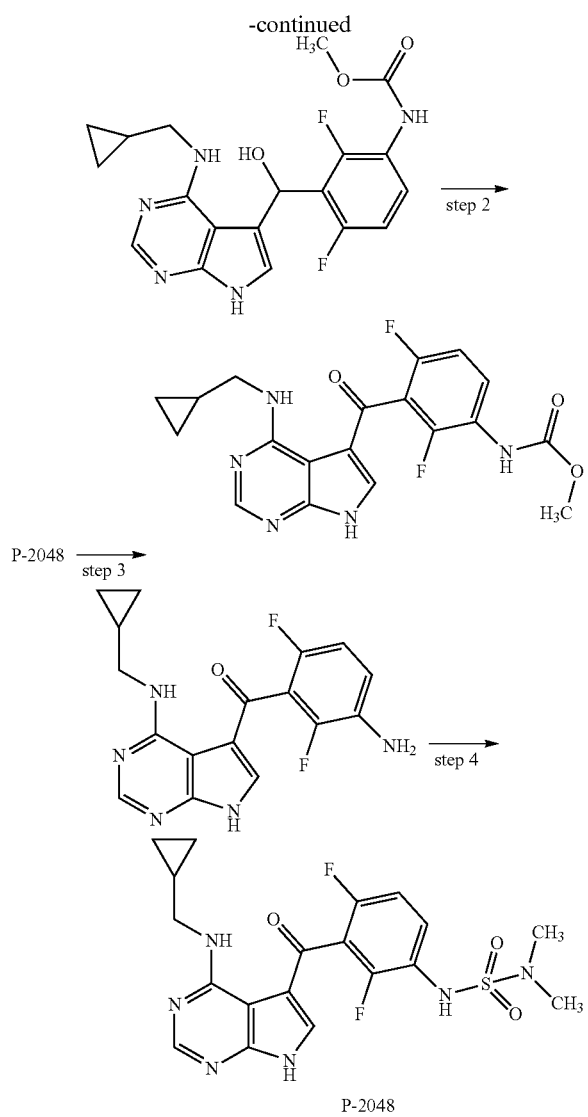

P-2048

Step 1.
methyl N-[3-[[4-(cyclopropylmethylamino)-7H-pyrrolo[2,3-d]pyrimidin-5-yl]-hydroxy-methyl]-2,4-difluoro-phenyl]carbamate. A mixture of [N-(cyclopropylmethyl)-7H-pyrrolo[2,3-d]pyrimidin-4-amine (0.62 g, 3.29 mmol), methyl N-(2,4-difluoro-3-formyl-phenyl)carbamate (0.92 g, 4.28 mmol), and potassium hydroxide (0.55 g, 9.88 mmol) in methanol (9 mL) was stirred at room temperature for 16 hours. The reaction mixture was neutralized with 1N HCl (aq) to pH 3 and extracted with ethyl acetate (2 times). The combined organic layers were washed with brine, dried over sodium sulfate, filtered, and concentrated. The crude material was purified by silica gel column chromatography eluting with methanol in dichloromethane. This provided methyl N-[3-[[4-(cyclopropylmethylamino)-7H-pyrrolo[2,3-d]pyrimidin-5-yl]-hydroxy-methyl]-2,4-difluoro-phenyl]carbamate (0.448 g). MS(ESI) [M+H+]+=403.9

Step 2.
methyl N-[3-[4-(cyclopropylmethylamino)-7H-pyrrolo[2,3-d]pyrimidine-5-carbonyl]-2,4-difluoro-phenyl]carbamate. To methyl N-[3-[[4-(cyclopropylmethylamino)-7H-pyrrolo[2,3-d]pyrimidin-5-yl]-hydroxy-methyl]-2,4-difluoro-phenyl]carbamate (446 mg, 1.11 mmol) in dimethyl sulfoxide (4 ml) was added 2-iodoxybenzoic acid (0.894 g). The resulting solution was stirred overnight. The reaction was poured into water and extracted with ethyl acetate (2 times). The combined organic layers were washed with brine, dried over sodium sulfate, filtered, and concentrated. The crude material was purified by silica gel flash chromatography eluting with methanol and dichloromethane. This provided 443 mg of methyl N-[3-[4-(cyclopropylmethylamino)-7H-pyrrolo[2,3-d]pyrimidine-5-carbonyl]-2,4-difluoro-phenyl]carbamate. MS(ESI) [M+H+]+=402.3.

Step 3.
(3-amino-2,6-difluoro-phenyl)-[4-(cyclopropylmethylamino)-7H-pyrrolo[2,3-d]pyrimidin-5-yl]methanone. To methyl N-[3-[4-(cyclopropylmethylamino)-7H-pyrrolo[2,3-d]pyrimidine-5-carbonyl]-2,4-difluoro-phenyl]carbamate (443 mg, 1.1 mmol) in tetrahydrofuran (4.5 ml), was added 5 M of sodium hydroxide in water (5.5 ml). The mixture was refluxed overnight. After the reaction mixture cooled to room temperature, it was neutralized with 6N HCl (aq). The resulting mixture was extracted with ethyl acetate (2 times). The combined organic layers were washed with brine, dried over sodium sulfate, filtered, and concentrated. The crude material was purified by silica gel flash chromatography eluting with methanol and dichloromethane. This provided 0.185 g of (3-amino-2,6-difluoro-phenyl)-[4-(cyclopropylmethylamino)-7H-pyrrolo[2,3-d]pyrimidin-5-yl]methanone. MS(ESI) [M+H+]+=344.3.

Step 4.
4-(cyclopropylmethylamino)-5-[3-(dimethylsulfamoylamino)-2,6-difluoro-benzoyl]-7H-pyrrolo[2,3-d]pyrimidine (P-2048). To (3-amino-2,6-difluoro-phenyl)-[4-(cyclopropylmethylamino)-7H-pyrrolo[2,3-d]pyrimidin-5-yl]methanone (500 mg, 1.46 mmol) dissolved in pyridine (5 ml) was added N,N-dimethylsulfamoyl chloride (230 mg, 1.60 mmol). The reaction was stirred at room temperature for 3 days. The solvent was then removed under vacuum and the resulting material was purified by silica gel flash chromatography eluting a gradient of methanol in dichloromethane (0-2% methanol). MS ESI [M+H+]+=450.9.

The following compounds were made according to the synthetic protocol set forth in Scheme 4b.

| Compound No. | Name | MH(+) |
|---|---|---|
| P-2037 | N-[2,4-difluoro-3-[4-(isopropylamino)-7H-pyrrolo[2,3-d]pyrimidine-5-carbonyl]phenyl]propane-2-sulfonamide | 438.0 |
| P-2038 | N-[2,4-difluoro-3-[4-(isopropylamino)-7H-pyrrolo[2,3-d]pyrimidine-5-carbonyl]phenyl]piperidine-1-sulfonamide | 479.0 |
| P-2039 | N-[2,4-difluoro-3-[4-(isopropylamino)-7H-pyrrolo[2,3-d]pyrimidine-5-carbonyl]phenyl]cyclohexanesulfonamide | 478.0 |
| P-2040 | N-[2,4-difluoro-3-[4-(isopropylamino)-7H-pyrrolo[2,3-d]pyrimidine-5-carbonyl]phenyl]cyclopentanesulfonamide | 464.0 |
| P-2041 | N-[2,4-difluoro-3-[4-(isopropylamino)-7H-pyrrolo[2,3-d]pyrimidine-5-carbonyl]phenyl]pyrrolidine-1-sulfonamide | 465.0 |

-continued

| Compound No. | Name | MH(+) |
|---|---|---|
| P-2042 | 5-[3-(diethylsulfamoylamino)-2,6-difluoro-benzoyl]-4-(isopropylamino)-7H-pyrrolo[2,3-d]pyrimidine | 467.5 |
| P-2043 | N-[2,4-difluoro-3-[4-(isopropylamino)-7H-pyrrolo[2,3-d]pyrimidine-5-carbonyl]phenyl]cyclobutanesulfonamide | 450.0 |
| P-2044 | N-[2,4-difluoro-3-[4-(isopropylamino)-7H-pyrrolo[2,3-d]pyrimidine-5-carbonyl]phenyl]morpholine-4-sulfonamide | 481.0 |
| P-2045 | 5-[3-(dimethylsulfamoylamino)-2,6-difluoro-benzoyl]-4-(isopropylamino)-7H-pyrrolo[2,3-d]pyrimidine | 439.0 |
| P-2046 | N-[3-[4-(cyclopropylmethylamino)-7H-pyrrolo[2,3-d]pyrimidine-5-carbonyl]-2,4-difluoro-phenyl]cyclopropanesulfonamide | 448.0 |
| P-2047 | N-[3-[4-(cyclopropylmethylamino)-7H-pyrrolo[2,3-d]pyrimidine-5-carbonyl]-2,4-difluoro-phenyl]propane-2-sulfonamide | 450.0 |
| P-2049 | N-[3-[4-(cyclopropylmethylamino)-7H-pyrrolo[2,3-d]pyrimidine-5-carbonyl]-2,4-difluoro-phenyl]cyclohexanesulfonamide | 490.5 |
| P-2050 | N-[3-[4-(cyclopropylmethylamino)-7H-pyrrolo[2,3-d]pyrimidine-5-carbonyl]-2,4-difluoro-phenyl]cyclopentanesulfonamide | 476.5 |
| P-2051 | N-[3-[4-(cyclopropylmethylamino)-7H-pyrrolo[2,3-d]pyrimidine-5-carbonyl]-2,4-difluoro-phenyl]pentane-2-sulfonamide | 478.0 |
| P-2052 | 4-(cyclopropylmethylamino)-5-[3-(diethylsulfamoylamino)-2,6-difluoro-benzoyl]-7H-pyrrolo[2,3-d]pyrimidine | 479.0 |
| P-2053 | N-[3-[4-(cyclopropylmethylamino)-7H-pyrrolo[2,3-d]pyrimidine-5-carbonyl]-2,4-difluoro-phenyl]cyclobutanesulfonamide | 462.5 |
| P-2054 | N-[3-[4-(cyclopropylmethylamino)-7H-pyrrolo[2,3-d]pyrimidine-5-carbonyl]-2,4-difluoro-phenyl]morpholine-4-sulfonamide | 493.1 |
| P-2055 | N-[3-[4-(cyclopropylmethylamino)-7H-pyrrolo[2,3-d]pyrimidine-5-carbonyl]-2,4-difluoro-phenyl]pyrrolidine-1-sulfonamide | 477.1 |
| P-2056 | N-[3-[4-(cyclopropylmethylamino)-7H-pyrrolo[2,3-d]pyrimidine-5-carbonyl]-2,4-difluoro-phenyl]butane-2-sulfonamide | 464.3 |
| P-2057 | N-[3-[4-(cyclopropylmethylamino)-7H-pyrrolo[2,3-d]pyrimidine-5-carbonyl]-2-fluoro-phenyl]pyrrolidine-1-sulfonamide | 459.4 |
| P-2058 | N-[3-[4-(cyclopropylmethylamino)-7H-pyrrolo[2,3-d]pyrimidine-5-carbonyl]-2,4-difluoro-phenyl]tetrahydropyran-4-sulfonamide | 492.5 |
| P-2061 | 4-(cyclopropylmethylamino)-5-[3-[[ethyl(methyl)sulfamoyl]amino]-2,6-difluoro-benzoyl]-7H-pyrrolo[2,3-d]pyrimidine | 465.1 |
| P-2062 | 5-[3-[[ethyl(methyl)sulfamoyl]amino]-2-fluoro-benzoyl]-4-(methylamino)-7H-pyrrolo[2,3-d]pyrimidine | 407.1 |
| P-2063 | 4-(cyclopropylamino)-5-[3-[[ethyl(methyl)sulfamoyl]amino]-2-fluoro-benzoyl]-7H-pyrrolo[2,3-d]pyrimidine | 433.2 |
| P-2064 | 4-(cyclopropylmethylamino)-5-[3-[[ethyl(methyl)sulfamoyl]amino]-2-fluoro-benzoyl]-7H-pyrrolo[2,3-d]pyrimidine | 447.0 |
| P-2065 | 5-[3-[[ethyl(methyl)sulfamoyl]amino]-2-fluoro-benzoyl]-4-(2,2,2-trifluoroethylamino)-7H-pyrrolo[2,3-d]pyrimidine | 475.0 |
| P-2066 | 5-[3-[[ethyl(methyl)sulfamoyl]amino]-2-fluoro-benzoyl]-4-(propylamino)-7H-pyrrolo[2,3-d]pyrimidine | 435.2 |
| P-2067 | 5-[3-[[ethyl(methyl)sulfamoyl]amino]-2-fluoro-benzoyl]-4-(isopropylamino)-7H-pyrrolo[2,3-d]pyrimidine | 435.4 |
| P-2068 | 4-[(4,4-difluorocyclohexyl)amino]-5-[3-[[ethyl(methyl)sulfamoyl]amino]-2-fluoro-benzoyl]-7H-pyrrolo[2,3-d]pyrimidine | 511.1 |
| P-2069 | 5-[3-[[ethyl(methyl)sulfamoyl]amino]-2-fluoro-benzoyl]-4-[(2-hydroxy-2-methyl-propyl)amino]-7H-pyrrolo[2,3-d]pyrimidine | 465.1 |
| P-2070 | N-[3-[4-(cyclopropylamino)-7H-pyrrolo[2,3-d]pyrimidine-5-carbonyl]-2-fluoro-phenyl]pyrrolidine-1-sulfonamide | 445.4 |
| P-2071 | N-[2-fluoro-3-[4-(methylamino)-7H-pyrrolo[2,3-d]pyrimidine-5-carbonyl]phenyl]pyrrolidine-1-sulfonamide | 419.3 |
| P-2072 | 4-(cyclobutylamino)-5-[3-[[ethyl(methyl)sulfamoyl]amino]-2-fluoro-benzoyl]-7H-pyrrolo[2,3-d]pyrimidine | 447.3 |
| P-2073 | 5-[3-[[ethyl(methyl)sulfamoyl]amino]-2-fluoro-benzoyl]-4-(2-methoxyethylamino)-7H-pyrrolo[2,3-d]pyrimidine | 451.3 |

-continued

| Compound No. | Name | MH(+) |
|---|---|---|
| P-2074 | 5-[3-[[ethyl(methyl)sulfamoyl]amino]-2-fluoro-benzoyl]-4-[[(2S)-tetrahydrofuran-2-yl]methylamino]-7H-pyrrolo[2,3-d]pyrimidine | 477.1 |
| P-2075 | 5-[3-[[ethyl(methyl)sulfamoyl]amino]-2-fluoro-benzoyl]-4-(tetrahydropyran-4-ylamino)-7H-pyrrolo[2,3-d]pyrimidine | 477.0 |
| P-2077 | N-[2-fluoro-3-[4-(2,2,2-trifluoroethylamino)-7H-pyrrolo[2,3-d]pyrimidine-5-carbonyl]phenyl]pyrrolidine-1-sulfonamide | 487.2 |
| P-2079 | 4-[[(1R)-1-cyclopropylethyl]amino]-5-[3-[[ethyl(methyl)sulfamoyl]amino]-2-fluoro-benzoyl]-7H-pyrrolo[2,3-d]pyrimidine | 461.1 |
| P-2080 | 4-[[(1S)-1-cyclopropylethyl]amino]-5-[3-[[ethyl(methyl)sulfamoyl]amino]-2-fluoro-benzoyl]-7H-pyrrolo[2,3-d]pyrimidine | 461.5 |
| P-2081 | N-[3-[4-(cyclobutylamino)-7H-pyrrolo[2,3-d]pyrimidine-5-carbonyl]-2-fluoro-phenyl]pyrrolidine-1-sulfonamide | 459.4 |
| P-2082 | N-[2-fluoro-3-[4-[[(2S)-tetrahydrofuran-2-yl]methylamino]-7H-pyrrolo[2,3-d]pyrimidine-5-carbonyl]phenyl]pyrrolidine-1-sulfonamide | 489.4 |
| P-2083 | N-[2-fluoro-3-[4-(tetrahydropyran-4-ylamino)-7H-pyrrolo[2,3-d]pyrimidine-5-carbonyl]phenyl]pyrrolidine-1-sulfonamide | 489.1 |
| P-2084 | N-[2-fluoro-3-(4-methoxy-7H-pyrrolo[2,3-d]pyrimidine-5-carbonyl)phenyl]pyrrolidine-1-sulfonamide | 419.9 |
| P-2092 | 5-[3-[[ethyl(methyl)sulfamoyl]amino]-2-fluoro-benzoyl]-4-methoxy-7H-pyrrolo[2,3-d]pyrimidine | 406.1 (MH−) |
| P-2094 | N-[3-[4-[[(1R)-1-cyclopropylethyl]amino]-7H-pyrrolo[2,3-d]pyrimidine-5-carbonyl]-2-fluoro-phenyl]pyrrolidine-1-sulfonamide | 473.4 |
| P-2095 | N-[3-[4-[(2,2-dimethyl-1,3-dioxolan-4-yl)methylamino]-7H-pyrrolo[2,3-d]pyrimidine-5-carbonyl]-2-fluoro-phenyl]pyrrolidine-1-sulfonamide | 519.1 |
| P-2096 | N-[3-[4-(2,3-dihydroxypropylamino)-7H-pyrrolo[2,3-d]pyrimidine-5-carbonyl]-2-fluoro-phenyl]pyrrolidine-1-sulfonamide | 479.1 |
| P-2097 | 1-[[5-[2-fluoro-3-(pyrrolidin-1-ylsulfonylamino)benzoyl]-7H-pyrrolo[2,3-d]pyrimidin-4-yl]amino]cyclopropanecarboxylic acid | 489.0 |
| P-2098 | N-[2-fluoro-3-[4-[(3-hydroxycyclobutyl)methylamino]-7H-pyrrolo[2,3-d]pyrimidine-5-carbonyl]phenyl]pyrrolidine-1-sulfonamide | 489.1 |
| P-2099 | 5-[3-[[ethyl(methyl)sulfamoyl]amino]-2,6-difluoro-benzoyl]-4-(propylamino)-7H-pyrrolo[2,3-d]pyrimidine | 453.2 |
| P-2100 | 5-[3-[[ethyl(methyl)sulfamoyl]amino]-2,6-difluoro-benzoyl]-4-(2-methoxyethylamino)-7H-pyrrolo[2,3-d]pyrimidine | 469.1 |
| P-2101 | 4-(cyclobutylamino)-5-[3-[[ethyl(methyl)sulfamoyl]amino]-2,6-difluoro-benzoyl]-7H-pyrrolo[2,3-d]pyrimidine | 465.0 |
| P-2102 | N-[3-[4-(2-aminoethylamino)-7H-pyrrolo[2,3-d]pyrimidine-5-carbonyl]-2-fluoro-phenyl]pyrrolidine-1-sulfonamide | 448.0 |
| P-2103 | ethyl 2-[[5-[2-fluoro-3-(pyrrolidin-1-ylsulfonylamino)benzoyl]-7H-pyrrolo[2,3-d]pyrimidin-4-yl]amino]acetate | 491.2 |
| P-2104 | N-[2-fluoro-3-[4-(2-methoxyethylamino)-7H-pyrrolo[2,3-d]pyrimidine-5-carbonyl]phenyl]pyrrolidine-1-sulfonamide | 463.2 |
| P-2105 | N-[2-fluoro-3-[4-(3-methoxypropylamino)-7H-pyrrolo[2,3-d]pyrimidine-5-carbonyl]phenyl]pyrrolidine-1-sulfonamide | 477.1 |
| P-2107 | methyl 2-[[5-[2-fluoro-3-(pyrrolidin-1-ylsulfonylamino)benzoyl]-7H-pyrrolo[2,3-d]pyrimidin-4-yl]amino]-4-methyl-pentanoate | 533.2 |
| P-2108 | N-[2-fluoro-3-[4-[(3-hydroxy-3-methyl-butyl)amino]-7H-pyrrolo[2,3-d]pyrimidine-5-carbonyl]phenyl]pyrrolidine-1-sulfonamide | 491.2 |
| P-2109 | 2-[[5-[2-fluoro-3-(pyrrolidin-1-ylsulfonylamino)benzoyl]-7H-pyrrolo[2,3-d]pyrimidin-4-yl]amino]acetic acid | 463.0 |
| P-2110 | N-[2-fluoro-3-[4-(2-morpholinoethylamino)-7H-pyrrolo[2,3-d]pyrimidine-5-carbonyl]phenyl]pyrrolidine-1-sulfonamide | 518.1 |
| P-2111 | N-[2-fluoro-3-[4-(3-morpholinopropylamino)-7H-pyrrolo[2,3-d]pyrimidine-5-carbonyl]phenyl]pyrrolidine-1-sulfonamide | 532.1 |
| P-2112 | N-[2-fluoro-3-[4-(3,3,3-trifluoropropylamino)-7H-pyrrolo[2,3-d]pyrimidine-5-carbonyl]phenyl]pyrrolidine-1-sulfonamide | 501.0 |
| P-2113 | N-[3-[4-[[3-(dimethylamino)-2,2-dimethyl-propyl]amino]-7H-pyrrolo[2,3-d]pyrimidine-5-carbonyl]-2-fluoro-phenyl]pyrrolidine-1-sulfonamide | 518.1 |
| P-2115 | 5-[3-[[ethyl(methyl)sulfamoyl]amino]-2-fluoro-benzoyl]-4-(3-methoxypropylamino)-7H-pyrrolo[2,3-d]pyrimidine | 465.1 |

-continued

| Compound No. | Name | MH(+) |
|---|---|---|
| P-2116 | 5-[3-[[ethyl(methyl)sulfamoyl]amino]-2,6-difluoro-benzoyl]-4-(3-methoxypropylamino)-7H-pyrrolo[2,3-d]pyrimidine | 483.1 |
| P-2117 | 5-[3-[[ethyl(methyl)sulfamoyl]amino]-2,6-difluoro-benzoyl]-4-(isopropylamino)-7H-pyrrolo[2,3-d]pyrimidine | 453.0 |
| P-2118 | 4-[[(1R)-1-cyclopropylethyl]amino]-5-[3-[[ethyl(methyl)sulfamoyl]amino]-2,6-difluoro-benzoyl]-7H-pyrrolo[2,3-d]pyrimidine | 479.0 |
| P-2119 | 5-[3-[[ethyl(methyl)sulfamoyl]amino]-2,6-difluoro-benzoyl]-4-(tetrahydropyran-4-ylamino)-7H-pyrrolo[2,3-d]pyrimidine | 495.3 |

Example 8: Preparation of N-(3-(2-(tert-butyl)-5-(2-methyl-1H-pyrrolo[2,3-b]pyridin-4-yl)thiazol-4-yl)-2-fluorophenyl)pyrrolidine-1-sulfonamide (P-2121)

Scheme 5

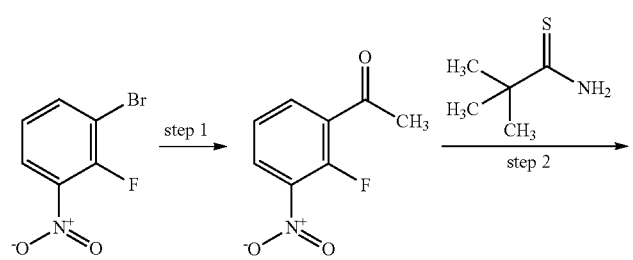

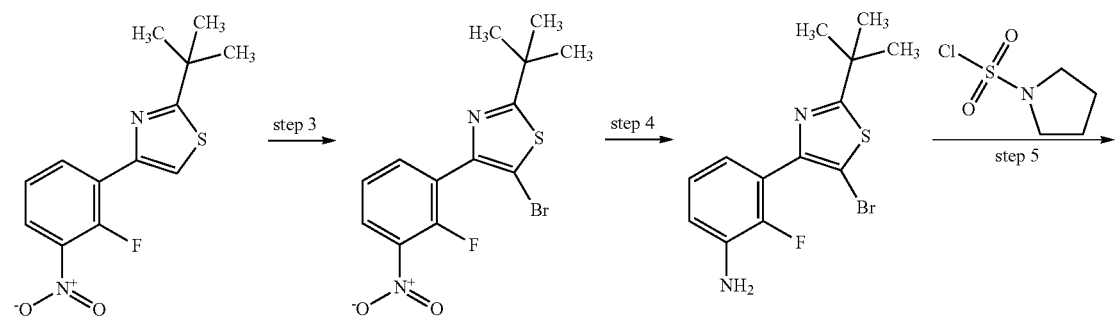

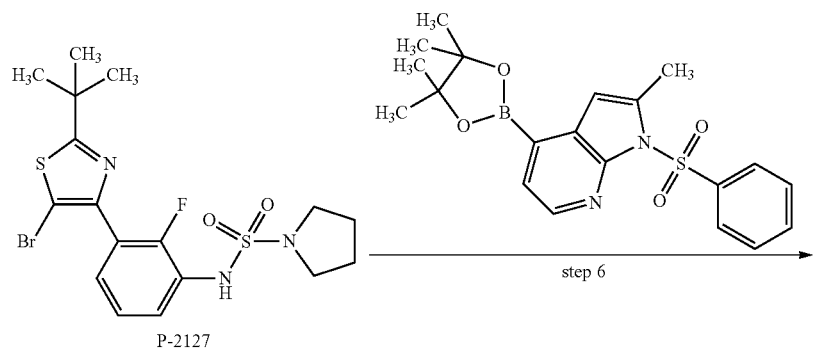

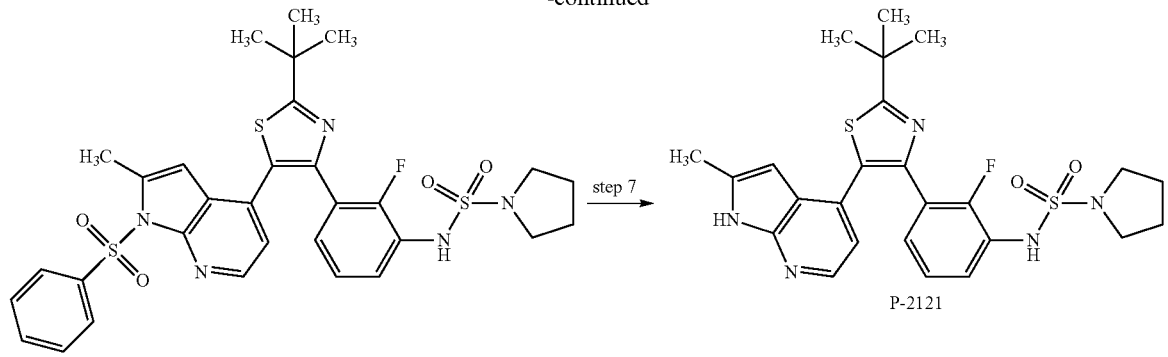

Step 1. 1-(2-Fluoro-3-nitrophenyl)ethanone: Bis(triphenylphosphine)palladium(II) dichloride (1.6 g, 2.28 mmol, 0.05 equiv) was added to a solution of 1-bromo-2-fluoro-3-nitrobenzene (10.0 g, 45.6 mmol, 1 equiv) and tri-n-butyl (1-ethoxyvinyl)stannane (15.4 mL, 45.6 mmol, 1 equiv) in dioxane (100 mL). The resulting turbid solution was heated at 90° C. for 4 hours during which time a dark brown solution formed. After TLC (30% MTBE/heptane) confirmed complete conversion, the reaction was cooled to room temperature. A saturated solution of KF (100 mL) and ethyl acetate (100 mL) were added and the biphasic mixture was stirred for 1 hour and filtered through Celite, washing with ethyl acetate. The organic layer was separated and dried over Na$_2$SO$_4$, filtered, and evaporated yielding the crude enol ether product as a brown oil. The crude product was dissolved in THF (50 mL) and 2 N HCl (50 mL) was added. The reaction was stirred at room temperature for 1.5 hours. The reaction was then saturated with NaCl and extracted with MTBE (2×150 mL). The organic layer was washed with brine (1×300 mL), dried over Na$_2$SO$_4$, filtered, and evaporated yielding crude material that was purified by silica gel column chromatography eluting with 0-40% ethyl acetate/heptanes gradient. Fractions containing product were evaporated under reduced pressure yielding compound 1-(2-Fluoro-3-nitrophenyl)ethanone (7.1 g, 86% yield) as a yellow oil.

Step 2. 2-(tert-Butyl)-4-(2-fluoro-3-nitrophenyl)thiazole: Copper (II) bromide (33.9 g, 152 mmol, 1.9 equiv) was suspended/dissolved in ethyl acetate (75 mL) with mechanical stirring. 1-(2-Fluoro-3-nitrophenyl)ethanone (14.4 g, 80.0 mmol, 1 equiv) was then added as a solution in CHCl$_3$ (75 mL) and the reaction was heated to reflux for 24 hours. The reaction was cooled to room temperature and filtered through a short plug of silica gel washing with ethyl acetate. The filtrate was evaporated leaving crude 2-bromo-1-(2-fluoro-3-nitrophenyl) ethanone which was dissolved in dimethylacetamide (150 mL) and 2,2-dimethylpropanethioamide (10.3 g, 88.0 mmol, 1 equiv). The reaction was stirred at room temperature for 1.5 hours. The reaction was heated to 60° C. for 2 hours, cooled to room temperature, and diluted with water (300 mL). The mixture was extracted with 15% MTBE in heptane (2×200 mL). The combined organic layers were washed with brine, dried over Na$_2$SO$_4$, filtered, and evaporated. The crude material was purified by silica gel column chromatography eluting with 0-15% ethyl acetate in heptane. Fractions containing product were evaporated yielding 2-(tert-Butyl)-4-(2-fluoro-3-nitrophenyl)thiazole (15.6 g, 70% yield over 2 steps) as an off-white solid.

Step 3. 5-Bromo-2-(tert-butyl)-4-(2-fluoro-3-nitrophenyl)thiazole: Bromine (5.8 mL, 113 mmol, 1.8 equiv) was added to a solution of 2-(tert-Butyl)-4-(2-fluoro-3-nitrophenyl)thiazole (17.6 g, 63 mmol, 1 equiv) in chloroform (250 mL). The reaction was heated at reflux for 18 hours. Trifluoroacetic acid (1 mL) was added and reaction was heated at reflux for an additional 24 hours. The reaction was then cooled to room temperature, diluted with DCM (250 mL), and washed with saturated aqueous Na$_2$S$_2$O$_3$ (1×500 mL) and saturated aqueous NaHCO$_3$ (1×250 mL). The organic layer was dried over Na$_2$SO$_4$, filtered, and evaporated. The resulting material was purified by silica gel column chromatography eluting with 0-20% MTBE in heptane yielding additional 5-Bromo-2-(tert-butyl)-4-(2-fluoro-3-nitrophenyl)thiazole (1.2 g, 18.6 g total, 82% yield).

Step 4. 3-(5-Bromo-2-(tert-butyl)thiazol-4-yl)-2-fluoroaniline: To a solution of 5-Bromo-2-(tert-butyl)-4-(2-fluoro-3-nitrophenyl)thiazole (18.6 g, 51.8 mmol, 1 equiv) in ethyl acetate/THF (150 mL/150 mL) was added SnCl$_2$ dihydrate (40.9 g, 181 mmol, 3.5 equiv) and the reaction was heated to 60° C. for 2.5 hours. The reaction was cooled to room temperature and quenched by the slow addition of saturated aqueous NaHCO$_3$ (500 mL). The biphasic mixture was filtered through Celite (very slow) washing with ethyl acetate. The filtrate was transferred to a separatory funnel and the phases separated. The organic phase was washed with brine (1×250 mL), dried over Na$_2$SO$_4$, filtered, and evaporated leaving a yellow oil. Heptane (90 mL) and MTBE (10 mL) were added to dissolve the oil. Crystallization of 3-(5-Bromo-2-(tert-butyl)thiazol-4-yl)-2-fluoroaniline provided (13.1 g) with an additional (2.0 g) isolated from the mother liquor by silica gel column chromatography (15.1 g total, 88% yield).

Step 5. N-(3-(5-Bromo-2-(tert-butyl)thiazol-4-yl)-2-fluorophenyl)pyrrolidine-1-sulfonamide: A solution of 3-(5-Bromo-2-(tert-butyl)thiazol-4-yl)-2-fluoroaniline (13.5 g, 41 mmol, 1 equiv), pyridine (10 mL, 123 mmol, 3 equiv), and pyrrolidine-1-sulfonyl chloride (21 g, 123 mmol, 3 equiv) in acetonitrile (230 mL) was heated at 60° C. for 18 hours. The reaction was cooled to room temperature and the solvent evaporated. The residue was partitioned between ethyl acetate (300 mL) and 1 N HCl (300 mL). The phases were separated and the organic layer was washed with brine (1×300 mL), dried over Na$_2$SO$_4$, filtered, and evaporated yielding a brown oil. Heptane (90 mL) and MTBE (10 mL). Crystallization of N-(3-(5-Bromo-2-(tert-butyl)thiazol-4-yl)-2-fluorophenyl)pyrrolidine-1-sulfonamide provided (8.45 g, 46% yield) as an off-white solid.

Step 6. N-(3-(2-(tert-butyl)-5-(2-methyl-1-(phenylsulfonyl)-1H-pyrrolo[2,3-b]pyridin-4-yl)thiazol-4-yl)-2-fluorophenyl)pyrrolidine-1-sulfonamide: A mixture of 1-(benzenesulfonyl)-2-methyl-4-(4,4,5,5-tetramethyl-1,3,2- dioxaborolan-2-yl)pyrrolo[2,3-b]pyridine (1.1 g, 1.381 mmol, ~50% purity), N-(3-(5-bromo-2-(tert-butyl)thiazol-4-yl)-2-fluorophenyl)pyrrolidine-1-sulfonamide (0.426 g, 0.921 mmol), potassium carbonate (0.382 g, 2.76 mmol) and [1,1'-bis(diphenylphosphino)ferrocene]dichloropalladium (II) (0.075 g, 0.092 mmol) in dioxane (12.27 mL) and water (6.14 mL) was heated at 90° C. for several hours. Upon cooling, the reaction mixture diluted with water and extracted with ethyl acetate. The organic layer was separated and concentrated under reduced pressure to give the crude product which was purified by silica gel column chromatography eluting with 0-100% ethyl acetate/heptane to give N-(3-(2-(tert-butyl)-5-(2-methyl-1-(phenylsulfonyl)-1H-pyrrolo[2,3-b]pyridin-4-yl)thiazol-4-yl)-2-fluorophenyl)pyrrolidine-1-sulfonamide (0.60 g, 0.918 mmol, 100% yield) as a yellow solid.

Step 7. N-(3-(2-(tert-butyl)-5-(2-methyl-1H-pyrrolo[2,3-b]pyridin-4-yl)thiazol-4-yl)-2-fluorophenyl)pyrrolidine-1-sulfonamide (P-2121): To a solution of N-(3-(2-(tert-butyl)-5-(2-methyl-1-(phenylsulfonyl)-1H-pyrrolo[2,3-b]pyridin-4-yl)thiazol-4-yl)-2-fluorophenyl)pyrrolidine-1-sulfonamide (0.60 g, 0.918 mmol) in THF (9.18 mL) was added TBAF trihydrate (1.448 g, 4.59 mmol) and stirred 40° C. for 4 hours. Additional TBAF trihydrate (1.448 g, 4.59 mmol) as added and the mixture was stirred overnight. The mixture was diluted with water/brine and ethyl acetate and the layers were separated. The organic layer was concentrated under reduced pressure to give crude product which was purified by silica gel column chromatography eluting with 0-10% methanol/DCM and triturated with MTBE/heptane and filtered washing with heptane and dried in a vacuum oven to give N-(3-(2-(tert-butyl)-5-(2-methyl-1H-pyrrolo[2,3-b]pyridin-4-yl)thiazol-4-yl)-2-fluorophenyl)pyrrolidine-1-sulfonamide (0.18 g, 0.350 mmol, 38% yield) as an off-white solid. MS (ESI) $[M+H^+]^+$=514.2.

The following compounds were made according to the synthetic protocol set forth in scheme 5.

| Compound No. | Name | MH(+) |
|---|---|---|
| P-2120 | N-[3-[2-tert-butyl-5-(1H-pyrrolo[2,3-b]pyridin-4-yl)thiazol-4-yl]-2-fluoro-phenyl]pyrrolidine-1-sulfonamide | 500.0 |
| P-2126 | N-[3-[2-tert-butyl-5-(2-methyl-3H-imidazo[4,5-b]pyridin-7-yl)thiazol-4-yl]-2-fluoro-phenyl]pyrrolidine-1-sulfonamide | 515.1 |

Example 9: Preparation of N-(3-(2-(tert-butyl)-5-(7H-pyrrolo[2,3-d]pyrimidin-4-yl)thiazol-4-yl)-2-fluorophenyl)pyrrolidine-1-sulfonamide (P-2122)

Scheme 6

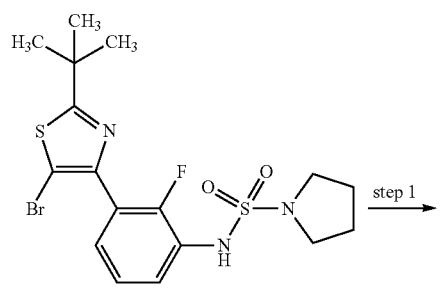

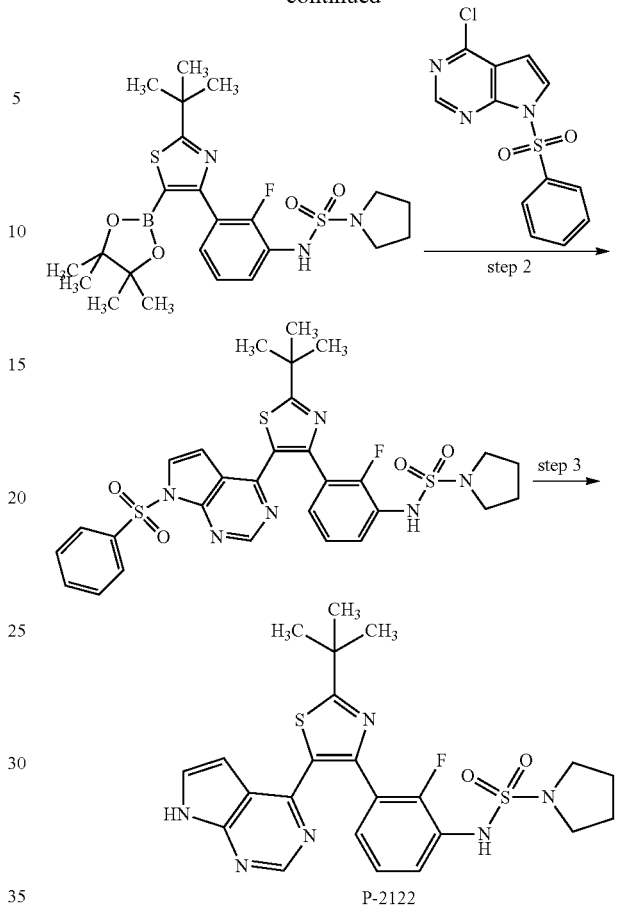

Step 1. N-(3-(2-(tert-butyl)-5-(4,4,5,5-tetramethyl-1,3,2-dioxaborolan-2-yl)thiazol-4-yl)-2-fluorophenyl)pyrrolidine-1-sulfonamide: To N-(3-(5-Bromo-2-(tert-butyl)thiazol-4-yl)-2-fluorophenyl)pyrrolidine-1-sulfonamide (1.50 g, 3.24 mmol) in dry THF (32.4 mL) was added sodium hydride 60% (0.162 g, 4.22 mmol) and the mixture was stirred at −78° C. for 30 minutes. Then n-butyllithium 2.5M hexanes (1.946 mL, 4.87 mmol) was added dropwise and the mixture was stirred at −78° C. for 30 minutes. Then, i-propylpinacol borate (3.31 mL, 16.22 mmol) was added and was allowed to warm to room temperature overnight. The reaction was poured into 1% aqueous HCl/brine and then extracted with ethyl acetate. The organic layer was separated and concentrated under reduced pressure to give N-(3-(2-(tert-butyl)-5-(4,4,5,5-tetramethyl-1,3,2-dioxaborolan-2-yl)thiazol-4-yl)-2-fluorophenyl)pyrrolidine-1-sulfonamide (1.65 g, 2.267 mmol, 69.9% yield) as an oil along with ~30% of the corresponding 5-protio thiazole which was used directly in the next step.

Step 2. N-(3-(2-(tert-butyl)-5-(7-(phenylsulfonyl)-7H-pyrrolo[2,3-d]pyrimidin-4-yl)thiazol-4-yl)-2-fluorophenyl)pyrrolidine-1-sulfonamide: 7-(benzenesulfonyl)-4-chloro-pyrrolo[2,3-d]pyrimidine (0.142 g, 0.483 mmol), N-(3-(2-(tert-butyl)-5-(4,4,5,5-tetramethyl-1,3,2-dioxaborolan-2-yl)thiazol-4-yl)-2-fluorophenyl)pyrrolidine-1-sulfonamide (0.551 g, 0.725 mmol), potassium carbonate (0.200 g, 1.450 mmol) and [1,1'-bis(diphenylphosphino)ferrocene]dichloro-palladium(II) (0.039 g, 0.048 mmol) in dioxane (6.45 mL) and water (3.22 mL) were heated at 100° C. for several hours. Upon cooling, the reaction mixture diluted with water and extracted with ethyl acetate. The organic layer was separated and concentrated under reduced pressure to give the crude product which was purified by silica gel column chromatography eluting with 0-100% ethyl acetate/heptane to give N-(3-(2-(tert-butyl)-5-(7-(phenylsulfonyl)-7H-pyrrolo[2,3-d]pyrimidin-4-yl)thiazol-4-yl)-2-fluorophenyl)pyrrolidine-1-sulfonamide (0.20 g, 0.312 mmol, 65% yield) as a clear semi-solid.

Step 3. N-(3-(2-(tert-butyl)-5-(7H-pyrrolo[2,3-d]pyrimidin-4-yl)thiazol-4-yl)-2-fluorophenyl)pyrrolidine-1-sulfonamide (P-2122): To a solution of N-(3-(2-(tert-butyl)-5-(7-(phenylsulfonyl)-7H-pyrrolo[2,3-d]pyrimidin-4-yl)thiazol-4-yl)-2-fluorophenyl)pyrrolidine-1-sulfonamide (0.20 g, 0.312 mmol) in THF (3.12 mL) was added TBAF trihydrate (1.083 g, 3.43 mmol) and stirred 40° C. overnight. The mixture was diluted with water/brine and ethyl acetate and the layers were separated. The organic layer was concentrated under reduced pressure to give crude product which was purified by silica gel column chromatography eluting with 0-10% methanol/DCM and triturated with MTBE/heptane and filtered washing with heptane and dried in a vacuum oven to give N-(3-(2-(tert-butyl)-5-(7H-pyrrolo[2,3-d]pyrimidin-4-yl)thiazol-4-yl)-2-fluorophenyl)pyrrolidine-1-sulfonamide (0.080 g, 0.160 mmol, 51% yield) as an off-white solid. MS (ESI) [M+H$^+$]$^+$=501.0.

The following compounds were made according to the synthetic protocol set forth in Scheme 6.

| Compound # | Name | MH(+) |
|---|---|---|
| P-2123 | N-[3-[2-tert-butyl-5-(6-methyl-7H-pyrrolo[2,3-d]pyrimidin-4-yl)thiazol-4-yl]-2-fluoro-phenyl]pyrrolidine-1-sulfonamide | 515.1 |
| P-2124 | N-[3-[2-tert-butyl-5-(8-methyl-9H-purin-6-yl)thiazol-4-yl]-2-fluoro-phenyl]pyrrolidine-1-sulfonamide | 516.3 |
| P-2125 | N-[3-[2-tert-butyl-5-(9H-purin-6-yl)thiazol-4-yl]-2-fluoro-phenyl]pyrrolidine-1-sulfonamide | 502.2 |

Example 10: N-(5-chloro-3-(5-(2-cyclopropylpyrimidin-5-yl)-1H-pyrrolo[2,3-b]pyridine-3-carbonyl)-2-fluorophenyl)pyrrolidine-1-sulfonamide (P-2180)

Scheme 7.

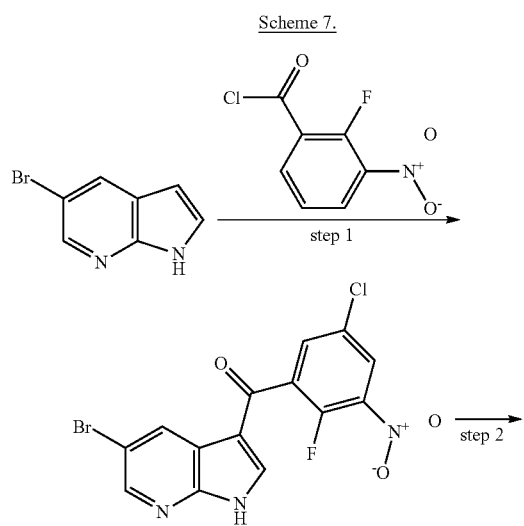

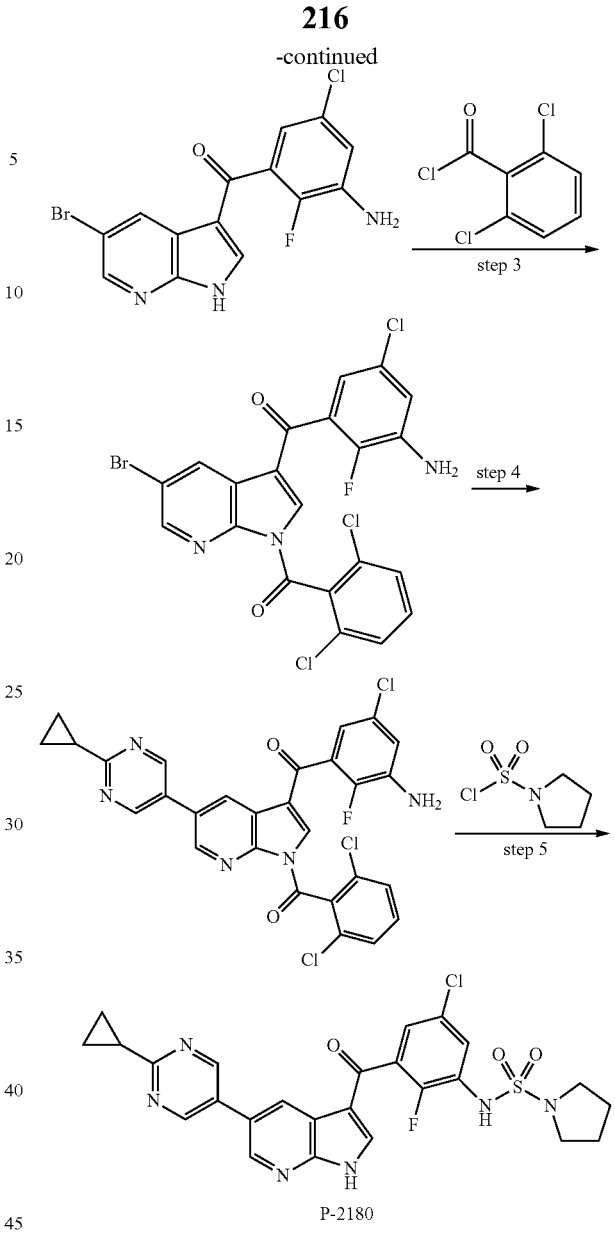

Step 1. (5-bromo-1H-pyrrolo[2,3-b]pyridin-3-yl)(5-chloro-2-fluoro-3-nitrophenyl)methanone: To 5-chloro-2-fluoro-3-nitrobenzoic acid (20 g, 91 mmol) was added thionyl chloride (66.5 mL, 911 mmol). The reaction was heated at 80° C. overnight and allowed to cool to room temperature. The volatiles were removed under reduced pressure and then azeotroped from toluene several times to give 2-fluoro-3-nitro-benzoyl chloride as an oil which was used directly. 5-bromo-1H-pyrrolo[2,3-b]pyridine (12 g, 60.9 mmol) and aluminum chloride (48.7 g, 365 mmol) in nitromethane (152 mL) were allowed to stir at room temperature for 1 hour. Then 2-fluoro-3-nitro-benzoyl chloride (21.74 g, 91 mmol) in nitromethane (152 mL) was added and the mixture was heated at 50° C. for 3 days. After cooling to 0° C., the reaction was quenched with methanol (~200 mL) resulting in a precipitate. The mixture was diluted with water (~200 mL) and then filtered. The crude product was triturated with MTBE and filtered washing with additional MTBE to give (5-bromo-1H-pyrrolo[2,3-b]pyridin-3-yl)(5-chloro-2-fluoro-3-nitrophenyl)methanone as a brown solid.

Step 2. (3-amino-5-chloro-2-fluorophenyl)(5-bromo-1H-pyrrolo[2,3-b]pyridin-3-yl)methanone: To (5-bromo-1H-pyrrolo[2,3-b]pyridin-3-yl)(5-chloro-2-fluoro-3-nitrophenyl)methanone (24.27 g, 60.9 mmol) in ethyl acetate (761 mL) and THF (761 mL) was treated portion wise with tin(II) chloride dihydrate (48.1 g, 213 mmol) while heating to 60° C. and held at this temperature overnight. After cooling to room temperature, the reaction mixture was quenched with half sat. aqueous sodium bicarbonate and filtered through Celite washing the cake with ethyl acetate. The layers were separated and the organic layer was concentrated under reduced pressure to give (3-amino-5-chloro-2-fluorophenyl)(5-bromo-1H-pyrrolo[2,3-b]pyridin-3-yl)methanone (8 g, 21.70 mmol, 35.6% yield) as a tan solid.

Step 3. (3-(3-amino-5-chloro-2-fluorobenzoyl)-5-bromo-1H-pyrrolo[2,3-b]pyridin-1-yl)(2,6-dichlorophenyl)methanone: To (3-amino-5-chloro-2-fluorophenyl) (5-bromo-1H-pyrrolo[2,3-b]pyridin-3-yl)methanon (8 g, 21.70 mmol) in THF (87 mL) was added DMAP (0.265 g, 2.170 mmol), DIPEA (7.56 mL, 43.4 mmol) and 2,6-dichlorobenzoyl chloride (3.42 mL, 23.87 mmol) and the reaction was stirred at 25° C. overnight. The reaction mixture was diluted with water and extracted with ethyl acetate. The organic layer was separated and concentrated under reduced pressure and the crude product was dissolved in DCM and purified by silica gel column chromatography eluting with 0-40% ethyl acetate/heptane and triturated with heptane and filtered to give (3-(3-amino-5-chloro-2-fluorobenzoyl)-5-bromo-1H-pyrrolo[2,3-b]pyridin-1-yl)(2,6-dichlorophenyl)methanone (5.1 g, 9.42 mmol, 43.4% yield) as a yellow solid.

Step 4. (3-(3-amino-5-chloro-2-fluorobenzoyl)-5-bromo-1H-pyrrolo[2,3-b]pyridin-1-yl)(2,6-dichlorophenyl)methanone: A mixture of (3-(3-amino-5-chloro-2-fluorobenzoyl)-5-bromo-1H-pyrrolo[2,3-b]pyridin-1-yl)(2,6-dichlorophenyl)methanone (4 g, 7.39 mmol), (2-cyclopropylpyrimidin-5-yl)boronic acid (2.422 g, 14.77 mmol), powdered potassium carbonate (3.06 g, 22.16 mmol) and bis(triphenylphosphine)palladium(II) dichloride (0.259 g, 0.369 mmol) in dioxane (39.4 mL) and water (19.70 mL) was heated at 90° C. for 1 hour. Upon cooling, the reaction mixture diluted with water and extracted with ethyl acetate. The organic layer was separated and concentrated under reduced pressure to give the crude product purified by silica gel column chromatography eluting with 0-100% ethyl acetate/heptane to give (3-(3-amino-5-chloro-2-fluorobenzoyl)-5-bromo-1H-pyrrolo[2,3-b]pyridin-1-yl)(2,6-dichlorophenyl)methanone (4.3 g, 7.40 mmol, 100% yield) as a yellow solid.

Step 5. N-(5-chloro-3-(5-(2-cyclopropylpyrimidin-5-yl)-1H-pyrrolo[2,3-b]pyridine-3-carbonyl)-2-fluorophenyl)pyrrolidine-1-sulfonamide (P-2180): To (3-(3-amino-5-chloro-2-fluorobenzoyl)-5-bromo-1H-pyrrolo[2,3-b]pyridin-1-yl) (2,6-dichlorophenyl)methanone (0.250 g, 0.430 mmol) in acetonitrile (2.460 mL) was added DMAP (5.26 mg, 0.043 mmol), pyridine (0.174 mL, 2.152 mmol) and pyrrolidine-1-sulfonyl chloride (0.292 g, 1.722 mmol) and the reaction was heated at 70° C. for 2 days. The reaction mixture was concentrated under reduced pressure and then was partitioned between water and ethyl acetate. The organic layer was concentrated under reduced pressure to give the crude product which was dissolved in a mixture of MeOH (2.87 mL) and dimethylacetamide (1.433 mL) and treated with ammonia 7 M MeOH (0.307 mL, 2.150 mmol) and heated at 50° C. overnight. The volatiles were removed under reduced pressure and the residue was partitioned between ethyl acetate and water/brine. The organic layer was concentrated under reduced pressure to give the crude product which was dissolved in THF (4 mL) and purified by reverse phase (55 g) column chromatography eluting with 0-100% acetonitrile/water and triturated with DCM/heptane and filtered to give N-(5-chloro-3-(5-(2-cyclopropylpyrimidin-5-yl)-1H-pyrrolo[2,3-b]pyridine-3-carbonyl)-2-fluorophenyl) pyrrolidine-1-sulfonamide (0.050 g, 0.092 mmol, 21.5% yield) as an off-white solid. MS (ESI) $[M+H^+]^+$=540.9

The following compounds were made according to the synthetic protocol set forth in Scheme 7.

| Compound No. | Name | MH(+) |
| --- | --- | --- |
| P-2171 | N-[3-[5-(2-cyclopropylpyrimidin-5-yl)-1H-pyrrolo[2,3-b]pyridine-3-carbonyl]-2,5-difluoro-phenyl]pyrrolidine-1-sulfonamide | 525.3 |
| P-2172 | (3R)-N-[3-[5-(2-cyclopropylpyrimidin-5-yl)-1H-pyrrolo[2,3-b]pyridine-3-carbonyl]-2,5-difluoro-phenyl]-3-fluoro-pyrrolidine-1-sulfonamide | 543.3 |
| P-2173 | 5-(2-cyclopropylpyrimidin-5-yl)-3-[3-(dimethylsulfamoylamino)-2,5-difluoro-benzoyl]-1H-pyrrolo[2,3-b]pyridine | 499.3 |
| P-2174 | (3R)-N-[5-chloro-3-[5-(2-cyclopropylpyrimidin-5-yl)-1H-pyrrolo[2,3-b]pyridine-3-carbonyl]-2-fluoro-phenyl]-3-fluoro-pyrrolidine-1-sulfonamide | 559.2 |
| P-2175 | 3-[5-chloro-3-(dimethylsulfamoylamino)-2-fluoro-benzoyl]-5-(2-cyclopropylpyrimidin-5-yl)-1H-pyrrolo[2,3-b]pyridine | 515.2 |
| P-2176 | N-[5-chloro-3-[5-(2-cyclopropylpyrimidin-5-yl)-1H-pyrrolo[2,3-b]pyridine-3-carbonyl]-2-fluoro-phenyl]-2,2,5,5-tetradeuterio-pyrrolidine-1-sulfonamide | 545.1 |
| P-2177 | N-[5-chloro-3-[5-(2-cyclopropylpyrimidin-5-yl)-1H-pyrrolo[2,3-b]pyridine-3-carbonyl]-2-fluoro-phenyl]-2,2,3,3,4,4,5,5-octadeuterio-pyrrolidine-1-sulfonamide | 549 |
| P-2178 | (3R)-N-[3-[5-(2-cyclopropylpyrimidin-5-yl)-1H-pyrrolo[2,3-b]pyridine-3-carbonyl]-2-fluoro-5-(trifluoromethyl)phenyl]-3-fluoro-pyrrolidine-1-sulfonamide | 593.1 |
| P-2179 | N-[3-[5-(2-cyclopropylpyrimidin-5-yl)-1H-pyrrolo[2,3-b]pyridine-3-carbonyl]-2-fluoro-5-(trifluoromethyl)phenyl]pyrrolidine-1-sulfonamide | 575.1 |

The following compounds were prepared according to the protocol set forth in Scheme 7 using the appropriate 7-azaindole in place of 8-bromo-7-azaindole.

| Compound # | Name | MH(+) |
|---|---|---|
| P-2001 | N-[2,4-difluoro-3-(4-methoxy-1H-pyrrolo[2,3-b]pyridine-3-carbonyl)phenyl]propane-2-sulfonamide | 409.9 |
| P-2002 | 3-[3-(dimethylsulfamoylamino)-2,6-difluoro-benzoyl]-4-methoxy-1H-pyrrolo[2,3-b]pyridine | 411.1 |
| P-2003 | N-[2,4-difluoro-3-(4-methoxy-1H-pyrrolo[2,3-b]pyridine-3-carbonyl)phenyl]pyrrolidine-1-sulfonamide | 437.1 |
| P-2004 | 3-[3-(diethylsulfamoylamino)-2,6-difluoro-benzoyl]-4-methoxy-1H-pyrrolo[2,3-b]pyridine | 439.1 |
| P-2005 | N-[2,4-difluoro-3-(4-methoxy-1H-pyrrolo[2,3-b]pyridine-3-carbonyl)phenyl]cyclohexanesulfonamide | 449.9 |
| P-2006 | N-[2,4-difluoro-3-(4-methoxy-1H-pyrrolo[2,3-b]pyridine-3-carbonyl)phenyl]butane-2-sulfonamide | 423.9 |
| P-2007 | 4-chloro-3-[3-(dimethylsulfamoylamino)-2,6-difluoro-benzoyl]-1H-pyrrolo[2,3-b]pyridine | 415.1 |
| P-2008 | N-[3-(4-chloro-1H-pyrrolo[2,3-b]pyridine-3-carbonyl)-2,4-difluoro-phenyl]cyclobutanesulfonamide | 425.9 |
| P-2009 | N-[2,4-difluoro-3-(4-methoxy-1H-pyrrolo[2,3-b]pyridine-3-carbonyl)phenyl]pentane-2-sulfonamide | 437.9 |
| P-2010 | N-[2,4-difluoro-3-(4-methoxy-1H-pyrrolo[2,3-b]pyridine-3-carbonyl)phenyl]cyclobutanesulfonamide | 421.9 |
| P-2011 | 4-chloro-3-[3-(diethylsulfamoylamino)-2,6-difluoro-benzoyl]-1H-pyrrolo[2,3-b]pyridine | 443.1 |
| P-2012 | 4-cyano-3-[3-(diethylsulfamoylamino)-2,6-difluoro-benzoyl]-1H-pyrrolo[2,3-b]pyridine | 433.9 |
| P-2013 | N-[3-(4-chloro-1H-pyrrolo[2,3-b]pyridine-3-carbonyl)-2,4-difluoro-phenyl]propane-2-sulfonamide | 413.9 |
| P-2014 | N-[3-(4-chloro-1H-pyrrolo[2,3-b]pyridine-3-carbonyl)-2,4-difluoro-phenyl]cyclohexanesulfonamide | 453.9 |
| P-2015 | N-[3-(4-chloro-1H-pyrrolo[2,3-b]pyridine-3-carbonyl)-2,4-difluoro-phenyl]cyclopentanesulfonamide | 439.9 |
| P-2016 | N-[3-(4-chloro-1H-pyrrolo[2,3-b]pyridine-3-carbonyl)-2,4-difluoro-phenyl]butane-2-sulfonamide | 427.9 |
| P-2017 | N-[3-(4-cyano-1H-pyrrolo[2,3-b]pyridine-3-carbonyl)-2,4-difluoro-phenyl]propane-2-sulfonamide | 405.1 |
| P-2018 | N-[3-(4-cyano-1H-pyrrolo[2,3-b]pyridine-3-carbonyl)-2,4-difluoro-phenyl]cyclohexanesulfonamide | 445.1 |
| P-2019 | N-[3-(4-cyano-1H-pyrrolo[2,3-b]pyridine-3-carbonyl)-2,4-difluoro-phenyl]pyrrolidine-1-sulfonamide | 431.9 |
| P-2020 | N-[3-(4-cyano-1H-pyrrolo[2,3-b]pyridine-3-carbonyl)-2,4-difluoro-phenyl]butane-2-sulfonamide | 419.1 |
| P-2021 | N-[3-(4-cyano-1H-pyrrolo[2,3-b]pyridine-3-carbonyl)-2,4-difluoro-phenyl]cyclobutanesulfonamide | 417.5 |
| P-2022 | N-[3-(4-cyano-1H-pyrrolo[2,3-b]pyridine-3-carbonyl)-2,4-difluoro-phenyl]morpholine-4-sulfonamide | 447.9 |
| P-2023 | N-[2,4-difluoro-3-(4-methoxy-1H-pyrrolo[2,3-b]pyridine-3-carbonyl)phenyl]morpholine-4-sulfonamide | 453.1 |
| P-2024 | N-[3-(4-chloro-1H-pyrrolo[2,3-b]pyridine-3-carbonyl)-2,4-difluoro-phenyl]morpholine-4-sulfonamide | 457.1 |
| P-2025 | N-[3-(4-chloro-1H-pyrrolo[2,3-b]pyridine-3-carbonyl)-2,4-difluoro-phenyl]pyrrolidine-1-sulfonamide | 441.1 |

Example 11: Synthesis of methyl N-[(1S)-2-[[4-[4-[5-chloro-2-fluoro-3-(1-piperidylsulfonylamino)phenyl]-1-isopropyl-pyrazol-3-yl]pyrimidin-2-yl]amino]-1-methyl-ethyl]carbamate Example 12: Synthesis of N-[3-[4-(cyclopropylmethylamino)-5-fluoro-1H-pyrrolo[2,3-b]pyridine-3-carbonyl]-2,4-difluoro-phenyl]pyrrolidine-1-sulfonamide (P-2060)

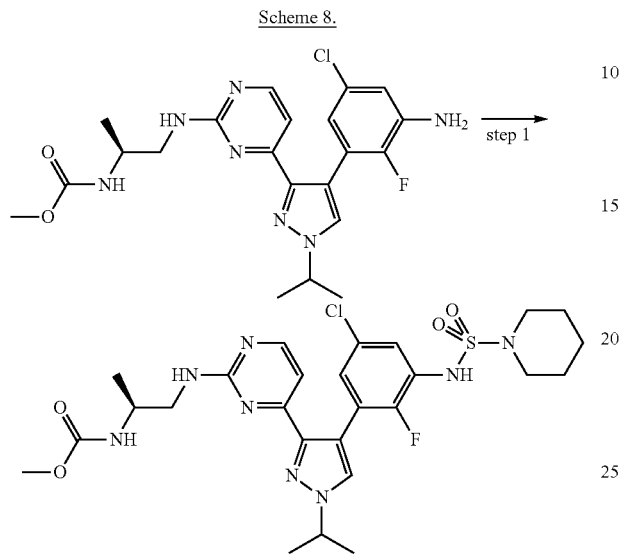

Scheme 8.

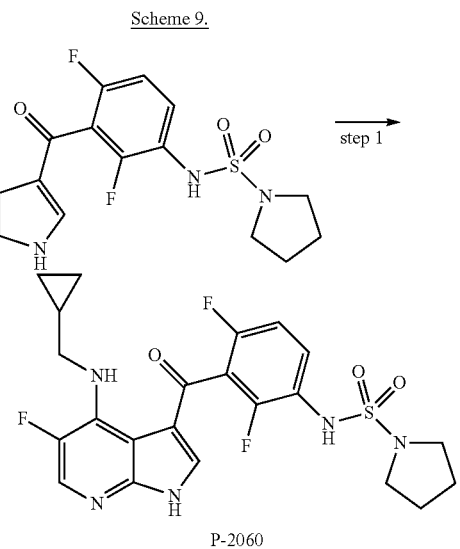

Scheme 9.

Step 1. Starting material prepared according to PCT publication No. WO/2011/025927, which is incorporated herein by reference in its entirety for all purposes.

The following compounds were prepared according to the synthetic protocol set forth in Scheme 8.

Step 1. N-[3-[4-(cyclopropylmethylamino)-5-fluoro-1H-pyrrolo[2,3-b]pyridine-3-carbonyl]-2,4-difluoro-phenyl]pyrrolidine-1-sulfonamide. To N-[2,4-difluoro-3-(5-fluoro-4-iodo-1H-pyrrolo[2,3-b]pyridine-3-carbonyl)phenyl]pyrrolidine-1-sulfonamide (95 mg, 0.17 mmol) in isopropyl

| Compound No. | Name | MH(+) |
|---|---|---|
| P-2001 | methyl N-[(1S)-2-[[4-[4-[5-chloro-2-fluoro-3-(pyrrolidin-1-ylsulfonylamino)phenyl]-1-isopropyl-pyrazol-3-yl]pyrimidin-2-yl]amino]-1-methyl-ethyl]carbamate | 409.9 |
| P-2002 | methyl N-[(1S)-2-[[4-[4-[5-chloro-2-fluoro-3-[[(3R)-3-fluoropyrrolidin-1-yl]sulfonylamino]phenyl]-1-isopropyl-pyrazol-3-yl]pyrimidin-2-yl]amino]-1-methyl-ethyl]carbamate | 411.1 |
| P-2003 | methyl N-[(1S)-2-[[4-[4-[5-chloro-2-fluoro-3-[[(3S)-3-fluoropyrrolidin-1-yl]sulfonylamino]phenyl]-1-isopropyl-pyrazol-3-yl]pyrimidin-2-yl]amino]-1-methyl-ethyl]carbamate | 437.1 |
| P-2004 | methyl N-[(1S)-2-[[4-[4-[3-(azetidin-1-ylsulfonylamino)-5-chloro-2-fluoro-phenyl]-1-isopropyl-pyrazol-3-yl]pyrimidin-2-yl]amino]-1-methyl-ethyl]carbamate | 439.1 |
| P-2005 | methyl N-[(1S)-2-[[4-[4-[5-chloro-3-[[ethyl(methyl)sulfamoyl]amino]-2-fluoro-phenyl]-1-isopropyl-pyrazol-3-yl]pyrimidin-2-yl]amino]-1-methyl-ethyl]carbamate | 449.9 |
| P-2006 | methyl N-[(1S)-2-[[4-[4-[5-chloro-3-(diethylsulfamoylamino)-2-fluoro-phenyl]-1-isopropyl-pyrazol-3-yl]pyrimidin-2-yl]amino]-1-methyl-ethyl]carbamate | 423.9 |
| P-2007 | methyl N-[(1S)-2-[[4-[4-[5-chloro-3-(dimethylsulfamoylamino)-2-fluoro-phenyl]-1-isopropyl-pyrazol-3-yl]pyrimidin-2-yl]amino]-1-methyl-ethyl]carbamate | 415.1 |
| P-2008 | methyl N-[(1S)-2-[[4-[4-[5-chloro-3-(cyclohexylsulfonylamino)-2-fluoro-phenyl]-1-isopropyl-pyrazol-3-yl]pyrimidin-2-yl]amino]-1-methyl-ethyl]carbamate | 425.9 |
| P-2009 | methyl N-[(1S)-2-[[4-[4-[5-chloro-3-(cyclopentylsulfonylamino)-2-fluoro-phenyl]-1-isopropyl-pyrazol-3-yl]pyrimidin-2-yl]amino]-1-methyl-ethyl]carbamate | 437.9 |
| P-2010 | methyl N-[(1S)-2-[[4-[4-[5-chloro-3-(cyclobutylsulfonylamino)-2-fluoro-phenyl]-1-isopropyl-pyrazol-3-yl]pyrimidin-2-yl]amino]-1-methyl-ethyl]carbamate | 421.9 |
| P-2011 | methyl N-[(1S)-2-[[4-[4-[5-chloro-3-(cyclopropylsulfonylamino)-2-fluoro-phenyl]-1-isopropyl-pyrazol-3-yl]pyrimidin-2-yl]amino]-1-methyl-ethyl]carbamate | 443.1 | alcohol (2 ml) was added cyclopropylmethanamine (49.11 mg, 0.69 mmol). The resulting solution was stirred at 90° C. overnight. The reaction mixture was concentrated under vacuum and purified by silica gel flash chromatography eluting with EtOAc/Hexane (0-65% gradient). Fractions containing desired product were pooled and the product was further purified by preparative HPLC. The pure fractions were combined to provide 6.5 mg N-[3-[4-(cyclopropylmethylamino)-5-fluoro-1H-pyrrolo[2,3-b]pyridine-3-carbonyl]-2,4-difluoro-phenyl]pyrrolidine-1-sulfonamide. MS (ESI) $[M+H]^+=494.4$.

Compounds of formula (I') or (I) or a compound of any of the subgeneric formulas of formula (I), for example, formulas (Ia), (Ia-1), (Ia-2), (Ib), (Ib-1), (Ib-2), (Ib-1a), (Ib-1b), (Ic), (Ic-1), (Ic-1a), (Ic-2), (Ic-2a), (Id), (Id-1), (Id-1a), (Id-2), (Id-2a), (Ie), (Ie-1), (Ie-1a), (Ie-2), (Ie-2a), (If), (If-1), (If-2), (If-3), (If-4), (Ig), (Ig-1), (Ig-2), (Ig-3), (Ig-4), (Ih), (Ih-1), (Ih-2), (Ih-3), (Ih-4), (Ij), (Ij-1) or (Ij-2), or any of the compounds as described herein can be prepared according to the protocols set forth in Examples 1-12. For example, compounds listed in Tables 1 and 2, such as compounds P-2001 to P-2183 were prepared according to the protocols set forth in Examples 1 to 12. The $^1$H NMR and mass spectroscopy data were consistent with the structures of the compounds.

Example 13: Compound Properties

While the inhibitory activity of the compounds on any Raf kinase is important to their activity in treating of disease, the compounds described herein show favorable properties that provide advantages as a pharmaceutical as well.

Assays for biochemical and cell based activity are known in the art, for example, as described in PCT publication WO 2007/002433, the disclosure of which is hereby incorporated by reference as it relates to such assays. For example, the biochemical activity $IC_{50}$ values are determined with respect to inhibition of BRAF V600E kinase activity or p-Erk kinase activity, where inhibition of phosphorylation of a peptide substrate is measured as a function of compound concentration. Compounds to be tested are diluted in dimethyl sulfoxide to a concentration of 0.1 mM. These are serially diluted 15 μL into 30 μL of dimethyl sulfoxide seven times in 96 well plates for a total of 8 dilution points, and for each dilution point 1 μL is added to a well of an assay plate. Plates are prepared such that each well in a 384 well plate contains 1 μL of compound in 10 μL volume with 0.1 nanograms Raf enzyme (i.e. any of BRAF, c-Raf-1 or BRAF V600E, Upstate Biotechnology or prepared by methods known to one of skill in the art), 50 mM HEPES, pH 7.0, 50 mM NaCl, 2 mM $MgCl_2$, 1 mM $MnCl_2$, 0.01% Tween-20, 1 mM DTT, and 100 nM biotin-MEK1 as substrate. The reaction is started with addition of 10 μL of 200 μM ATP (i.e. final 100 μM ATP). After incubation of the kinase reaction for 45 minutes at room temperature, 5 μL/well of Stop Solution is added (25 mM Hepes pH 7.5, 100 mM EDTA, 0.01% BSA with donor beads (Streptavidin coated beads, Perkin Elmer), acceptor beads (Protein A coated, Perkin Elmer), and anti-phosphor MEK1/2 antibody (CellSignal), each at final concentration 10 μg/mL). The plates are incubated for 3 hours at room temperature and read on Envision reader (Perkin Elmer). Phosphorylation of Mek1 results in binding of the anti-phosphor-MEK1/2antibody and association of the donor and acceptor beads such that signal correlates with kinase activity. The signal versus compound concentration is used to determine the $IC_{50}$.

Compounds are assessed in a variety of cell based assays. For example human cell lines with BRAF V600E mutation (A375 melanoma, SKMEL3 melanoma, and COLO205 colon adenocarcinoma), as well as tumorigenic cell lines with wild-type BRAF (SW620 colon adenocarcinoma) or with Ras mutations (SKMEL2 melanoma and IPC298 melanoma). Similar assays may be used to assess additional tumorigenic cell lines with Ras mutations, including, but not limited to, M202, M207, M243, M244, M296, 5117, HCT116, HCT15, DLD1, MiaPaCa, A549, NCI-H23, NCI-H460, HOP62, MDA-MB231, Hs-578T, HL60, MOLT-4, and CCRF-CEM.

On day 1, cells are counted, then centrifuged in a conical tube for 5 minutes at 1000 rpm. The supernatant is removed and cells are re-suspended as follows:

SW620 (ATCC catalog # CCL-27): resuspended in Leibovitz's L-15 medium, 2 mM L-glutamine, 10% fetal bovine serum to $6 \times 10^4$ cells/mL.

A375 (ATCC catalog # CRL-1619): resuspend in Dulbecco's modified Eagle's medium, 4 mM L-glutamine, 4.5 g/L D-glucose, 10% fetal bovine serum to $6 \times 10^4$ cells/mL.

COLO205 (ATCC catalog # CCL-222): resuspend in RPMI 1640, 2 mM L-glutamine, 1.5 g/L sodium bicarbonate, 4.5 g/L D-glucose, 10 mM HEPES, 1.0 mM sodium pyruvate, 10% fetal bovine serum to $6 \times 10^4$ cells/mL.

SKMEL2 (ATCC catalog # HTB-68): resuspend in Minimum Eagle essential medium, 2 mM L-glutamine, 1.5 g/L sodium bicarbonate, 0.1 mM non-essential amino acids, 1.0 mM sodium pyruvate, 10% fetal bovine serum to $6 \times 10^4$ cells/mL.

SKMEL3 (ATCC catalog # HTB-69): resuspend in McCoy's 5A medium, 1.5 mM L-glutamine, 15% fetal bovine serum to $6 \times 10^4$ cells/mL.

IPC298 (DSMZ catalog # ACC 251): resuspend in RPMI 1640, 2 mM L-glutamine, 10% fetal bovine serum to $6 \times 10^4$ cells/mL.

The cells are plated, 50 μL in each well of a 96-well dish (Corning 3610) and incubated at 37° C. in 5% $CO_2$ overnight, cells plated to a final concentration of cells as follows:
SW620: 5,000 cells per well.
A375: 2,000 cells per well.
COLO205: 2,000 cells per well.
SKMEL2: 2,000 cells per well.
SKMEL3: 3,000 cells per well.
IPC298: 2,000 cells per well.

On day 2, compound at a maximum concentration of 5 mM is serially diluted 1:3 (e.g. 10 μL with 30 μL dimethyl sulfoxide) for a total of 8 point titration with DMSO as a control. A 1 μL aliquot of each dilution point and control is added to 249 μL growth media and 50 μL is added to a well containing cells, providing 10 μM compound at the maximum concentration point. The cells are incubated for 3 days at 37° C. in 5% $CO_2$.

On day 5, ATPlite 1 step Luminescence Assay System (Perkin Elmer #6016739) is brought to room temperature along with the cell cultures. ATPlite is added 25 μL to each well, shake for 2 minutes, and the cells are incubated at room temperature for 10 minutes, then luminescence is read on Safire reader. The measured luminescence correlates directly with cell number, such that the reading as a function of compound concentration is used to determine the $IC_{50}$ value.

B9 is a squamous cell carcinoma cell line expressing activated HRAS that was isolated from a DMBA/TPA-induced mouse model of skin carcinogenesis (Stoler, et al. *The Journal of Cell Biology*, 1993, 122(5), 1103-17). IPC- 298 is a human melanoma cell line that expresses activated NRAS (Aubert, et al. *International Journal of Cancer*, 1993, 54(5), 784-92). To determine whether compounds induce phosphorylated ERK and MEK, cells are plated in a 96-well dish and treated with an 8-point titration of compound for one hour at 37° C. The media is then removed and the cells are incubated with lysis buffer containing protease and phosphatase inhibitors. Phosphorylated ERK and MEK in the resulting lysates is detected using AlphaScreen™ technology. To detect phosphorylated ERK, cell lysates are incubated with streptavidin-coated donor beads, anti-mouse IgG acceptor beads, a biotinylated anti-ERK1/2 rabbit antibody, and a mouse antibody that recognizes ERK1/2 only when it is phosphorylated on Thr202 and Tyr204. The biotinylated ERK1/2 antibody will bind to both the streptavidin-coated donor beads and to ERK1/2 (regardless of its phosphorylation state), and the phospho-ERK1/2 antibody will bind to the acceptor beads and to ERK1/2 that is phosphorylated at Thr202/Tyr204. Excitation of the beads with laser light at 680 nm produces singlet oxygen, which is rapidly quenched unless the beads are in close proximity. When ERK is phosphorylated, both antibodies can bind the same protein, bringing the donor and acceptor beads into close proximity, producing a signal that can be measured at 580 nm. MEK phosphorylation is detected using a similar approach, only with antibodies directed against total MEK1/2 and MEK1/2 that is phosphorylated at Ser217 and Ser221.

The assay data for the compounds in Tables 1 and 2 has been disclosed in PCT patent publication No. WO 2012/109075, which is incorporated herein by reference in its entirety for all purposes.

The following table provides data indicating the BRAF V600E biochemical inhibitory activity, B9 and IPC-298_P-ERK cell activation activity, A375_P-ERK cell growth inhibitory activity for exemplary compounds as described herein. In the table below, inhibitory activity in the BRAF mutant assays is provided as follows: +++=0.0001 $\mu M < IC_{50} < 1$ $\mu M$; ++=1 $\mu M < IC_{50} < 10$ $\mu M$; +=10 $\mu M < IC_{50}$.

| Compound number | Biochemical activity (IC$_{50}$ μM) V600E | Cell activity (EC$_{50}$ μM) IPC-298_P-ERK | B9_pERK | Cell activity (IC$_{50}$ μM) A375 |
|---|---|---|---|---|
| P-2001 | +++ | >10 | >10 | + |
| P-2002 | +++ | >10 | >10 | +++ |
| P-2003 | +++ | >10 | >10 | +++ |
| P-2004 | ++ | >10 | >10 | + |
| P-2005 | +++ | >10 | >10 | ++ |
| P-2006 | +++ | >10 | >10 | +++ |
| P-2007 | +++ | >10 | >10 | +++ |
| P-2008 | +++ | >10 | >10 | +++ |
| P-2009 | +++ | >10 | >10 | ++ |
| P-2010 | +++ | >10 | >10 | ++ |
| P-2011 | +++ | >10 | >10 | ++ |
| P-2012 | +++ | >10 | >10 | ++ |
| P-2013 | +++ | | | +++ |
| P-2014 | +++ | >10 | >10 | +++ |
| P-2015 | +++ | >10 | >10 | + |
| P-2016 | +++ | >10 | >10 | +++ |
| P-2017 | +++ | >10 | >10 | +++ |
| P-2018 | +++ | >10 | >10 | + |
| P-2019 | +++ | >10 | >10 | +++ |
| P-2020 | +++ | >10 | >10 | +++ |
| P-2021 | +++ | >10 | >10 | + |
| P-2022 | +++ | >10 | >10 | +++ |
| P-2023 | +++ | >10 | >10 | ++ |
| P-2024 | +++ | >10 | >10 | +++ |
| P-2025 | +++ | >10 | >10 | +++ |
| P-2026 | ++ | >10 | >10 | + |
| P-2027 | +++ | >10 | >10 | +++ |
| P-2028 | +++ | >10 | >10 | + |
| P-2029 | +++ | >10 | >10 | +++ |
| P-2030 | ++ | >10 | >10 | ++ |
| P-2031 | ++ | >10 | >10 | + |
| P-2032 | +++ | >10 | >10 | +++ |
| P-2033 | +++ | >10 | >10 | + |
| P-2034 | +++ | >10 | >10 | ++ |
| P-2035 | +++ | >10 | >10 | ++ |
| P-2036 | ++ | >10 | >10 | ++ |
| P-2037 | +++ | >10 | >10 | +++ |
| P-2038 | +++ | >10 | >10 | +++ |
| P-2039 | +++ | >10 | >10 | +++ |
| P-2040 | +++ | >10 | >10 | +++ |
| P-2042 | +++ | >10 | >10 | +++ |
| P-2043 | ++ | >10 | >10 | ++ |
| P-2044 | +++ | >10 | >10 | +++ |
| P-2045 | +++ | >10 | >10 | +++ |
| P-2047 | +++ | | | +++ |
| P-2048 | +++ | >10 | | +++ |
| P-2049 | +++ | >10 | >10 | +++ |
| P-2051 | +++ | | | +++ |
| P-2052 | +++ | >10 | >10 | +++ |
| P-2054 | +++ | >10 | >10 | +++ |
| P-2056 | +++ | >10 | >10 | +++ |
| P-2057 | +++ | >10 | >10 | +++ |
| P-2058 | +++ | >10 | >10 | +++ |
| P-2061 | +++ | >10 | >10 | +++ |
| P-2062 | +++ | >10 | >10 | +++ |
| P-2063 | +++ | >10 | >10 | +++ |
| P-2064 | +++ | >10 | >10 | +++ |
| P-2065 | +++ | >10 | >10 | +++ |
| P-2066 | +++ | >10 | >10 | +++ |
| P-2067 | +++ | >10 | >10 | +++ |
| P-2068 | +++ | >10 | >10 | +++ |
| P-2069 | +++ | >10 | >10 | +++ |
| P-2070 | +++ | >10 | >10 | +++ |
| P-2071 | +++ | >10 | >10 | +++ |
| P-2072 | +++ | >10 | >10 | +++ |
| P-2073 | +++ | >10 | >10 | +++ |
| P-2074 | +++ | >10 | >10 | +++ |
| P-2075 | +++ | >10 | >10 | +++ |
| P-2076 | +++ | >10 | >10 | +++ |
| P-2077 | +++ | >10 | | +++ |
| P-2078 | +++ | >10 | >10 | +++ |
| P-2079 | +++ | >10 | >10 | +++ |
| P-2080 | +++ | >10 | >10 | +++ |
| P-2081 | +++ | >10 | >10 | +++ |
| P-2082 | +++ | >10 | >10 | +++ |
| P-2083 | +++ | >10 | >10 | +++ |
| P-2084 | +++ | >10 | >10 | +++ |
| P-2085 | ++ | >10 | >10 | +++ |
| P-2086 | +++ | >10 | >10 | +++ |
| P-2087 | +++ | >10 | >10 | ++ |
| P-2088 | +++ | >10 | >10 | +++ |
| P-2089 | +++ | >1 | >1 | +++ |
| P-2090 | +++ | >10 | >10 | +++ |
| P-2091 | +++ | >10 | >10 | +++ |
| P-2092 | +++ | >10 | >10 | +++ |
| P-2093 | +++ | >1 | >1 | +++ |
| P-2094 | +++ | >10 | >10 | +++ |
| P-2095 | | >10 | >10 | +++ |
| P-2096 | +++ | >10 | >10 | + |
| P-2097 | ++ | >10 | >10 | + |
| P-2098 | +++ | >10 | >10 | +++ |
| P-2099 | +++ | >10 | >10 | +++ |
| P-2100 | +++ | >10 | >10 | +++ |
| P-2101 | +++ | >10 | >10 | +++ |
| P-2102 | +++ | >10 | >10 | ++ |
| P-2103 | +++ | >10 | >10 | +++ |
| P-2104 | +++ | >10 | >10 | +++ |
| P-2105 | +++ | >10 | >10 | +++ |

-continued

| Compound number | Biochemical activity (IC$_{50}$ µM) V600E | Cell activity (EC$_{50}$ µM) IPC-298_P-ERK | B9_pERK | Cell activity (IC$_{50}$ µM) A375 |
|---|---|---|---|---|
| P-2106 | +++ | >10 | >10 | +++ |
| P-2107 | +++ | >10 | >10 | ++ |
| P-2108 | +++ | >10 | >10 | +++ |
| P-2109 | +++ | >10 | >10 | ++ |
| P-2110 | +++ | >10 | >10 | +++ |
| P-2111 | +++ | >10 | >10 | +++ |
| P-2112 | +++ | >10 | | +++ |
| P-2113 | +++ | >10 | >10 | +++ |
| P-2115 | +++ | >10 | >10 | +++ |
| P-2116 | +++ | >10 | >10 | +++ |
| P-2117 | +++ | >10 | >10 | +++ |
| P-2118 | +++ | >10 | >10 | +++ |
| P-2119 | +++ | >10 | >10 | +++ |
| P-2120 | +++ | >10 | >10 | ++ |
| P-2121 | +++ | >10 | >10 | +++ |
| P-2122 | +++ | >10 | >10 | +++ |
| P-2123 | +++ | >10 | >10 | +++ |
| P-2124 | +++ | >1 | >10 | +++ |
| P-2125 | +++ | >1 | >10 | +++ |
| P-2126 | +++ | | >10 | +++ |
| P-2127 | +++ | >10 | >10 | + |
| P-2129 | +++ | +++ | +++ | +++ |
| P-2130 | +++ | +++ | +++ | +++ |
| P-2138 | +++ | | >10 | +++ |
| P-2152 | +++ | +++ | | +++ |
| P-2153 | +++ | +++ | +++ | +++ |
| P-2160 | +++ | +++ | | +++ |
| P-2161 | +++ | >10 | +++ | +++ |
| P-2163 | ++ | >10 | >10 | ++ |
| P-2164 | +++ | >10 | | +++ |
| P-2165 | +++ | >10 | >10 | +++ |
| P-2166 | +++ | >10 | +++ | +++ |
| P-2169 | +++ | +++ | +++ | +++ |
| P-2170 | +++ | +++ | +++ | +++ |
| P-2171 | +++ | >1 | >10 | +++ |
| P-2172 | +++ | >10 | >1 | +++ |
| P-2173 | +++ | >1 | >10 | +++ |
| P-2174 | +++ | >10 | >10 | +++ |
| P-2175 | +++ | >10 | | +++ |
| P-2176 | +++ | >10 | >10 | +++ |
| P-2177 | +++ | >10 | >10 | +++ |
| P-2178 | +++ | >10 | >10 | ++ |
| P-2179 | ++ | >10 | >10 | + |
| P-2180 | +++ | >10 | >10 | ++++ |
| P-2181 | +++ | +++ | >10 | +++ |
| P-2182 | +++ | >10 | >10 | |
| P-2183 | +++ | >10 | >10 | |

Biochemical Assays and Kinome Selectivity Profiling.

As described herein, compound A is a compound of formula (I). For example, compound A is a compound set forth in Tables 1 and 2.

The in vitro RAF kinase activities were determined by measuring phosphorylation of a biotinylated substrate peptide as described previously (Tsai, J. et al. *Proc Natl Acad Sci USA* 105, 3041-3046 (2008)). Compounds of formula (I), e.g., compound A, was also tested against a panel of 287 kinases at concentrations of 1 µM in duplicate. Kinases inhibited by over 50% were followed up by IC$_{50}$ determination. The 287 kinases represent all major branches of the kinome phylogenetic tree. The inhibition screen of 287 kinases was carried out under contract as complementary panels at Invitrogen (Life Technologies, WI, USA) SelectScreen™ profiling service, DiscoverX (CA, USA) KINOMEScan™ service, and Reaction Biology Corporation (PA, USA) Kinase HotSpot™ service.

Cell Culture, pERK Assay, Growth Inhibition Assay, and Phototoxicity Assay

The B9 cell line was a gift from Allan Balmain (University of California, San Francisco, Calif., USA). The IPC-298 cell line was purchased from DSMZ (Braunschweig, Germany). The SK-MEL-239 and KS-MEL-239 cell lines were kindly provided by Neal Rosen (Memorial Sloan-Kettering Cancer Center, New York, N.Y., USA). All other cell lines were purchased from ATCC.

Phospho-ERK AlphaScreen® assay. To determine the effects of compound treatment upon phosphorylation of ERK1/2, cells were plated in a 96-well dish and treated with an 8-point titration of compound for one hour at 37° C. before lysis. To detect pERK, cell lysates were incubated with streptavidin-coated AlphaScreen® donor beads, anti-mouse IgG AlphaScreen® acceptor beads, a biotinylated anti-ERK1/2 rabbit antibody, and a mouse antibody that recognizes ERK1/2 only when it is phosphorylated on Thr202 and Tyr204. The biotinylated ERK1/2 antibody binds to both the streptavidin-coated AlphaScreen® donor beads and to ERK1/2 (regardless of its phosphorylation state), and the phospho-ERK1/2 antibody binds to the acceptor beads and to ERK1/2 that is phosphorylated at Thr202/Tyr204. An increase in ERK1/2 phosphorylation at Thr202/Tyr204 brings the donor and acceptor AlphaScreen® beads into close proximity, generating a signal that can be quantified on an EnVision reader (Perkin Elmer).

Phospho-ERK immunoblot analysis. Western blots were performed by standard techniques and analyzed on an Odyssey Infrared Scanner (Li-COR Biosciences). The following antibodies were used: pERK1/2 (T202/Y204) and ERK1/2 (Cell Signaling).

Growth inhibition assay. Cells were plated into a 96-well plate at a density of 3000 cells per well and allowed to adhere overnight. Compounds were dissolved in DMSO, diluted 3-fold to create an 8-point titration, and added to cells. After a 72 h incubation, cell viability was examined using CellTiter-Glo® (Promega). Data presented represent the average of at least three independent experiments.

Anchorage-independent growth assay. $2.5 \times 10^4$ B9 cells were plated in each well of a six-well plate with a bottom layer of 1% and a top layer of 0.4% low melting agar (Sigma A4018, Dallas, Tex.) containing RPMI1640 medium with 10% FBS. For RAF inhibitor study, B9 cells grown in soft agar were treated with vemurafenib, compound P-1000 or compound A at indicated concentration or dimethyl sulfoxide (DMSO) for 3 weeks. For EGFR ligand study, B9 cells grown in soft agar were treated with AREG (R&D systems 989-AR, Minneapolis, Minn.), TGFα (R&D systems 239-A, Minneapolis, Minn.) or HB-EGF (R&D systems 259-HE, Minneapolis, Minn.) at the indicated concentrations for 3 weeks. For vemurafenib and erlotinib combination study, B9 cells grown in soft agar were treated with vemurafenib, erlotinib or a combination of the two compounds at the indicated concentrations or DMSO for 3 weeks. Anchorage-independent colonies ≥100 µm were scored using AxioVision Rel 4.8 software (CarlZeiss, Wake Forest, N.C.).

B9 cells grown in soft agar were treated with AREG, TGFα or HBEGF at the indicated concentrations for 3 weeks. Anchorage-independent colonies ≥100 µm were scored. B9 cells grown in soft agar were treated with vemurafenib or a combination of vemurafenib and erlotinib at the indicated concentrations for 3 weeks. Anchorage-independent colonies ≥100 µm were scored.

Phototoxicity assay. The NIH 3T3 phototoxicity assay was developed based on Organization for Economic Co-operation and Development test guidelines No. 432 (OECD Guidelines for the Testing of Chemicals/Test No. 432: In Vitro 3T3 NRU Phototoxicity Test, 2004) with minor modifications. Two collagen-coated 96-well plates with $10^4$ NIH 3T3 cells per well in DMEM with 10% calf serum were pre-incubated with eight different concentrations of the test chemical for 1 hour. Thereafter one of the two plates (+UV) is exposed to the non-cytotoxic UVA irradiation dose (1.7 mW/cm2=5 J/cm2) through the lid for 50 minutes whereas the other plate is kept in the dark. Cytotoxicity in this test is expressed as a concentration-dependent reduction of the uptake of the Vital dye Neutral Red (NR) when measured 24 hours after treatment with the test chemical and irradiation. To predict the phototoxic potential, the concentration responses obtained in the presence and in the absence of irradiation are compared at the $IC_{50}$ level, i.e., the concentration reducing cell viability to 50% compared to the untreated controls.

Microarray Gene Expression Analysis

B9 cells were plated in DMSO control or 1 µM of vemurafenib or compound A and incubated for 16 hours. Cells were harvested, total RNA was isolated (RNeasy Mini Kit, Qiagen), and gene expression was measured using Affymetrix Mouse420_2 chips (Santa Clara, Calif.) following the manufacturer's instructions. Vemurafenib response genes were identified by requiring the ratio between the treated and vehicle control samples be more than 1.9 (up-regulated) or less than 0.54 (downregulated).

Western Blot (EGFR Ligand Assay)

$2 \times 10^4$ B9 cells were plated in each well of a 96-well plate and treated with DMSO control or compounds at indicated concentration for 48 hours. Cell supernatants were collected and cells were lysed using 1× cell lysis buffer (CST 9803, Beverly, Mass.). The amount of AREG, TGFα and HB-EGF in cell supernatants or cell lysates were determined with the use of ELISA Development kits (R&D systems DY989, DY239 and 259-HE-050, Minneapolis, Minn.) according to the manufacturer's instructions.

RAF Dimerization Assays

Immunoprecipitation-Western blot assay. Cells were plated on 15-cm dishes and allowed to adhere overnight at 37° C. Cells were treated with compound or DMSO for one hour at 37° C. prior to lysis in RIPA buffer containing protease and phosphatase inhibitors. The lysates were clarified by centrifugation and equal amounts were immunoprecipitated with antibodies for either BRAF (Santa Cruz) or CRAF (BD Biosciences) overnight at 4° C. The immunoprecipitated complexes were separated by SDS-PAGE and transferred to PVDF. Western blots were performed with BRAF and CRAF antibodies, as noted, and were visualized on a LI-COR Odyssey imaging system.

AlphaScreen assay using recombinant kinase domains. Recombinant human Braf protein with N-terminal GST-Tag and C-terminal His-tag (GST-BRAF-His, residues 432-727), recombinant human RAF1 protein with N-terminal His-tag (His-RAF1, residues 325-648) or recombinant human RAF1 protein with N-terminal GST tag and C-terminal His-tag (GST-RAF1-His, residues 325-648) were expressed in Sf9 insect cells via a baculovirus expression system as previously described (Ref). His-RAF1 protein was in vitro biotinylated. BRAF-RAF1 and RAF1-RAF1 interaction was measured quantitatively using Alpha technology.

Tumor Xenograft Studies

All animal studies were conducted in accordance with the Institute for Laboratory Animal Research Guide for the Care and Use of Laboratory Animals and the USDA Animal Welfare Act. The same formulation was used for both COLO205 and B9 xenograft studies. The powder of test compound was dissolved in pure N-methyl-2-pyrrolidone (NMP). Diluent consists of PEG400: TPGS:Poloxamer 407: Water (40:5:5:50). Before gavage administration, fresh stock of NMP compound solution (or NMP for vehicle) was thoroughly mixed with the diluents to make a uniform suspension. Dosing volume is 5 µl/g. On the last day of the efficacy study, blood samples were collected at 0, 2, 4, and 8 hrs after last dosing, 2 animals/time point, for PK analysis.

COLO205 tumor cells were cultured in Dulbecco's Modified Eagle's Medium supplemented with 10% FBS, bovine insulin, 100 U/ml penicillin and 100 g/ml streptomycin at 37° C. BALB/C nude mice, female, 6-8 weeks old, weighing approximately 18-22 g, were inoculated subcutaneously at the right flank with COLO205 tumor cells ($5 \times 10^6$) in 0.1 ml of PBS mixed with matrigel (50:50) for tumor development. The treatment was started when mean tumor size reached approximately 100 $mm^3$, with eight mice in each treatment group randomized to balance the average weight and tumor size. Thereafter tumor sizes were measured twice weekly.

B9 cells were expanded in DMEM 10% FBS 1% Penicillin/Streptomycin. Upon trypsinization the cells were washed three times with 20 ml RPMI and after the final centrifugation re-suspended, counted and adjusted by volume to a final concentration of $5 \times 10^7$ cells/mL. B9 xenografts were started by injection of $5 \times 10^6$ cells subcutaneously in 6-7 week old female nude BALB/c mice Animals were fed a standard rodent diet and water was supplied ad libitum. Tumor measurements were taken with an electronic microcaliper three times weekly. Also body weights were recorded at these times. Compound dosing started when the average size of tumors reached 50-70 $mm^3$. Animals were equally distributed over treatment groups (n=10) to balance the average tumor size Animals were dosed orally for day 1-14 twice daily and day 15-28 once daily with vehicle, vemurafenib 50 mg/kg or Compound A 50 mg/kg. TPA was put twice a week on the skin of all mice during weeks 3 and 4 at a dose of 2 µg in 200 µl acetone.

Crystallization and Structure Determination

Expression and purification of BRAF and $BRAF^{V600E}$ were carried out as previously described (Tsai, J. et al. *Proc Natl Acad Sci USA* 105, 3041-3046 (2008)). Crystallization drops were prepared by mixing the protein solution with 1 mM of compound and the same amount of reservoir, and drops were incubated by vapor diffusion (sitting drops) at 4° C. The mother liquor used to obtain co-crystals of compound A, dabrafenib and compound P-0352 with $BRAF^{V600E}$ consists of 0.1 M BisTris at pH 6.0, 12.5% 2,5-hexabediol, 12% PEG3350. All co-crystals were flash-frozen with liquid nitrogen, but $BRAF^{V600E}$ co-crystals were soaked in a solution containing the mother liquor plus 20% glycerol, prior to flash-freezing. X-ray diffraction data were collected at beamline 8.3.1 at the Advanced Light Source (Lawrence Berkeley Laboratory, CA, USA) and beamline 9.1 at Stanford Synchrotron Radiation Lightsource (Stanford University, CA USA). Data were processed and scaled using MOSFLM (Powell, H. R. *Acta Crystallogr D Biol Crystallogr* 55, 1690-1695 (1999)) and SCALA in the CCP4 package (Winn, M. D. et al. *Acta Crystallogr D Biol Crystallogr* 67, 235-242 (2011)). All co-structures were solved using molecular replacement with the program MOL-REP (Vagin, A. et al. *Acta Crystallogr D Biol Crystallogr* 66, 22-25 (2010)). The starting models used for are the inhibitor bound $BRAF^{V600E}$ and $BRAF^{WT}$, respectively (Protein Data Bank accession codes 4FK3, 1UWJ). The final models were obtained after several rounds of manual rebuilding and refinement with PHENIX (Adams, P. D. et al. *Acta Crystallogr D Biol Crystallogr* 66, 213-221 (2010)) and REFMAC (Murshudov, G. N. et al. *Acta Crystallogr D Biol Crystallogr* 53, 240-255 (1997)). A summary of the crystallography statistics is included in Table 5.

TABLE 3

Kinase inhibitory activity of compound A versus a panel of kinases[a] (% inhibition at single concentration at 1 μM and $IC_{50}$)

| Clan | Family | Kinase | % Inhibition | $IC_{50}$ (μM) |
|---|---|---|---|---|
| TK | SRC/Other | PTK6_(Brk) | 98.5 | 0.061 |
| TK | SRC/Other | SRMS_(Srm) | 98.5 | <0.039 |
| TKL | RIPK-LRRK | RIPK2 | 96.4 | 0.023 |
| TK | SRC/Fyn | FGR | 94 | <0.039 |
| TKL | RIPK-LRRK | RIPK3 | 86 | ND |
| TK | SRC/Fyn | YES1 | 83 | 0.0495 |
| TKL | RAF | BRAF | 83 | 0.14 |
| TKL | MLK-ZAK | ZAK | 81 | 0.062 |
| TK | SRC/Lyn | LCK | 80.5 | 0.036 |
| TKL | RAF | RAF1_(CRAF) | 80 | 0.091 |
| TK | SRC/Fyn | SRC_N1 | 78.5 | 0.052 |
| STE | MAP4K/GCK-MST | MAP4K5_(KHS1) | 69.5 | 0.41 |
| TK | SRC/Lyn | BLK | 68 | 0.32 |
| TK | CSK | CSK | 67 | 0.14 |
| TKL | LIMK-TESK | LIMK1 | 65 | 0.24 |
| TK | SRC/Lyn | LYN_B | 64.5 | 0.16 |
| TK | EGFR/ACK | ACK1 | 64 | 0.26 |
| TK | SRC/Lyn | LYN_A | 64 | 0.12 |
| Atypical | PI3K | PIK3CD/PIK3R1_(p110d/p85a) | 60.5 | 0.34 |
| Atypical | PI4K | PI4KB_(PI4K_beta) | 60 | 1.1 |
| TK | SRC/Fyn | FYN | 57.5 | 0.18 |
| TKL | TGFBR | TGFBR1_(ALK5) | 57.5 | 0.36 |
| TKL | RIPK-LRRK | RIPK5 | 57 | ND |
| Atypical | PI3K | PIK3C2A_(PI3KC2a) | 53.5 | 0.41 |
| Atypical | PI3K | PIK3C2B_(PI3KC2b) | 52.5 | 0.59 |

[a]Lists of kinases minimally affected by compound A is included below.

Kinases with <50% Inhibition at 1 μM Compound a

SRC, FRK_PTK5), WNK2, ACVR2B, HCK, MAP3K8_(COT), LIMK2, PDGFRA, AMPK_A2/B1/G1, CLK4, PRKCN_(PKD3), CHEK1_(CHK1), ACVR1_(ALK2)

Kinases with <20% Inhibition at 1 μM Compound a

MET, BMPR1A_(ALK3), CAMK2A_(CaMKII_alpha), MAP4K2_(GCK), DNA-PK, ABL2_(Arg), KDR_(VEGFR2), CDK8/cyclinC, GSK3A, EPHA5, RIPK4, PRKCB1_(PKCbeta_I), PRKC_(PKC_alpha), MARK2, PRKCQ_(PKC_theta), PIK3CA/PIK3R1_(p110a/p85a), CLK2, ABL1, EPHB2, RET, SPHK2, EPHA8, FES_(FPS), PKN1_(PRK1), CDC42_BPB_(MRCKB), SNF1LK2, NEK1, PAK7_(KIAA1264), BMX, MARK1_(MARK), NUAK1_(ARK5), CLK3, MAPK9_(JNK2), AURKB_(Aurora_B), MATK_(HYL), ERBB4_(HER4), EPHA1, PRKG1, CSNK1G2_(CK1_gamma_2), HIPK4, AXL, FLT3, TEK_(Tie2), BRSK1_(SAD1), STK16, PAK3, MUSK, PHKG1, MYLK2_(skMLCK), MAPKAPK3, CDK9/CyclinT1, SLK, TAOK2_(TAO1), IGF1R, SGK_SGK1), PRKCB2_(PKCbetaII), CDK7/CyclinH/MNAT1, MAPK8_(JNK1), MAPK12_(p38_gamma), MAPK13_(p38_delta), PLK1, TTK, STK4_(MST1), IRAK1, RIPK1

Kinases with <20% Inhibition at 1 μM Compound a

GRK4, PRKCI_(PKC_iota), CAMK2B_(CaMKIIbeta), CAMK2Q(CaMKII_delta), DYRK3, MAP2K2_(MEK2), PAK1, EPHB1, INSRR_(IRR), NTRK3_(TRKC), PDGFRB_(PDGFRbeta), AKT2_(PKBb), SGKL_(SGK3), CAMK4_(CaMKIV), GSK3B, MERTK_(cMER), FGFR1, CAMK1D_(CaMKI_delta), PRKD1_(PKC_mu), CDK2/CyclinA, SRPK1, MAPK11_(p38_beta), NEK2, NEK4, FER, FLT4_(VEGFR3), IRAK4, AKT3_(PKBg), SGK2, ADRBK1_(GRK2), RPS6KA3_(RSK2), PRKD2_(PKD2), SRPK2, STK23_(MSSK1), DYRK1A, AURKC_(Aurora_C), PIM1, MINK1, ERBB2_(HER2), PTK2_(FAK), CSF1R_(FMS), DMPK, CSNK2A1_(CK2_alpha_1), CSNK2A2_(CK2_alpha_2), PTK2B_(PYK2), FGFR2, FLT1_(VEGFR1), PRKG2_(PKG2), PRKCD_(PKC_delta), PRKCG_(PKC_gamma), RPS6KA5_(MSK1), CDK1/CyclinB, HIPK2, AURKA_(Aurora_A), TBK1, NEK6, MAP2K1_(MEK1), MAP3K2_(MEKK2), ITK, EPHA7, LTK_(TYK1), INSR, NTRK2_(TRKB), KIT, PRKCH_(PKCeta), STK25_(YSK1), MAP4K4_(HGK), EPHA3, ROS1, MAP3K10_(MLK2), RPS6KA4_(MSK2), EEF2K, CHEK2_(CHK2), DAPK3_(ZIPK), MAPK1_(ERK2), NEK9, MAP3K7_(TAK1-TAB1), BTK, JAK2_(H1_JH2, FGFR3, MELK, PRKCZ_(PKC_zeta), RPS6KA2_(RSK3), CSNK1A 1_(CK1_alpha_1), MAPK14_(p38_alpha), TXK, EPHB3, JAK1, FGFR4, AKT1_(PKBa), AMPK_A1/B1/G1, CSNK1G1_(CK1_gamma_1), CDK9/cyclinK, PAK2_(PAK65), EPHB4, DDR1, MST1R_(RON), MAPK3_(ERK1), PIK3C3_(hVPS34), CSNK1E_(CK1_epsilon), DYRK1B, MST4, LRRK2, RPS6KA1_(RSK1), MARK3, CLK1, HIPK3_(YAK1), PRKX, PHKG2, MKNK2_(MNK2), STK33, CDK5_p35, CHUK_(IKKa), EPHA2, EPHA4, GRK7, ROCK2, DCAMKL2_(DCK2), MKNK1_(MNK1), NEK7, PLK2, MAP2K3_(MEK3), TYRO3_(RSE), JAK2, JAK3, PRKCE_(PKC_epsilon), RPS6KA6_(RSK4), PIK3CG_(p110g), MAPKAPK5_(PRAK), CDK5_p25, MAPK10_(JNK3), CAMKK1, IKBKE_(IKK_epsilon), PASK, SYK, MAPKAPK2, GSG2_(Haspin), PAK4, MAP3K9_(MLK1), RPS6KB1_(p70S6K), STK17A_(DRAK1), PAK6, TEC, ZAP70, ADRBK2_(GRK3), PRKACA_(PKA), DAPK1, MLCK_(MLCK2), MYLK_(MLCK), CSNK1D_(CK1_delta), HIPK1_(Myak), MAP3K3_(MEKK3), MAP3K14_(NIK), TAOK3_(JIK), EGFR_(ErbB1), DDR2, MAP3K11_(MLK3), ROCK1, FRAP1_(mTOR), MARK4, STK22B_(TSSK2), STK22D_(TSSK1), CSNK1G3_(CK1_gamma_3), PDK1, DYRK4, CAMKK2, CDC42_BPA_(MRCKA), NLK, PLK3, WEE1, STK3_(MST2), MAP3K5_(ASK1), IKBKB_(IKK_beta), PI4KA_(PI4K_alpha), PIM2, TYK2, GRK6, STK24_(MST3), GRK5, MAP2K6_(MKK6), NTRK1_(TRKA), SPHK1, ACVR1B_(ALK4), CAMK1

TABLE 4

Affymetrix Mouse gene probes that respond to vemurafenib and/or Compound A treatments.

| | Vemurafenib | | Compound A | | | |
|---|---|---|---|---|---|---|
| Probe Set ID | Repl. 1 | Repl. 2 | Repl. 1 | Repl. 2 | Gene Symbol | Gene Title |
| 1426181_a_at | 5.52 | 4.76 | 1.35 | 1.11 | Il24 | interleukin 24 |
| 1416325_at | 5.15 | 4.39 | 1.05 | 1.27 | Crisp1 | cysteine-rich secretory protein 1 |
| 1449367_at | 4.45 | 4.68 | 1.35 | 0.99 | Trex2 | three prime repair exonuclease 2 |
| 1450241_a_at | 4.78 | 4.27 | 1.44 | 1.44 | Evi2a | ecotropic viral integration site 2a |
| 1450791_at | 4.55 | 4.39 | 1.30 | 1.31 | Nppb | natriuretic peptide precursor type B |

TABLE 4-continued

Affymetrix Mouse gene probes that respond to vemurafenib and/or Compound A treatments.

| Probe Set ID | Vemurafenib Repl. 1 | Vemurafenib Repl. 2 | Compound A Repl. 1 | Compound A Repl. 2 | Gene Symbol | Gene Title |
|---|---|---|---|---|---|---|
| 1417065_at | 4.13 | 4.50 | 1.82 | 1.33 | Egr1 | early growth response 1 |
| 1424090_at | 4.08 | 4.46 | 1.22 | 1.35 | Sdcbp2 | syndecan binding protein (syntenin) 2 |
| 1437199_at | 4.17 | 4.31 | 1.39 | 1.25 | — | — |
| 1421134_at | 4.28 | 4.16 | 1.65 | 1.47 | Areg | amphiregulin |
| 1421679_a_at | 4.27 | 4.13 | 1.42 | 1.36 | Cdkn1a | cyclin-dependent kinase inhibitor 1A (P21) |
| 1453345_at | 3.86 | 3.92 | 1.15 | 1.20 | Nipal1 | NIPA-like domain containing 1 |
| 1435331_at | 3.91 | 3.71 | 1.22 | 1.11 | Pyhin1 | pyrin and HIN domain family, member 1 |
| 1457666_s_at | 3.60 | 3.89 | 0.99 | 1.06 | Ifi202b | interferon activated gene 202B |
| 1453055_at | 3.32 | 4.08 | 1.52 | 2.15 | Sema6d | sema domain, transmembrane domain (TM), and cytoplasmic domain, (semaphorin) 6D |
| 1420450_at | 3.42 | 3.93 | 1.25 | 1.31 | Mmp10 | matrix metallopeptidase 10 |
| 1419816_s_at | 3.87 | 3.39 | 1.48 | 1.29 | Errfi1 | ERBB receptor feedback inhibitor 1 |
| 1449545_at | 3.88 | 3.38 | 0.79 | 0.81 | Fgf18 | fibroblast growth factor 18 |
| 1421551_s_at | 3.58 | 3.42 | 1.09 | 0.99 | Ifi202b | interferon activated gene 202B |
| 1436584_at | 3.28 | 3.54 | 1.75 | 1.82 | Spry2 | sprouty homolog 2 (Drosophila) |
| 1423690_s_at | 3.37 | 3.20 | 1.11 | 1.22 | Gpsm1 | G-protein signalling modulator 1 (AGS3-like, C. elegans) |
| 1422273_at | 3.30 | 3.17 | 1.52 | 1.35 | Mmp1b | matrix metallopeptidase 1b (interstitial collagenase) |
| 1448978_at | 3.21 | 3.24 | 1.25 | 1.28 | Ngef | neuronal guanine nucleotide exchange factor |
| 1416129_at | 3.31 | 3.11 | 1.36 | 1.26 | Errfi1 | ERBB receptor feedback inhibitor 1 |
| 1456321_at | 3.42 | 2.99 | 1.25 | 1.46 | Nipal1 | NIPA-like domain containing 1 |
| 1440559_at | 3.39 | 2.95 | 1.36 | 1.32 | Hmga2-ps1 | high mobility group AT-hook 2, pseudogene 1 |
| 1420352_at | 3.07 | 3.13 | 1.24 | 1.12 | Prss22 | protease, serine, 22 |
| 1426037_a_at | 3.19 | 2.93 | 1.22 | 1.05 | Rgs16 | regulator of G-protein signaling 16 |
| 1439878_at | 3.09 | 2.90 | 1.25 | 1.40 | Ivl | involucrin |
| 1418349_at | 3.29 | 2.70 | 1.23 | 1.16 | Hbegf | heparin-binding EGF-like growth factor |
| 1417130_s_at | 3.10 | 2.79 | 1.29 | 1.26 | Angptl4 | angiopoietin-like 4 |
| 1451798_at | 3.05 | 2.76 | 1.33 | 1.16 | Il1rn | interleukin 1 receptor antagonist |
| 1448562_at | 2.68 | 2.99 | 1.42 | 1.28 | Upp1 | uridine phosphorylase 1 |
| 1450430_at | 2.66 | 2.97 | 0.87 | 1.09 | Mrc1 | mannose receptor, C type 1 |
| 1429700_at | 3.18 | 2.47 | 1.29 | 0.96 | 3110040M04Rik | RIKEN cDNA 3110040M04 gene |
| 1436329_at | 2.75 | 2.77 | 1.14 | 1.33 | Egr3 | early growth response 3 |
| 1416401_at | 2.87 | 2.64 | 1.39 | 1.12 | Cd82 | CD82 antigen |
| 1450501_at | 3.02 | 2.48 | 1.13 | 1.37 | Itga2 | integrin alpha 2 |
| 1449038_at | 2.96 | 2.51 | 1.06 | 1.43 | Hsd11b1 | hydroxysteroid 11-beta dehydrogenase 1 |
| 1455104_at | 2.60 | 2.85 | 0.93 | 1.38 | Mxd1 | MAX dimerization protein 1 |
| 1449965_at | 2.83 | 2.61 | 1.23 | 1.37 | Mcpt8 | mast cell protease 8 |
| 1424638_at | 2.76 | 2.67 | 1.02 | 1.27 | Cdkn1a | cyclin-dependent kinase inhibitor 1A (P21) |
| 1419529_at | 2.84 | 2.53 | 1.45 | 1.28 | Il23a | interleukin 23, alpha subunit p19 |
| 1448532_at | 2.70 | 2.67 | 1.02 | 1.20 | Prl8a9 | prolactin family8, subfamily a, member 9 |
| 1450276_a_at | 2.73 | 2.63 | 1.14 | 1.25 | Scin | scinderin |
| 1427364_a_at | 2.73 | 2.62 | 1.33 | 1.19 | Odc1 | ornithine decarboxylase, structural 1 |
| 1421668_x_at | 2.74 | 2.60 | 1.17 | 1.40 | Speer3 | spermatogenesis associated glutamate (E)-rich protein 3 |
| 1449133_at | 2.53 | 2.78 | 0.89 | 0.73 | Sprr1a | small proline-rich protein 1A |
| 1460521_a_at | 3.03 | 2.32 | 1.30 | 1.34 | Obfc2a | oligonucleotide/oligosaccharide-binding fold containing 2A |
| 1424383_at | 2.58 | 2.69 | 1.62 | 1.45 | Tmem51 | transmembrane protein 51 |
| 1422139_at | 2.45 | 2.82 | 1.02 | 1.28 | Plau | plasminogen activator, urokinase |
| 1449268_at | 2.82 | 2.36 | 1.06 | 1.21 | Gfpt1 | glutamine fructose-6-phosphate transaminase 1 |
| 1419317_x_at | 2.53 | 2.58 | 0.99 | 0.76 | Lce3c | late cornified envelope 3C |
| 1418350_at | 2.66 | 2.46 | 1.39 | 1.30 | Hbegf | heparin-binding EGF-like growth factor |
| 1428114_at | 2.61 | 2.47 | 1.12 | 0.90 | Slc14a1 | solute carrier family 14 (urea transporter), member 1 |
| 1427527_a_at | 2.73 | 2.37 | 1.01 | 0.84 | Pthlh | parathyroid hormone-like peptide |
| 1427512_a_at | 2.61 | 2.47 | 1.12 | 1.09 | Lama3 | laminin, alpha 3 |

TABLE 4-continued

Affymetrix Mouse gene probes that respond to vemurafenib and/or Compound A treatments.

| Probe Set ID | Vemurafenib Repl. 1 | Vemurafenib Repl. 2 | Compound A Repl. 1 | Compound A Repl. 2 | Gene Symbol | Gene Title |
|---|---|---|---|---|---|---|
| 1419322_at | 2.60 | 2.45 | 1.17 | 1.12 | Fgd6 | FYVE, RhoGEF and PH domain containing 6 |
| 1419188_s_at | 2.62 | 2.36 | 1.02 | 0.81 | Ccl27a/// Gm13306 | chemokine (C-C motif) ligand 27A///predicted gene 13306 |
| 1417812_a_at | 2.60 | 2.38 | 1.10 | 1.16 | Lamb3 | laminin, beta 3 |
| 1431688_at | 2.56 | 2.41 | 1.18 | 0.95 | LOC73899 | hypothetical LOC73899 |
| 1420537_at | 2.36 | 2.58 | 1.35 | 1.22 | Kctd4 | potassium channel tetramerisation domain containing 4 |
| 1425452_s_at | 2.41 | 2.53 | 1.32 | 1.55 | Fam84a | family with sequence similarity 84, member A |
| 1422138_at | 2.73 | 2.19 | 1.10 | 1.06 | Plau | plasminogen activator, urokinase |
| 1424306_at | 2.51 | 2.35 | 1.04 | 1.09 | Elovl4 | elongation of very long chain fatty acids (FEN1/Elo2, SUR4/Elo3, yeast)-like 4 |
| 1434109_at | 2.50 | 2.33 | 1.14 | 1.01 | Sh3bgrl2 | SH3 domain binding glutamic acid-rich protein like 2 |
| 1436659_at | 2.44 | 2.37 | 1.33 | 1.42 | Dclk1 | doublecortin-like kinase 1 |
| 1426300_at | 2.35 | 2.44 | 1.39 | 1.59 | Alcam | activated leukocyte cell adhesion molecule |
| 1422222_at | 2.50 | 2.27 | 1.43 | 1.15 | Ivl | involucrin |
| 1435330_at | 2.34 | 2.38 | 1.18 | 1.16 | Pyhin1 | pyrin and HIN domain family, member 1 |
| 1450262_at | 2.62 | 2.12 | 1.47 | 1.19 | Clcf1 | cardiotrophin-like cytokine factor 1 |
| 1451308_at | 2.50 | 2.21 | 1.04 | 1.01 | Elovl4 | elongation of very long chain fatty acids (FEN1/Elo2, SUR4/Elo3, yeast)-like 4 |
| 1450976_at | 2.23 | 2.47 | 1.06 | 1.29 | Ndrg1 | N-myc downstream regulated gene 1 |
| 1456248_at | 2.26 | 2.45 | 1.40 | 1.21 | Lce3f/// LOC630971 | late cornified envelope 3F/// hypothetical protein LOC630971 |
| 1452352_at | 2.37 | 2.30 | 1.28 | 1.08 | Ctla2b | cytotoxic T lymphocyte-associated protein 2 beta |
| 1423635_at | 2.41 | 2.23 | 1.31 | 1.40 | Bmp2 | bone morphogenetic protein 2 |
| 1441315_s_at | 2.46 | 2.18 | 1.12 | 1.10 | Slc19a2 | solute carrier family 19 (thiamine transporter), member 2 |
| 1423017_a_at | 2.63 | 2.03 | 1.13 | 1.04 | Il1rn | interleukin 1 receptor antagonist |
| 1421269_at | 2.46 | 2.16 | 1.33 | 1.05 | Ugcg | UDP-glucose ceramide glucosyltransferase |
| 1417677_at | 2.18 | 2.39 | 1.37 | 1.37 | Opn3 | opsin 3 |
| 1437486_at | 2.49 | 2.08 | 1.10 | 1.50 | Gprc5a | G protein-coupled receptor, family C, group 5, member A |
| 1454254_s_at | 2.37 | 2.18 | 1.18 | 1.06 | 1600029D21Rik | RIKEN cDNA 1600029D21 gene |
| 1430700_a_at | 2.36 | 2.18 | 1.38 | 1.10 | Pla2g7 | phospholipase A2, group VII (platelet-activating factor acetylhydrolase, plasma) |
| 1416488_at | 2.23 | 2.31 | 1.29 | 1.18 | Ccng2 | cyclin G2 |
| 1452087_at | 2.20 | 2.32 | 1.27 | 1.19 | Epsti1 | epithelial stromal interaction 1 (breast) |
| 1420407_at | 2.29 | 2.24 | 1.36 | 1.13 | Ltb4r1 | leukotriene B4 receptor 1 |
| 1437092_at | 2.37 | 2.13 | 1.26 | 1.14 | Clip4 | CAP-GLY domain containing linker protein family, member 4 |
| 1427885_at | 2.20 | 2.27 | 1.18 | 1.10 | Pold4 | polymerase (DNA-directed), delta 4 |
| 1428195_at | 2.42 | 2.06 | 1.71 | 1.87 | Ahcyl2 | S-adenosylhomocysteine hydrolase-like 2 |
| 1436100_at | 2.12 | 2.35 | 1.28 | 1.21 | Sh2d5 | SH2 domain containing 5 |
| 1451501_a_at | 2.21 | 2.25 | 1.24 | 1.15 | Ghr | growth hormone receptor |
| 1431611_a_at | 2.15 | 2.31 | 1.72 | 1.35 | Cadm1 | cell adhesion molecule 1 |
| 1428419_at | 2.16 | 2.28 | 1.02 | 0.78 | 5430411K18Rik | RIKEN cDNA 5430411K18 gene |
| 1454710_at | 2.39 | 2.03 | 1.29 | 1.07 | Spink2 | serine peptidase inhibitor, Kazal type 2 |
| 1452521_a_at | 2.33 | 2.09 | 1.28 | 1.15 | Plaur | plasminogen activator, urokinase receptor |
| 1439797_at | 2.09 | 2.32 | 1.23 | 1.02 | Ppard | peroxisome proliferator activator receptor delta |
| 1422324_a_at | 2.11 | 2.28 | 1.03 | 0.94 | Pthlh | parathyroid hormone-like peptide |
| 1434059_at | 2.26 | 2.10 | 0.99 | 0.84 | B230312A22Rik | RIKEN cDNA B230312A22 gene |
| 1415936_at | 2.21 | 2.16 | 1.18 | 1.30 | Bcar3 | breast cancer anti-estrogen resistance 3 |
| 1417837_at | 2.26 | 2.11 | 1.33 | 1.08 | Phlda2 | pleckstrin homology-like domain, family A, member 2 |
| 1442350_at | 2.22 | 2.13 | 1.01 | 1.13 | — | — |

TABLE 4-continued

Affymetrix Mouse gene probes that respond to vemurafenib and/or Compound A treatments.

| Probe Set ID | Vemurafenib Repl. 1 | Vemurafenib Repl. 2 | Compound A Repl. 1 | Compound A Repl. 2 | Gene Symbol | Gene Title |
|---|---|---|---|---|---|---|
| 1435066_at | 2.04 | 2.32 | 1.29 | 1.22 | Pitpnc1 | phosphatidylinositol transfer protein, cytoplasmic 1 |
| 1435695_a_at | 2.16 | 2.19 | 1.24 | 1.18 | Ggct | gamma-glutamyl cyclotransferase |
| 1426708_at | 2.19 | 2.15 | 1.21 | 1.16 | Antxr2 | anthrax toxin receptor 2 |
| 1426806_at | 2.33 | 2.02 | 1.06 | 1.17 | Obfc2a | oligonucleotide/oligosaccharide-binding fold containing 2A |
| 1451529_at | 1.91 | 2.47 | 1.27 | 1.49 | Sgtb | small glutamine-rich tetratricopeptide repeat (TPR)-containing, beta |
| 1421279_at | 2.23 | 2.11 | 1.14 | 1.13 | Lamc2 | laminin, gamma 2 |
| 1417962_s_at | 2.19 | 2.14 | 1.14 | 1.21 | Ghr | growth hormone receptor |
| 1426972_at | 2.06 | 2.26 | 1.01 | 1.29 | Sec24d | Sec24 related gene family, member D (S. cerevisiae) |
| 1448810_at | 2.16 | 2.16 | 1.33 | 0.87 | Gne | glucosamine |
| 1428228_at | 2.18 | 2.13 | 1.34 | 1.16 | Pgm3 | phosphoglucomutase 3 |
| 1448364_at | 2.30 | 2.01 | 1.41 | 1.38 | Ccng2 | cyclin G2 |
| 1428851_at | 2.30 | 2.01 | 1.21 | 1.11 | 1300014I06Rik | RIKEN cDNA 1300014I06 gene |
| 1449125_at | 2.14 | 2.10 | 1.24 | 1.00 | Tnfaip8l1 | tumor necrosis factor, alpha-induced protein 8-like 1 |
| 1448617_at | 2.24 | 1.99 | 1.27 | 1.45 | Cd53 | CD53 antigen |
| 1417328_at | 2.20 | 2.01 | 1.19 | 0.99 | Ercc1 | excision repair cross-complementing rodent repair deficiency, complementation group 1 |
| 1450376_at | 2.20 | 2.00 | 0.94 | 0.96 | Mxi1 | Max interacting protein 1 |
| 1433909_at | 2.02 | 2.17 | 0.99 | 1.06 | Syt17 | synaptotagmin XVII |
| 1416811_s_at | 2.28 | 1.92 | 1.03 | 1.02 | Ctla2a///Ctla2b | cytotoxic T lymphocyte-associated protein 2 alpha///cytotoxic T lymphocyte-associated protein 2 beta |
| 1424022_at | 2.27 | 1.92 | 1.18 | 1.09 | Osgin1 | oxidative stress induced growth inhibitor 1 |
| 1417488_at | 2.09 | 2.05 | 1.30 | 0.93 | Fosl1 | fos-like antigen 1 |
| 1449408_at | 2.04 | 2.08 | 1.22 | 1.11 | Jam2 | junction adhesion molecule 2 |
| 1441917_s_at | 2.00 | 2.11 | 1.05 | 0.96 | Tmem40 | transmembrane protein 40 |
| 1419149_at | 2.13 | 1.99 | 1.11 | 1.01 | Serpine1 | serine (or cysteine) peptidase inhibitor, Glade E, member 1 |
| 1436917_s_at | 2.22 | 1.89 | 0.86 | 0.78 | Gpsm1 | G-protein signalling modulator 1 (AGS3-like, C. elegans) |
| 1454649_at | 2.02 | 2.08 | 1.29 | 1.36 | Srd5a1 | steroid 5 alpha-reductase 1 |
| 1418538_at | 2.08 | 2.02 | 1.11 | 0.97 | Kdelr3 | KDEL (Lys-Asp-Glu-Leu) endoplasmic reticulum protein retention receptor 3 |
| 1452058_a_at | 2.07 | 2.02 | 1.28 | 1.13 | Rnf11 | ring finger protein 11 |
| 1437100_x_at | 2.03 | 2.05 | 1.35 | 1.21 | Pim3 | proviral integration site 3 |
| 1416246_a_at | 1.90 | 2.19 | 1.42 | 1.19 | Coro1a | coronin, actin binding protein 1A |
| 1417902_at | 2.00 | 2.07 | 1.14 | 1.10 | Slc19a2 | solute carrier family 19 (thiamine transporter), member 2 |
| 1423933_a_at | 2.06 | 2.01 | 1.12 | 0.99 | 1600029D21Rik | RIKEN cDNA 1600029D21 gene |
| 1431422_a_at | 2.14 | 1.93 | 1.08 | 0.94 | Dusp14 | dual specificity phosphatase 14 |
| 1417625_s_at | 2.03 | 2.03 | 1.06 | 1.17 | Cxcr7 | chemokine (C-X-C motif) receptor 7 |
| 1456284_at | 2.10 | 1.95 | 1.32 | 1.06 | Tmem171 | transmembrane protein 171 |
| 1424471_at | 2.18 | 1.89 | 1.31 | 1.30 | Rapgef3 | Rap guanine nucleotide exchange factor (GEF) 3 |
| 1426306_a_at | 2.18 | 1.87 | 1.10 | 0.97 | LOC100046560///Maged2 | similar to melanoma antigen family D, 2///melanoma antigen, family D, 2 |
| 1437271_at | 2.09 | 1.96 | 1.22 | 0.93 | Clcf1 | cardiotrophin-like cytokine factor 1 |
| 1431416_a_at | 2.12 | 1.93 | 1.14 | 1.03 | Jam2 | junction adhesion molecule 2 |
| 1442363_at | 2.08 | 1.96 | 1.30 | 1.23 | 1110012J17Rik | RIKEN cDNA 1110012J17 gene |
| 1422028_a_at | 2.13 | 1.91 | 1.04 | 0.96 | Ets1 | E26 avian leukemia oncogene 1, 5' domain |
| 1435460_at | 2.07 | 1.96 | 1.37 | 1.28 | Prkg2 | protein kinase, cGMP-dependent, type II |
| 1438038_at | 2.10 | 1.93 | 1.19 | 1.06 | 4930402H24Rik | RIKEN cDNA 4930402H24 gene |
| 1448855_at | 1.97 | 2.05 | 1.33 | 1.22 | Rassf1 | Ras association (RalGDS/AF-6) domain family member 1 |
| 1427278_at | 1.98 | 2.03 | 1.00 | 1.07 | Clip4 | CAP-GLY domain containing linker protein family, member 4 |
| 1431691_a_at | 1.98 | 2.04 | 1.41 | 1.13 | Rab31 | RAB31, member RAS oncogene family |

TABLE 4-continued

Affymetrix Mouse gene probes that respond to vemurafenib and/or Compound A treatments.

| Probe Set ID | Vemurafenib Repl. 1 | Vemurafenib Repl. 2 | Compound A Repl. 1 | Compound A Repl. 2 | Gene Symbol | Gene Title |
|---|---|---|---|---|---|---|
| 1421403_at | 2.04 | 1.96 | 1.37 | 1.11 | Pi15 | peptidase inhibitor 15 |
| 1448894_at | 2.01 | 1.99 | 1.18 | 1.05 | Akr1b8 | aldo-keto reductase family 1, member B8 |
| 1425660_at | 2.08 | 1.92 | 1.39 | 1.32 | Btbd3 | BTB (POZ) domain containing 3 |
| 1430623_s_at | 2.11 | 1.88 | 1.00 | 1.05 | Obfc2a | oligonucleotide/oligosaccharide-binding fold containing 2A |
| 1434601_at | 2.11 | 1.89 | 1.14 | 1.00 | Amigo2 | adhesion molecule with Ig like domain 2 |
| 1453278_a_at | 2.00 | 1.99 | 1.02 | 1.03 | Clip4 | CAP-GLY domain containing linker protein family, member 4 |
| 1456150_at | 1.99 | 1.99 | 1.24 | 1.27 | Jhdm1d | jumonji C domain-containing histone demethylase 1 homolog D (*S. cerevisiae*) |
| 1439434_x_at | 2.06 | 1.91 | 0.87 | 1.08 | Sh2d5 | SH2 domain containing 5 |
| 1452203_at | 2.07 | 1.90 | 1.20 | 1.23 | Obfc2a | oligonucleotide/oligosaccharide-binding fold containing 2A |
| 1422101_at | 2.04 | 1.93 | 0.95 | 0.88 | Tnfrsf23 | tumor necrosis factor receptor superfamily, member 23 |
| 1419722_at | 2.02 | 1.94 | 1.17 | 1.21 | Klk8 | kallikrein related-peptidase 8 |
| 1422924_at | 2.01 | 1.94 | 1.65 | 1.27 | Tnfsf9 | tumor necrosis factor (ligand) superfamily, member 9 |
| 1434252_at | 1.99 | 1.95 | 1.21 | 1.12 | Tmcc3 | transmembrane and coiled coil domains 3 |
| 1420760_s_at | 1.90 | 2.04 | 0.95 | 0.96 | Ndrg1 | N-myc downstream regulated gene 1 |
| 1422240_s_at | 1.95 | 1.98 | 1.04 | 1.11 | Sprr2h | small proline-rich protein 2H |
| 1434092_at | 2.04 | 1.89 | 0.99 | 0.77 | Atg9b | ATG9 autophagy related 9 homolog B (*S. cerevisiae*) |
| 1415828_a_at | 2.05 | 1.88 | 1.27 | 1.11 | Serp1 | stress-associated endoplasmic reticulum protein 1 |
| 1456174_x_at | 1.92 | 2.00 | 0.94 | 0.95 | Ndrg1 | N-myc downstream regulated gene 1 |
| 1460472_at | 1.91 | 1.99 | 1.29 | 1.35 | Cdk3 | cyclin-dependent kinase 3 |
| 1423597_at | 2.02 | 1.88 | 0.94 | 1.11 | Atp8a1 | ATPase, aminophospholipid transporter (APLT), class I, type 8A, member 1 |
| 1448613_at | 2.00 | 1.89 | 1.12 | 1.02 | Ecm1 | extracellular matrix protein 1 |
| 1420913_at | 1.92 | 1.96 | 1.05 | 1.07 | Slco2a1 | solute carrier organic anion transporter family, member 2a1 |
| 1421943_at | 1.93 | 1.92 | 1.20 | 1.06 | Tgfa | transforming growth factor alpha |
| 1418539_a_at | 1.94 | 1.89 | 1.12 | 1.09 | Ptpre | protein tyrosine phosphatase, receptor type, E |
| 1423543_at | 1.88 | 1.95 | 1.09 | 0.90 | Swap70 | SWA-70 protein |
| 1438699_at | 1.89 | 1.87 | 1.19 | 1.18 | Srd5a1 | steroid 5 alpha-reductase 1 |
| 1446791_at | 1.12 | 0.48 | 0.40 | 0.28 | Pi15 | peptidase inhibitor 15 |
| 1426848_at | 0.69 | 0.75 | 0.51 | 0.49 | LOC100047481///Sec24b | similar to SEC24 related gene family, member B (*S. cerevisiae*)///Sec24 related gene family, member B (*S. cerevisiae*) |
| 1421888_x_at | 0.65 | 0.63 | 0.42 | 0.36 | Aplp2 | amyloid beta (A4) precursor-like protein 2 |
| 1440169_x_at | 0.53 | 0.53 | 0.69 | 0.69 | Ifnar2 | interferon (alpha and beta) receptor 2 |
| 1429844_at | 0.52 | 0.53 | 0.90 | 0.82 | 2310043J07Rik | RIKEN cDNA 2310043J07 gene |
| 1456874_at | 0.52 | 0.54 | 0.83 | 0.91 | Flrt2 | fibronectin leucine rich transmembrane protein 2 |
| 1422537_a_at | 0.53 | 0.49 | 1.00 | 0.82 | Id2 | inhibitor of DNA binding 2 |
| 1417533_a_at | 0.50 | 0.51 | 0.97 | 0.88 | Itgb5 | integrin beta 5 |
| 1436944_x_at | 0.53 | 0.48 | 0.69 | 0.80 | Pisd///Pisd-ps1///Pisd-ps3/// | phosphatidylserine decarboxylase phosphatidylserine decarboxylase, pseudogene 1///phosphatidylserine decarboxylase, pseudogene 3 |
| 1457042_at | 0.48 | 0.52 | 1.03 | 0.96 | AI256396 | EST AI256396 |
| 1417495_x_at | 0.48 | 0.51 | 0.99 | 1.16 | Cp | ceruloplasmin |
| 1430567_at | 0.46 | 0.53 | 0.88 | 0.78 | Spink5 | serine peptidase inhibitor, Kazal type 5 |
| 1445758_at | 0.47 | 0.52 | 0.88 | 0.84 | — | — |
| 1460302_at | 0.49 | 0.50 | 0.78 | 0.80 | Thbs1 | thrombospondin 1 |
| 1460695_a_at | 0.51 | 0.48 | 0.92 | 0.80 | 2010111I01Rik | RIKEN cDNA 2010111I01 gene |
| 1456725_x_at | 0.48 | 0.49 | 0.62 | 0.59 | Ezr | ezrin |
| 1437982_x_at | 0.51 | 0.45 | 0.63 | 0.79 | Cox15 | COX15 homolog, cytochrome c oxidase assembly protein (yeast) |

TABLE 4-continued

Affymetrix Mouse gene probes that respond to vemurafenib and/or Compound A treatments.

| Probe Set ID | Vemurafenib Repl. 1 | Vemurafenib Repl. 2 | Compound A Repl. 1 | Compound A Repl. 2 | Gene Symbol | Gene Title |
|---|---|---|---|---|---|---|
| 1447661_at | 0.53 | 0.43 | 0.54 | 0.81 | — | — |
| 1439109_at | 0.45 | 0.50 | 0.76 | 0.66 | Ccdc68 | coiled-coil domain containing 68 |
| 1419671_a_at | 0.49 | 0.45 | 1.01 | 0.89 | Il17rc | interleukin 17 receptor C |
| 1455299_at | 0.50 | 0.44 | 0.73 | 0.72 | Vgll3 | vestigial like 3 (*Drosophila*) |
| 1455241_at | 0.44 | 0.50 | 0.78 | 0.91 | BC037703 | cDNA sequence BC037703 |
| 1422771_at | 0.46 | 0.47 | 0.90 | 0.81 | Smad6 | MAD homolog 6 (*Drosophila*) |
| 1438664_at | 0.44 | 0.49 | 0.96 | 0.94 | Prkar2b | protein kinase, cAMP dependent regulatory, type II beta |
| 1457568_at | 0.44 | 0.50 | 0.83 | 0.79 | Hnrnpd | heterogeneous nuclear ribonucleoprotein D |
| 1447845_s_at | 0.46 | 0.46 | 0.75 | 0.84 | Vnn1 | vanin 1 |
| 1430010_at | 0.43 | 0.49 | 0.89 | 0.72 | Ncapd2 | non-SMC condensin I complex, subunit D2 |
| 1435176_a_at | 0.44 | 0.46 | 0.70 | 0.75 | Id2 | inhibitor of DNA binding 2 |
| 1434957_at | 0.44 | 0.46 | 1.05 | 0.74 | Cdon | cell adhesion molecule-related/down-regulated by oncogenes |
| 1416527_at | 0.42 | 0.48 | 1.03 | 0.97 | Rab32 | RAB32, member RAS oncogene family |
| 1449297_at | 0.41 | 0.47 | 0.89 | 0.94 | Casp12 | caspase 12 |
| 1455981_at | 0.41 | 0.46 | 0.47 | 0.99 | Gm11263///Gm12242///Gm13654///Gm14138///Gm16406///Gm4796///Gm6476///Gm9143///LOC100043734///LOC236932///LOC623245///LOC639593///Rps6 | predicted gene 11263///predicted gene 12242///predicted gene 13654///40S ribosomal protein S6 (Phosphoprotein NP33)///ribosomal protein S6 pseudogene///predicted gene 4796///predicted gene 6476///predicted gene 9143///similar to ribosomal protein S6///similar to 40S ribosomal protein S6///similar to 40S ribosomal protein S6///similar to 40S ribosomal protein S6///ribosomal protein S6 |
| 1454048_a_at | 0.40 | 0.46 | 0.74 | 0.79 | 4931408A02Rik///LOC630876 | RIKEN cDNA 4931408A02 gene///similar to Protein C21orf63 homolog precursor |
| 1454699_at | 0.50 | 0.37 | 0.70 | 0.70 | LOC100047324///Sesn1 | similar to Sesn1 protein///sestrin 1 |
| 1454780_at | 0.42 | 0.44 | 0.95 | 0.74 | Galntl4 | UDP-N-acetyl-alpha-D-galactosamine: polypeptide N-acetylgalactosaminyltransferase-like 4 |
| 1449334_at | 0.43 | 0.42 | 0.80 | 0.82 | Timp3 | tissue inhibitor of metalloproteinase 3 |
| 1451446_at | 0.41 | 0.43 | 0.68 | 0.84 | Antxr1 | anthrax toxin receptor 1 |
| 1420955_at | 0.38 | 0.47 | 0.88 | 0.83 | Vsnl1 | visinin-like 1 |
| 1426260_a_at | 0.39 | 0.45 | 1.21 | 1.15 | Ugt1a1///Ugt1a10///Ugt1a2///Ugt1a5///Ugt1a6a///Ugt1a6b///Ugt1a7c///Ugt1a9 | UDP glucuronosyltransferase 1 family, polypeptide A1///UDP glycosyltransferase 1 family, polypeptide A10///UDP glucuronosyltransferase 1 family, polypeptide A2///UDP glucuronosyltransferase 1 family, polypeptide A5///UDP glucuronosyltransferase 1 family, polypeptide A6A///UDP glucuronosyltransferase 1 family, polypeptide A6B///UDP glucuronosyltransferase 1 family, polypeptide A7C///UDP glucuronosyltransferase 1 family, polypeptide A9 |
| 1439016_x_at | 0.40 | 0.42 | 0.99 | 0.80 | Sprr2a | small proline-rich protein 2A |
| 1454877_at | 0.40 | 0.42 | 1.03 | 0.97 | Sertad4 | SERTA domain containing 4 |
| 1424783_a_at | 0.39 | 0.43 | 1.03 | 0.95 | Ugt1a1///Ugt1a10///Ugt1a2///Ugt1a5///Ugt1a6a///Ugt1a6b///Ugt1a7c///Ugt1a9 | UDP glucuronosyltransferase 1 family, polypeptide A1///UDP glycosyltransferase 1 family, polypeptide A10///UDP glucuronosyltransferase 1 family, polypeptide A2///UDP glucuronosyltransferase 1 family, polypeptide A5///UDP glucuronosyltransferase 1 family, |

TABLE 4-continued

Affymetrix Mouse gene probes that respond to vemurafenib and/or Compound A treatments.

| Probe Set ID | Vemurafenib Repl. 1 | Vemurafenib Repl. 2 | Compound A Repl. 1 | Compound A Repl. 2 | Gene Symbol | Gene Title |
|---|---|---|---|---|---|---|
| | | | | | | polypeptide A6A///UDP glucuronosyltransferase 1 family, polypeptide A6B///UDP glucuronosyltransferase 1 family, polypeptide A7C///UDP glucuronosyltransferase 1 family, polypeptide A9 |
| 1417494_a_at | 0.39 | 0.43 | 0.63 | 0.72 | Cp | ceruloplasmin |
| 1443536_at | 0.39 | 0.40 | 0.49 | 0.76 | Slc7a11 | solute carrier family 7 (cationic amino acid transporter, y + system), member 11 |
| 1451006_at | 0.40 | 0.39 | 0.77 | 0.75 | Xdh | xanthine dehydrogenase |
| 1460220_a_at | 0.40 | 0.38 | 0.77 | 0.91 | Csf1 | colony stimulating factor 1 (macrophage) |
| 1420380_at | 0.37 | 0.41 | 1.06 | 0.94 | Ccl2 | chemokine (C-C motif) ligand 2 |
| 1418497_at | 0.39 | 0.38 | 0.82 | 0.83 | Fgf13 | fibroblast growth factor 13 |
| 1450618_a_at | 0.36 | 0.41 | 0.88 | 0.73 | Sprr2a | small proline-rich protein 2A |
| 1449815_a_at | 0.38 | 0.38 | 0.95 | 0.89 | Ssbp2 | single-stranded DNA binding protein 2 |
| 1440147_at | 0.34 | 0.38 | 0.99 | 0.99 | Lgi2 | leucine-rich repeat LGI family, member 2 |
| 1427747_a_at | 0.36 | 0.35 | 0.84 | 0.82 | Lcn2 | lipocalin 2 |
| 1438931_s_at | 0.35 | 0.33 | 0.53 | 0.80 | LOC100047324/// Sesn1 | similar to Sesn1 protein///sestrin 1 |
| 1427183_at | 0.30 | 0.37 | 0.56 | 0.76 | Efemp1 | epidermal growth factor-containing fibulin-like extracellular matrix protein 1 |
| 1448734_at | 0.31 | 0.30 | 0.88 | 0.89 | Cp | ceruloplasmin |
| 1449335_at | 0.24 | 0.36 | 0.73 | 0.70 | Timp3 | tissue inhibitor of metalloproteinase 3 |
| 1418240_at | 0.30 | 0.28 | 0.75 | 0.81 | Gbp2 | guanylate binding protein 2 |
| 1419089_at | 0.26 | 0.31 | 0.74 | 0.76 | Timp3 | tissue inhibitor of metalloproteinase 3 |
| 1438988_x_at | 0.26 | 0.27 | 0.26 | 0.63 | Hn1 | hematological and neurological expressed sequence 1 |
| 1449227_at | 0.25 | 0.29 | 0.84 | 0.84 | Ch25h | cholesterol 25-hydroxylase |
| 1435906_x_at | 0.21 | 0.30 | 0.85 | 0.79 | Gbp2 | guanylate binding protein 2 |
| 1416454_s_at | 0.23 | 0.20 | 0.74 | 0.57 | Acta2 | actin, alpha 2, smooth muscle, aorta |
| 1460250_at | 0.23 | 0.20 | 0.99 | 0.83 | Sostdc1 | sclerostin domain containing 1 |
| 1449340_at | 0.17 | 0.20 | 0.99 | 1.02 | Sostdc1 | sclerostin domain containing 1 |
| 1416612_at | 0.19 | 0.16 | 0.50 | 0.49 | Cyp1b1 | cytochrome P450, family 1, subfamily b, polypeptide 1 |

TABLE 5

Chromosomal translocations affecting RAF genes create oncogenic BRAF fusion proteins [a]

| | Fusion partner [b] | BRAF exons | CRAF exons | Protein length [c] | Frequency |
|---|---|---|---|---|---|
| Thyroid cancer | AKAP9 | 9-18 | | 1473 (386) | 11% radiation-induced papillary carcinomas [7] |
| Pilocytic astrocytoma | KIAA159 | 9-18 | | 2135 (386) | 66% pilocytic astrocytomas [8] |
| Pilocytic astrocytoma | FAM131B | 9-18 | | 404 (386) | 2-3% (3 out of 125) [9] |
| Prostate cancer | SLC45A3 | 8-18 | | 329 (329) | 1-2% (6 out of 349) [10] |
| Prostate cancer | ESRP1 | | 6-17 | 1060 (454) | 1% (4 out of 450) [10] |
| Gastric cancer | AGTRAP | 8-18 | | 597 (439) | 2% (2 out of 105) [10] |

[a] Fusion results in the loss of the N-terminus RAS binding domain (RBD) and expression of truncated RAF protein retaining the entire functional kinase domain.
[b] Gene symbols: SLC45A3, solute carrier family 45, member 3 (also known as prostein or prostate associated protein 6); ESRP1, epithelial splicing regulatory factor-1; AGTRAP, type-1 angiotensin II receptor associated protein;
[c] The number of amino acid in the protein encoded by the fusion gene. The number of amino acid from RAF is shown in parenthesis.
[7] Ciampi, R. et al. Oncogenic AKAP9-BRAF fusion is a novel mechanism of MAPK pathway activation in thyroid cancer. *J Clin Invest* 115, 94-101 (2005).

TABLE 5-continued

Chromosomal translocations affecting RAF genes create oncogenic BRAF fusion proteins [a]

| Fusion partner [b] | BRAF exons | CRAF exons | Protein length [c] | Frequency |
|---|---|---|---|---|

[8] Jones, D. T. et al. Tandem duplication producing a novel oncogenic BRAF fusion gene defines the majority of pilocytic astrocytomas. *Cancer Res* 68, 8673-8677 (2008).
[9] Cin, H. et al. Oncogenic FAM131B-BRAF fusion resulting from 7q34 deletion comprises an alternative mechanism of MAPK pathway activation in pilocytic astrocytoma. *Acta Neuropathol* 121, 763-774 (2011).
[10] Palanisamy, N. et al. Rearrangements of the RAF kinase pathway in prostate cancer, gastric cancer and melanoma. *Nat Med* 16, 793-798 (2010).

TABLE 6

Data collection and refinement statistics

|  | BRAF$^{V600E}$-Compound A | BRAF$^{V600E}$-Dabrafenib | BRAF$^{V600E}$-P-0352 |
|---|---|---|---|
| Data collection |  |  |  |
| Space group | P2$_1$2$_1$2$_1$ | P2$_1$2$_1$2$_1$ | P2$_1$2$_1$2$_1$ |
| Cell dimensions |  |  |  |
| a, b, c (Å) | 50.3, 104.8, 110.2 | 53.7, 105.7, 109.7 | 51.9, 105.4, 111.3 |
| Resolution (Å)[a] | 76.0-2.47 | 109.7-2.50 | 111.3-2.80 |
|  | (2.47-2.58) | (2.64-2.5) | (2.95-2.80) |
| R$_{sym}$ or R$_{merge}$ | 0.077 (0.743) | 0.071 (0.531) | 0.108 (0.591) |
| I/σI | 7.8 (1.0) | 8.1 (1.4) | 5.1 (1.5) |
| Completeness (%) | 100.0 (100.0) | 99.9 (99.9) | 99.9 (100.0) |
| Redundancy | 5.8 (5.9) | 6.1 (6.2) | 4.6 (4.8) |
| Refinement |  |  |  |
| Resolution (Å) | 76.0-2.47 | 54.9-2.50 | 55.7-2.8 |
| No. reflections | 22,006 | 22,263 | 15,592 |
| R$_{work}$/R$_{free}$ | 0.234/0.273 | 0.212/0.244 | 0.258/0.296 |
| R.m.s deviations |  |  |  |
| Bond lengths (Å) | 0.003 | 0.003 | 0.003 |
| Bond angles (°) | 0.7 | 0.7 | 0.7 |
| Most favored region (%)[b] | 95.1 | 96.5 | 94.8 |
| Additional allowed region (%)[b] | 4.9 | 3.5 | 4.6 |
| Disallowed region (%)[b] | 0.0 | 0.0 | 0.7 |

[a]Highest resolution shell is shown in parenthesis.
[b]In the Ramachandran plot All patents, patent applications and other references cited in the specification are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the disclosure is well adapted to obtain the ends and advantages mentioned, as well as those inherent therein. The methods, variances, and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

While this disclosure has been made with reference to specific embodiments, it is apparent that other embodiments and variations of this disclosure may be devised by others skilled in the art without departing from the true spirit and scope of the disclosure.

In addition, where features or aspects of the disclosure are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any two different values as the endpoints of a range. Such ranges are also within the scope of the disclosure.

What is claimed is:

1. A compound having formula (Ic-1a)

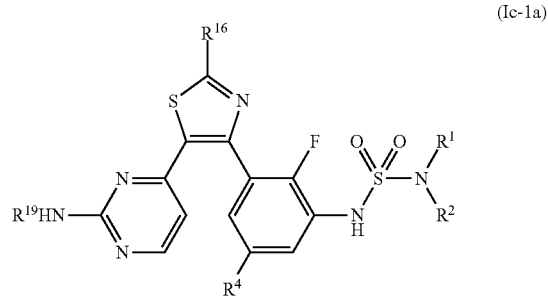

(Ic-1a)

or a pharmaceutically acceptable salt, a solvate, a tautomer or a stereoisomer thereof, wherein:

$R^{16}$ is hydrogen, optionally substituted aryl or optionally substituted $C_{1-6}$alkyl;

$R^{19}$ is hydrogen or 2-(methoxycarbonylamino)propyl;

$R^4$ is hydrogen, fluoro, chloro, —CH$_3$, —CN, or —CF$_3$; and $R^1$ and $R^2$ are each independently optionally substituted alkyl.

2. The compound of claim 1, wherein $R^{19}$ is hydrogen.

3. The compound of claim 1, wherein $R^4$ is hydrogen.

4. A pharmaceutical composition comprising a compound according to claim 1 and a pharmaceutical acceptable carrier, diluent or excipient.

5. The pharmaceutical composition of claim 4, further comprising another therapeutic agent.

6. A method for treating a subject suffering from a metastatic melanoma, a thyroid cancer, a colorectal cancer, a lung cancer or an ovarian cancer, said method comprising:
administering to the subject in need thereof an effective amount of a compound of claim 1.

7. A compound selected from the group consisting of:

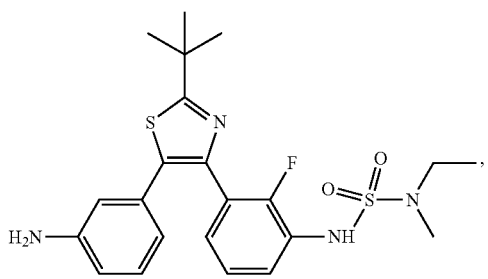

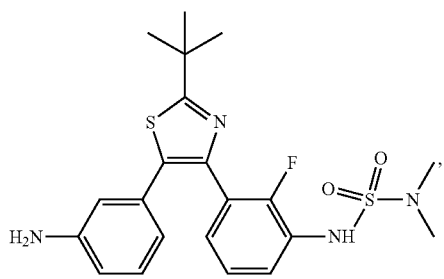

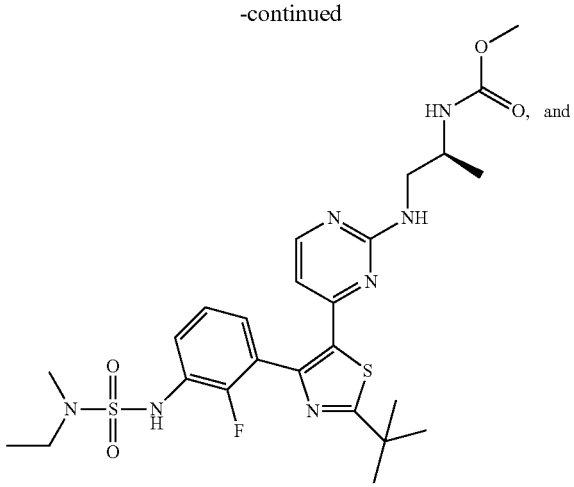

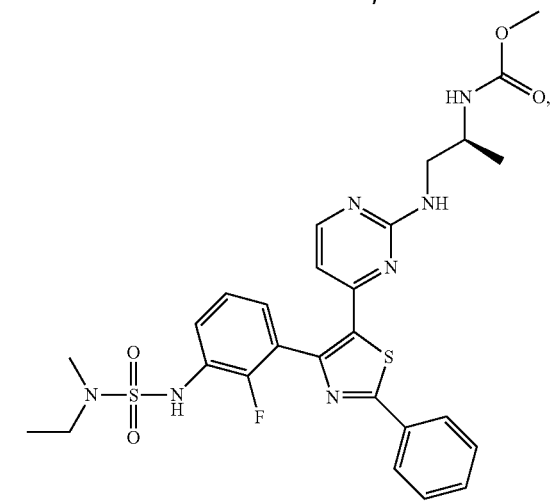

or a pharmaceutically acceptable salt, a solvate, a tautomer or a stereoisomer thereof.

8. A method for treating a subject suffering from a metastatic melanoma, a thyroid cancer, a colorectal cancer, a lung cancer or an ovarian cancer, said method comprising:
administering to the subject in need thereof an effective amount of a compound of claim 7 or a pharmaceutically acceptable salt, a solvate, a tautomer or a stereoisomer thereof.

* * * * *